US007253160B2

(12) United States Patent
Njoroge et al.

(10) Patent No.: US 7,253,160 B2
(45) Date of Patent: Aug. 7, 2007

(54) DEPEPTIDIZED INHIBITORS OF HEPATITIS C VIRUS NS3 PROTEASE

(75) Inventors: F. George Njoroge, Warren, NJ (US); Srikanth Venkatraman, Woodbridge, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 156 days.

(21) Appl. No.: 10/993,394

(22) Filed: Nov. 19, 2004

(65) Prior Publication Data
US 2005/0164921 A1 Jul. 28, 2005

Related U.S. Application Data

(60) Provisional application No. 60/523,715, filed on Nov. 20, 2003.

(51) Int. Cl.
C07K 5/12 (2006.01)
C07K 5/08 (2006.01)
A61K 38/06 (2006.01)
A61K 38/12 (2006.01)
A61P 31/14 (2006.01)

(52) U.S. Cl. .............................. 514/222.5; 514/226.5; 514/309; 514/312; 540/456; 540/460; 546/141; 546/153

(58) Field of Classification Search ............... 540/456, 540/460; 546/141, 153; 514/222.5, 226.5, 514/309, 312
See application file for complete search history.

(56) References Cited

U.S. PATENT DOCUMENTS 5,712,145 A 1/1998 Houghton
6,608,027 B1 8/2003 Tsantrizos

FOREIGN PATENT DOCUMENTS

| EP | 0 381 216 B1 | 12/1995 |
|---|---|---|
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/09543 | 2/2000 |
| WO | WO 00/59929 | 10/2000 |
| WO | WO 01/74768 A2 | 10/2001 |
| WO | WO 01/77113 A2 | 10/2001 |
| WO | WO 01/81325 A2 | 11/2001 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/48172 A2 | 6/2002 |

OTHER PUBLICATIONS

International Search report for PCT/US2004/039131 dated Nov. 19, 2004 for IN06122US01—5 Pages.
Berenguer, Marina, et al., "Hepatitis B and C Viruses: Molecular Identification and Targeted Antiviral Therapies," Proceedings of the Association of American Physicians, 110(2):98-112 (1998).
Dimasi, Nazzareno, et al., "Characterization of Engineered Hepatitis C Virus NS3 Protease Inhibitors Affinity Selected from Human Pancreatic Secretory Trypsin Inhibitor and Minibody Repertoires," Journal of Virology 71(10):7461-7469 (1997).
Elzouki, Abdul-Nasser, et al., "Serine protease inhibitors in patients with chronic viral hepatitis," Journal of Hepatology 27:42-48 (1997).
Failla, Cristina Maria, et al., "Redesigning the substrate specificity of the hepatitis C virus NS3 protease," Folding & Design 1(1):35-42 (1996).
Han, Wei, et al., "Alpha-Ketoamides, Alpha-Ketoesters and Alpha-Diketones as HCV NS3 Protease Inhibitors," Bioorganic & Medicinal Chemistry Letters 10:711-713 (2000).
Hoofnagle, Jay H., et al., "The Treatment of Chronic Viral Hepatitis," Drug Therapy 336(5):347-356 (Jan. 30, 1997).
Ingallinella, Paolo, et al., "Potent Peptide Inhibitors of Human Hepatitis C Virus NS3 Protease Are Obtained by Optimizing the Cleavage Products," Biochemistry 37:8906-8914 (1998).
Kolykhalov, Alexander A., et al., "Specificity of the Hepatitis C Virus NS3 Serine Protease: Effects of Substitutions at the 3/4A, 4A/4B, 4B/5A and 5A/5B Cleavage Sites on Polyprotein Processing," Journal of Virology 68(11):7525-7533 (Nov. 1994).
Komoda, Yasumasa, et al., "Substrate Requirements of Hepatitis C Virus Serine Proteinase for Intermolecular Polypeptide Cleavage in *Escherichia coli*," Journal of Virology 68(11):7351-7357 (Nov. 1994).
Landro, James A., et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping," Biochemistry 36:9340-9348 (1997).

(Continued)

Primary Examiner—Bruck Kifle
(74) Attorney, Agent, or Firm—Serena Farquharson-Torres

(57) ABSTRACT

The present invention discloses novel depeptidized compounds which have HCV protease inhibitory activity as well as pharmaceutical compositions comprising such compounds and methods of using them to treat disorders associated with the HCV protease.

44 Claims, No Drawings

OTHER PUBLICATIONS

Llinas-Brunet, Montse, et al., "Peptide-Based Inhibitors of the Hepatitis C Virus Serine Protease," Bioorganic & Medicinal Chemistry Letters 8:1713-1718 (1998).

Marchetti, Antonella, et al., "Synthesis of Two Novel Cyclic Biphenyl Ether Analogs of an Inhibitor of HCV NS3 Protease," Synlett S1:1000-1002 (1999).

Martin, F., et al., "Affinity selection of camelized VH domain antibody inhibitor of hepatitis C NS3 protease," Protein Engineering 10(5):607-614 (1997).

Martin, Franck, et al., "Design of Selective Eglin Inhibitors HCV NS3 Proteinease," Biochemistry 37:11459-11468 (1998).

Pizzi, Elisabetta, et al., "Molecular model of the specificity pocket of the hepatitis C virus protease: Implications for substrate recognition," Proc. Natl. Acad. Sci. USA 91:888-892 (Feb. 1994).

BioWorld Today 9(217):4 (Nov. 10, 1998).

U.S. Appl. No. 10/052,386, filed Jan. 18, 2002.

DEPEPTIDIZED INHIBITORS OF HEPATITIS C VIRUS NS3 PROTEASE

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel macrocyclic compounds as inhibitors of the HCV NS3/NS4a serine protease. This application claims priority from U.S. provisional patent application Ser. No. 60/523,715 filed Nov. 20, 2003.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids, and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), cV$_H$E2 (a "camelized" variable domain antibody fragment) (Martin et al.(1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608,027, Assignee: Boehringer Ingelheim (Canada) Ltd.; Published Oct. 12, 2000) which discloses peptide derivatives of the formula:

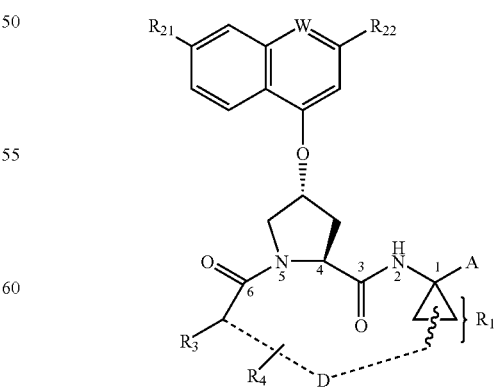

Reference is made to A. Marchetti et al, *Synlett*, S1, 1000-1002 (1999) describing the synthesis of bicylic analogs of an inhibitor of HCV NS3 protease. A compound disclosed therein has the formula:

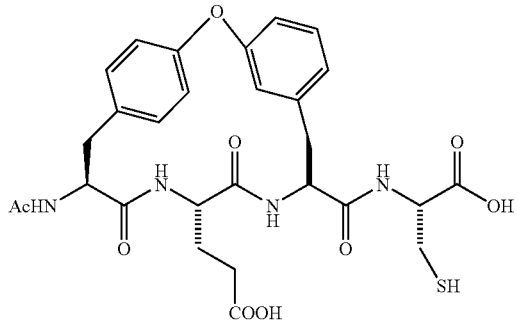

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

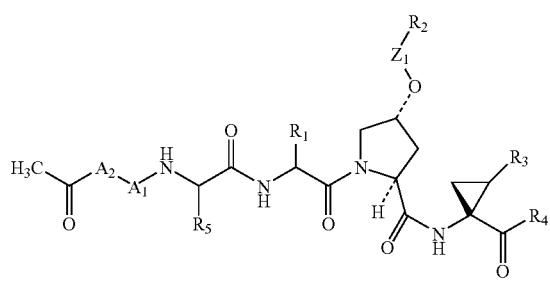

where the various elements are defined therein. An illustrative compound of that series is:

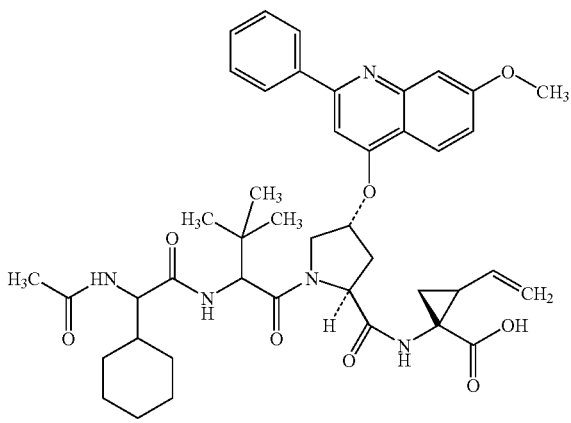

Reference is also made to WO 00/09543 (Assignee: Boehringer Ingelheim Limited; Published Feb. 24, 2000) which discloses peptide derivatives of the formula:

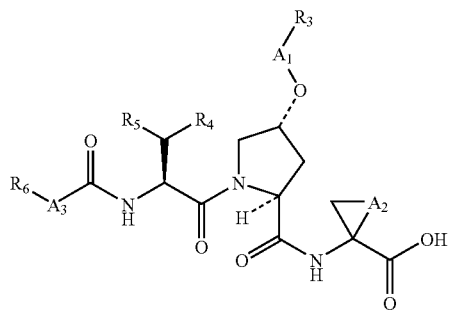

where the various elements are defined therein. An illustrative compound of that series is:

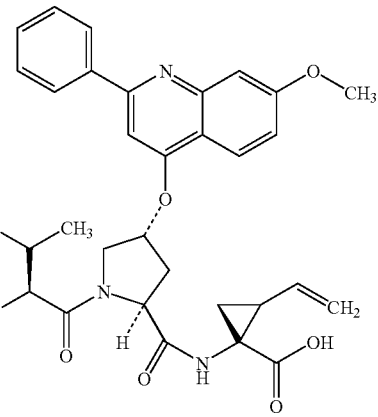

Reference is also made to U.S. Pat. No. 6,608,027 (Boehringer Ingelheim, Canada) which discloses NS3 protease inhibitors of the type:

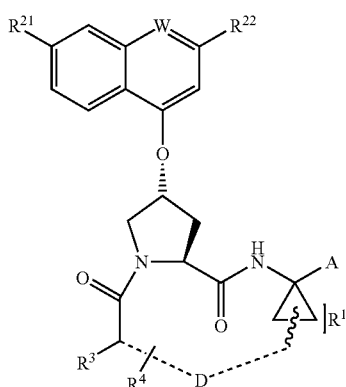

wherein the various moieties are defined therein.

Current therapies for hepatitis C include interferon-α ($INF_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

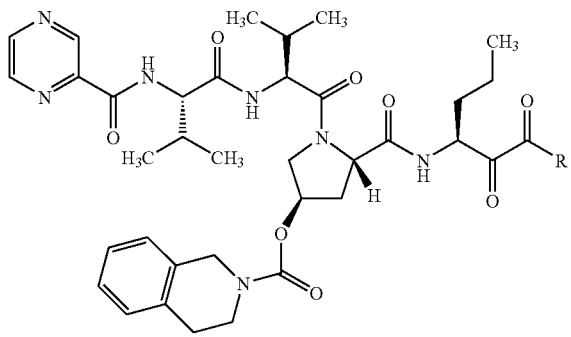

A specific compound disclosed in the afore-mentioned WO 01/74768 has the following formula:

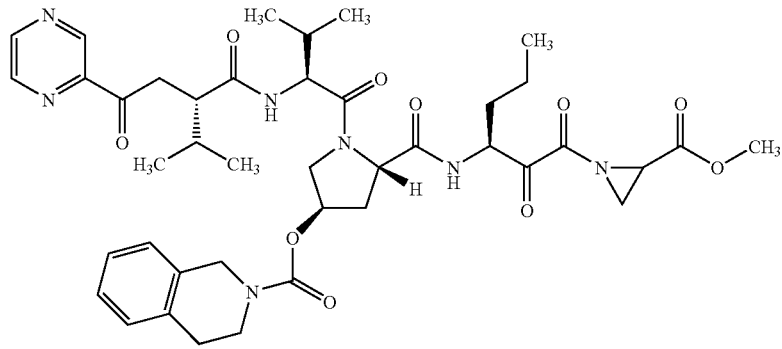

PCT Publications WO 01/77113; WO 01/081325; WO 02/08198; WO 02/08256; WO 02/08187; WO 02/08244; WO 02/48172; WO 02/08251; and pending U.S. patent application, Ser. No.10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds having the general structure shown in either structural Formula 1, structural Formula 2 or structural Formula 3:

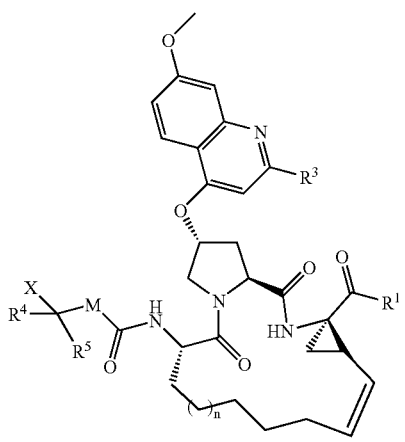

Formula 1

-continued

Formula 2

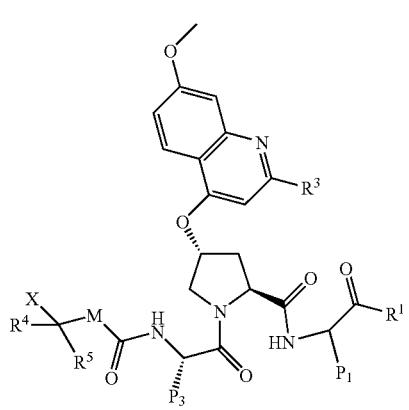

Formula 3

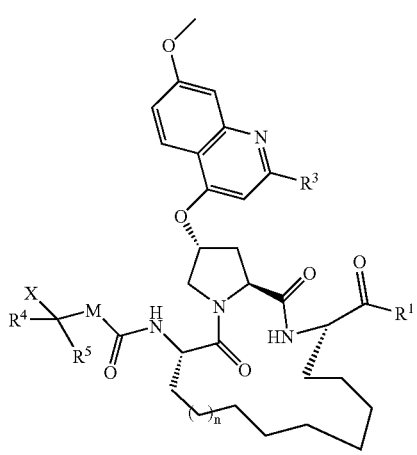

or a pharmaceutically acceptable salt, solvate or ester thereof, wherein,

M is O, N(H), or CH$_2$;

n is 0-4;

R$^1$ is —OR$^6$, —NR$^6$R$^7$ or

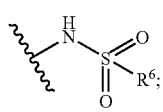

where R$^6$ and R$^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

P$_1$ is selected from the group consisting of alkyl, alkenyl, alkynyl, cycloalkyl haloalkyl;

P$_3$ is selected from the group consisting of alkyl, cycloalkyl, aryl and cycloalkyl fused with aryl;

R$^4$ and R$^5$ can be the same or different, each being independently selected from the group consisting of H, alkyl, aryl and cycloalkyl; or alternatively R$^4$ and R$^5$ together form part of a cyclic 5- to 7-membered ring such that the moiety

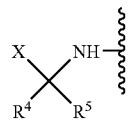

is represented by

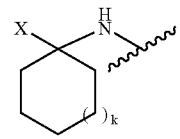

where k is 0 to 2;

X is selected from the group consisting of:

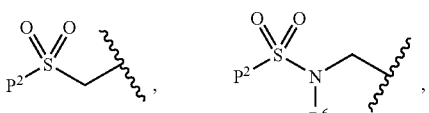

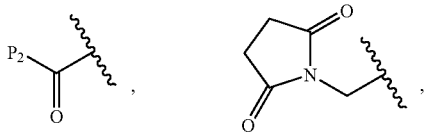

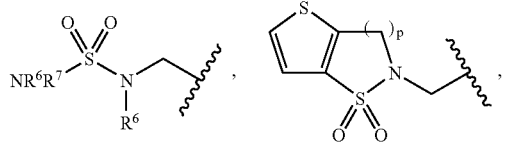

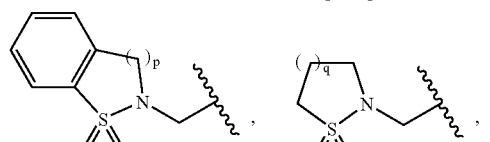

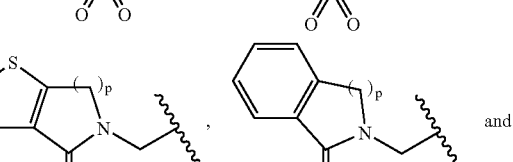

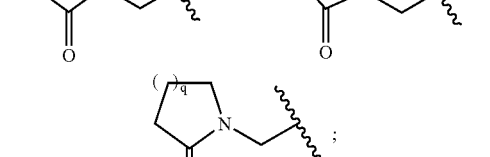

where p is 1 to 2, q is 1 to 3, and P$^2$ is alkyl, aryl, heteroaryl, heteroalkyl, cycloalkyl, dialkylamino, alkylamino, arylamino or cycloalkylamino;

and

R$^3$ is selected from the group consisting of: aryl, heterocyclyl, heteroaryl,

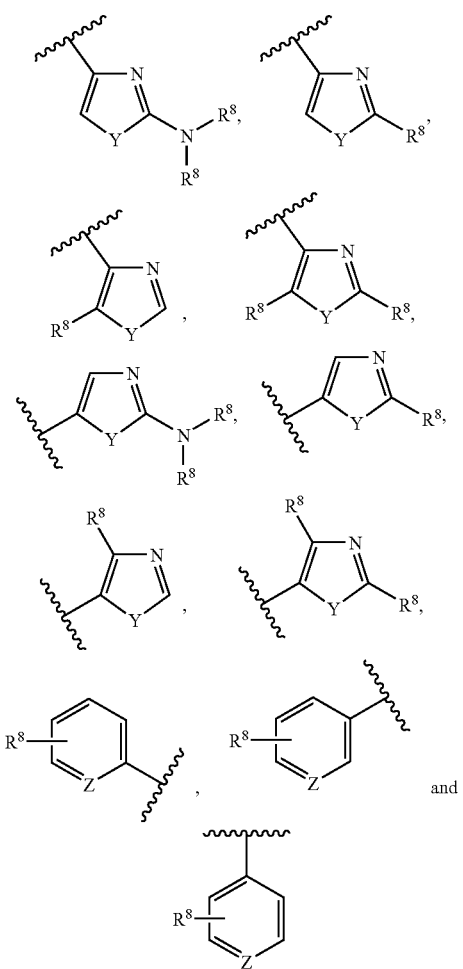

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

Each of the compounds represented by Formulas 1, 2 and 3, by itself or in combination with one or more compounds selected from the compounds of Formula 1, 2 and 3 and/or with other suitable agents disclosed herein, can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention depeptidized compounds which are represented by structural Formulas 1, 2 or 3, or a pharmaceutically acceptable salt, solvate or ester thereof, wherein the various moieties are as defined above.

In another embodiment, M is NH or O.

In another embodiment, n is 0-3.

In another embodiment, $R^1$ is $OR^6$ or $NR^6R^7$, where $R^6$ and $R^7$ can be the same or different, each being independently selected from the group consisting of H, alkyl, alkenyl, cycloalkyl, alkylamino and cycloalkylalkyl.

In another embodiment, $P^1$ is selected from the group consisting of:

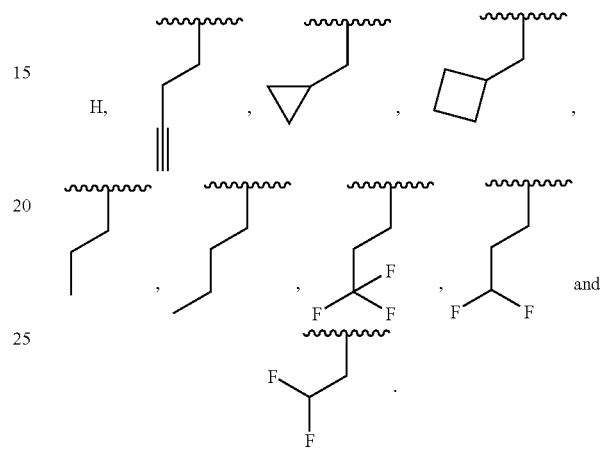

In another embodiment, $P^3$ is selected from the group consisting of:

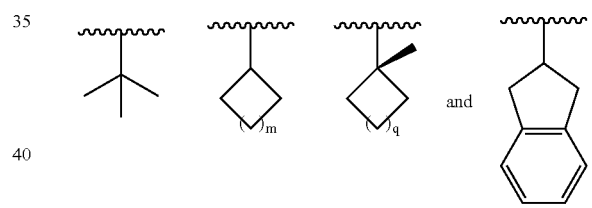

where m is 0 to 3 and q is 1 to 3.

In another embodiment, $R^4$ and $R^5$ are the same or different, each being independently selected from the group consisting of:

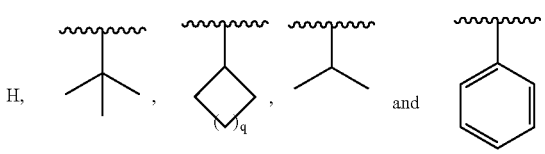

where q is 1 to 3, or $R^4$ and $R^5$ form part of a 5- or 6-membered ring as stated above.

In an additional embodiment, M is NH.

In an additional embodiment, n is 0 or 1.

In an additional embodiment, $R^1$ is OH, $NH_2$ or N(H)(alkyl).

In an additional embodiment, $P_1$ is cyclopropylalkyl, cyclobutylalkyl, n-propyl, n-butyl, 1,1,-difluoroethyl, 1,1-difluoropropyl or 1,1,1-trifluoropropyl.

In an additional embodiment, $P_3$ is t-butyl, cyclobutyl, cyclohexyl, or indanyl.

In an additional embodiment, $R^4$ and $R^5$ are the same or different, each being independently selected from the group consisting of t-butyl, cyclobutyl or phenyl, or $R^4$ and $R^5$ together form a 6-membered ring as stated above.
Yet another embodiment of the invention discloses compounds in Table 1 as belonging to Formula 1:
TABLE 1
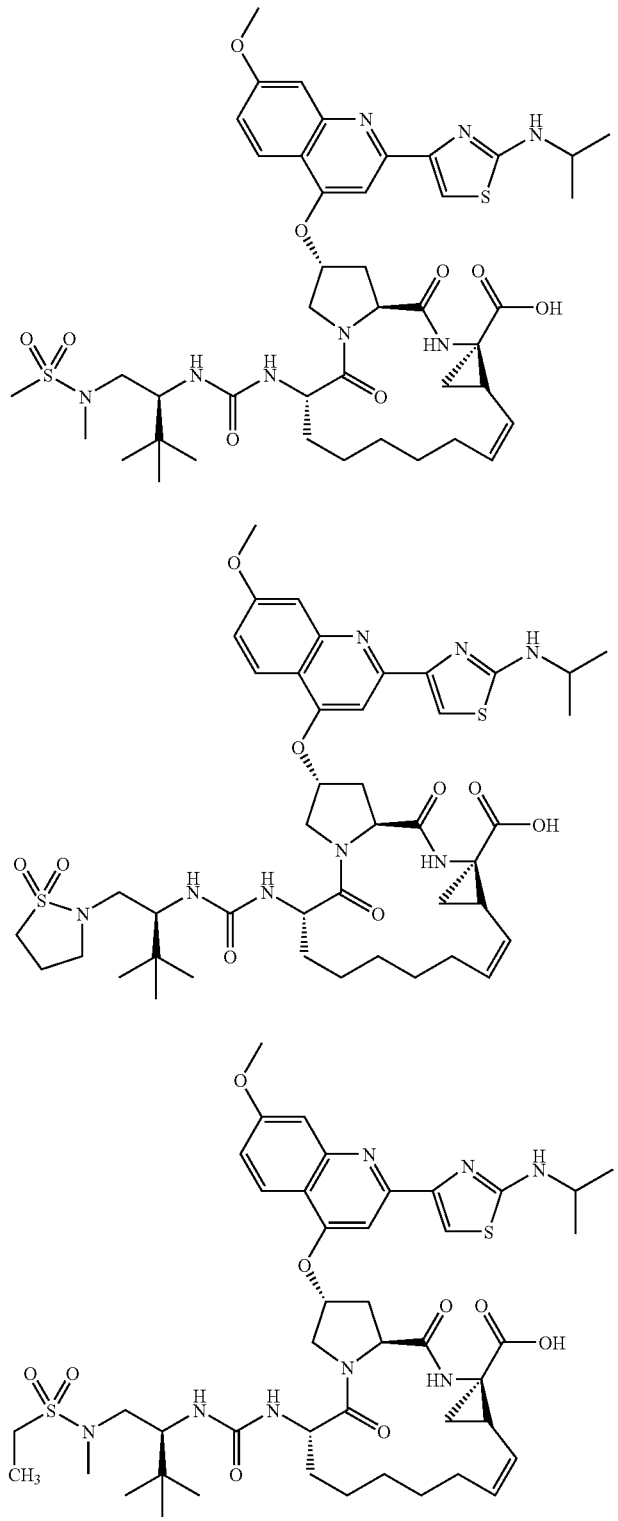

TABLE 1-continued
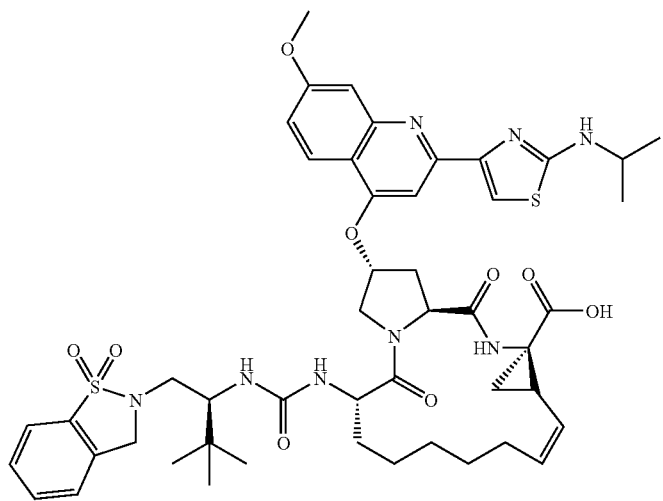
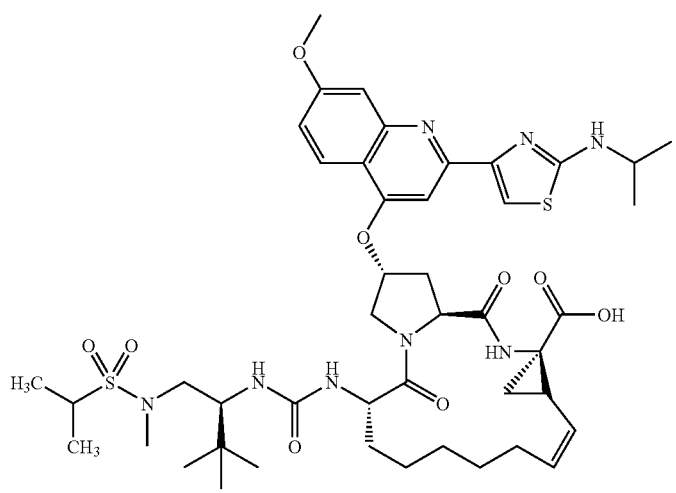
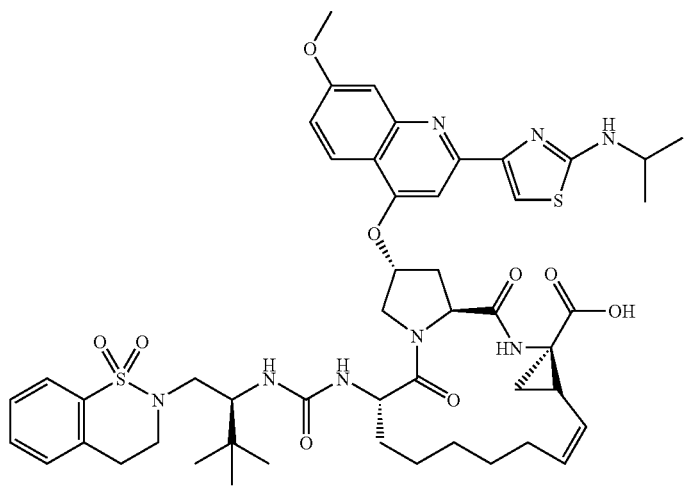

TABLE 1-continued
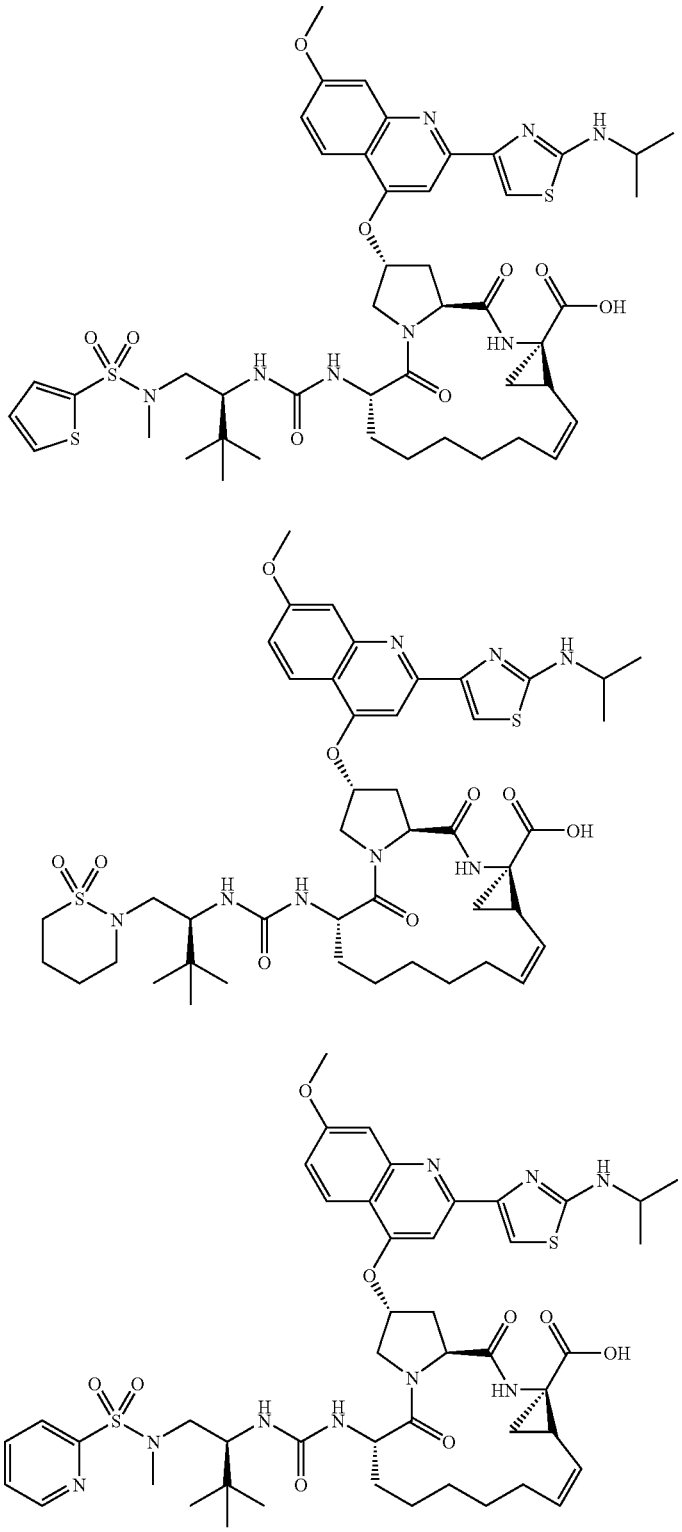

TABLE 1-continued
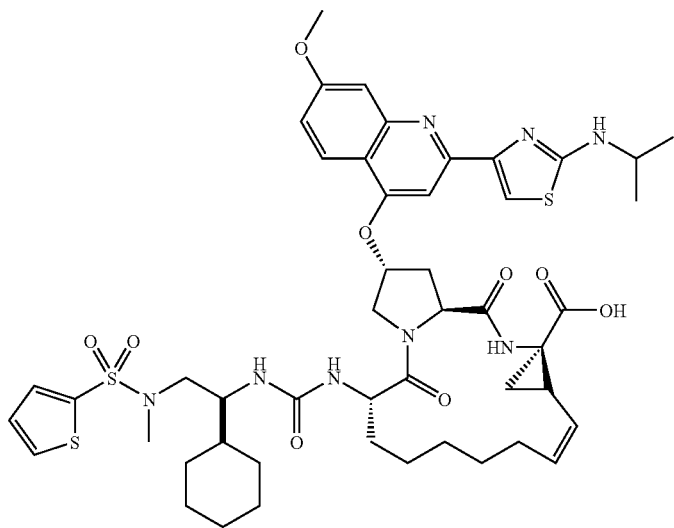
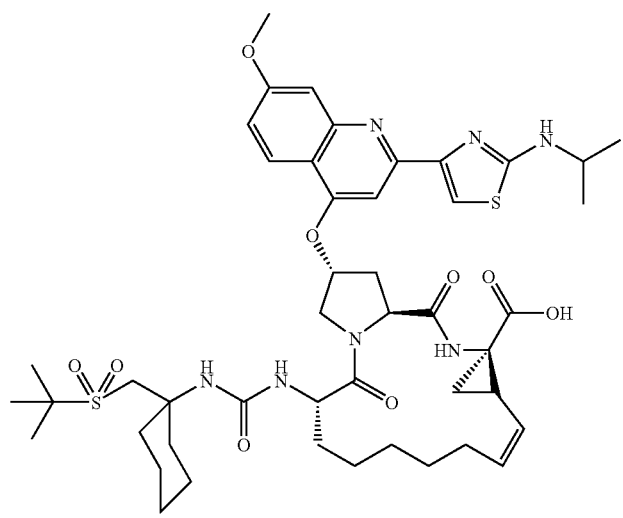
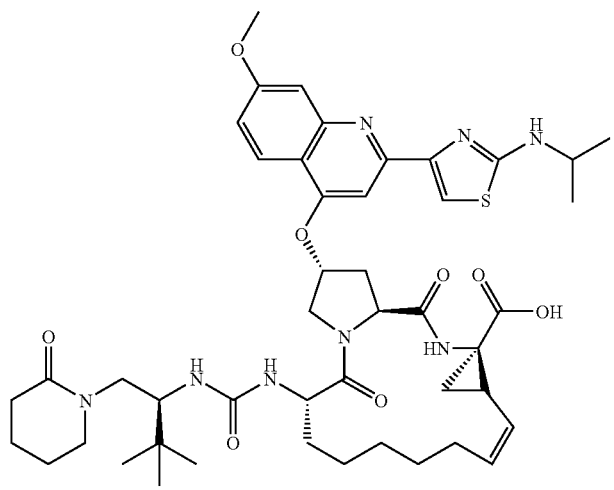

TABLE 1-continued
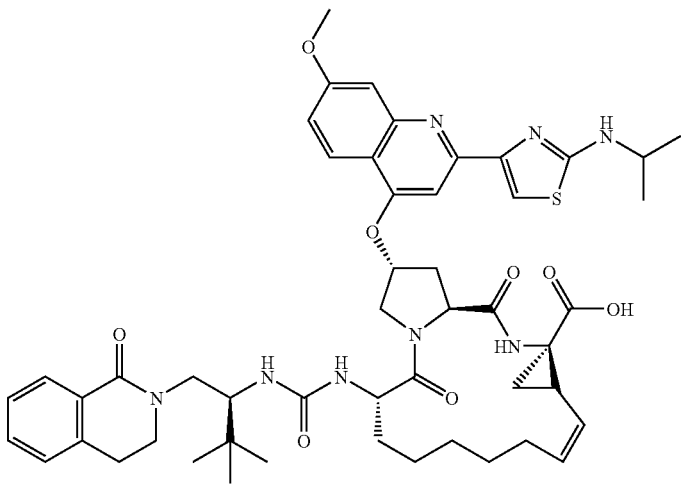
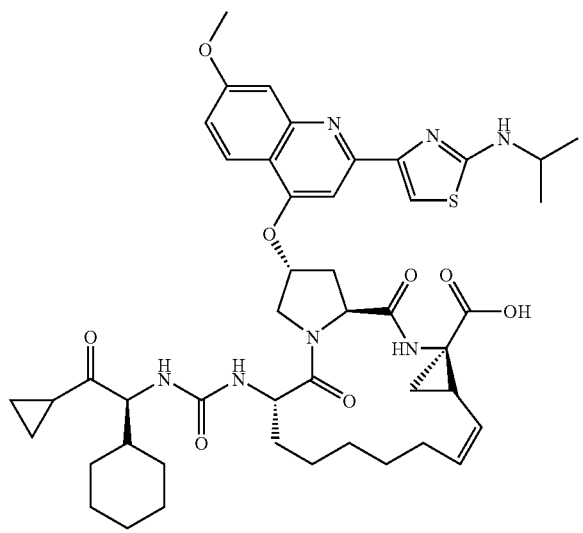
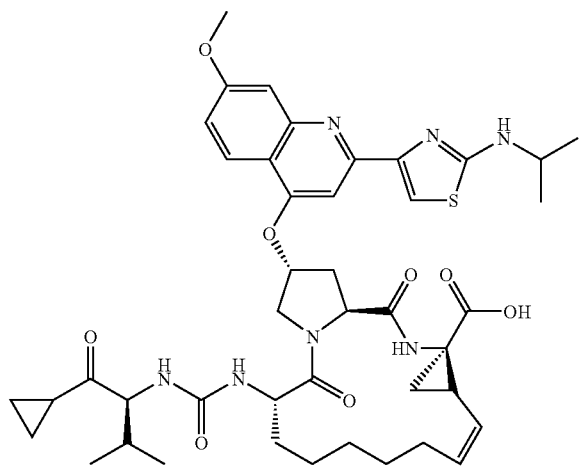

TABLE 1-continued
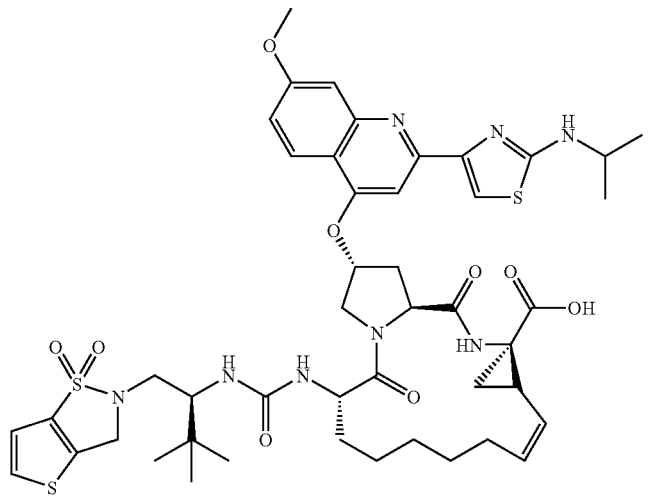
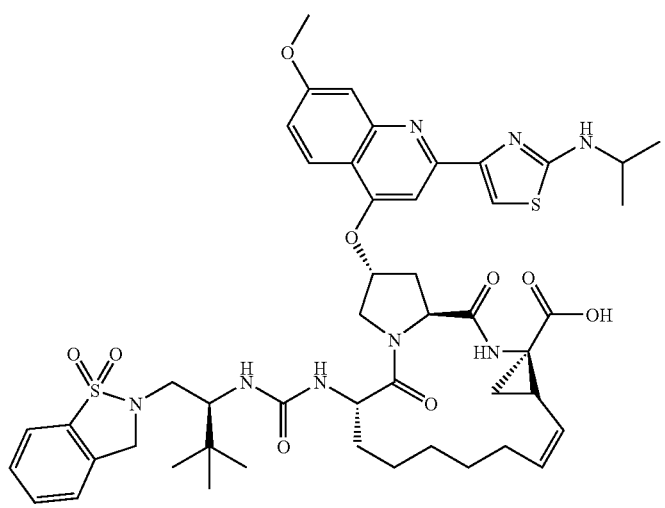
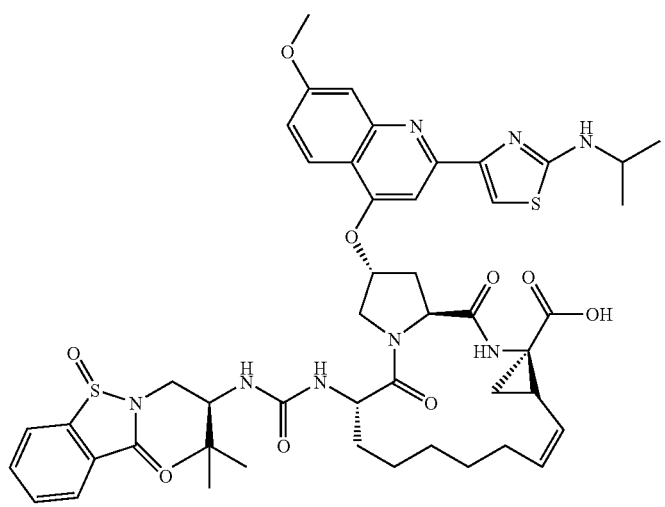

TABLE 1-continued
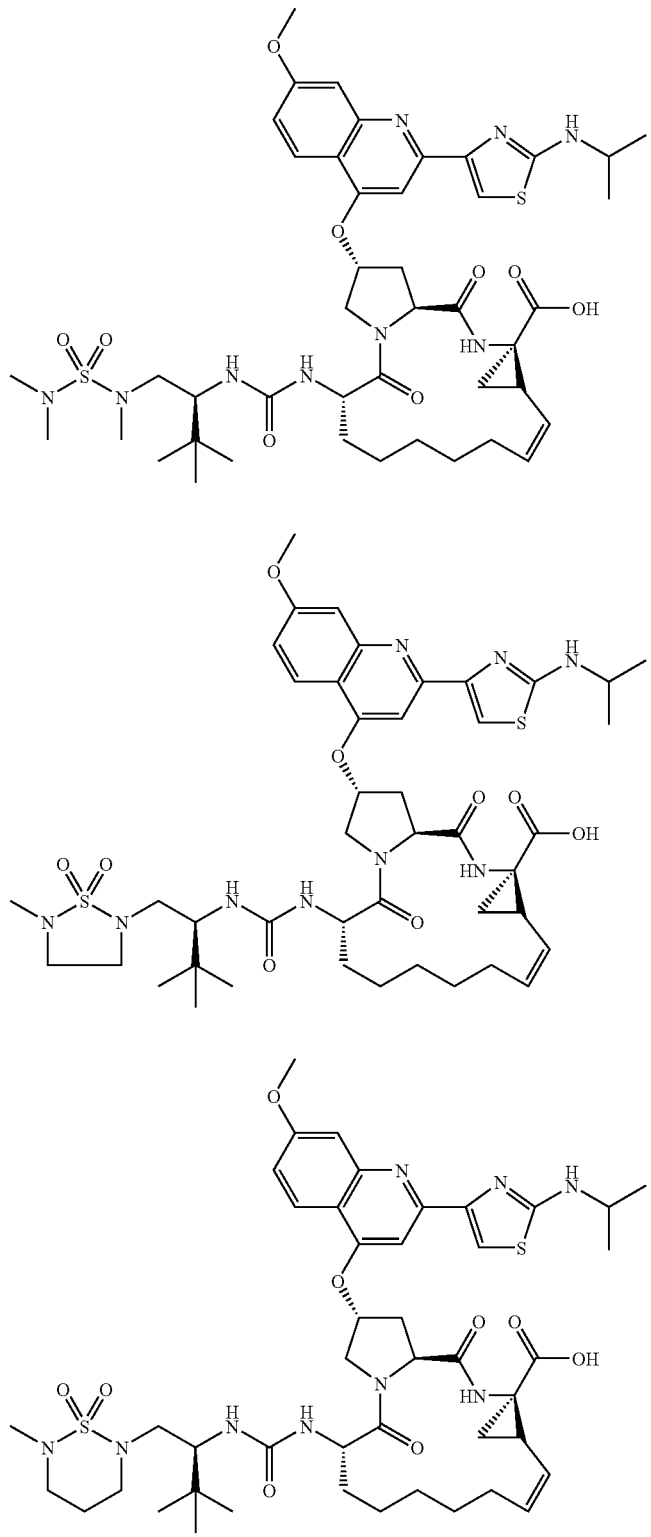

TABLE 1-continued
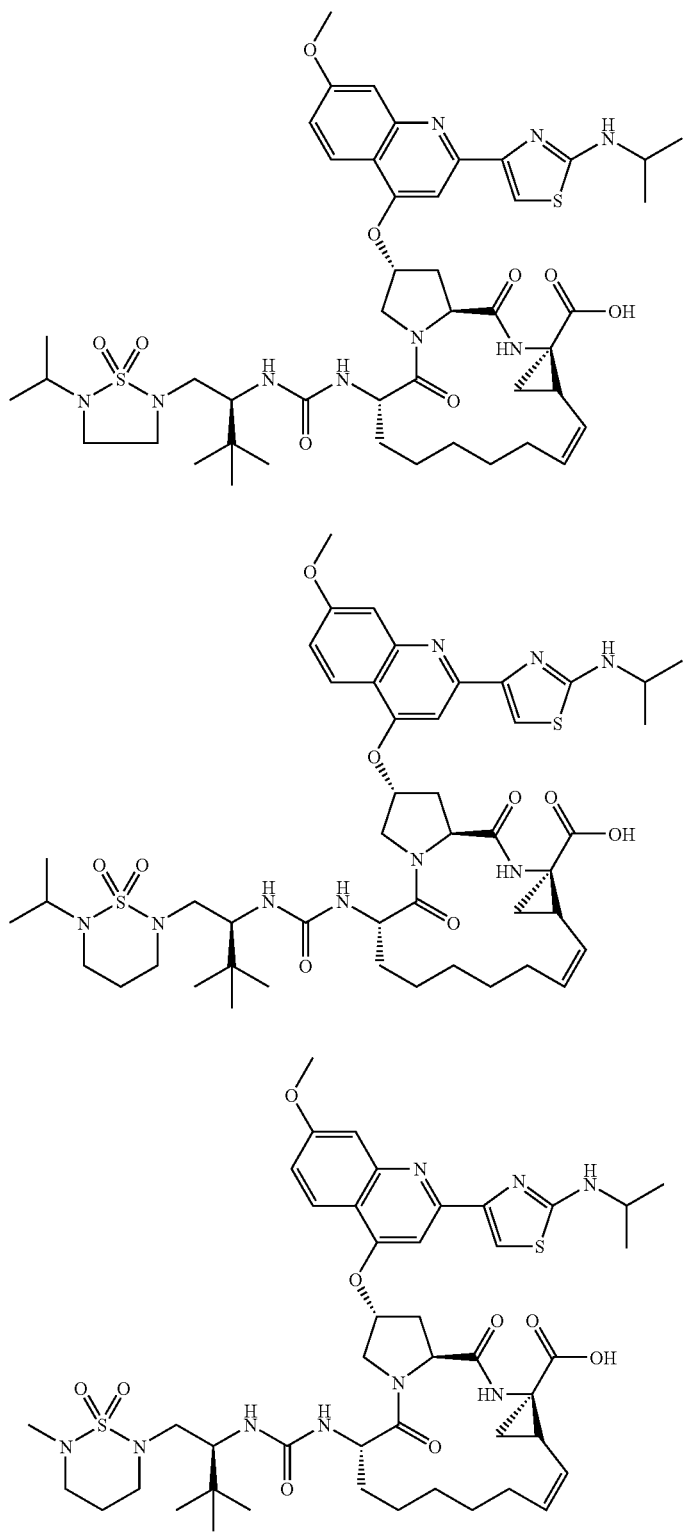

TABLE 1-continued
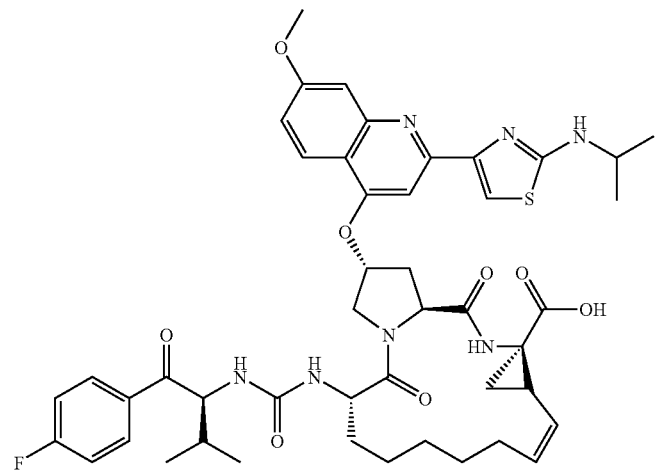
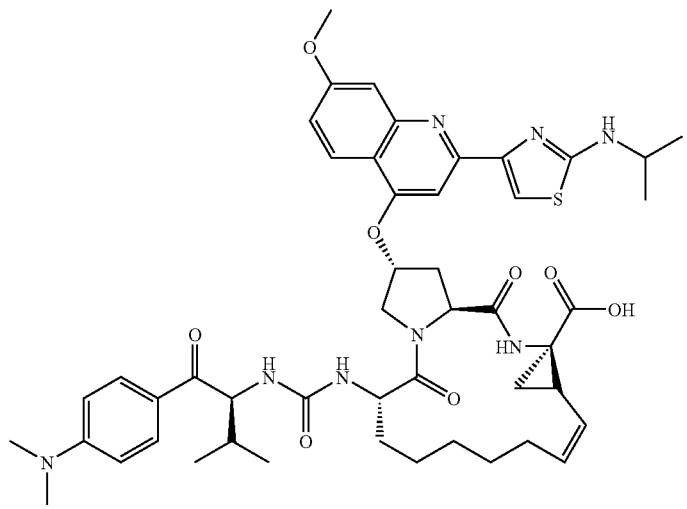
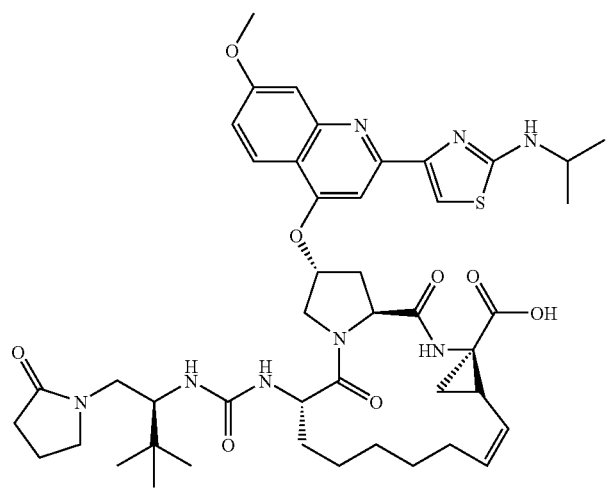

TABLE 1-continued
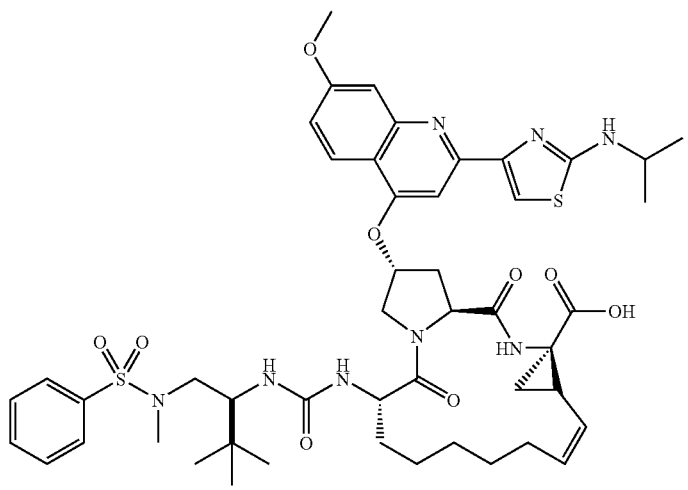
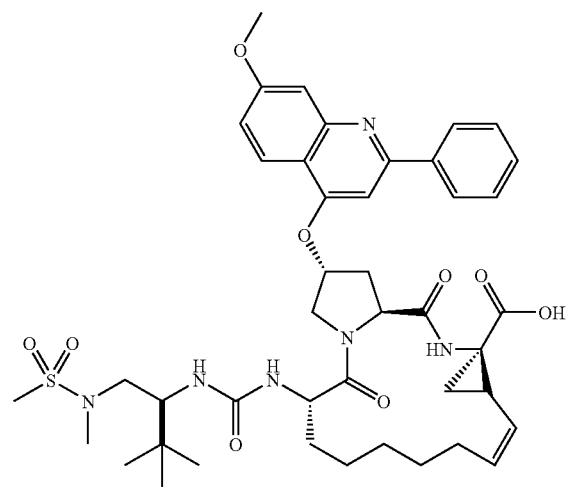
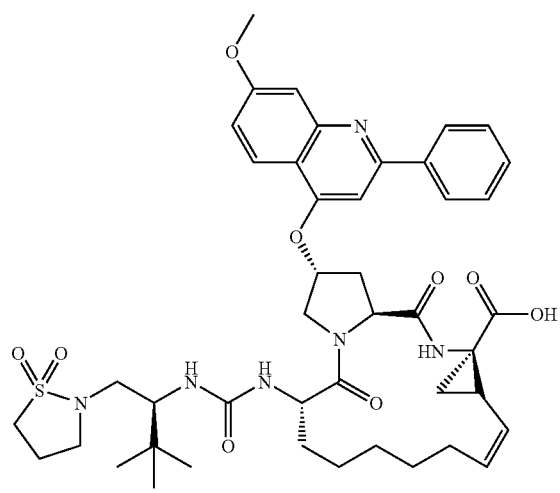

TABLE 1-continued
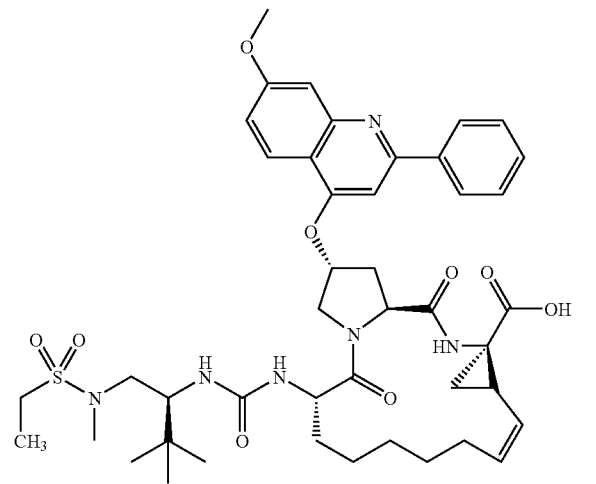
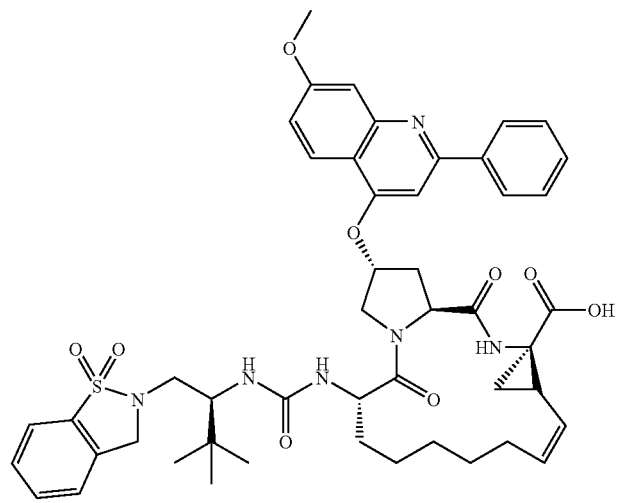
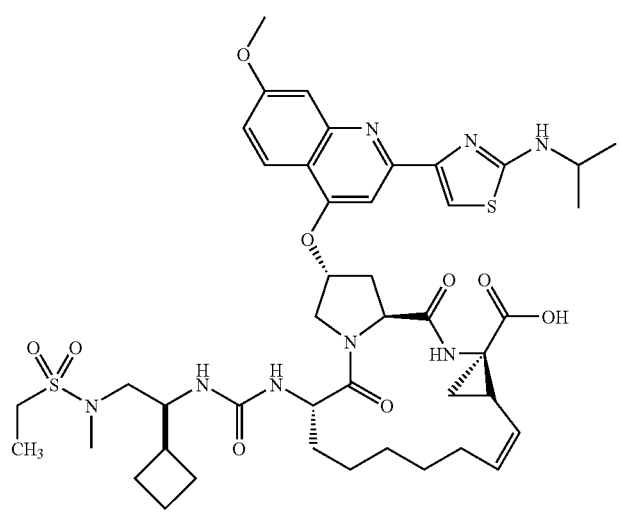

TABLE 1-continued
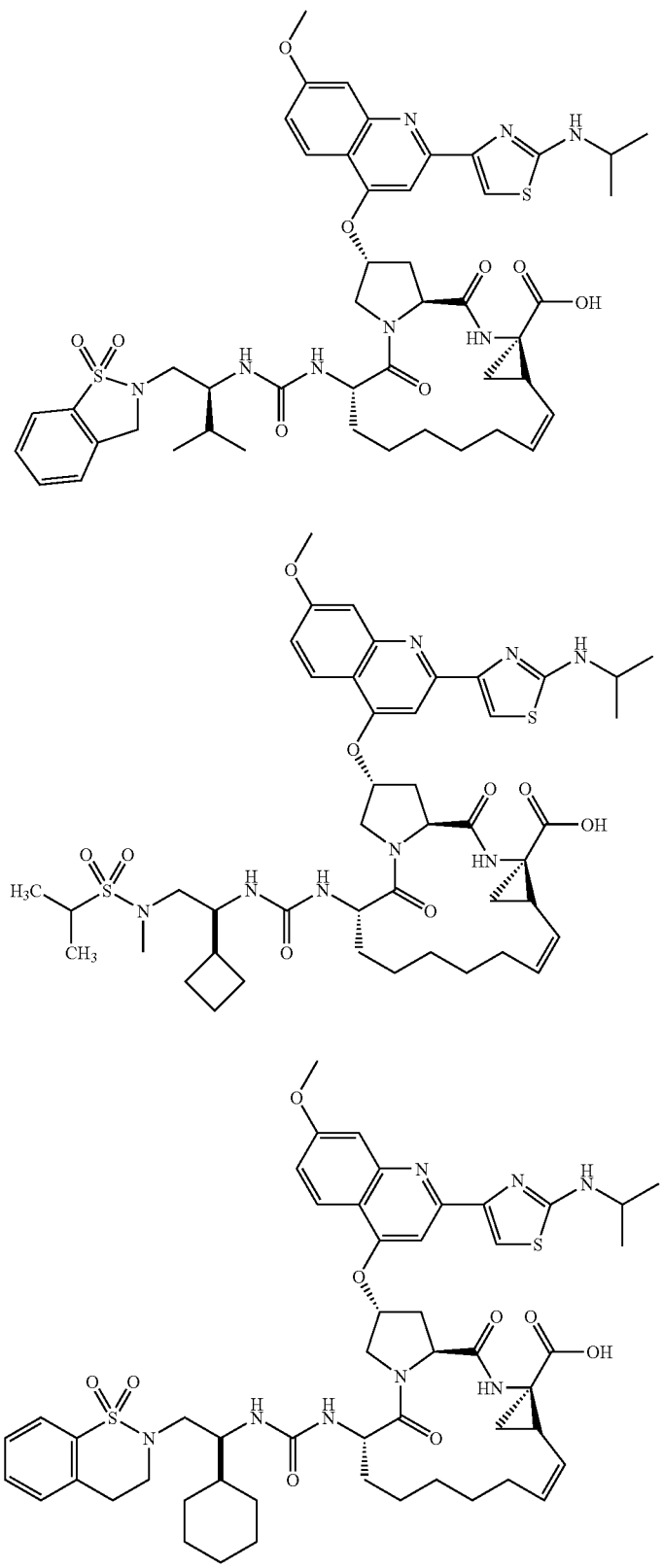

TABLE 1-continued
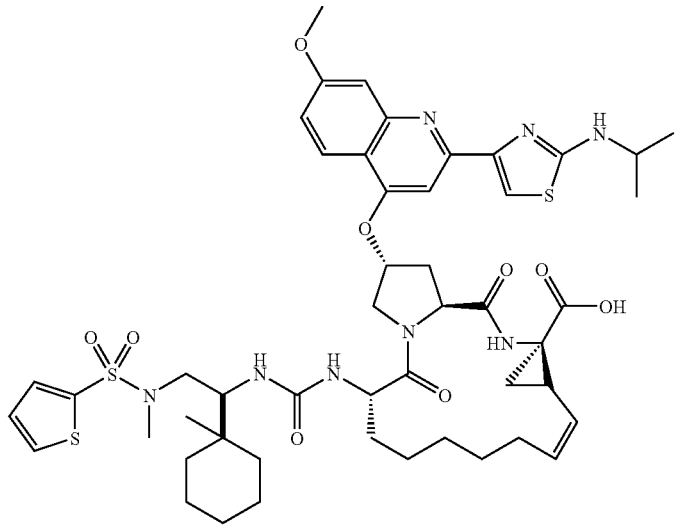
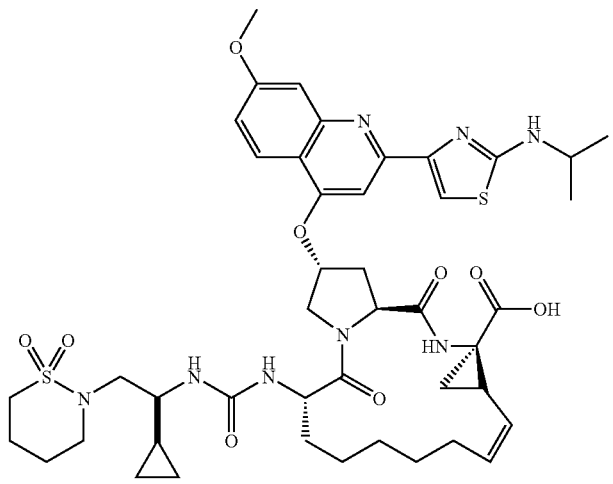
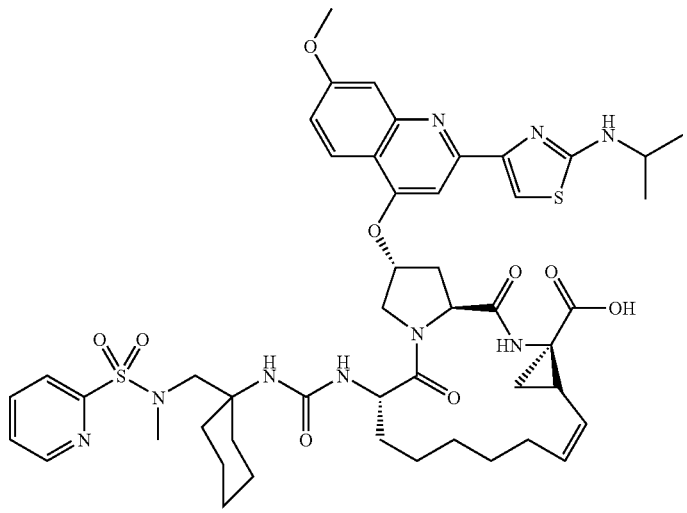

TABLE 1-continued
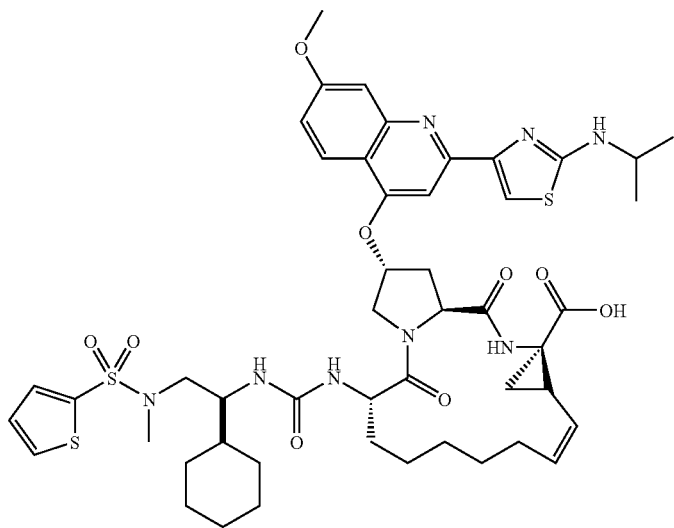
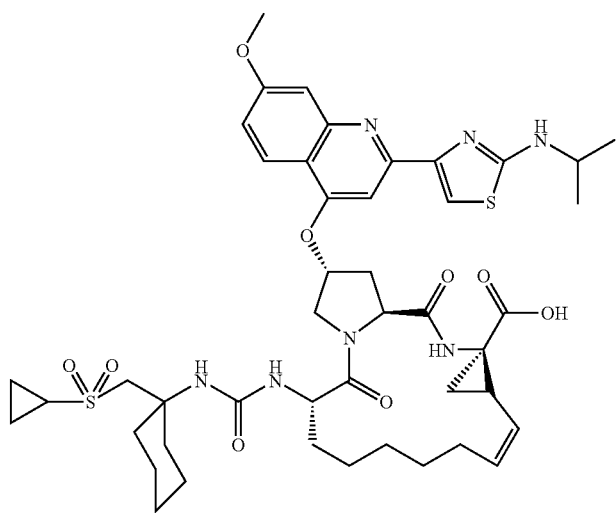
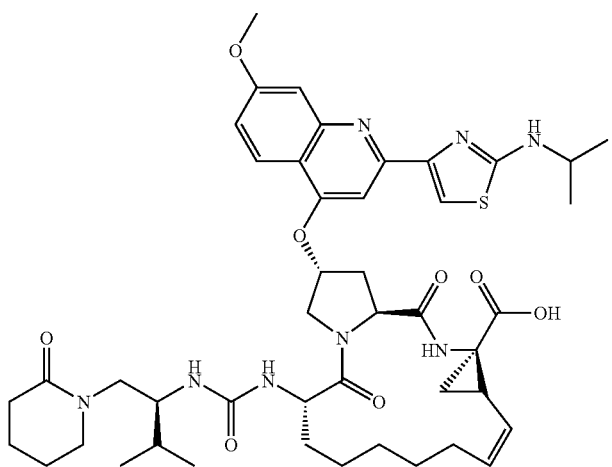

TABLE 1-continued
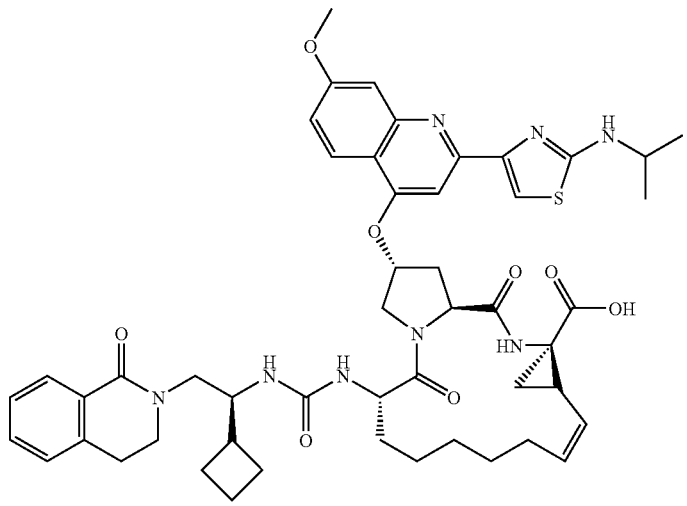
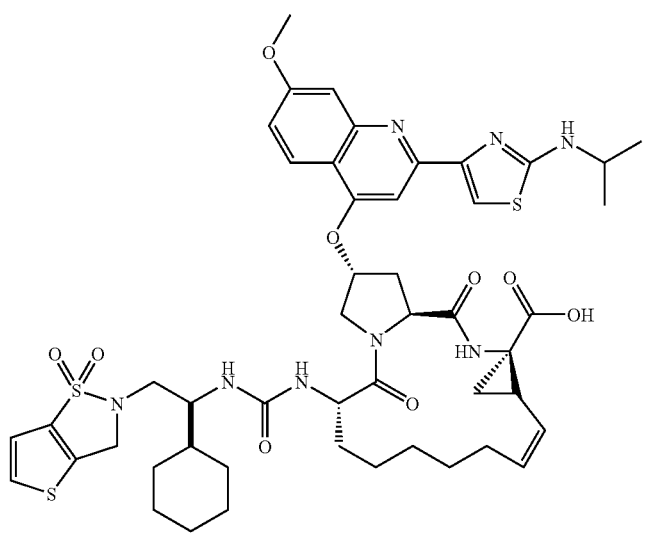
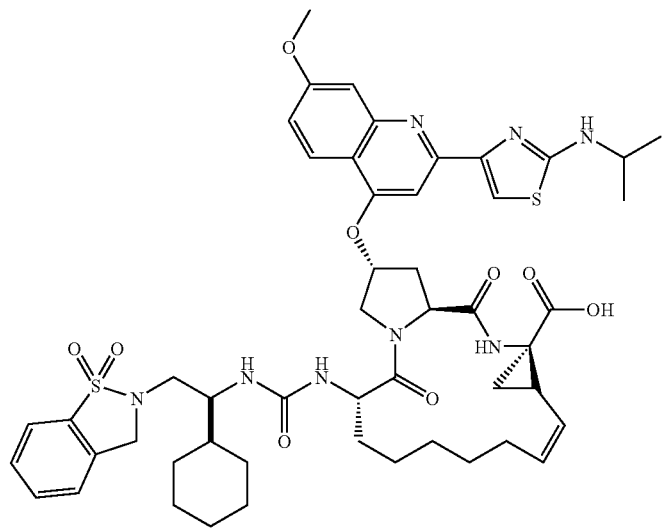

TABLE 1-continued
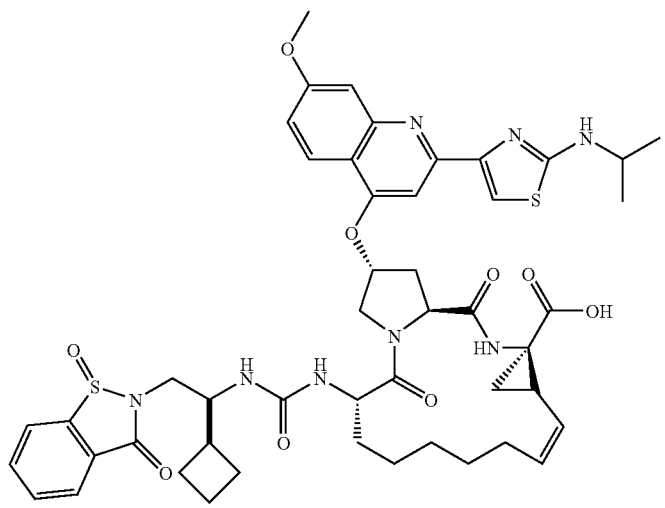
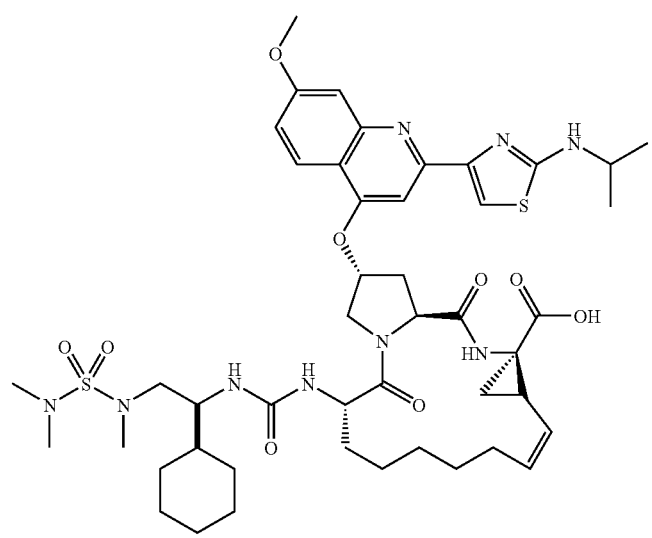
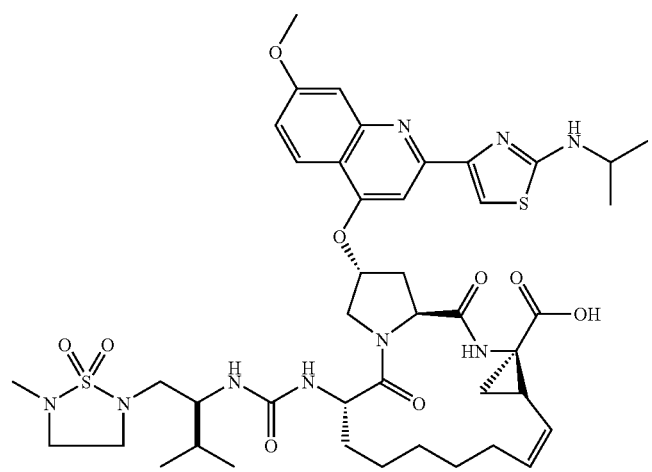

TABLE 1-continued
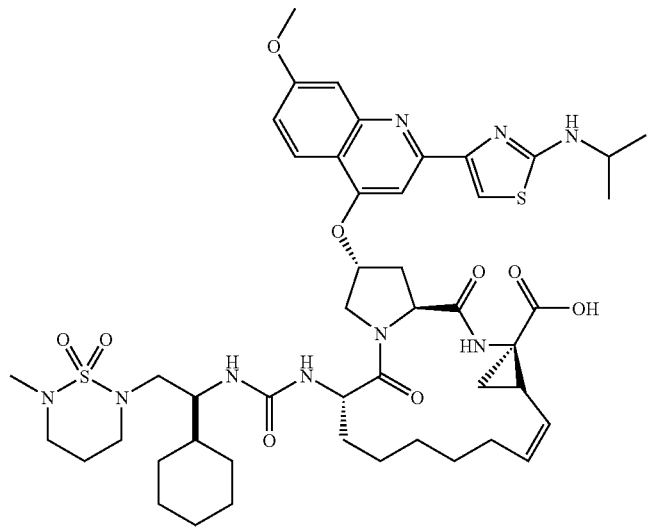
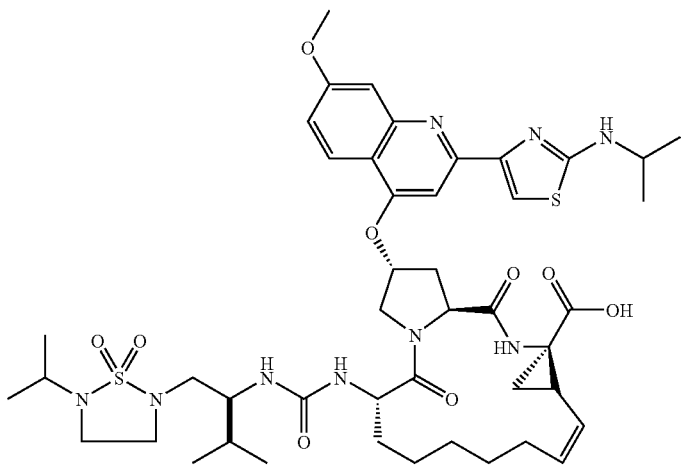
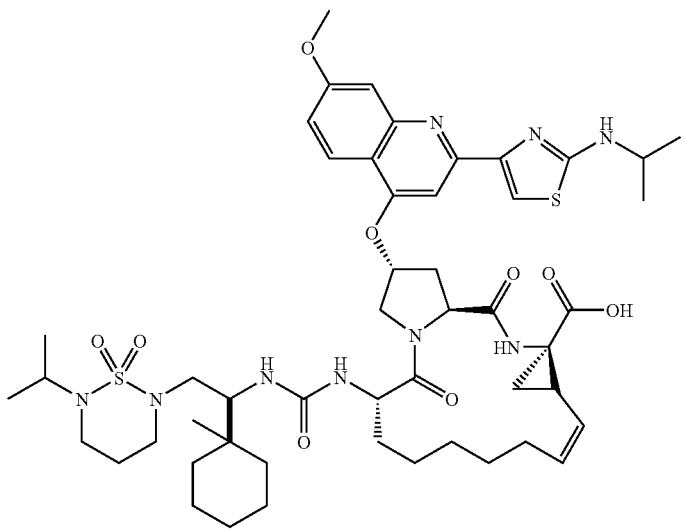

TABLE 1-continued
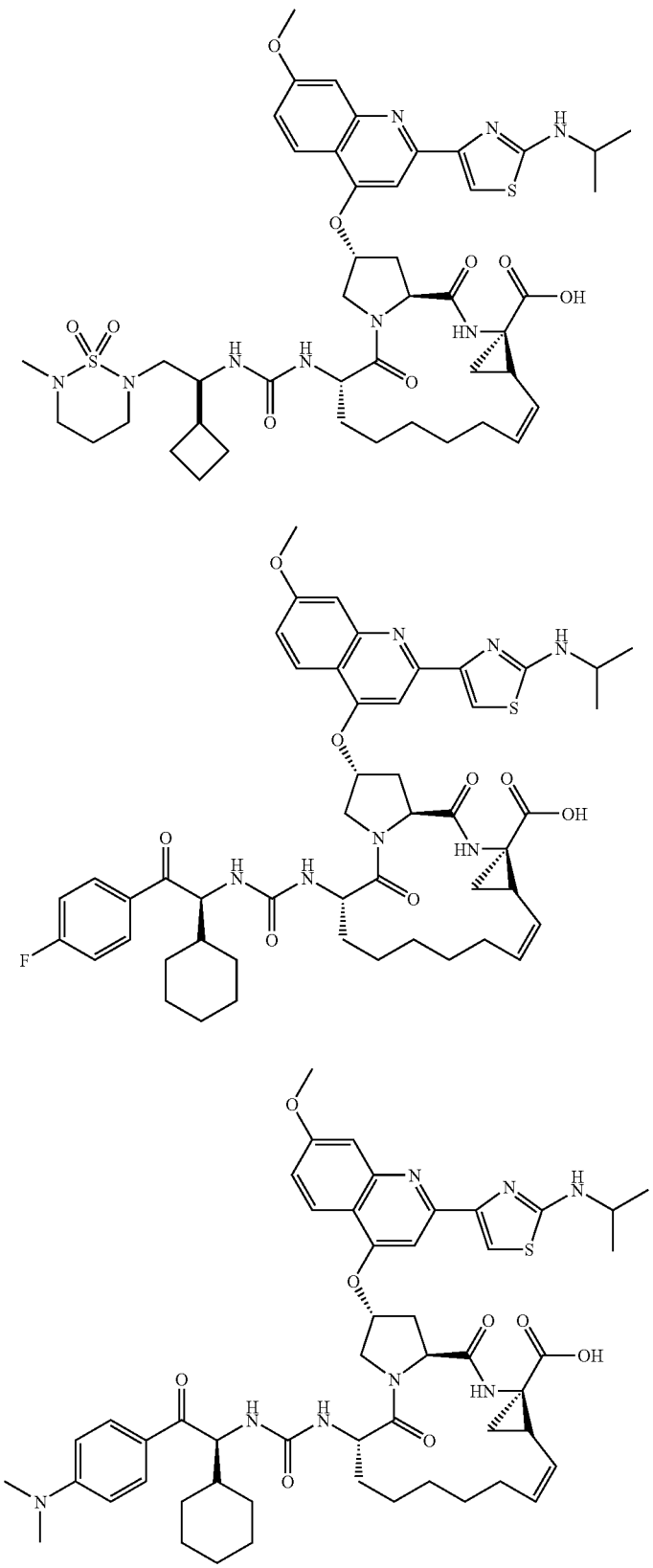

TABLE 1-continued
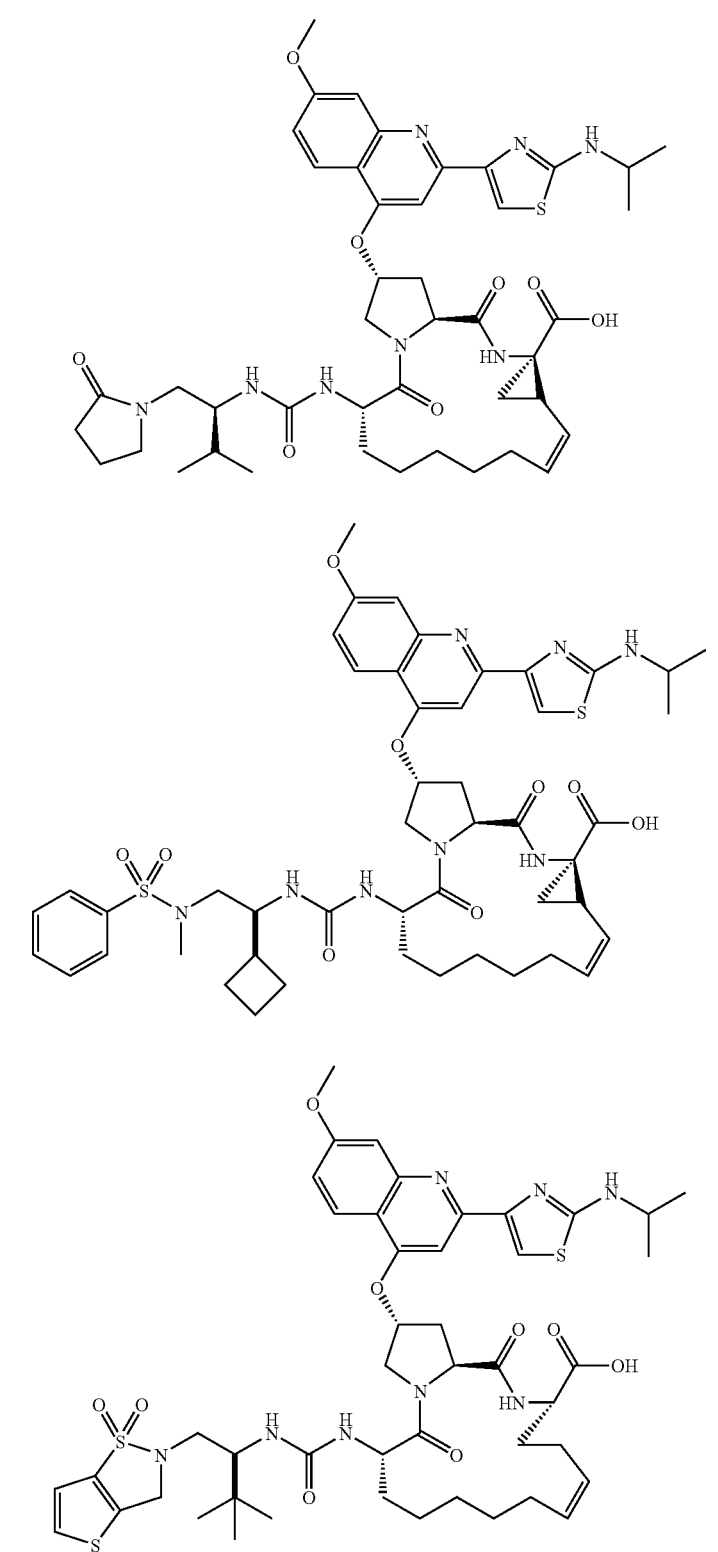

TABLE 1-continued
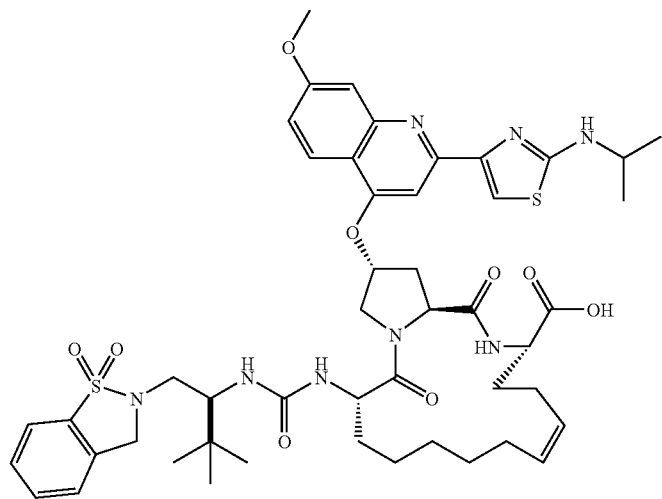
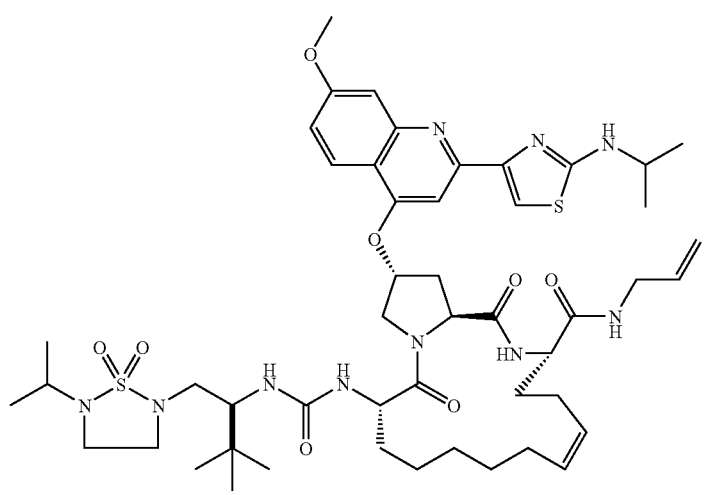
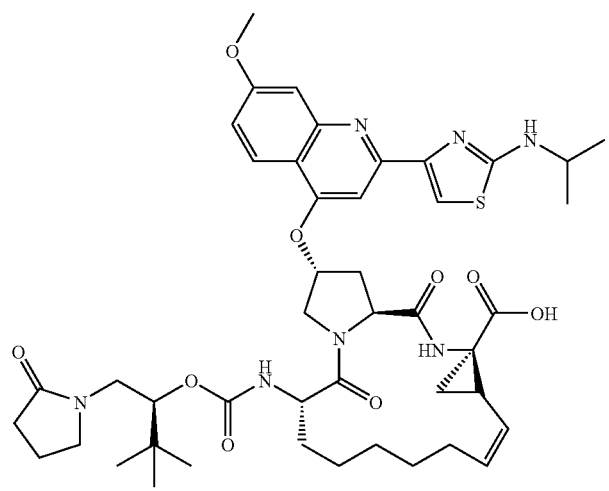

TABLE 1-continued
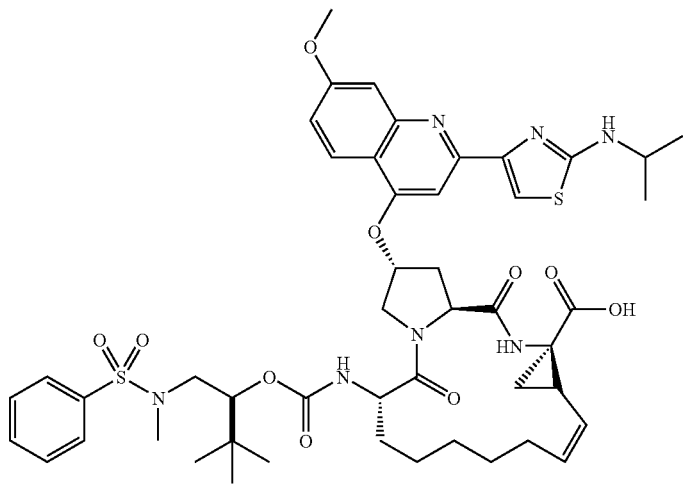
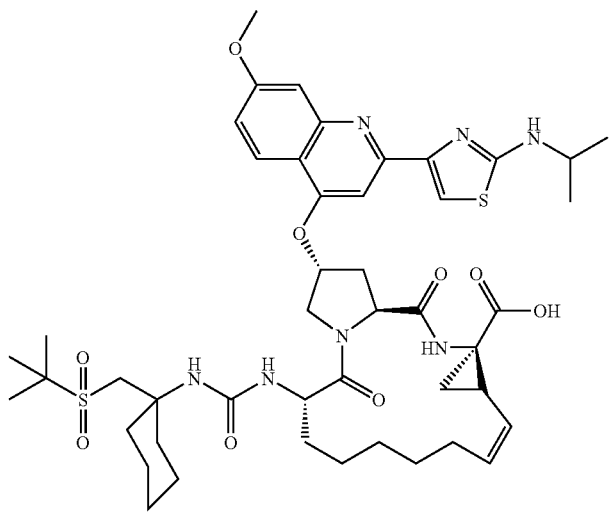
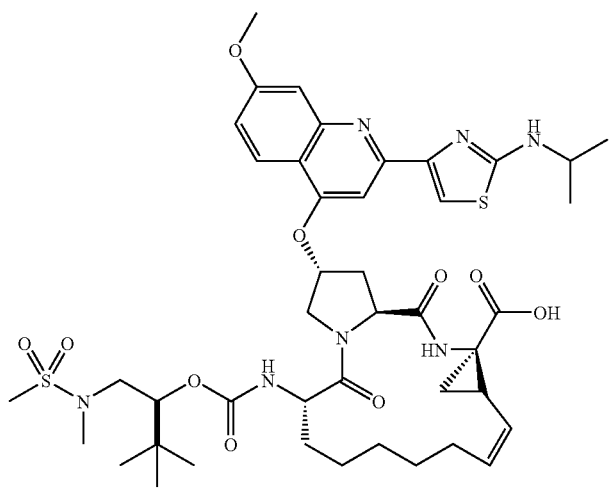

TABLE 1-continued
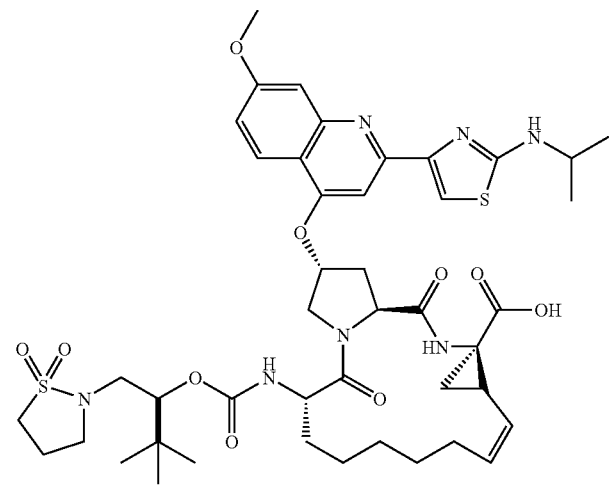
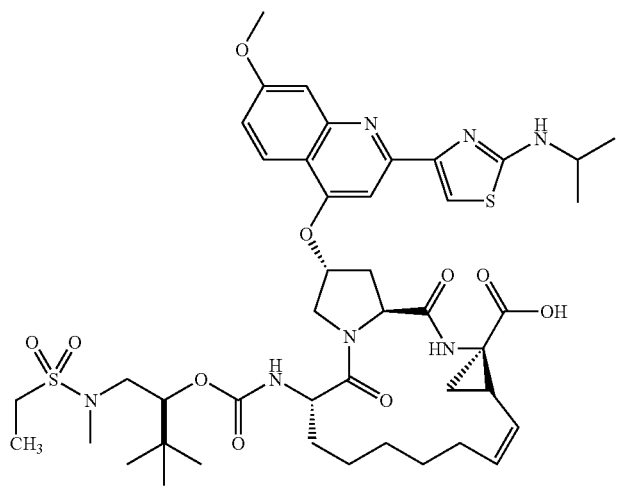
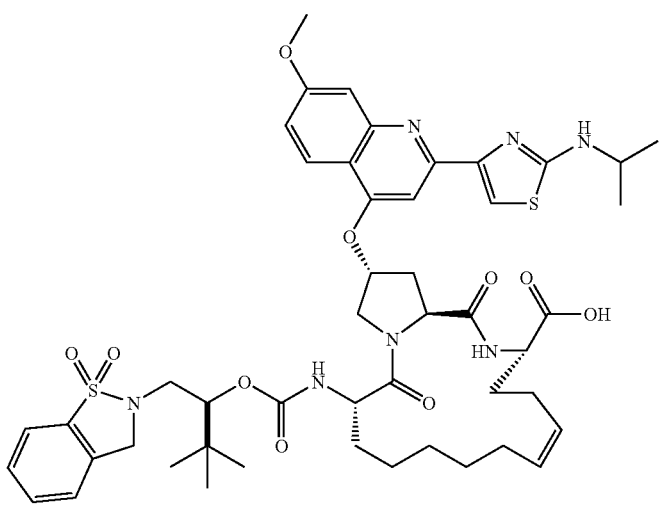

TABLE 1-continued
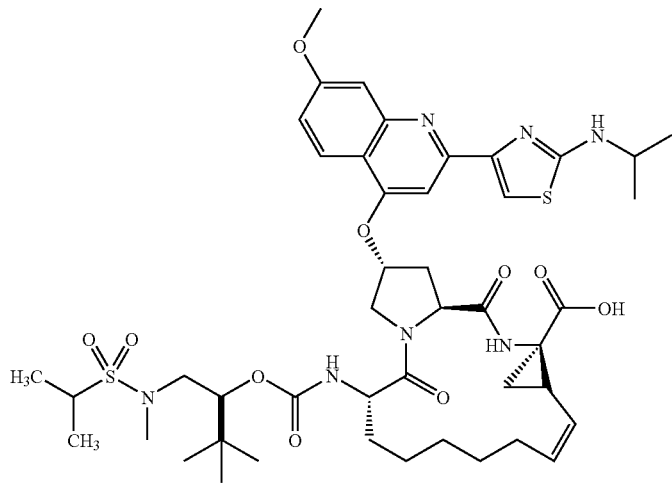
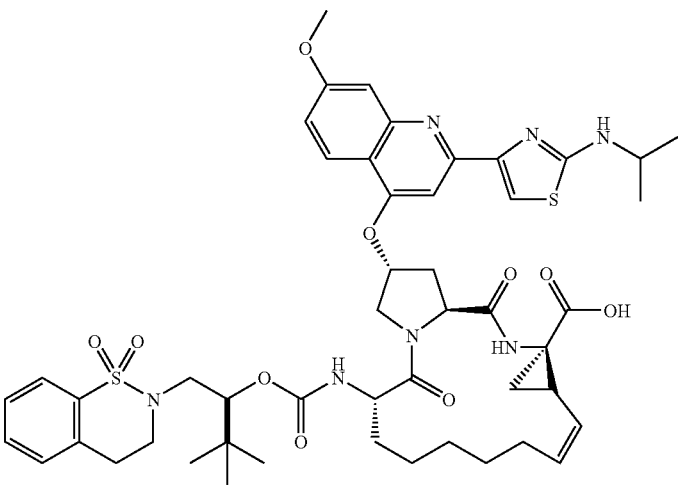
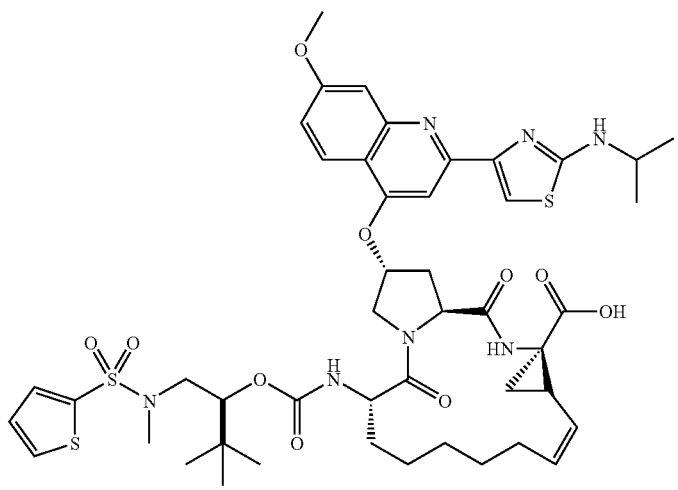

TABLE 1-continued
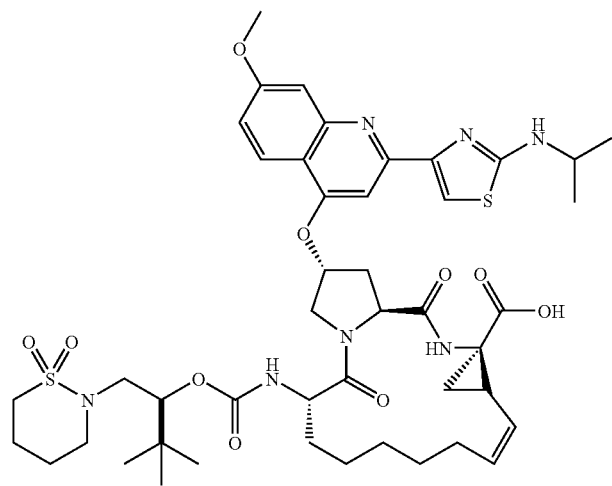
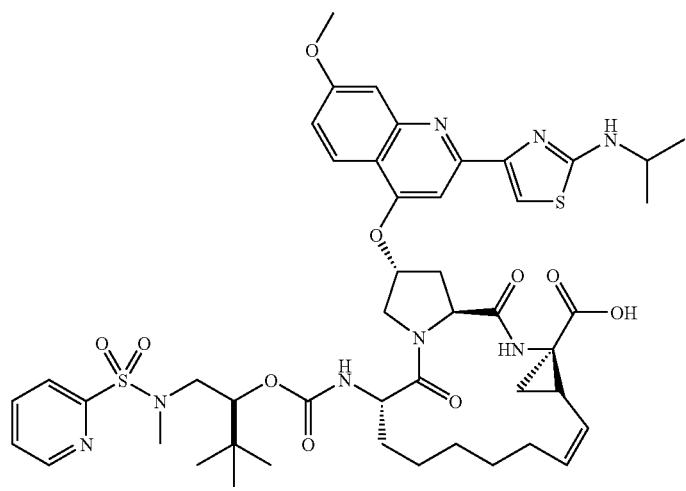
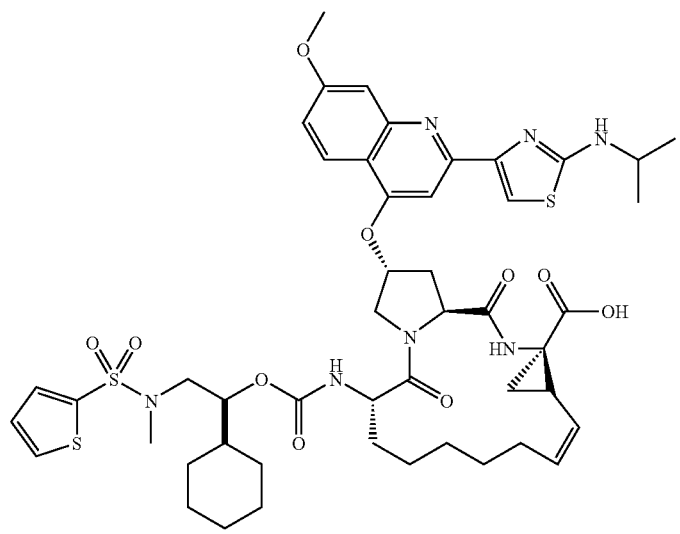

TABLE 1-continued
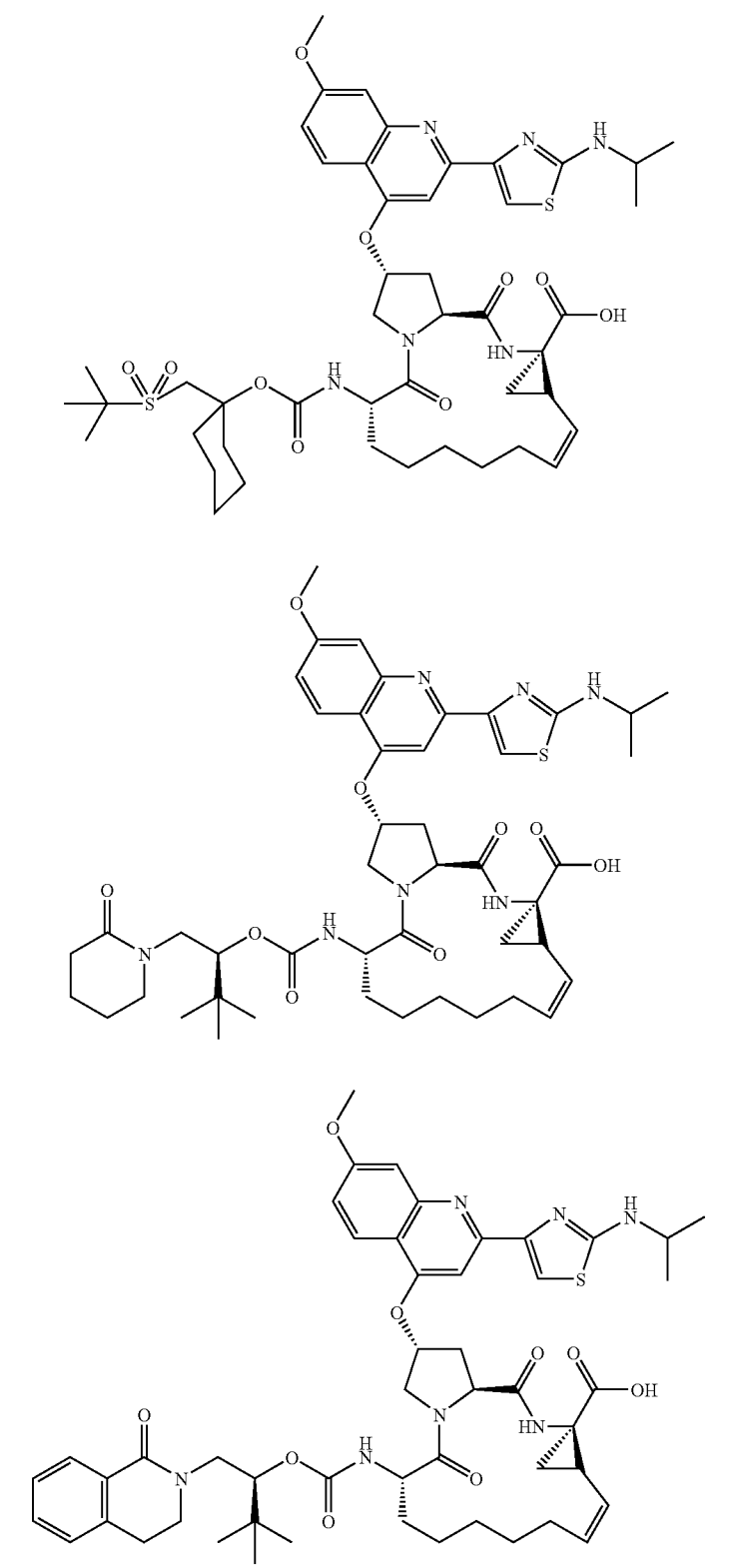

TABLE 1-continued
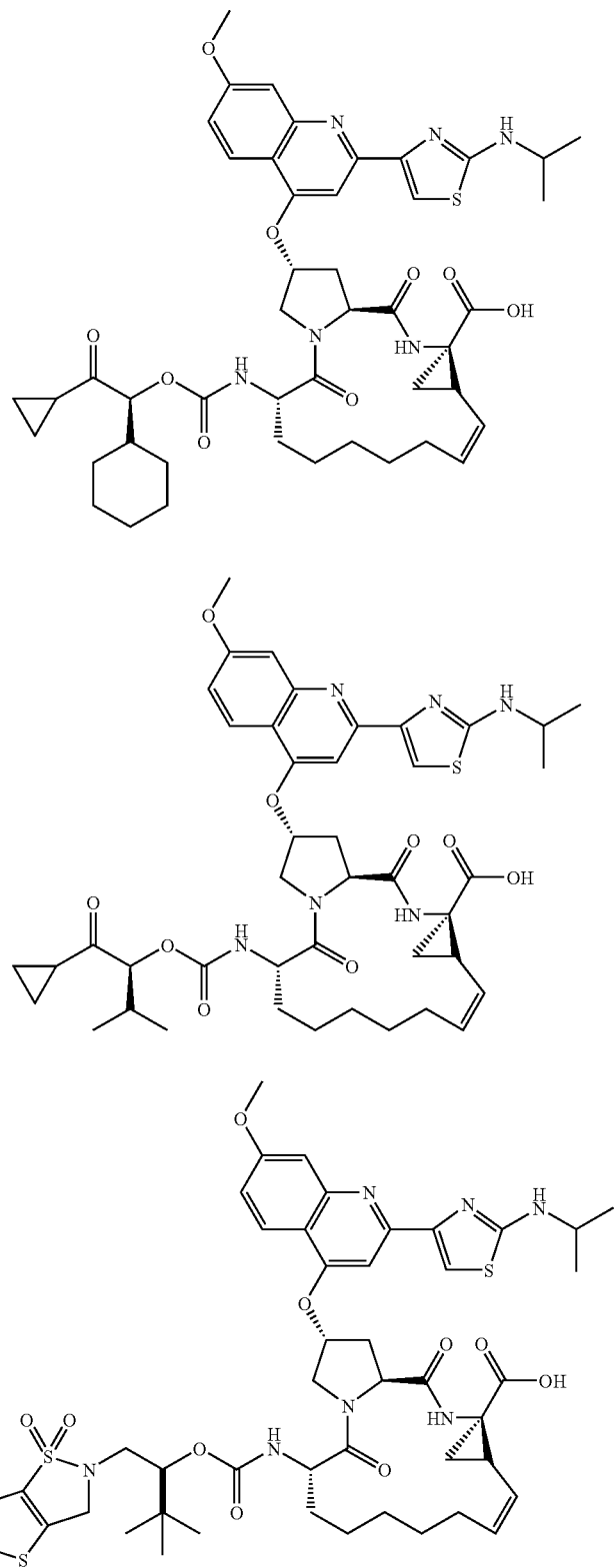

TABLE 1-continued
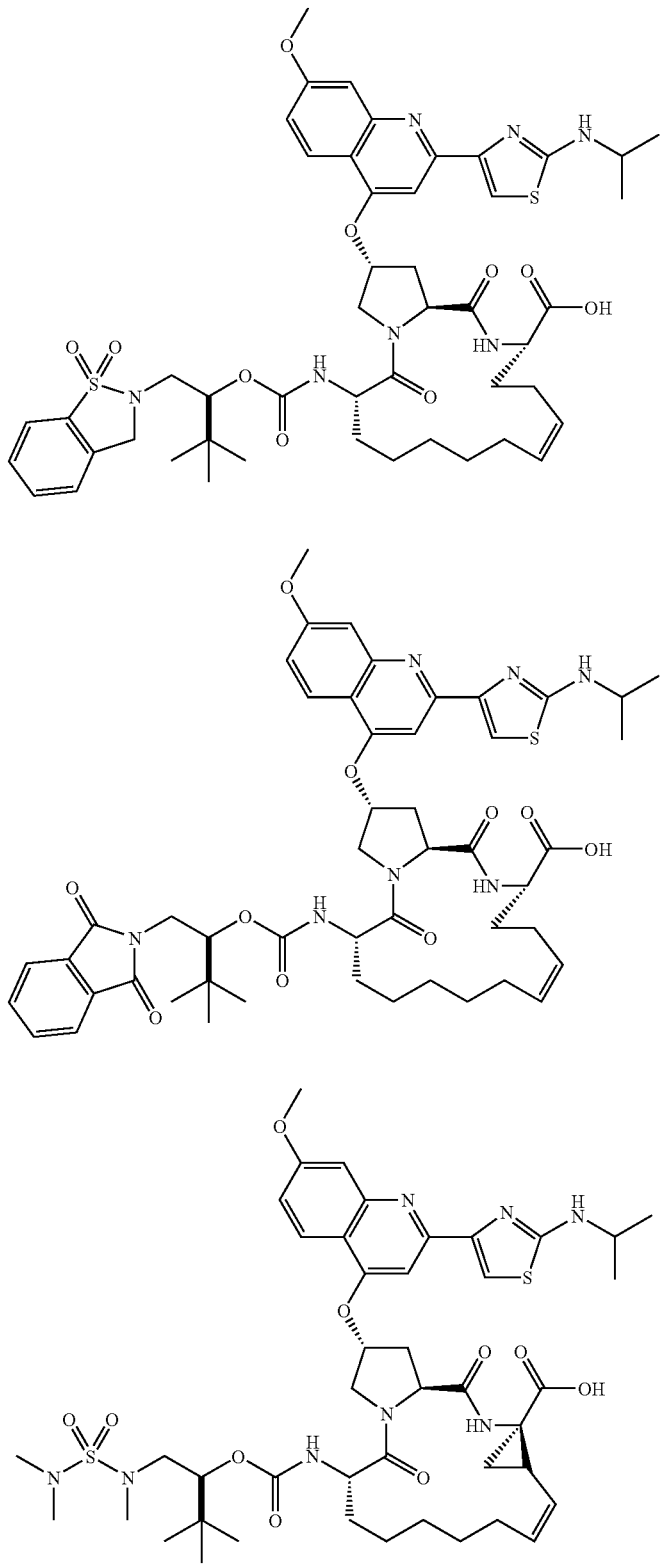

TABLE 1-continued
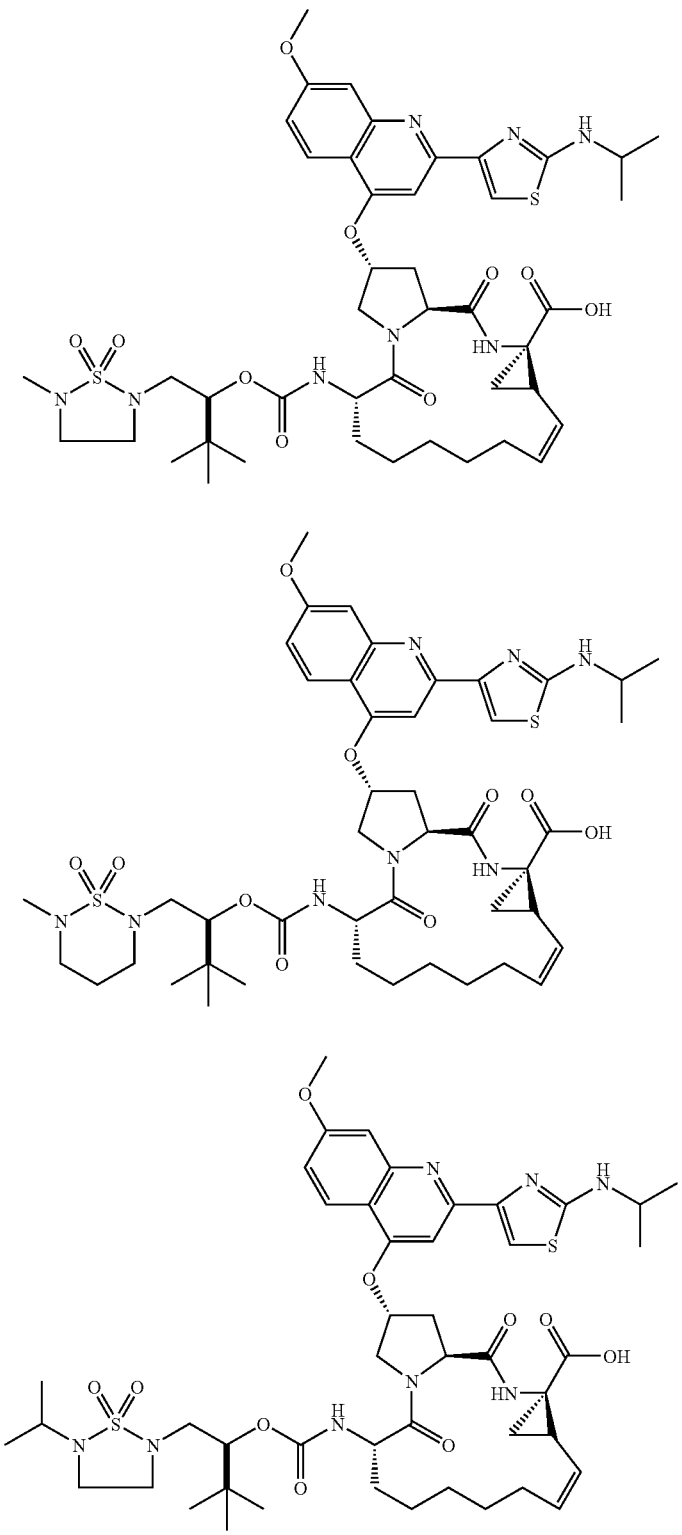

TABLE 1-continued
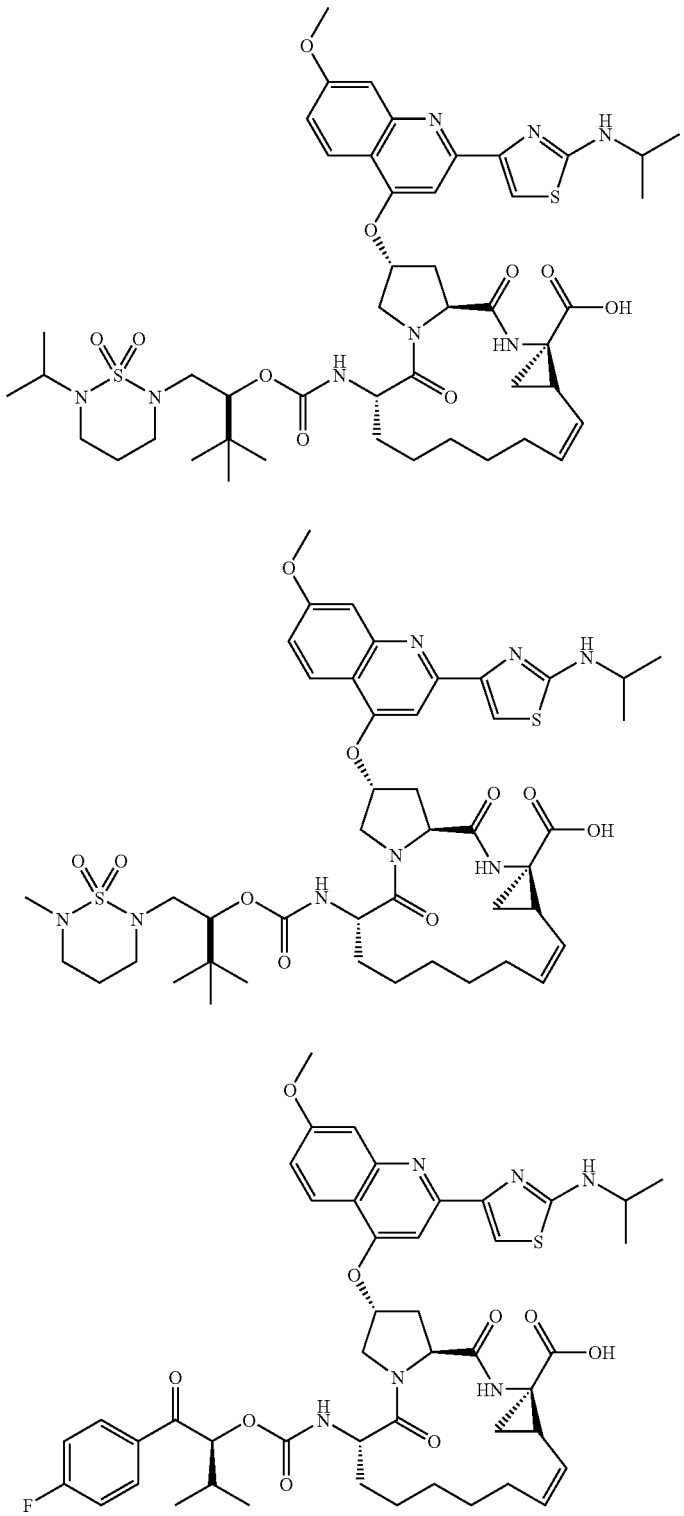

TABLE 1-continued
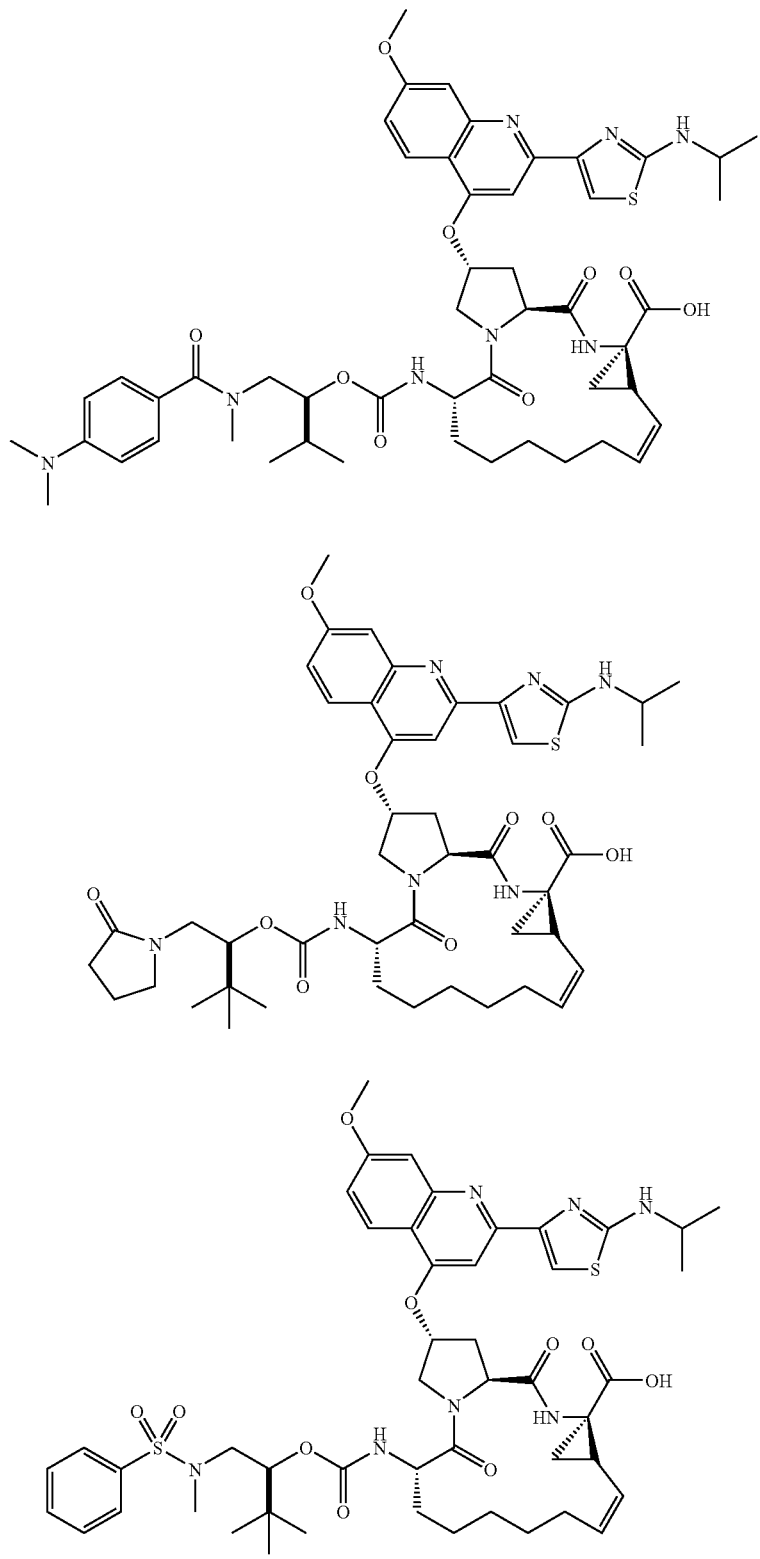

TABLE 1-continued
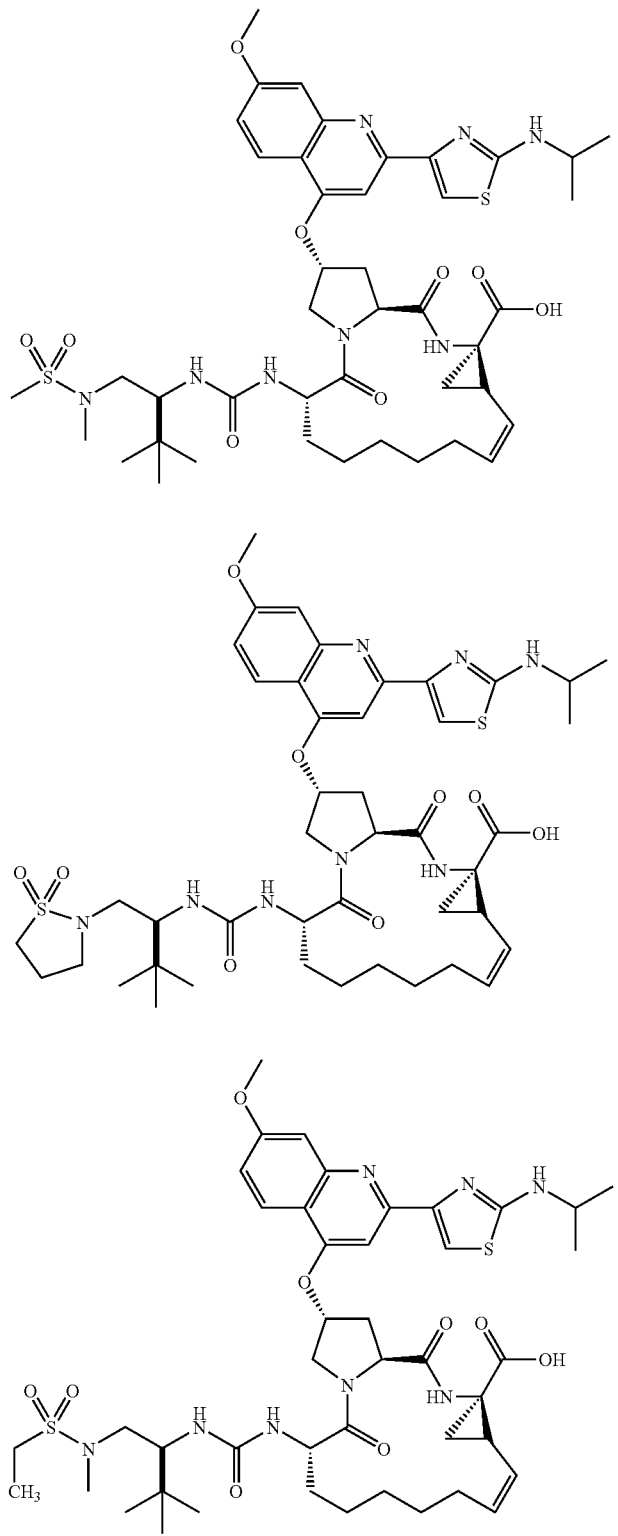

TABLE 1-continued
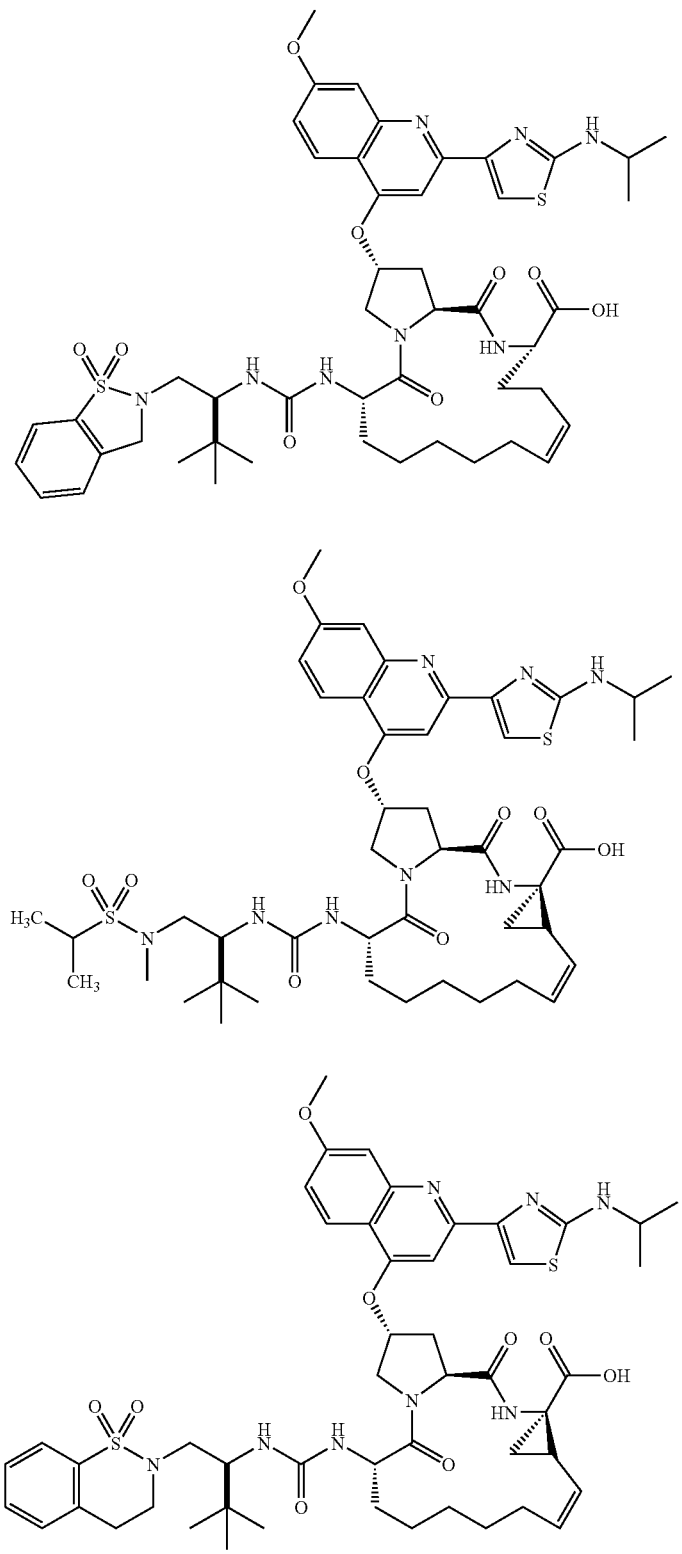

TABLE 1-continued
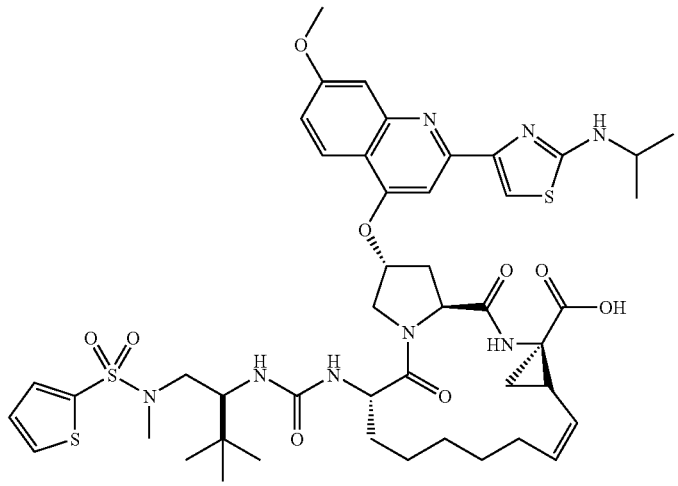
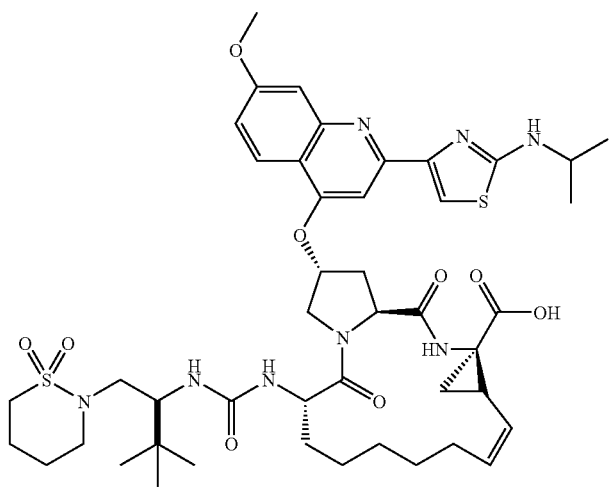
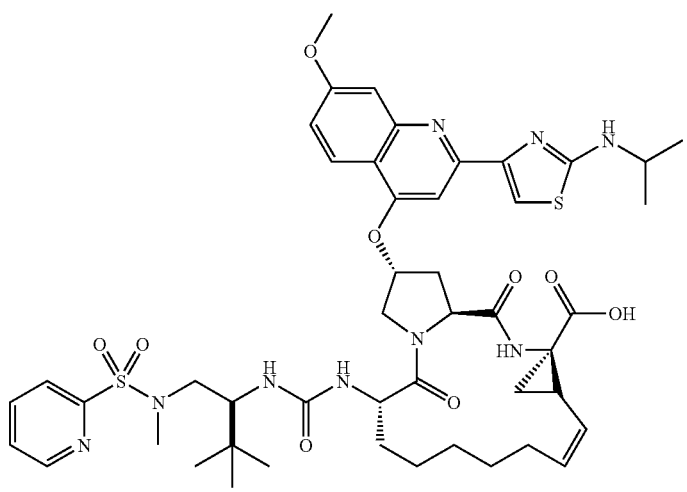

TABLE 1-continued
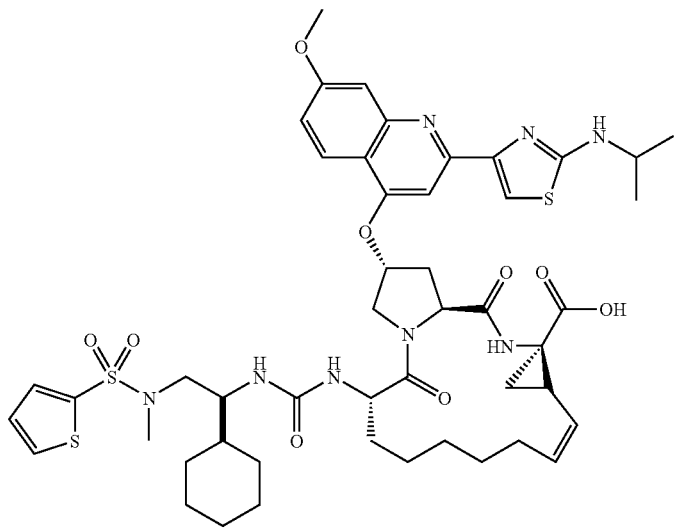
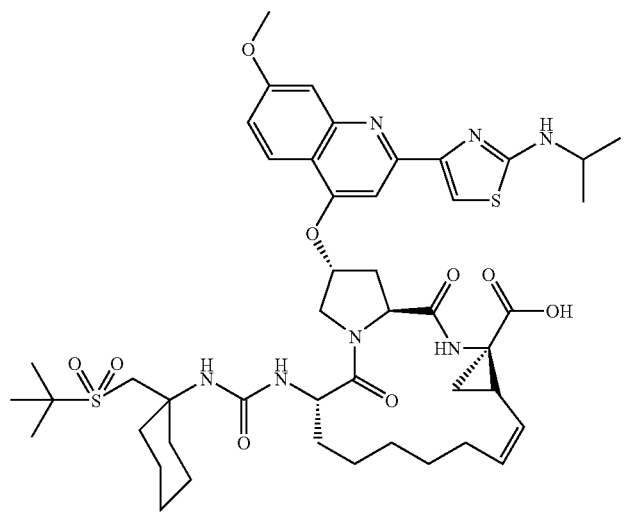
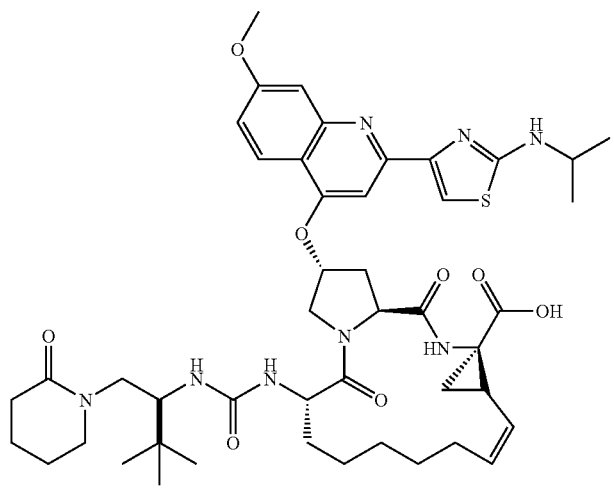

TABLE 1-continued
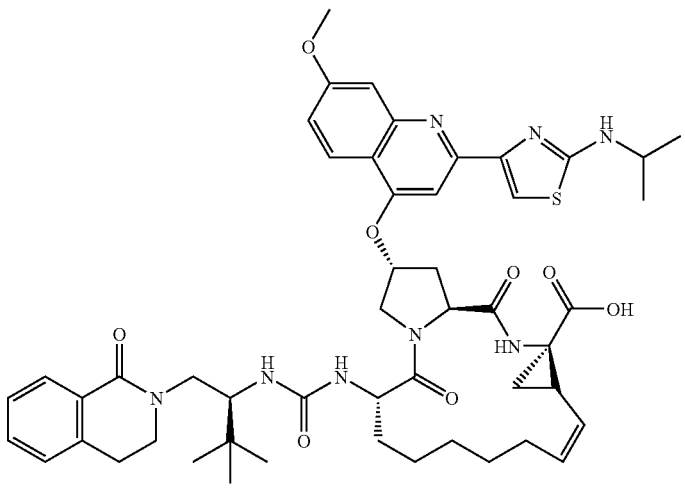
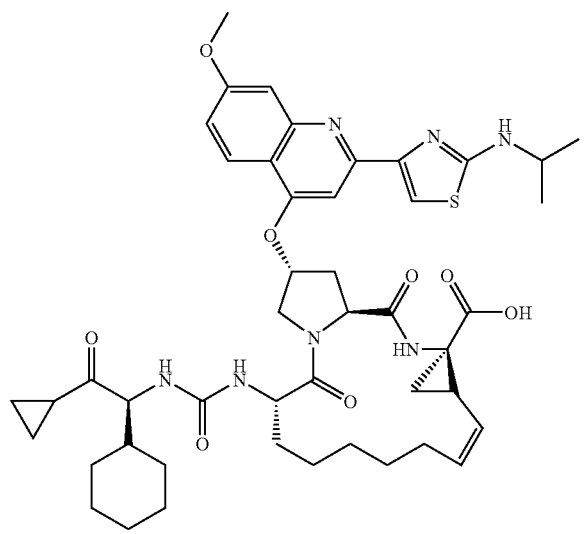
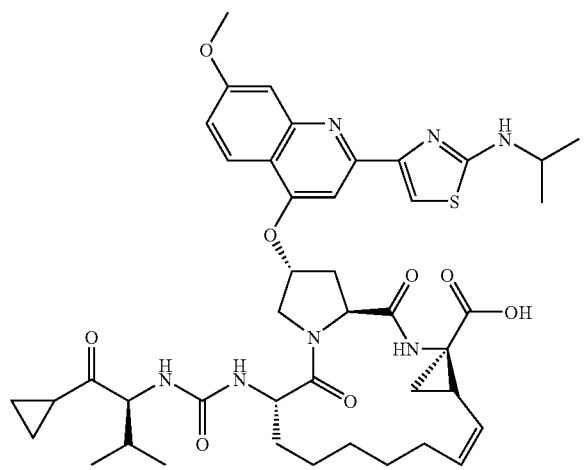

TABLE 1-continued
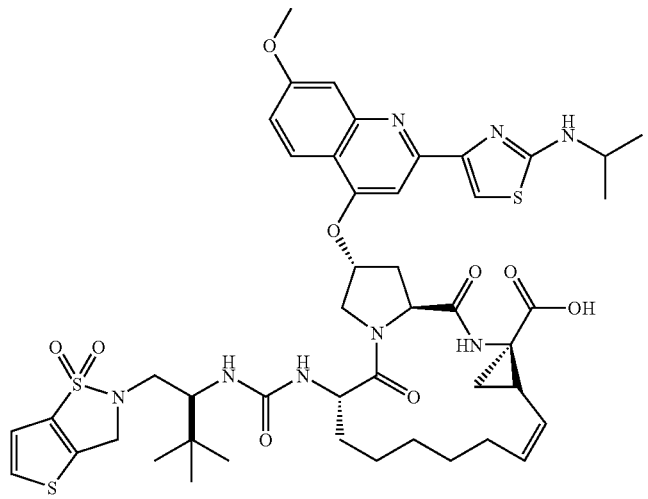
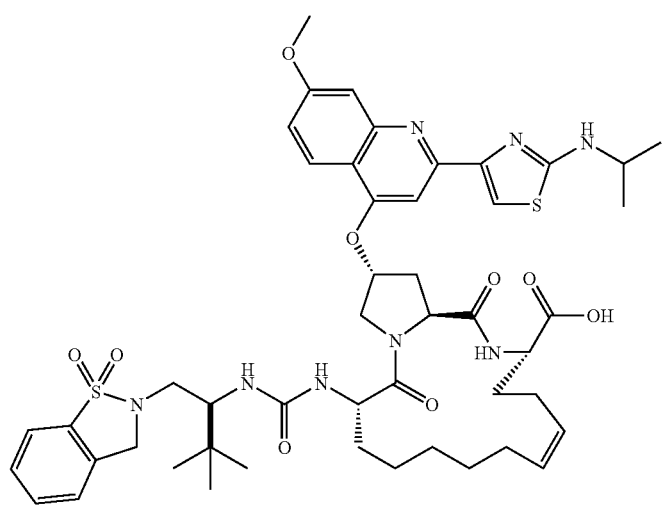
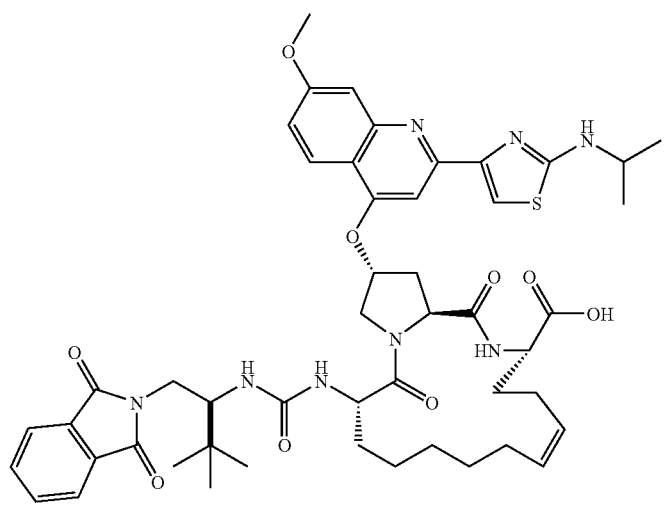

TABLE 1-continued
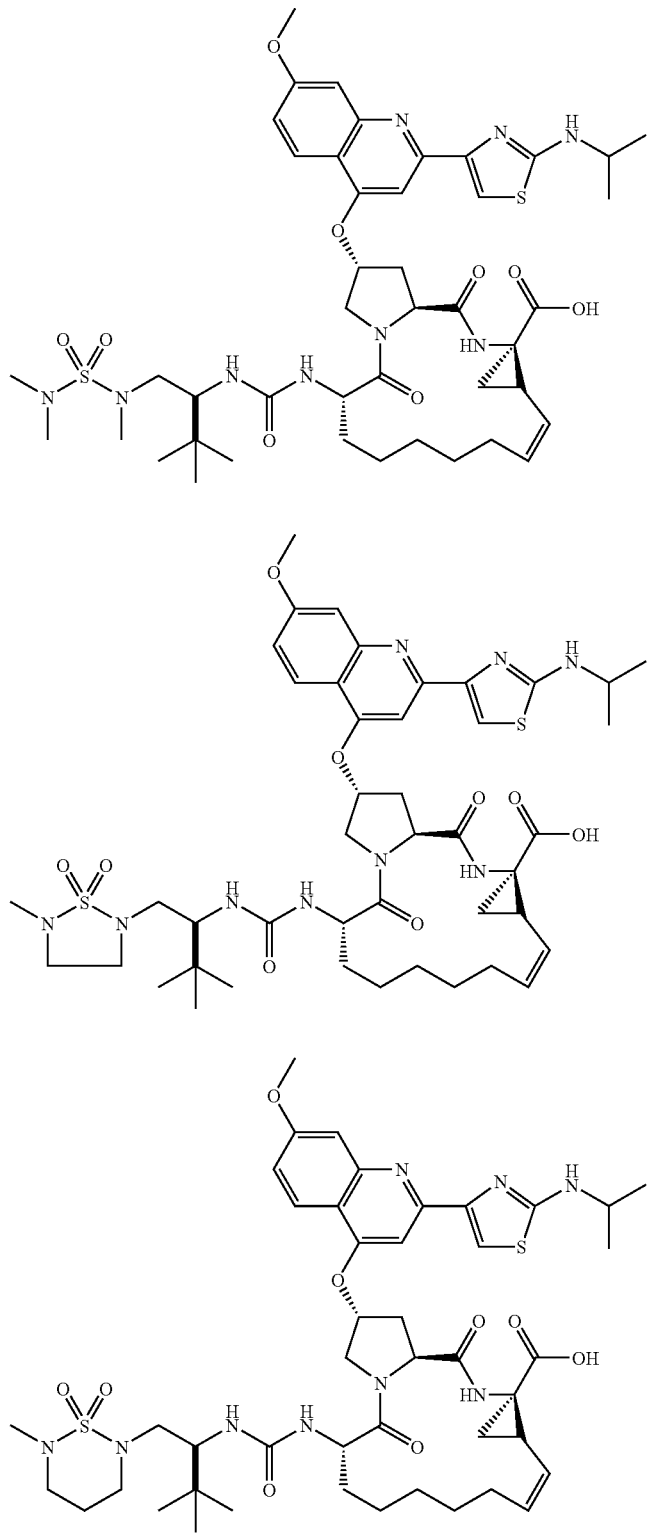

TABLE 1-continued
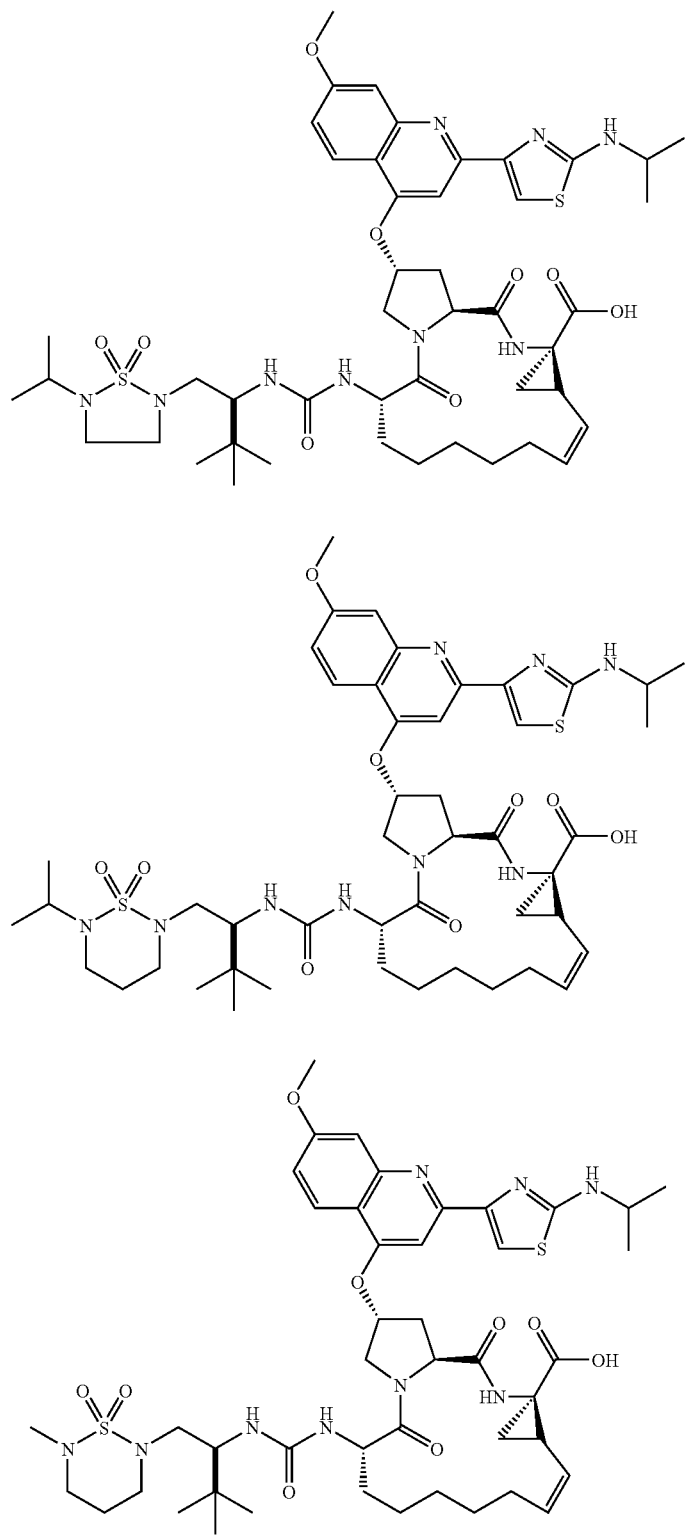

TABLE 1-continued
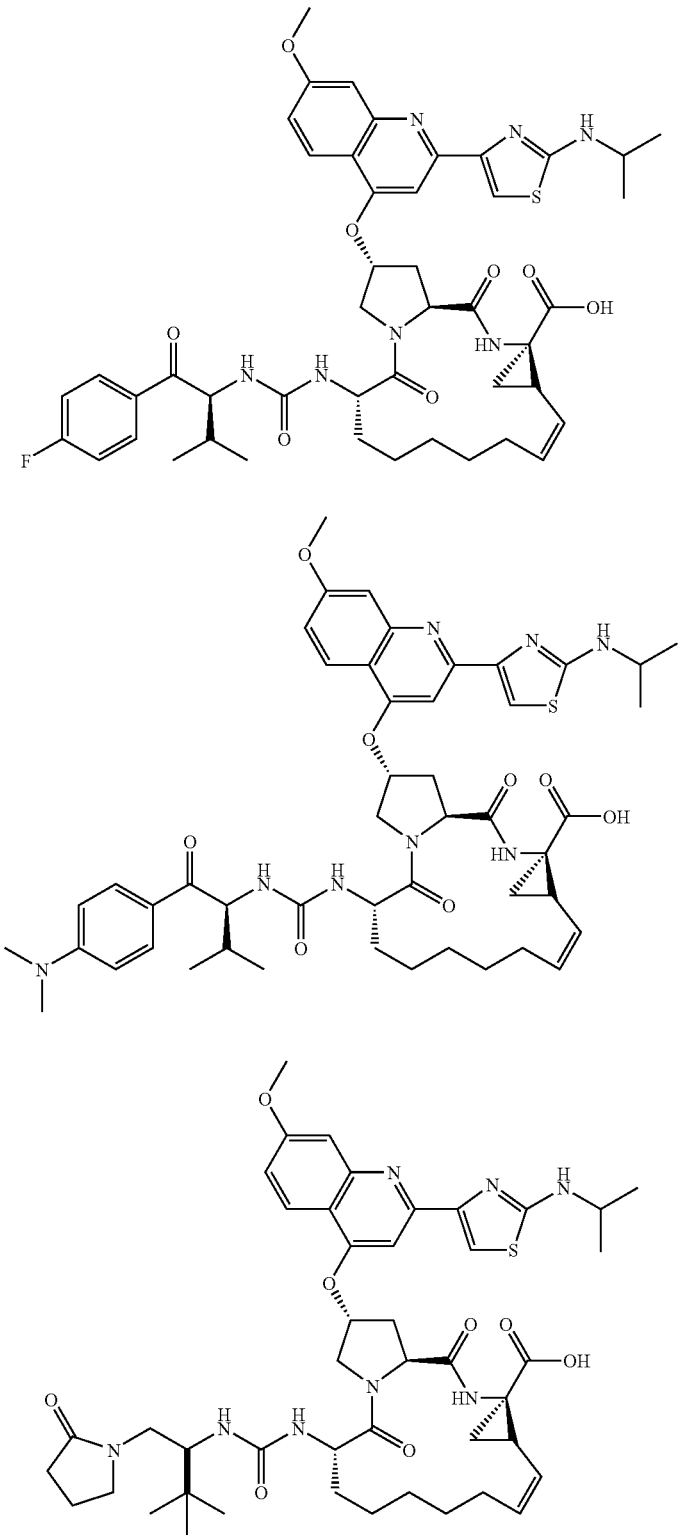

TABLE 1-continued
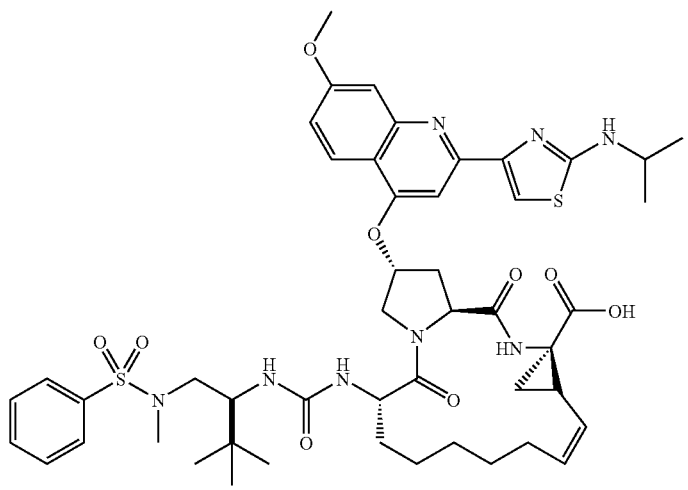
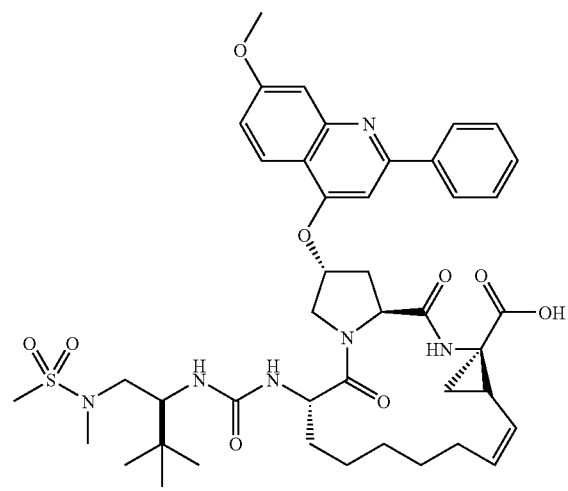
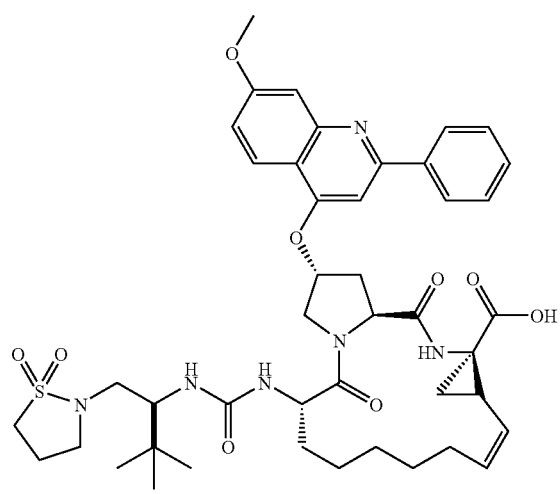

TABLE 1-continued
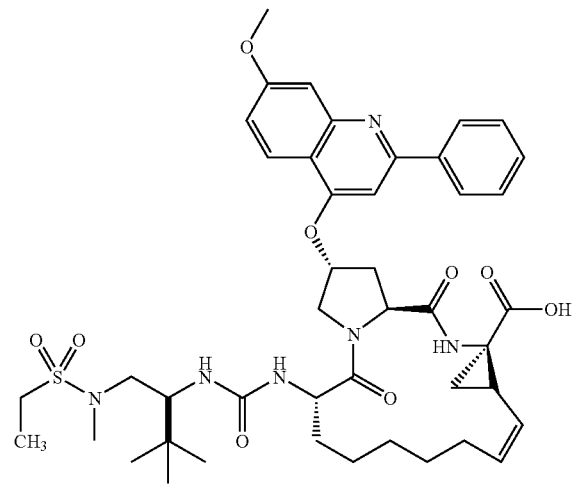
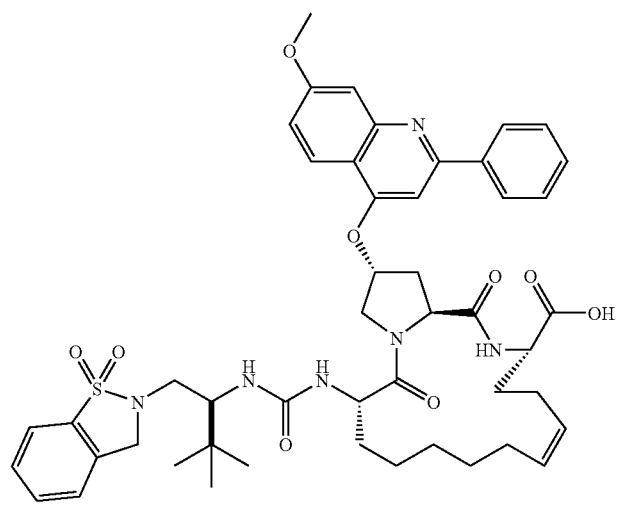
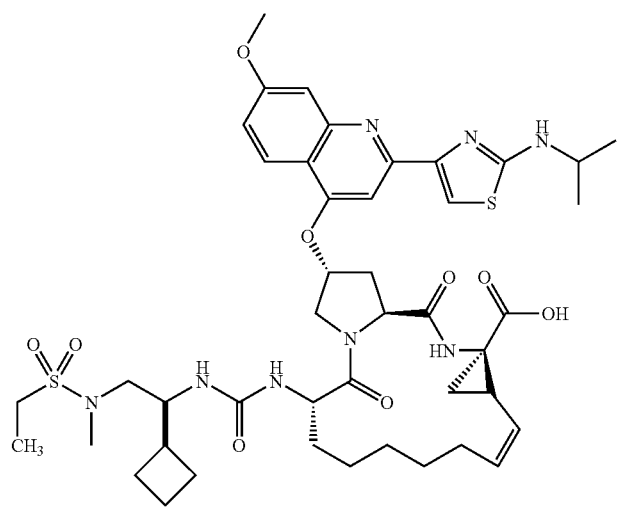

TABLE 1-continued
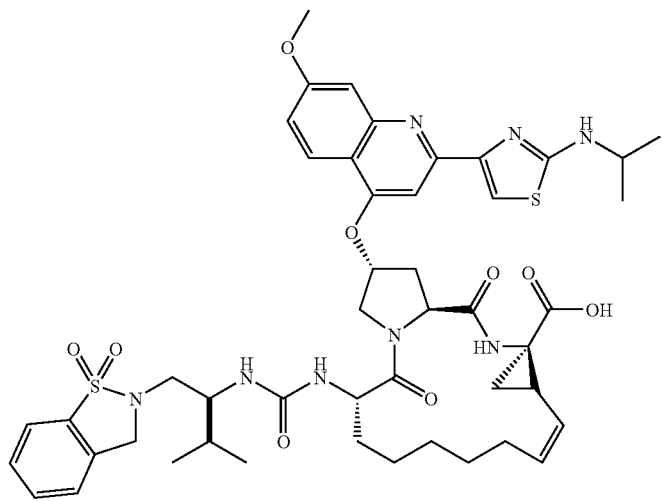
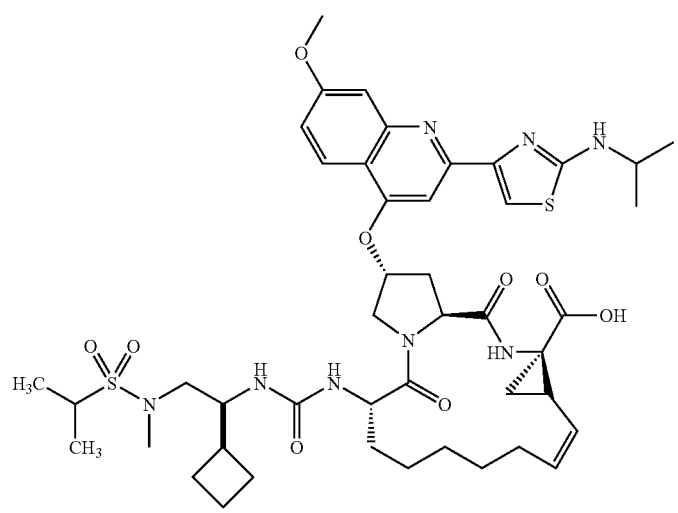
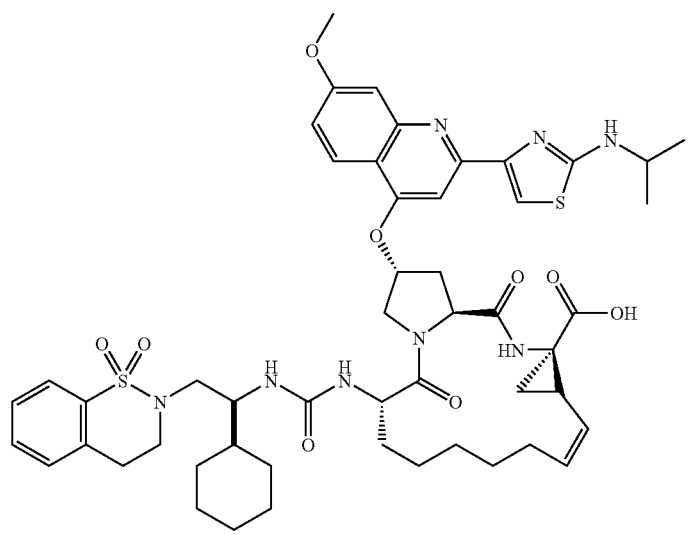

TABLE 1-continued
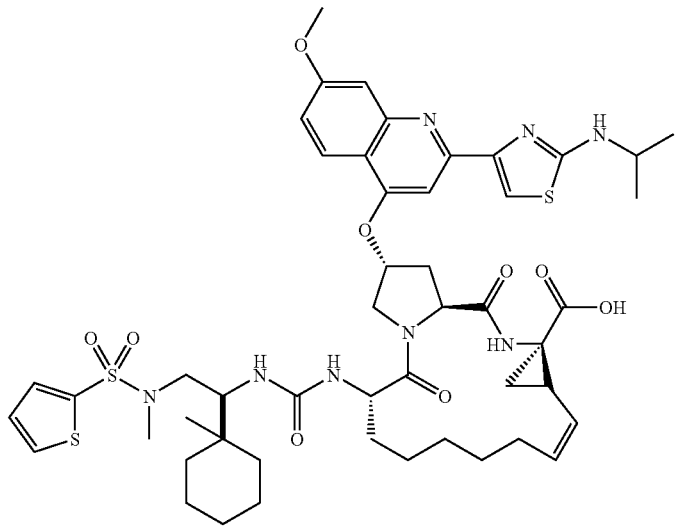
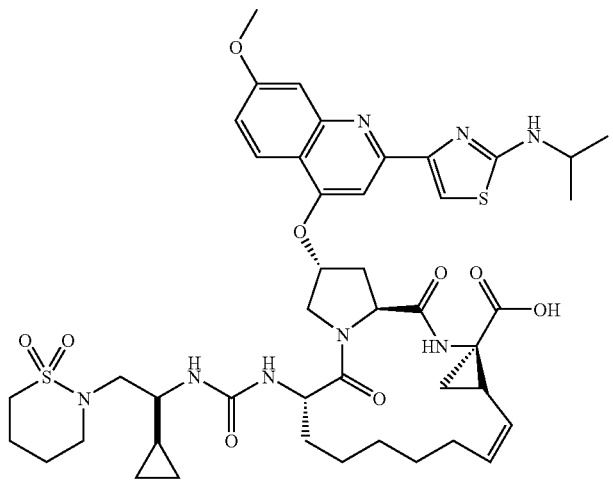
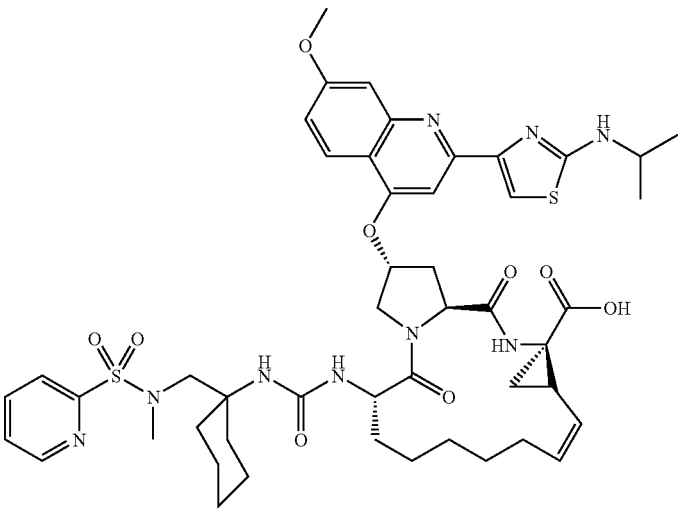

TABLE 1-continued
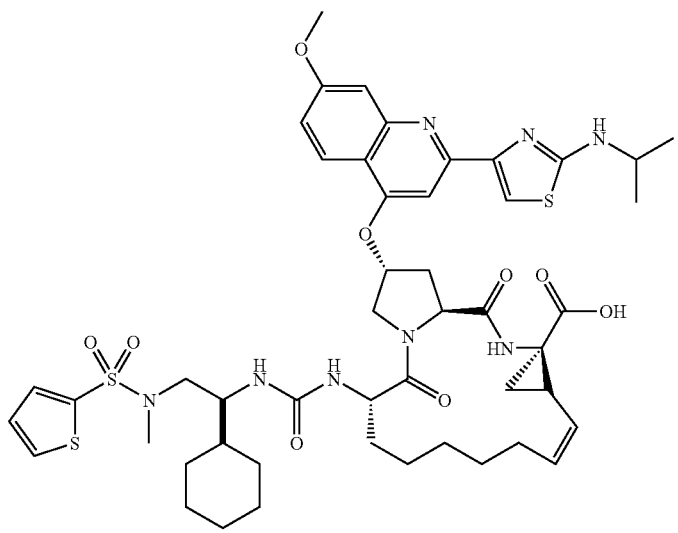
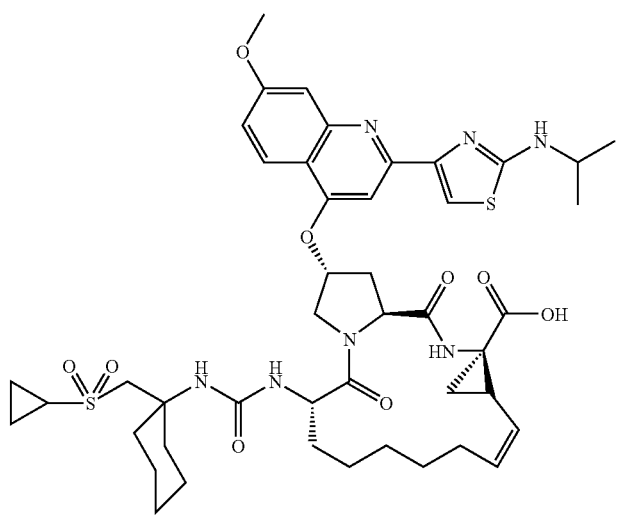
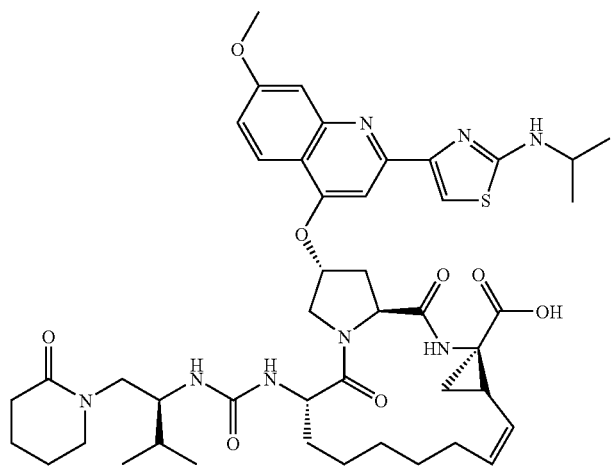

TABLE 1-continued
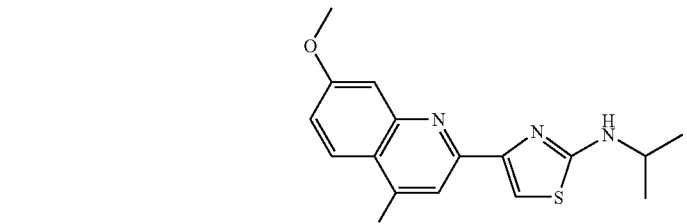
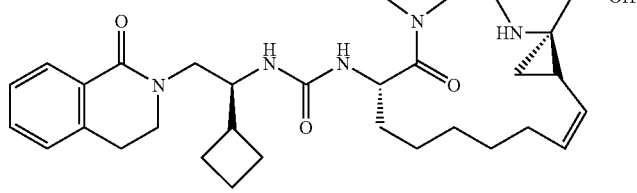
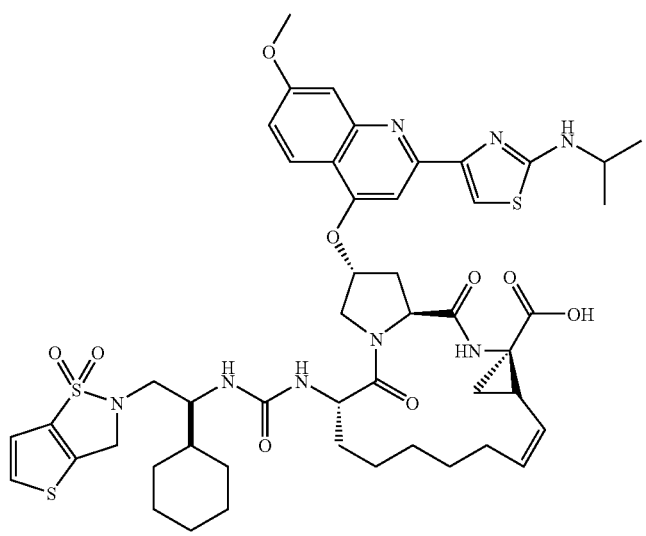
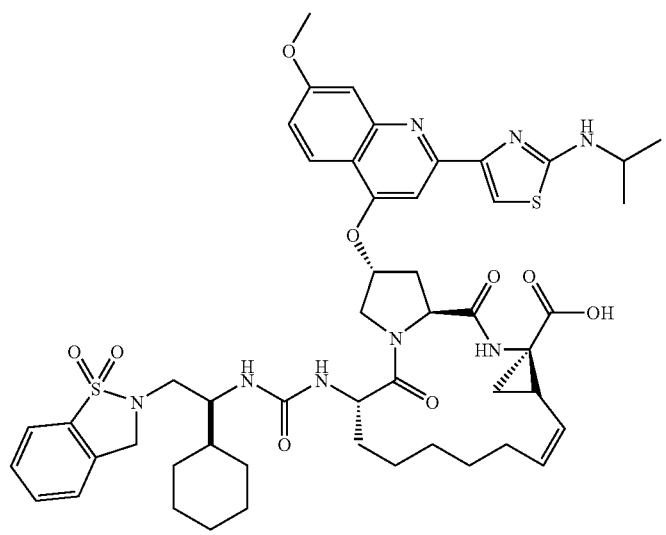

TABLE 1-continued
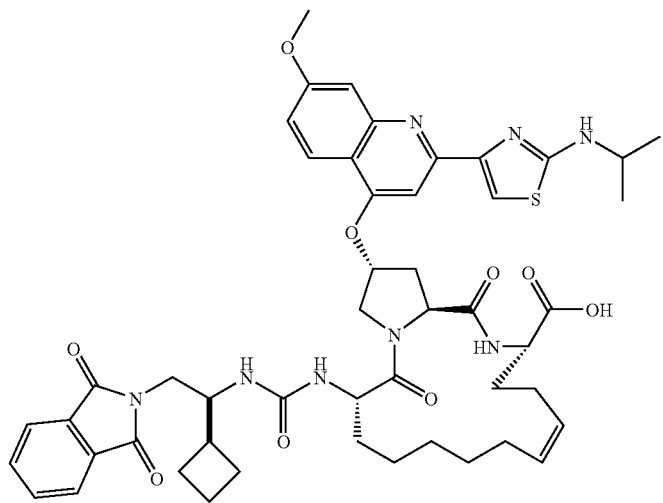
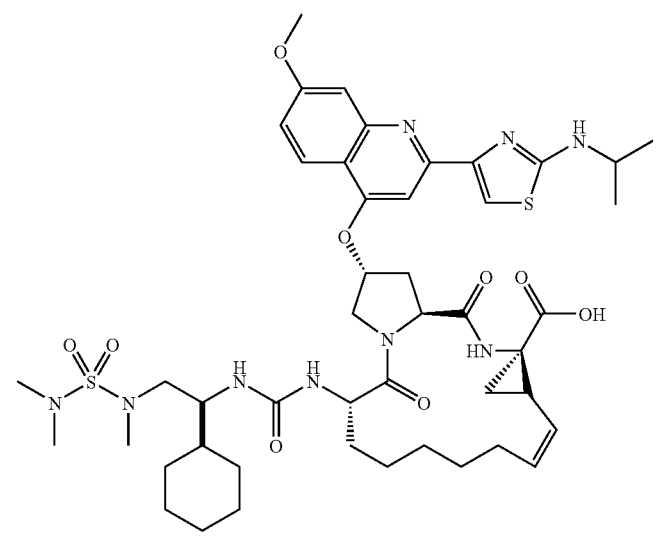
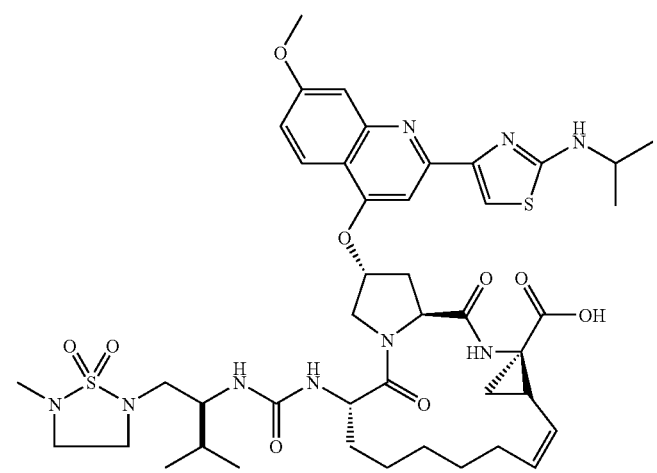

TABLE 1-continued
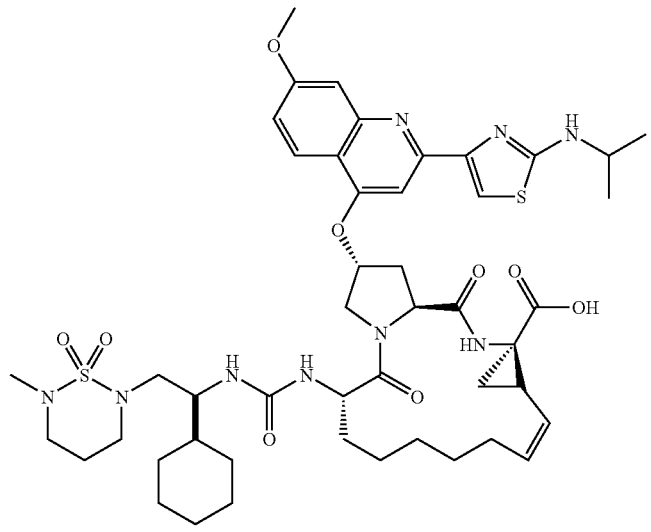
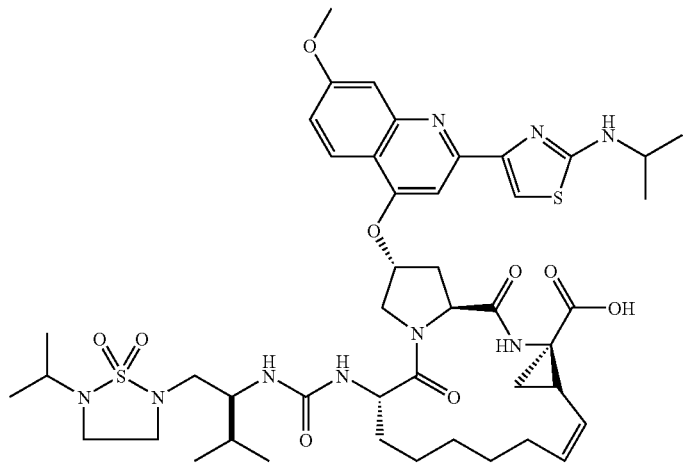
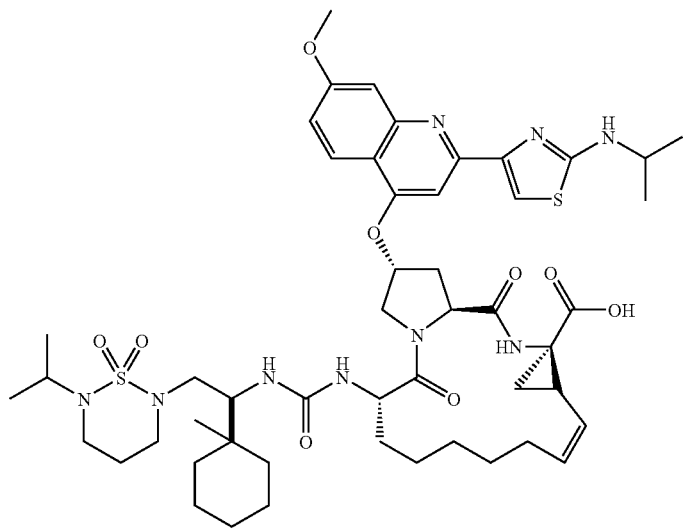

TABLE 1-continued
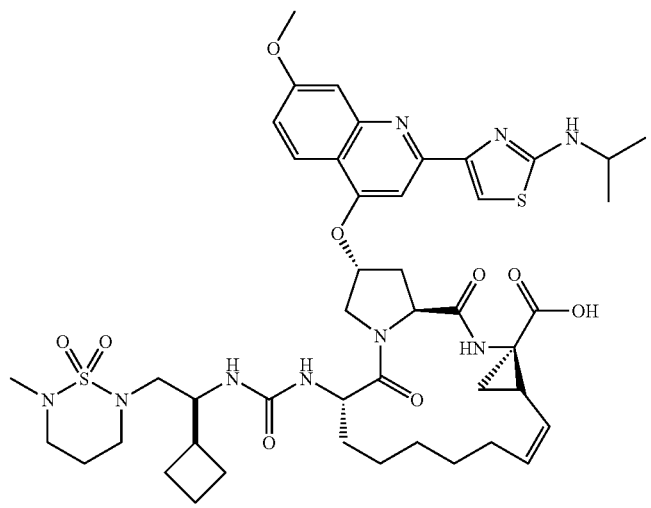
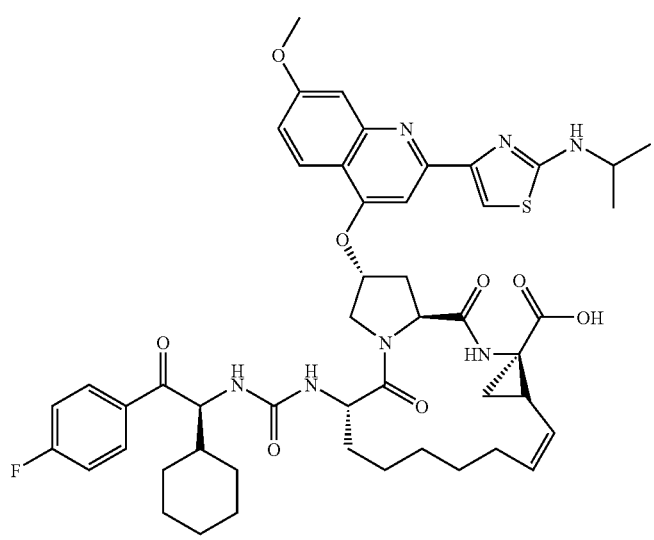
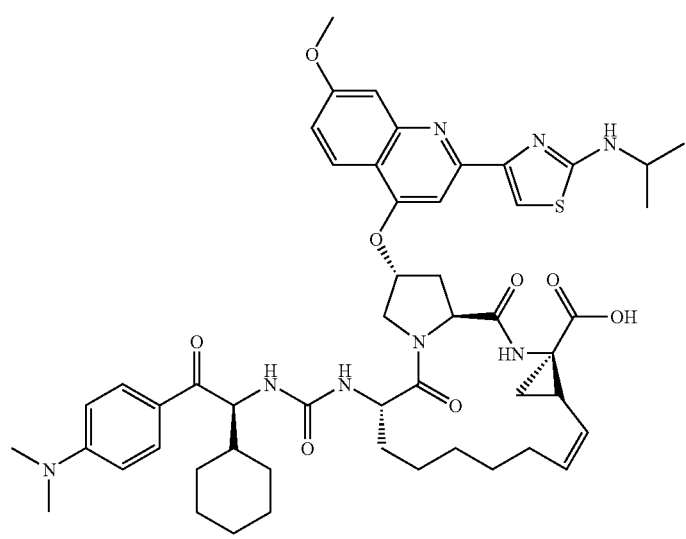

TABLE 1-continued
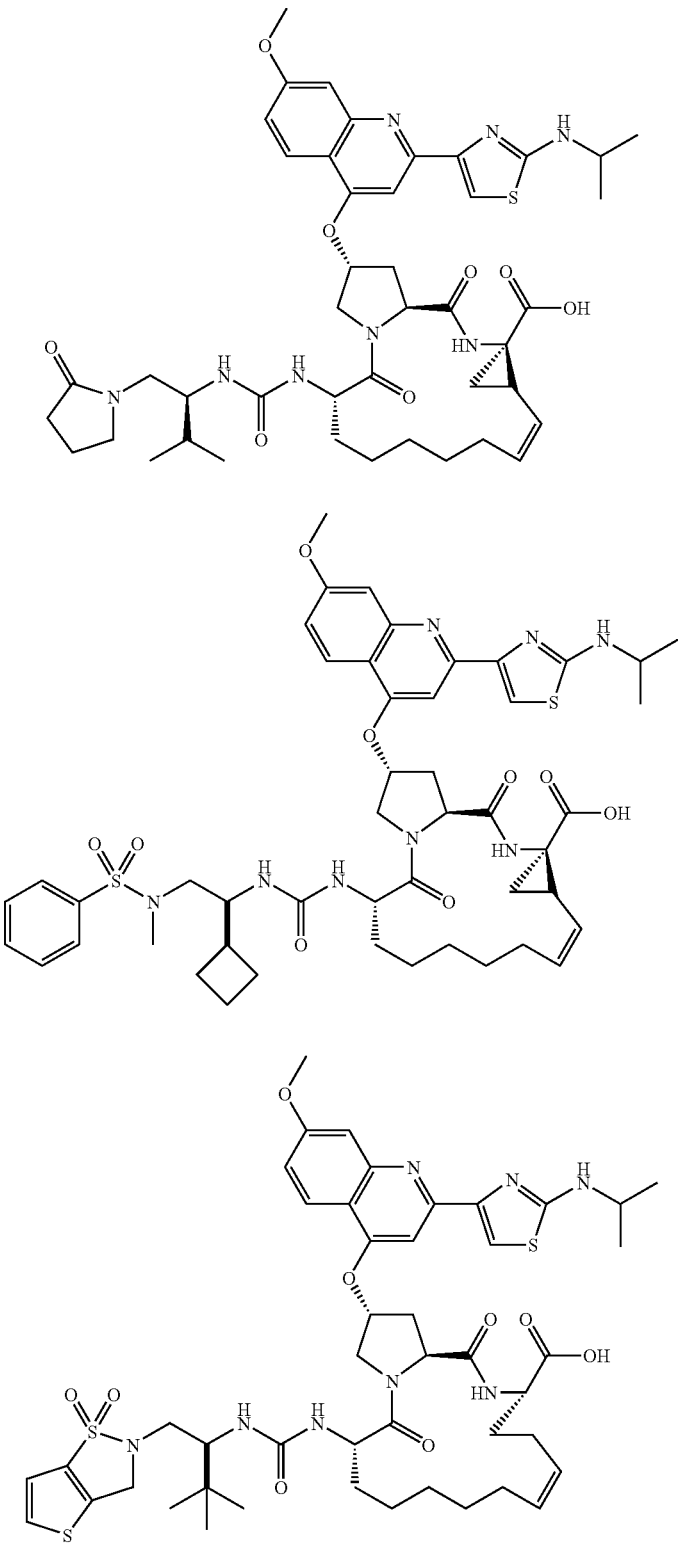

TABLE 1-continued
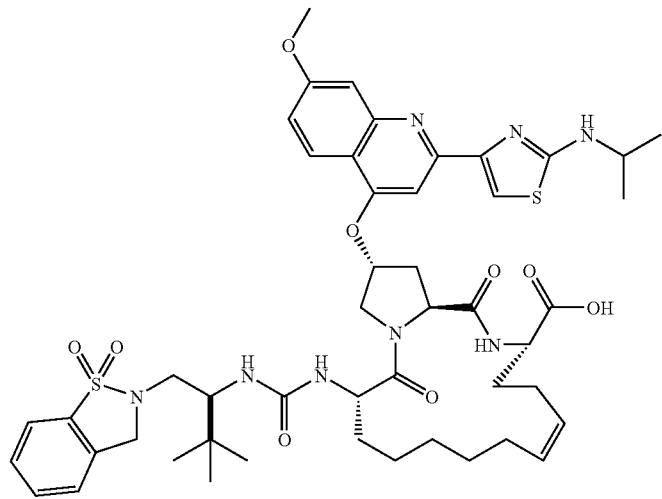
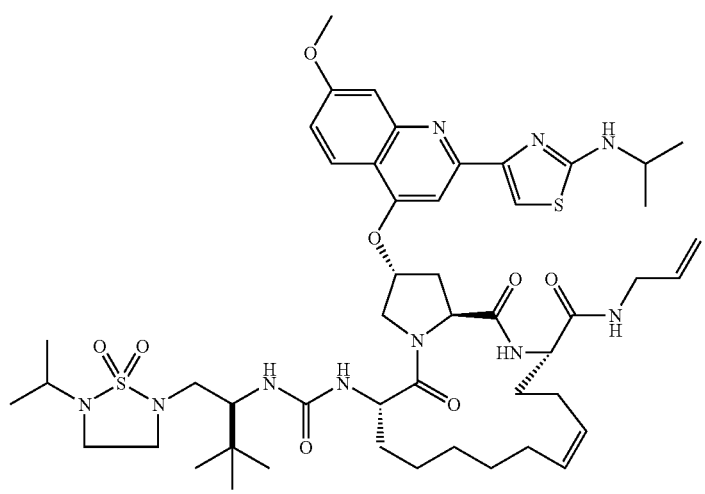
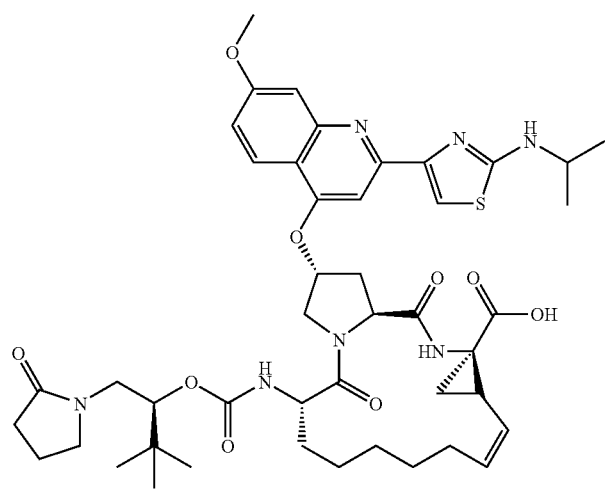

TABLE 1-continued
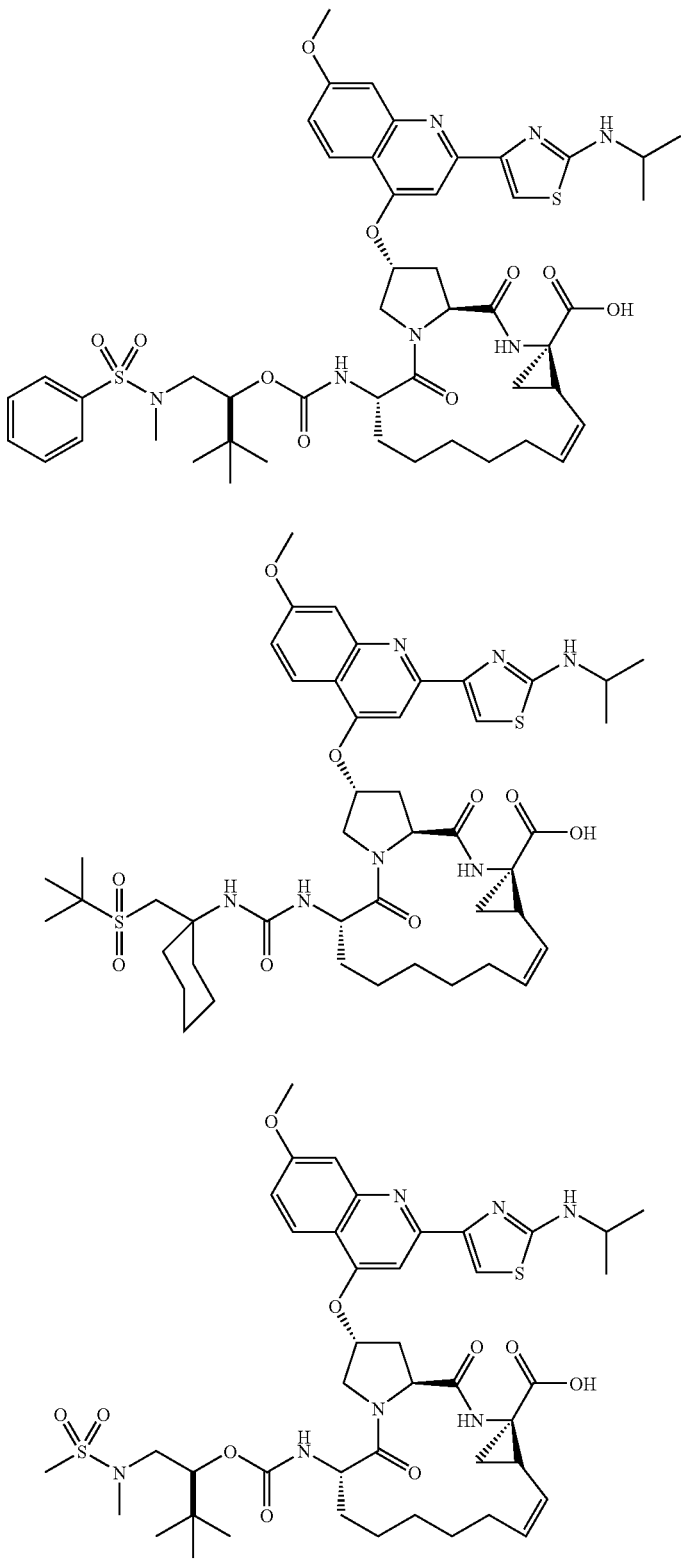

TABLE 1-continued
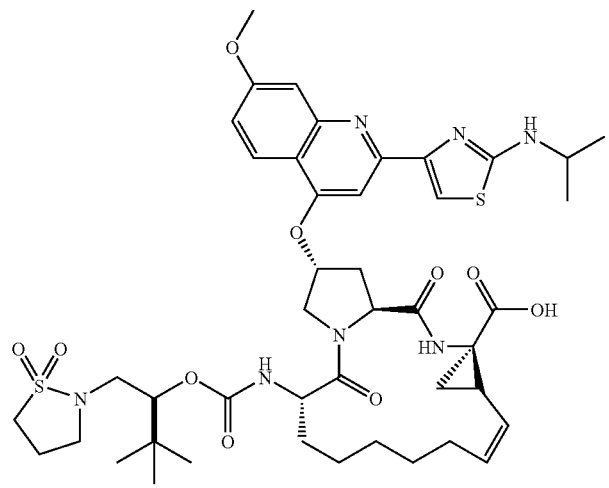
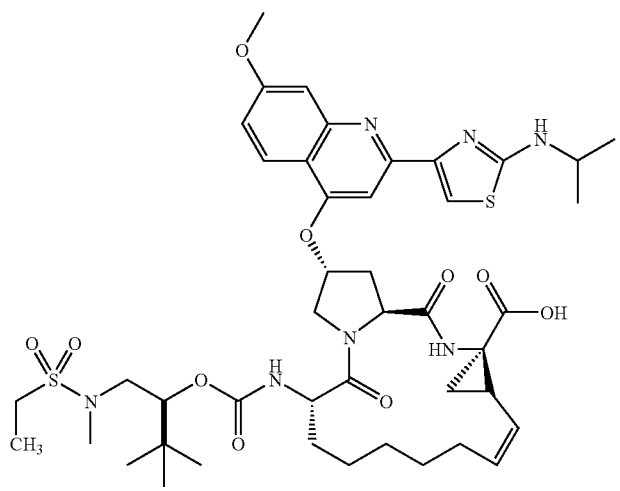
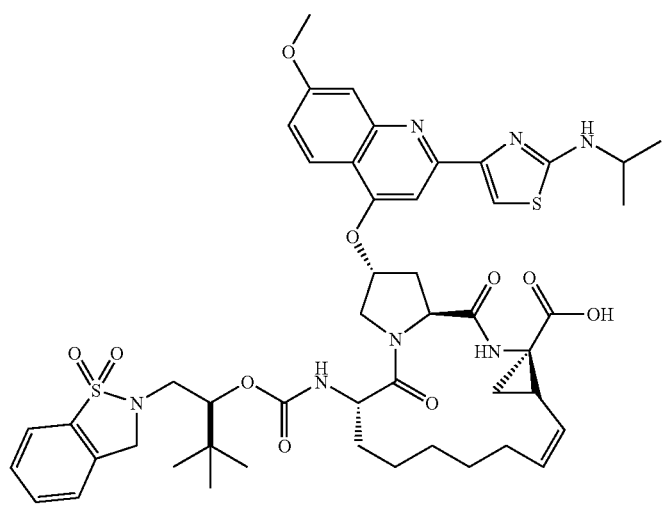

TABLE 1-continued
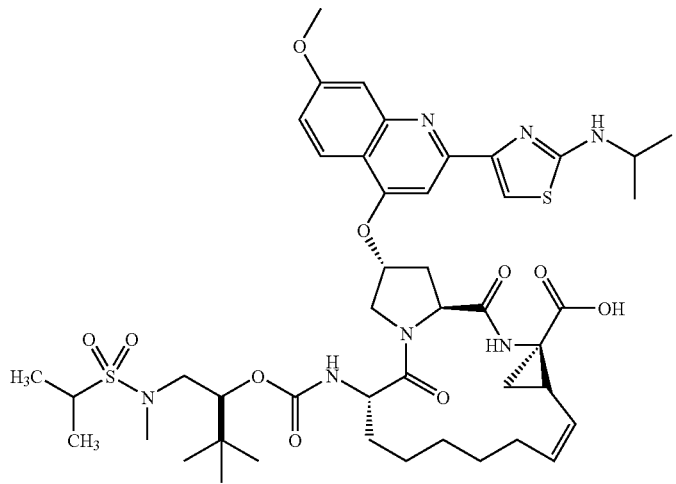
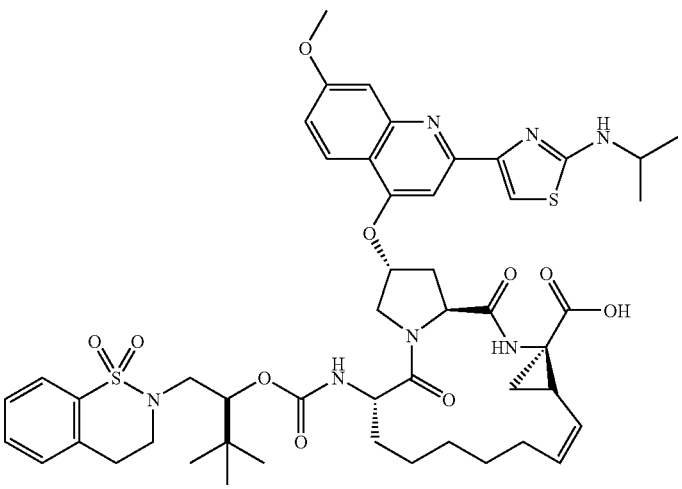
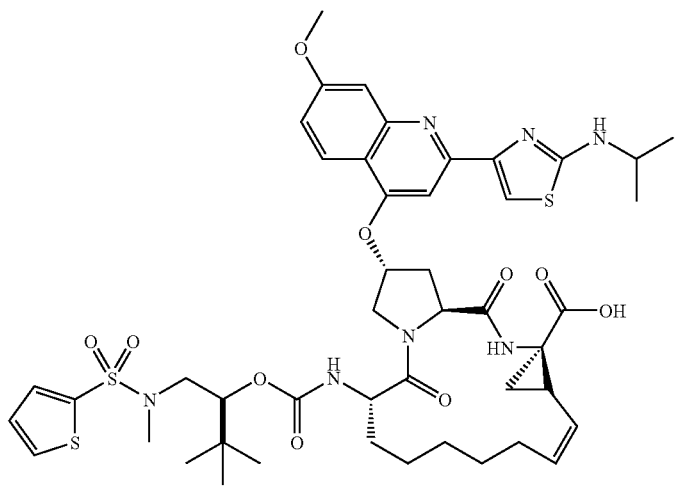

TABLE 1-continued
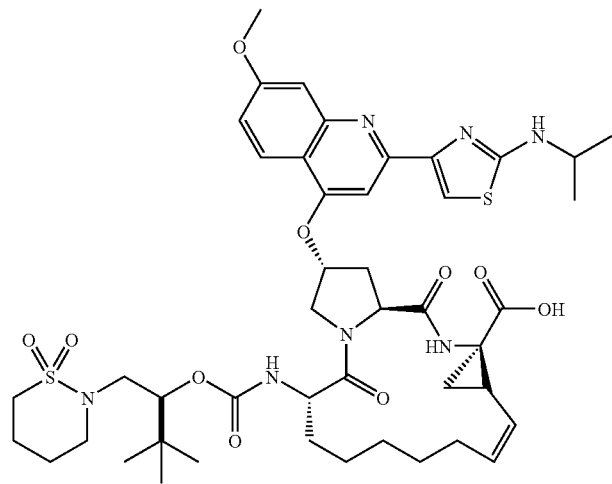
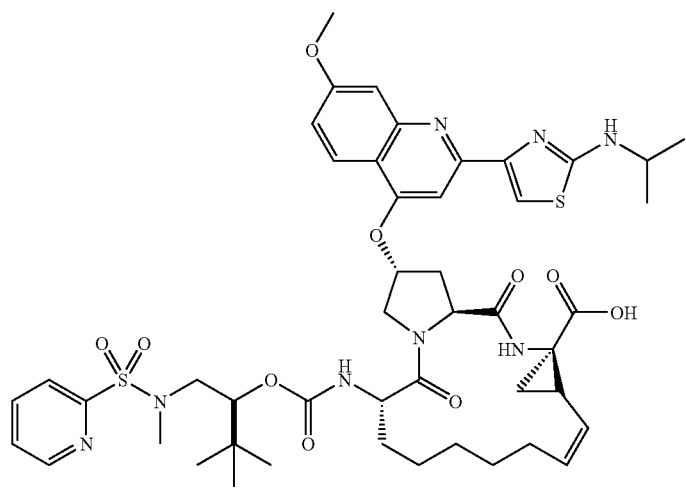
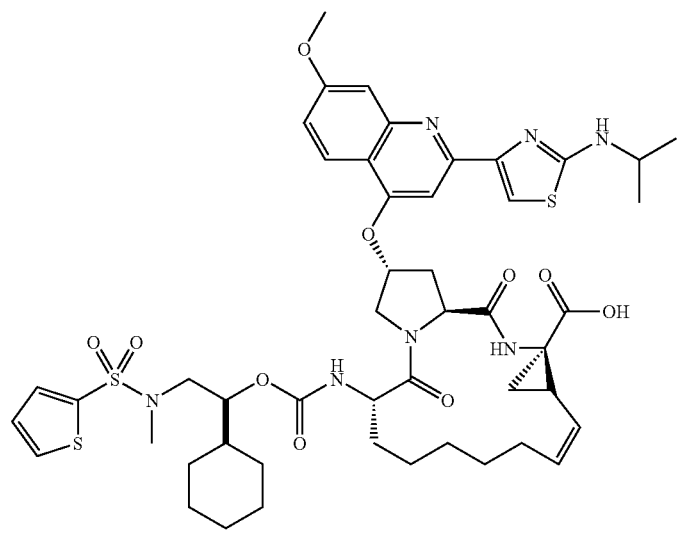

TABLE 1-continued
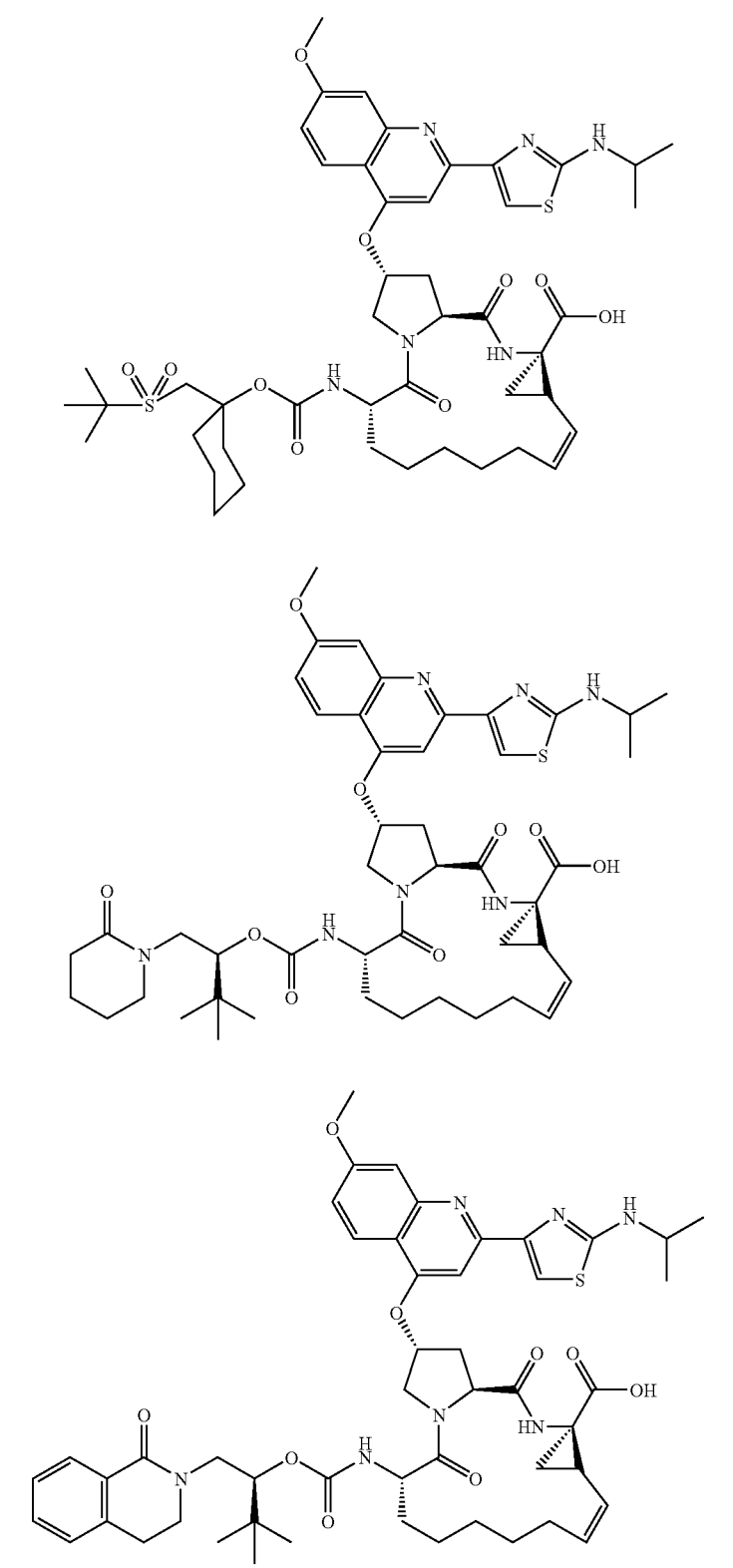

TABLE 1-continued
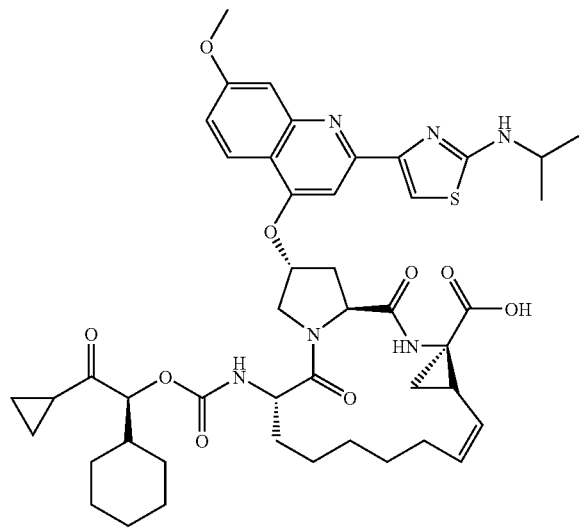
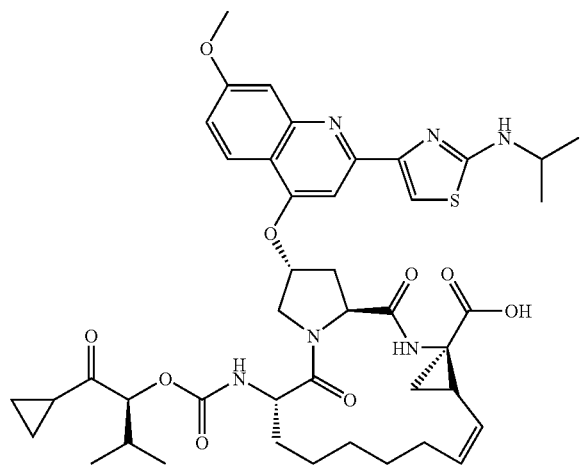
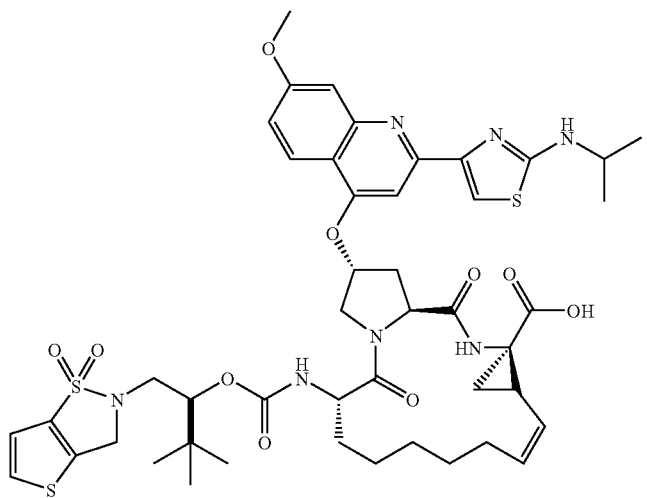

TABLE 1-continued
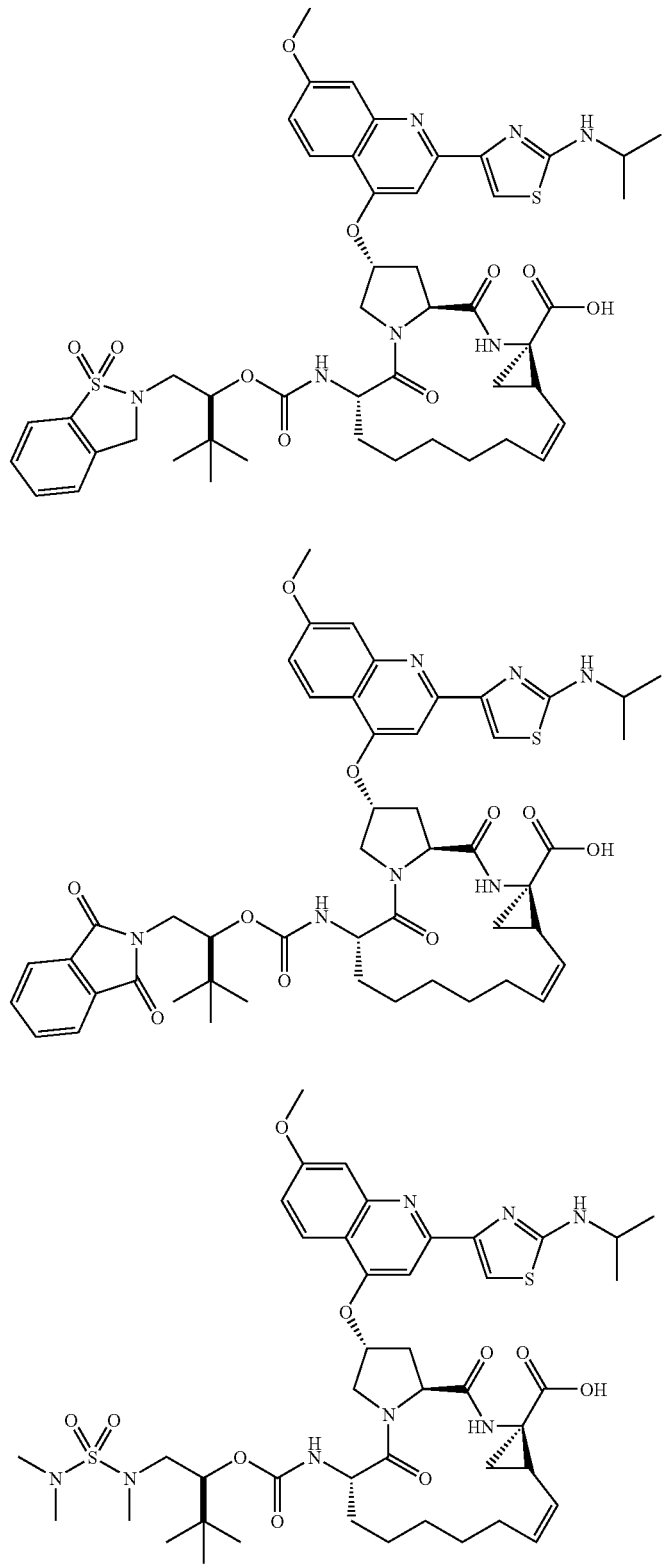

TABLE 1-continued
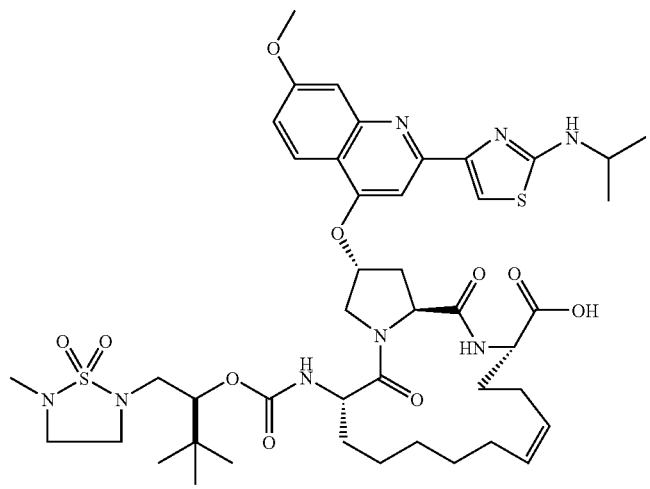
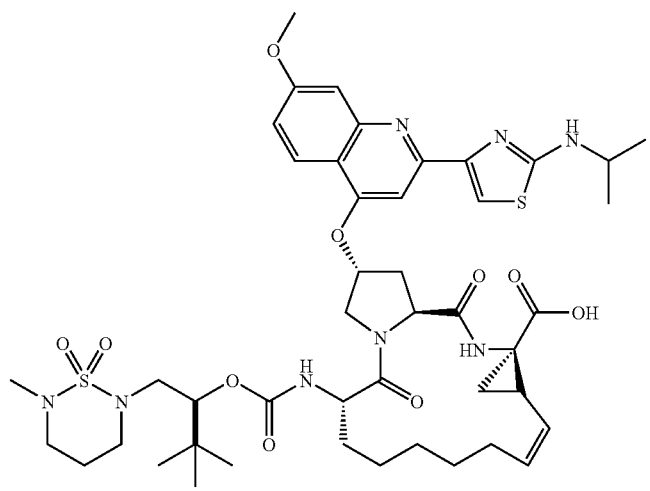
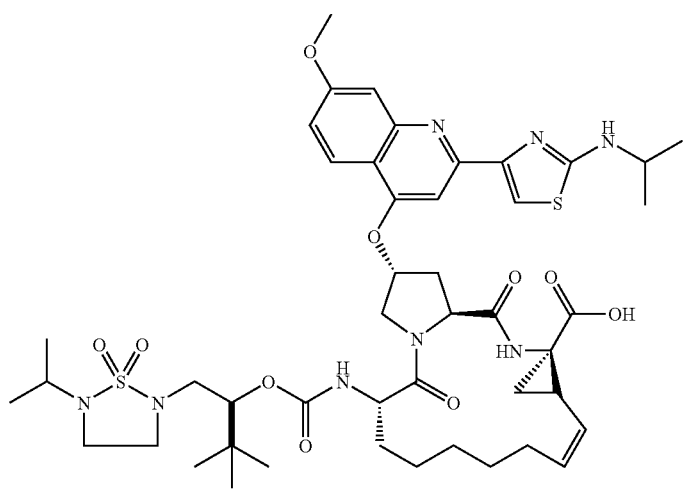

TABLE 1-continued
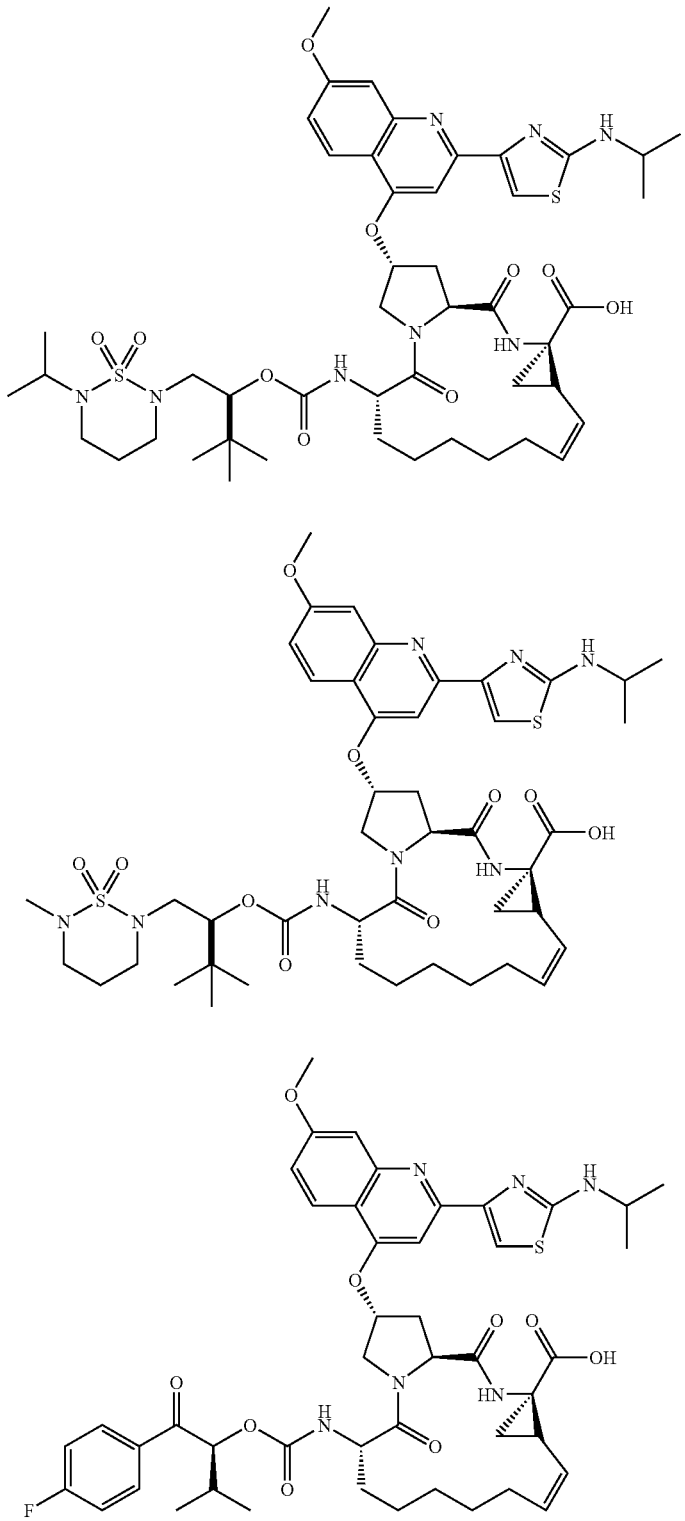

TABLE 1-continued
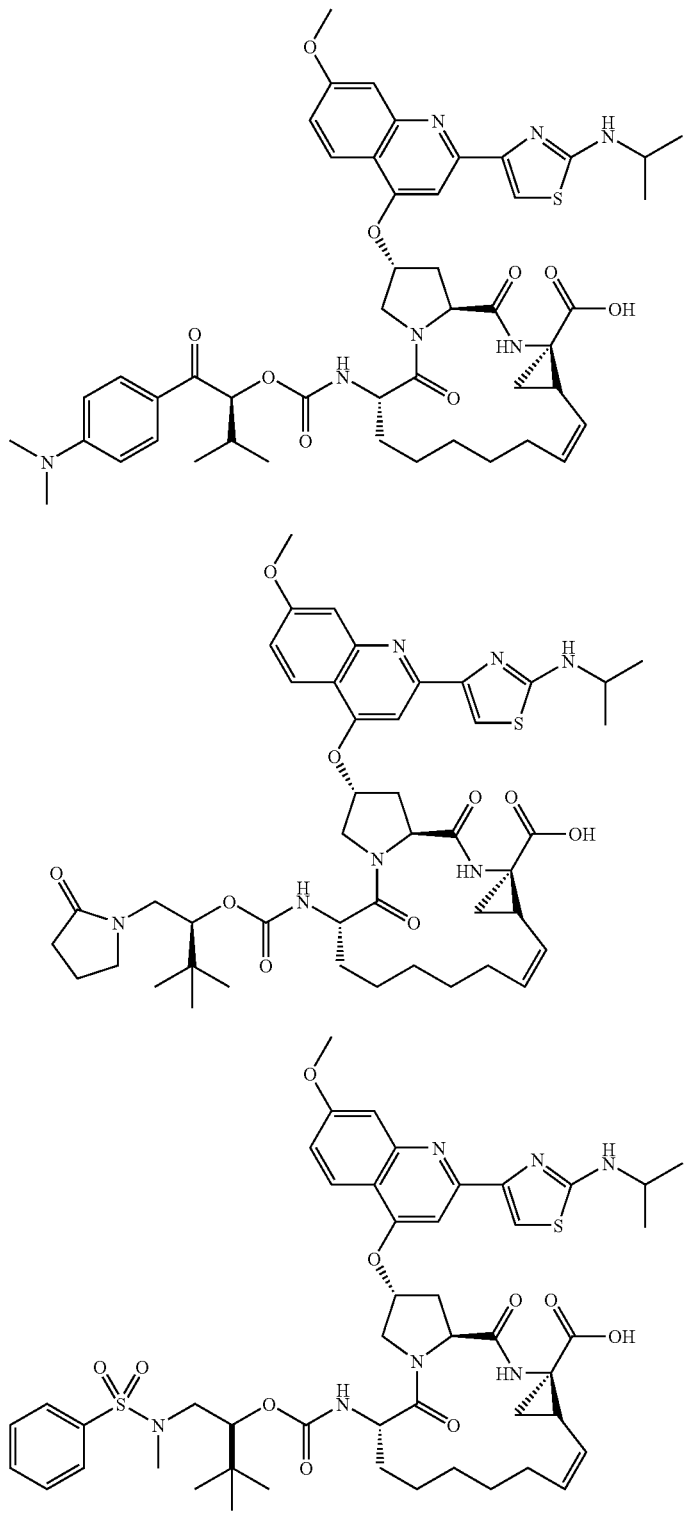
Yet another embodiment of the invention discloses compounds in Table 2 as belonging to Formula 2:

TABLE 2
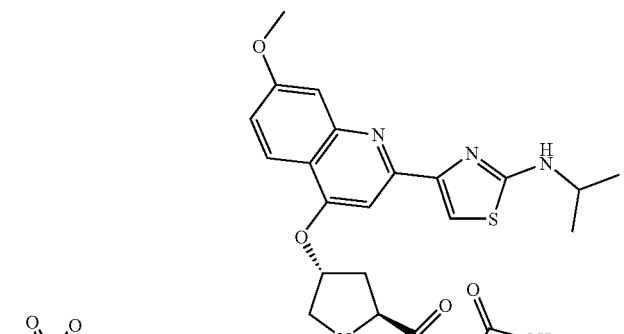
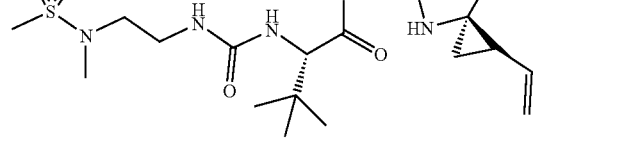
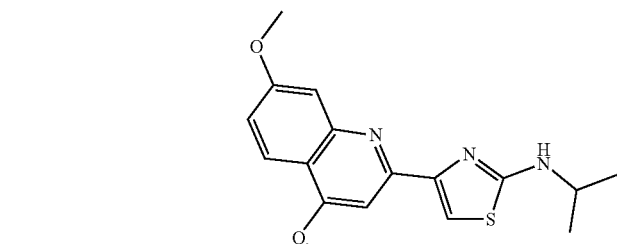
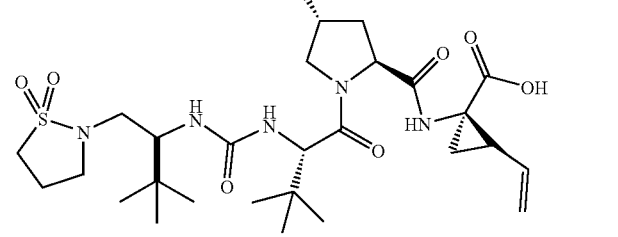
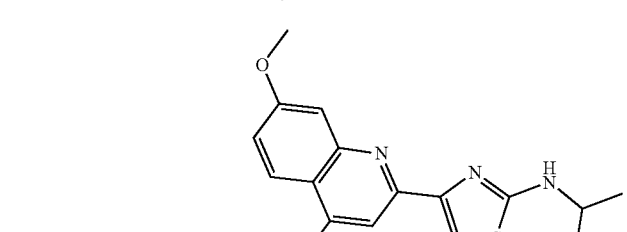
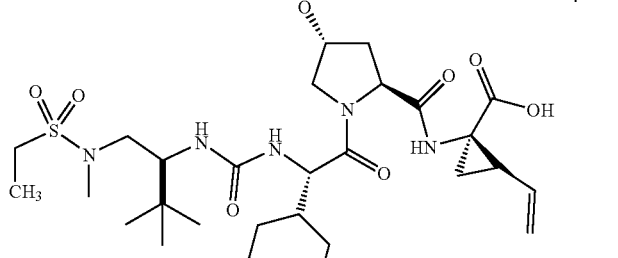

Yet another embodiment of the invention discloses compounds in Table 3 as belonging to Formula 3:
TABLE 3
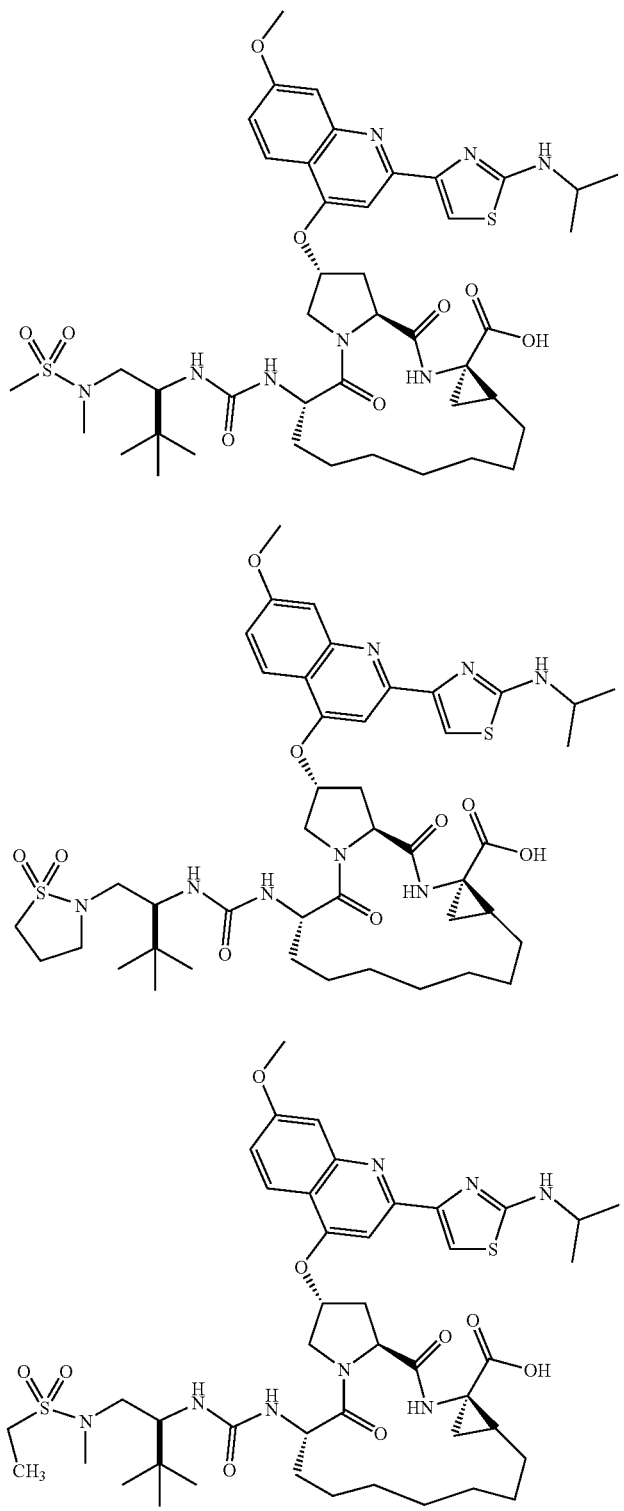

TABLE 3-continued
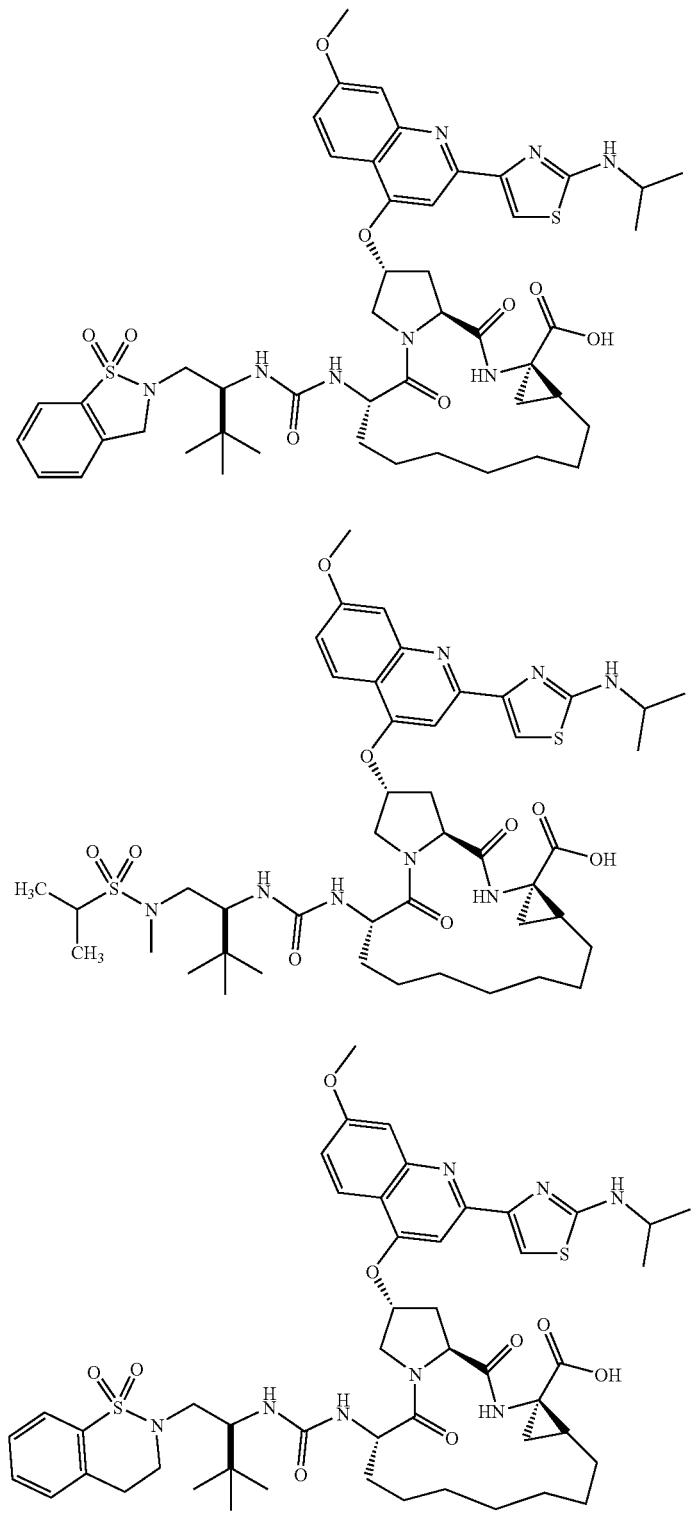

TABLE 3-continued
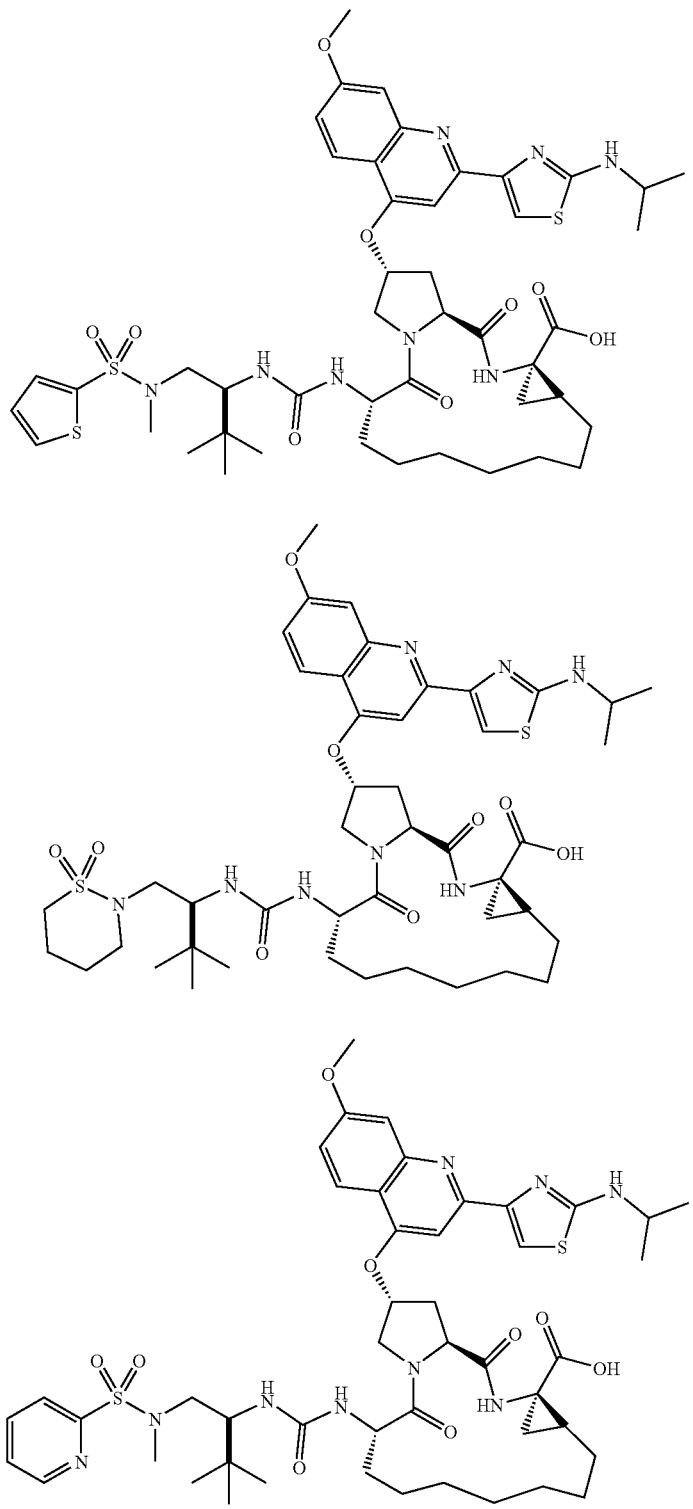

TABLE 3-continued
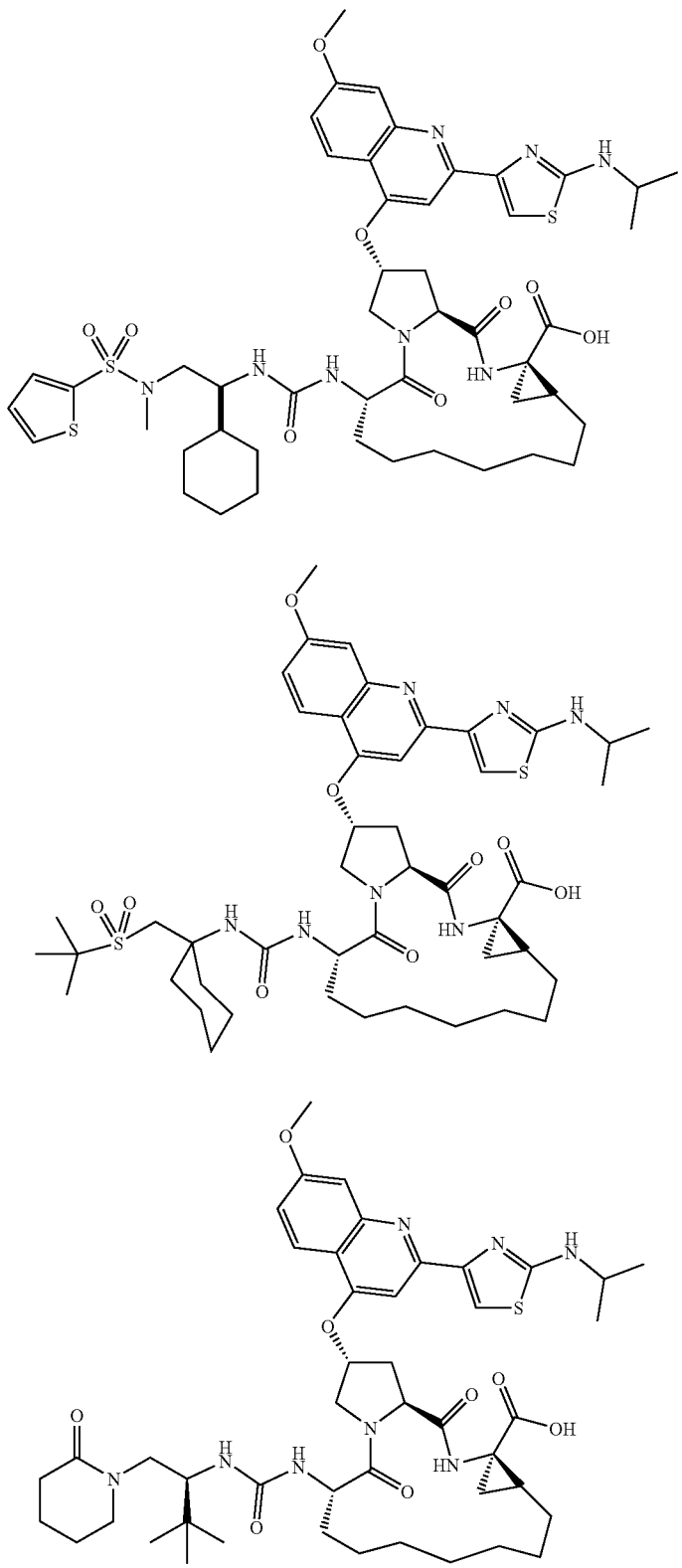

TABLE 3-continued
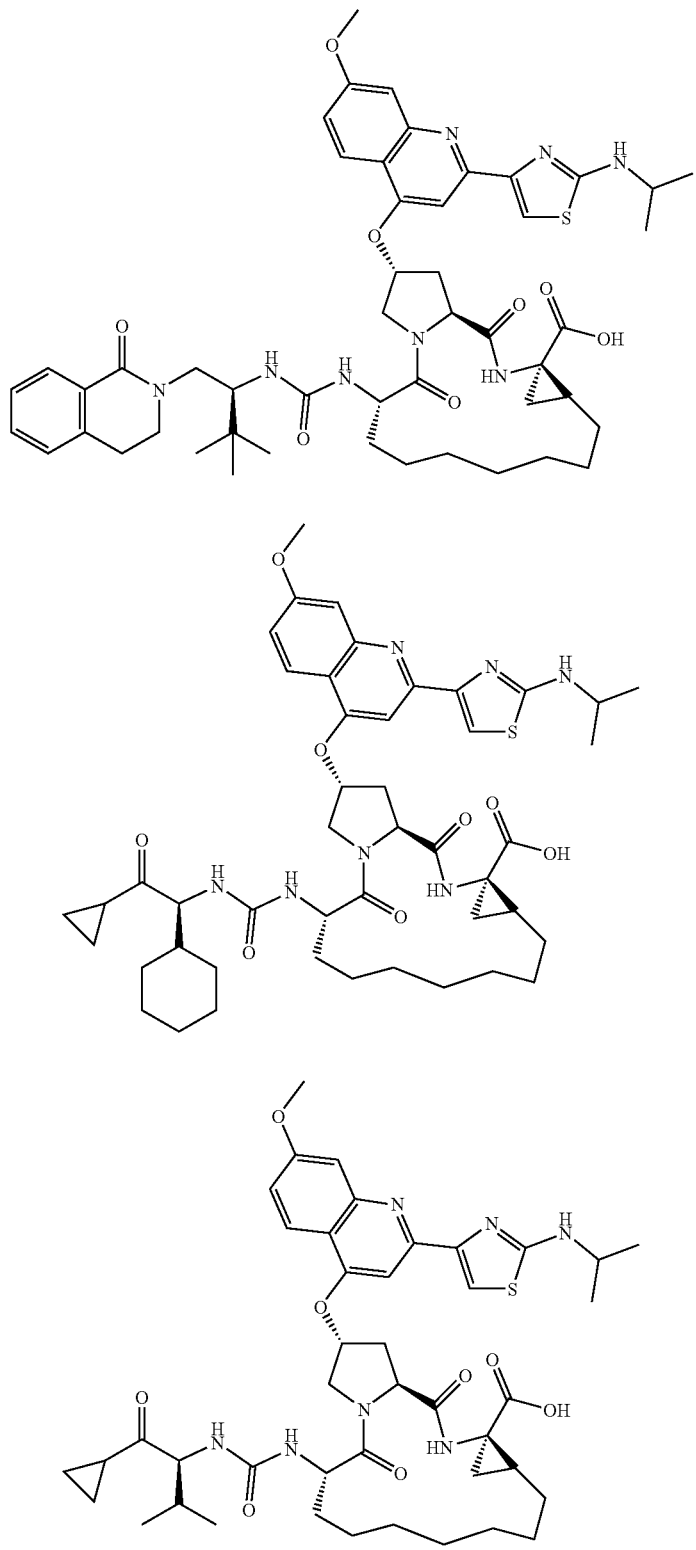

TABLE 3-continued
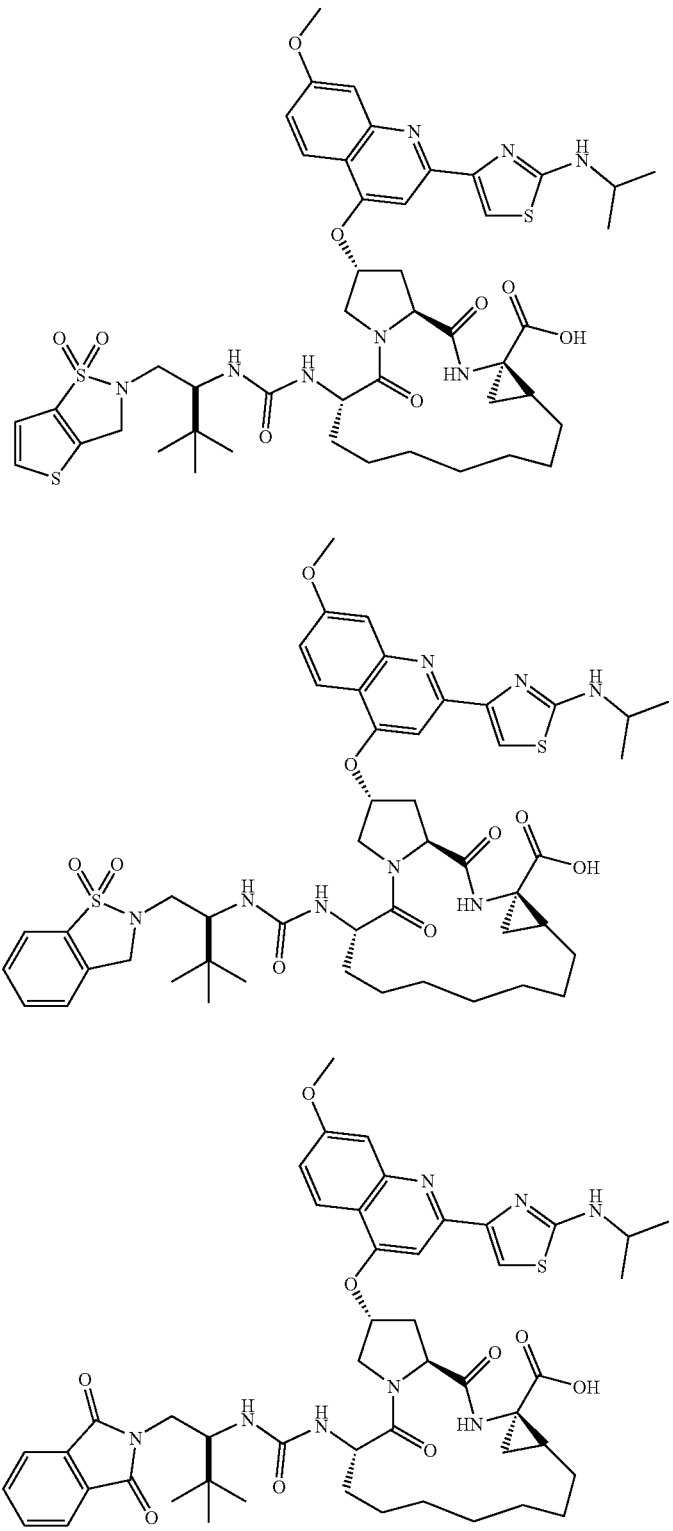

TABLE 3-continued
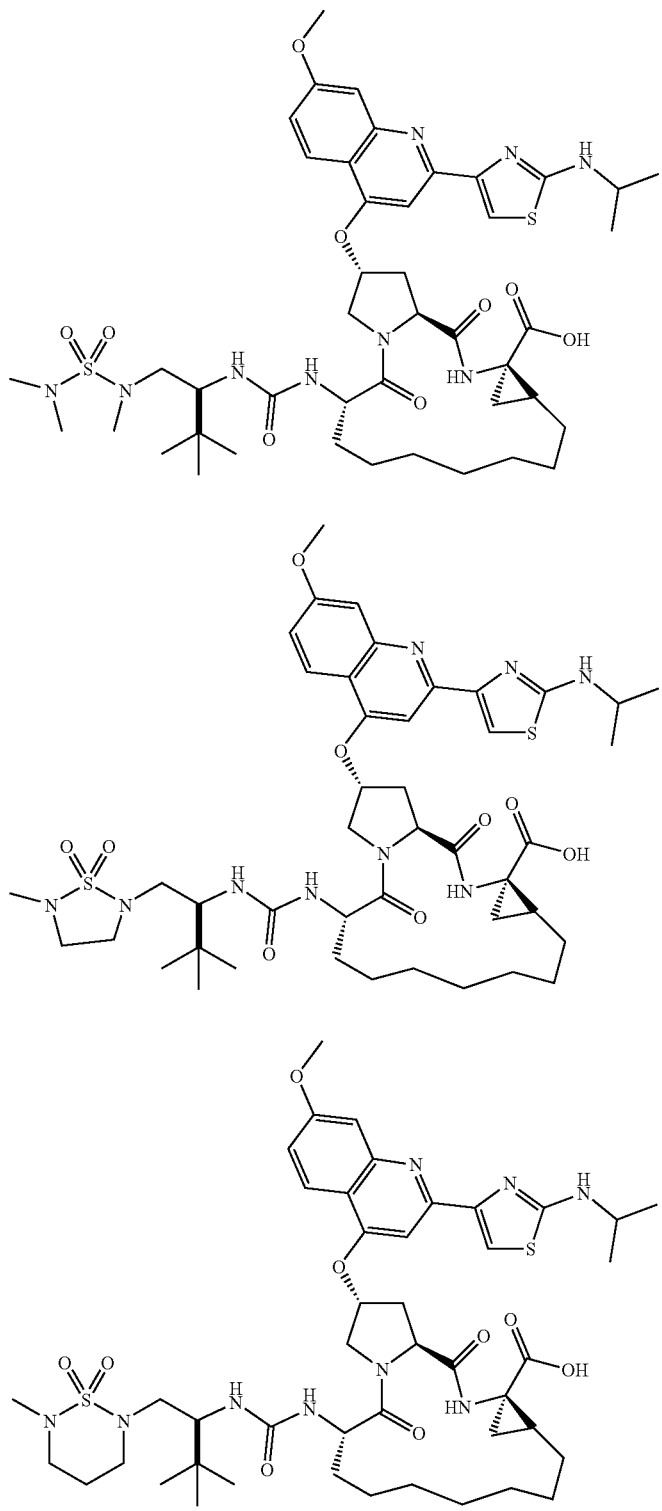

TABLE 3-continued
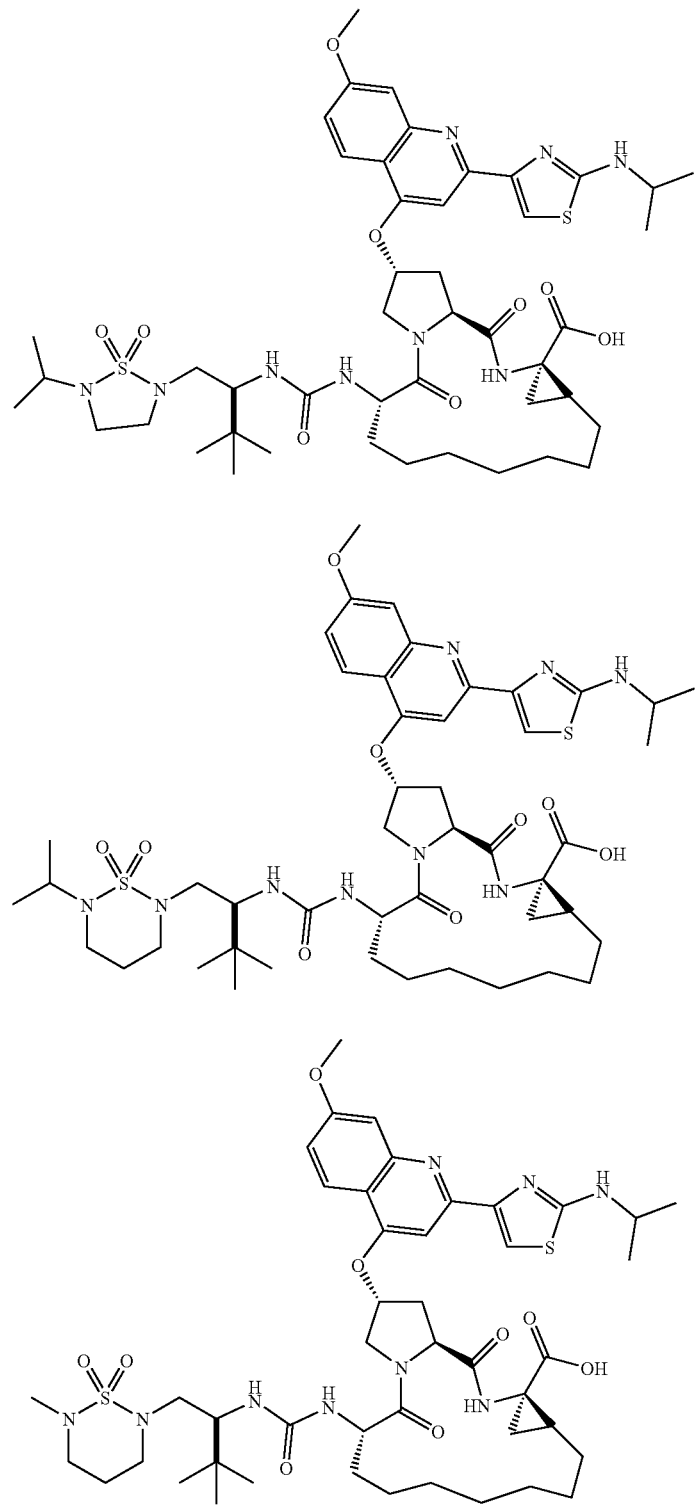

TABLE 3-continued
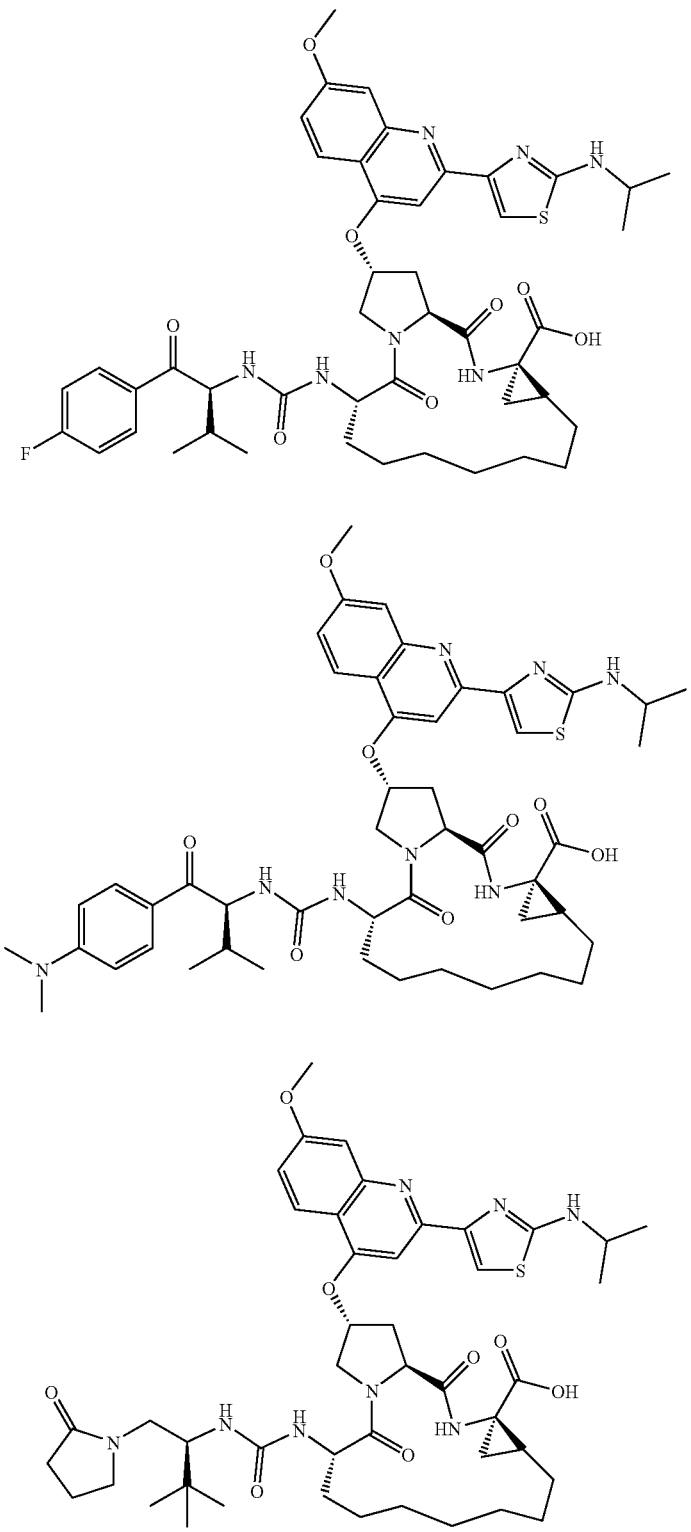

TABLE 3-continued
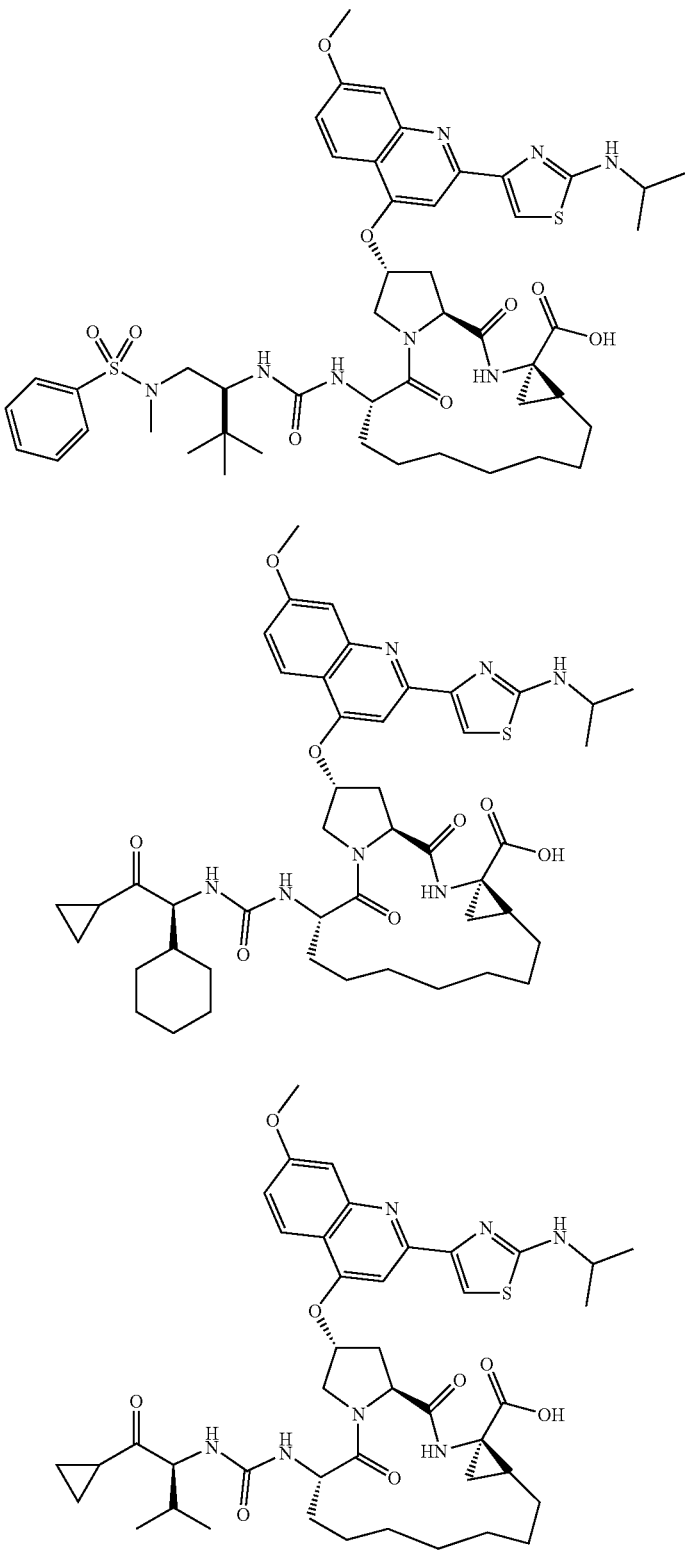

TABLE 3-continued
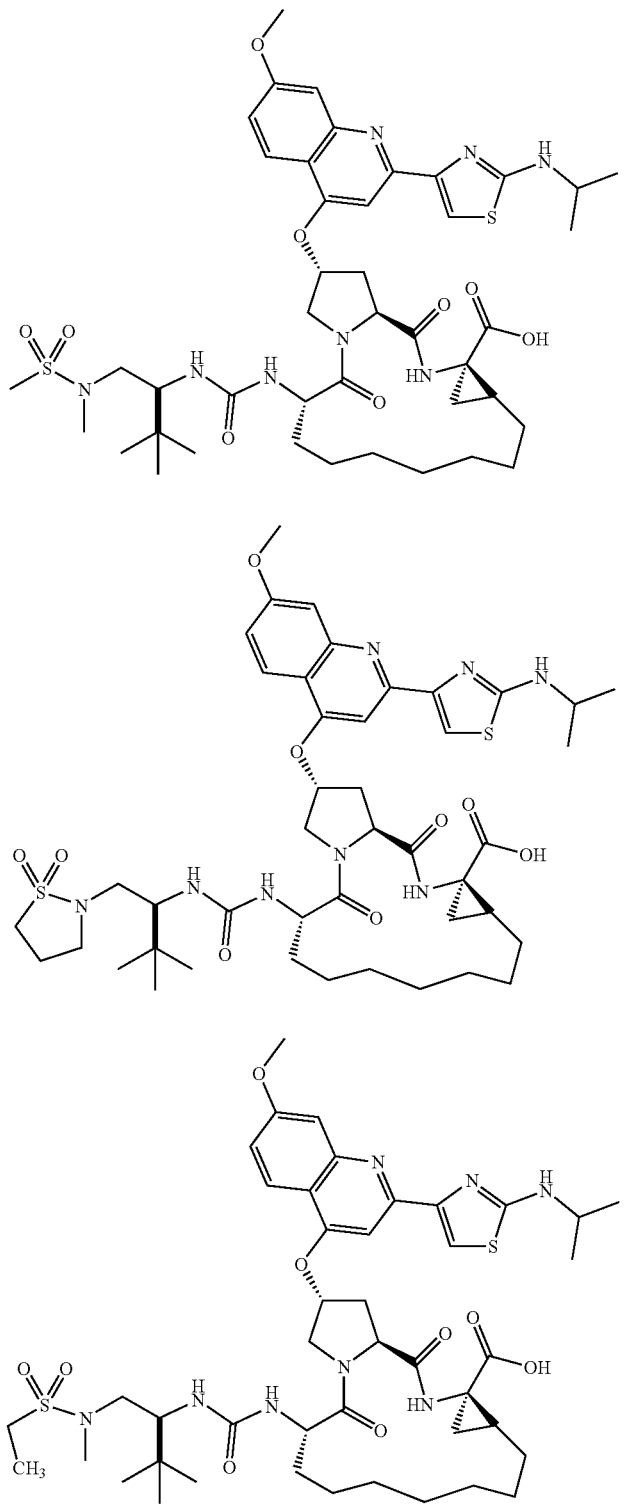

TABLE 3-continued
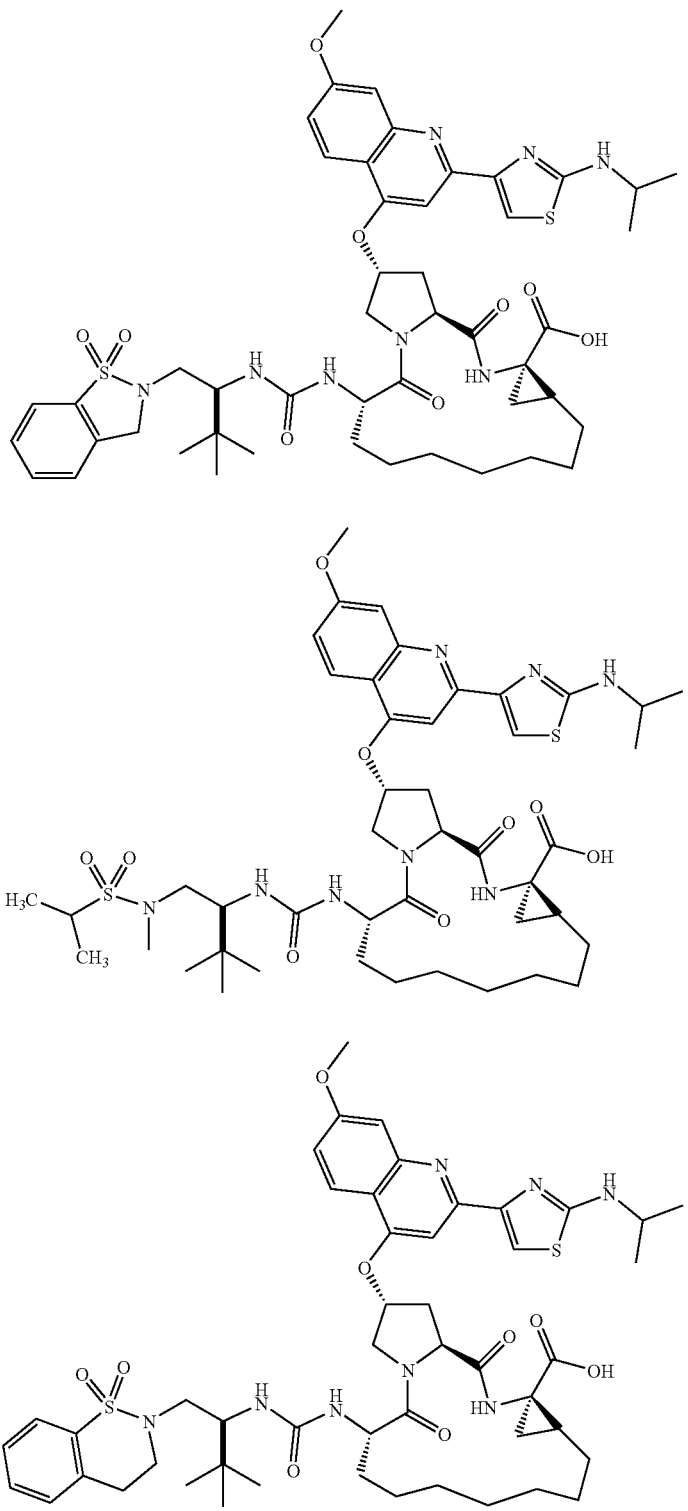

TABLE 3-continued
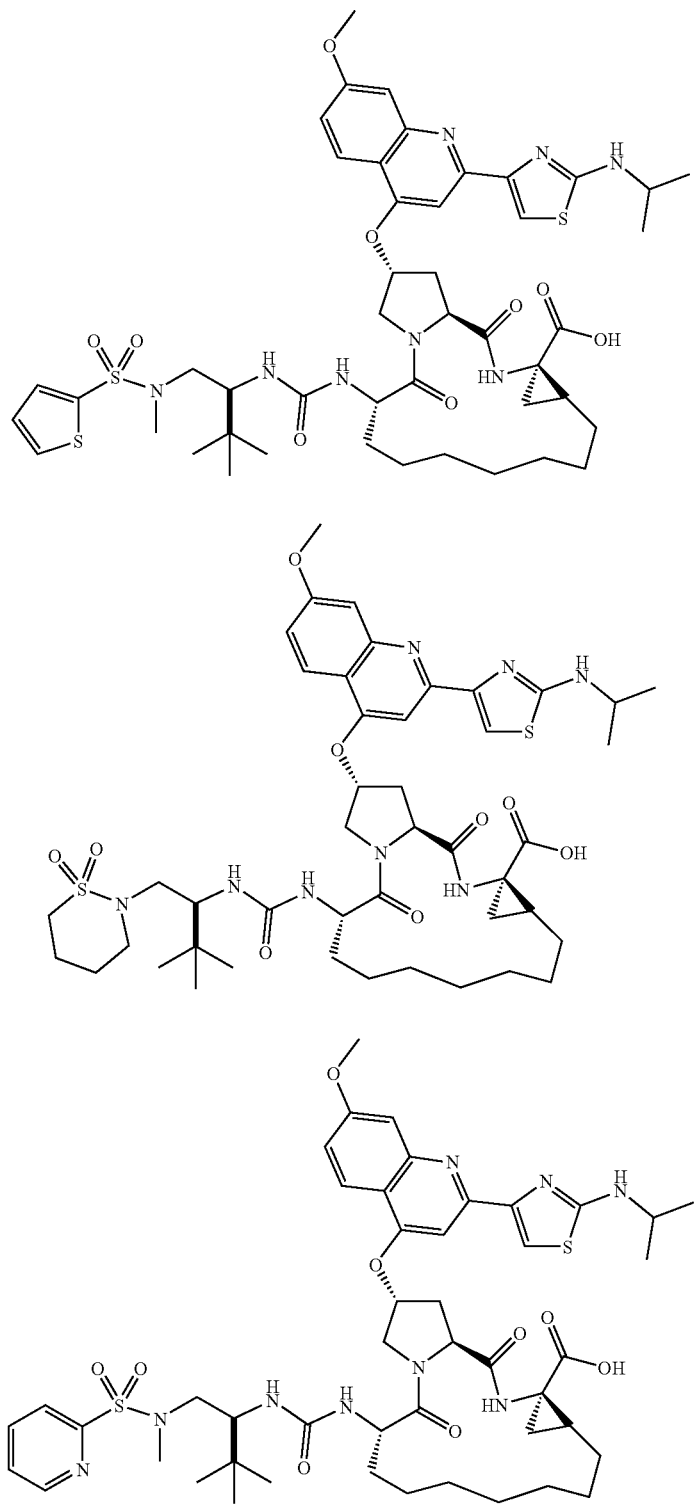

TABLE 3-continued
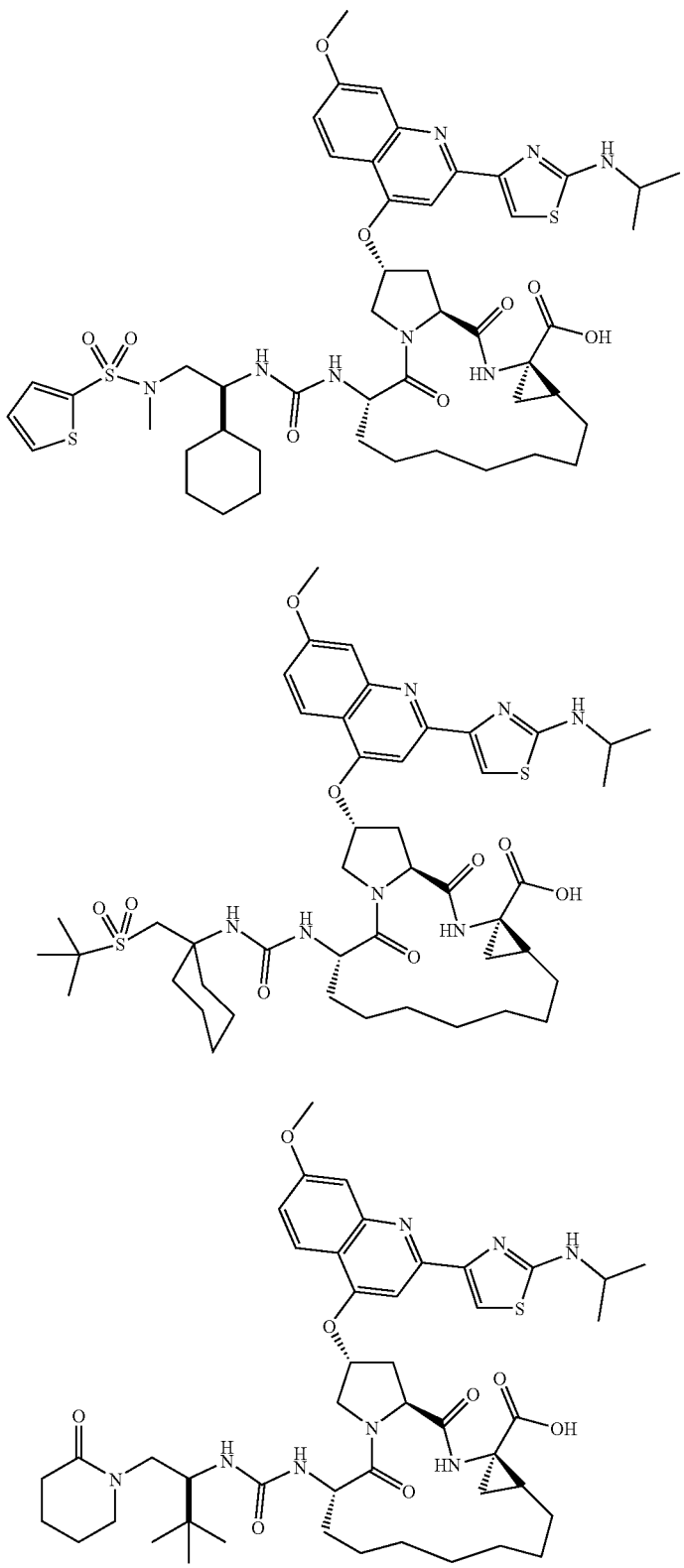

TABLE 3-continued
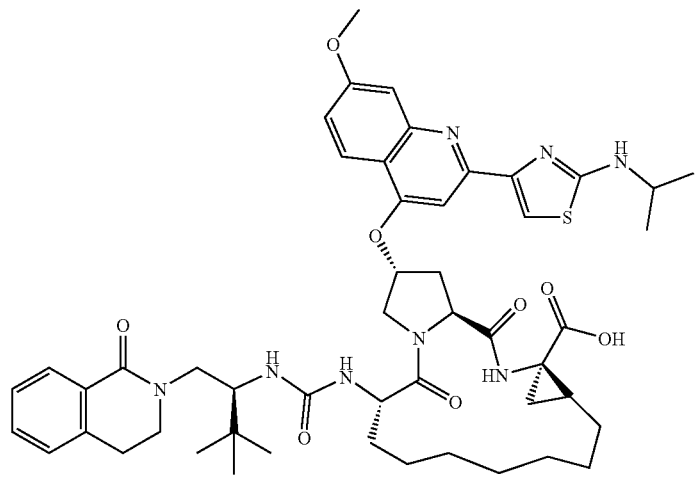
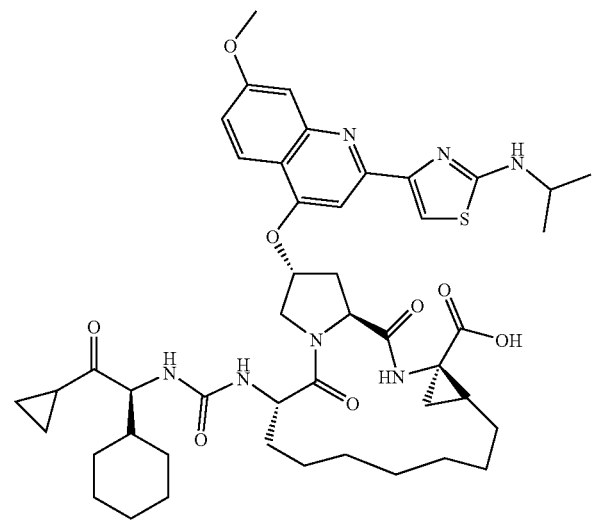
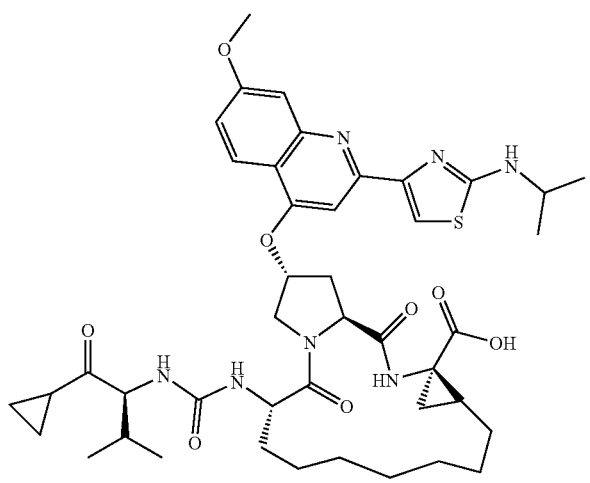

TABLE 3-continued
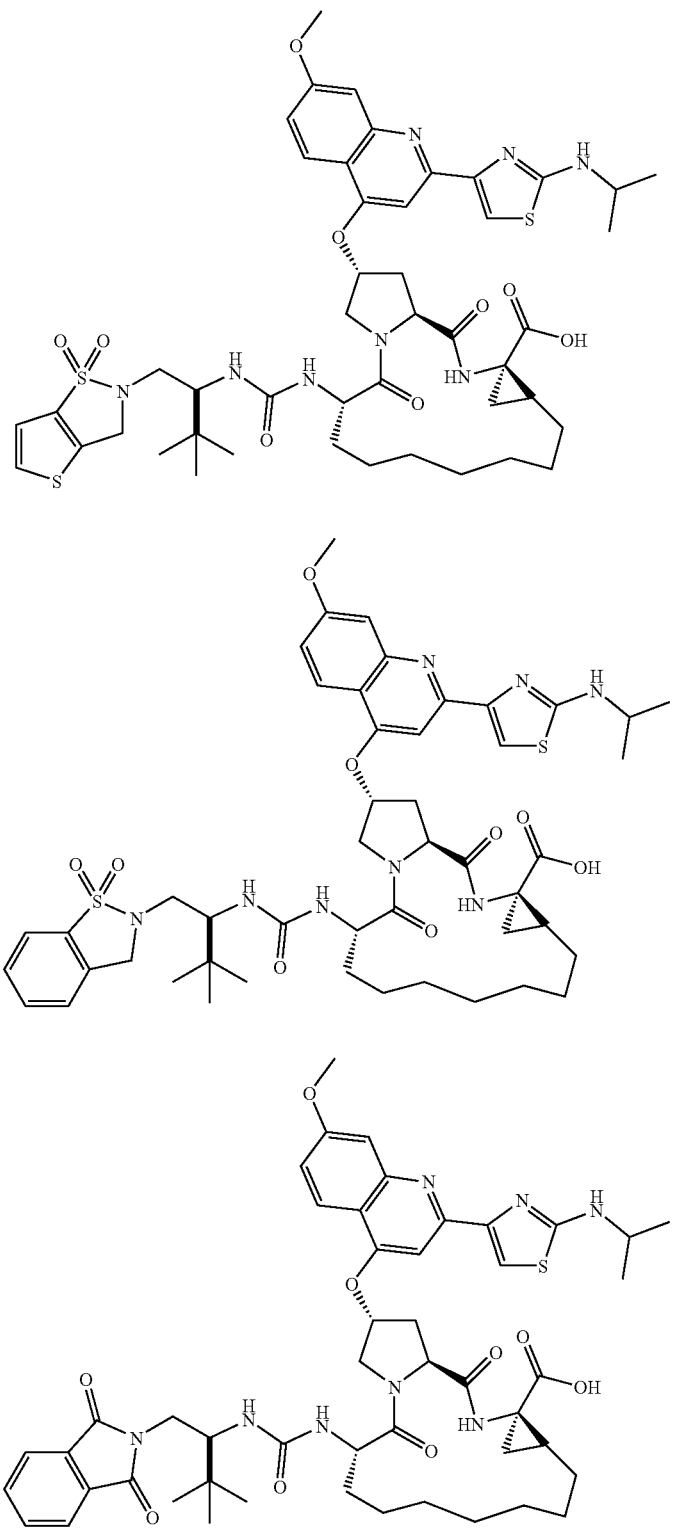

TABLE 3-continued
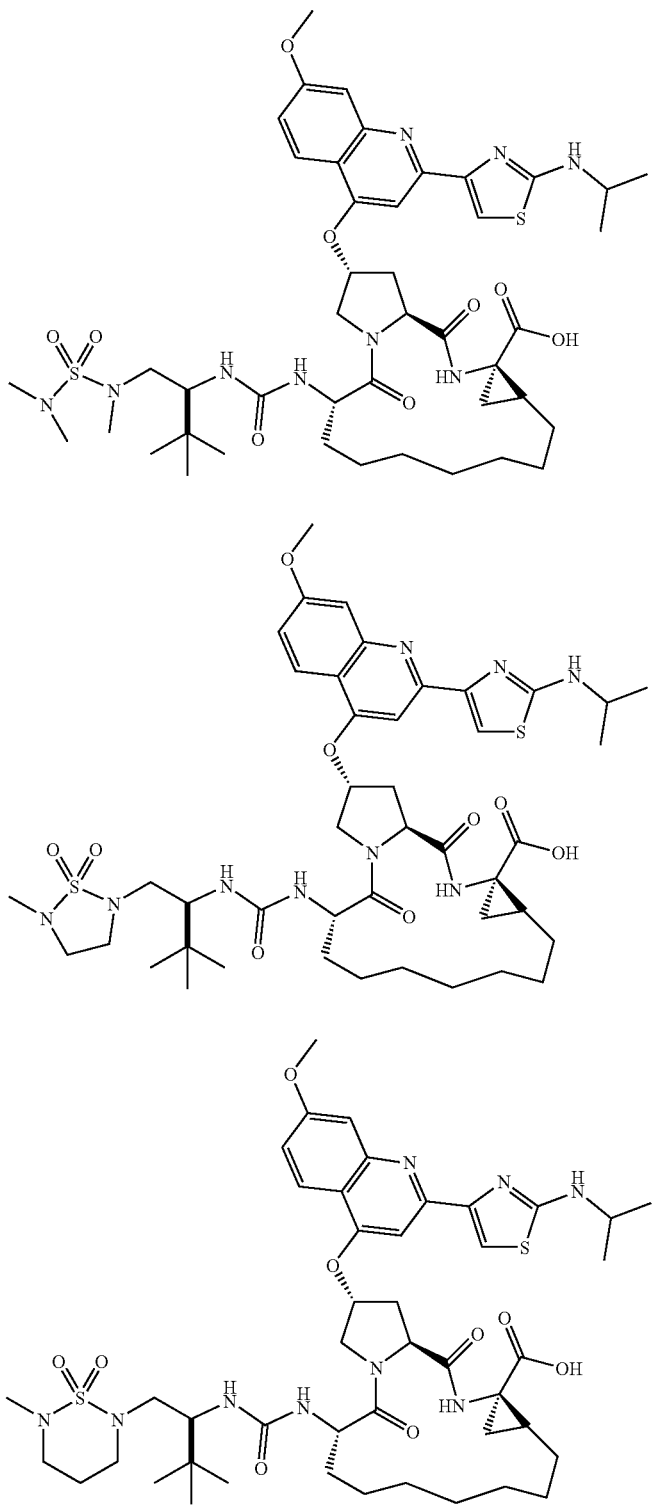

TABLE 3-continued
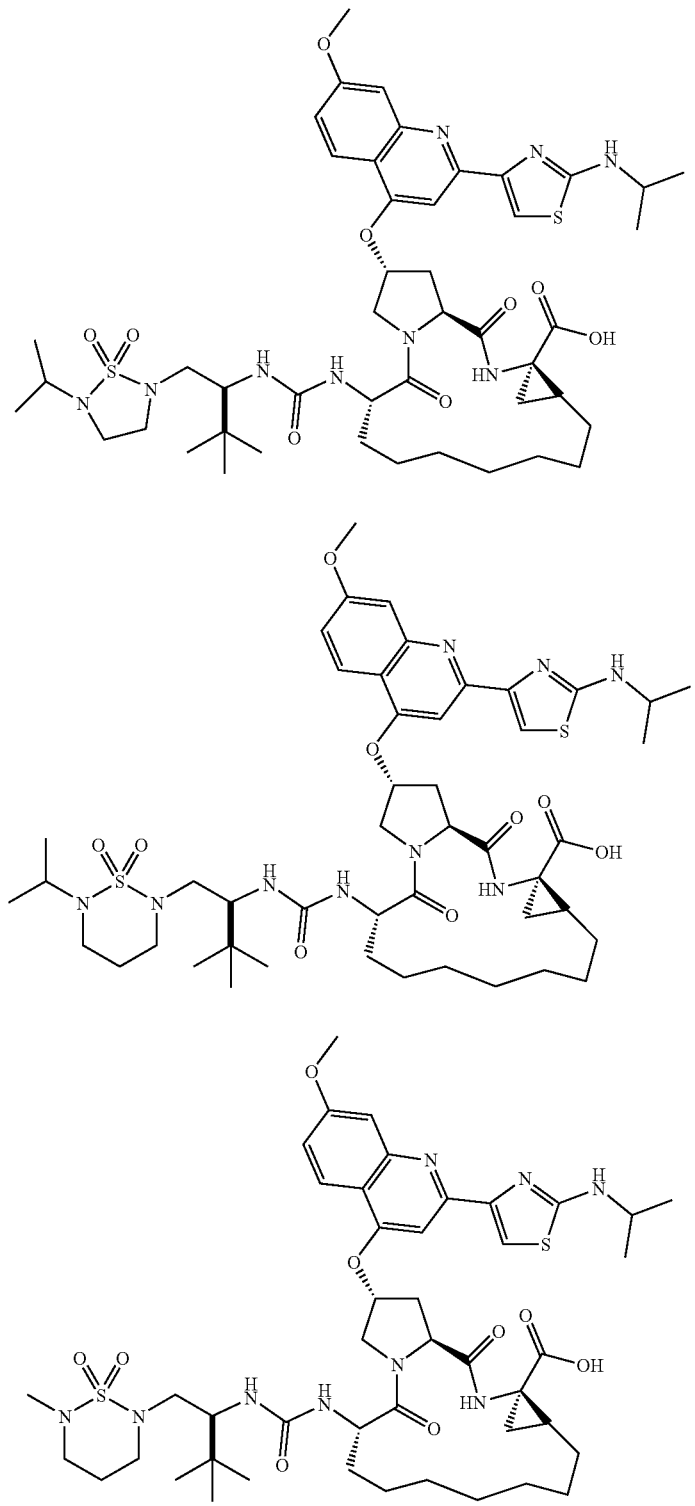

TABLE 3-continued
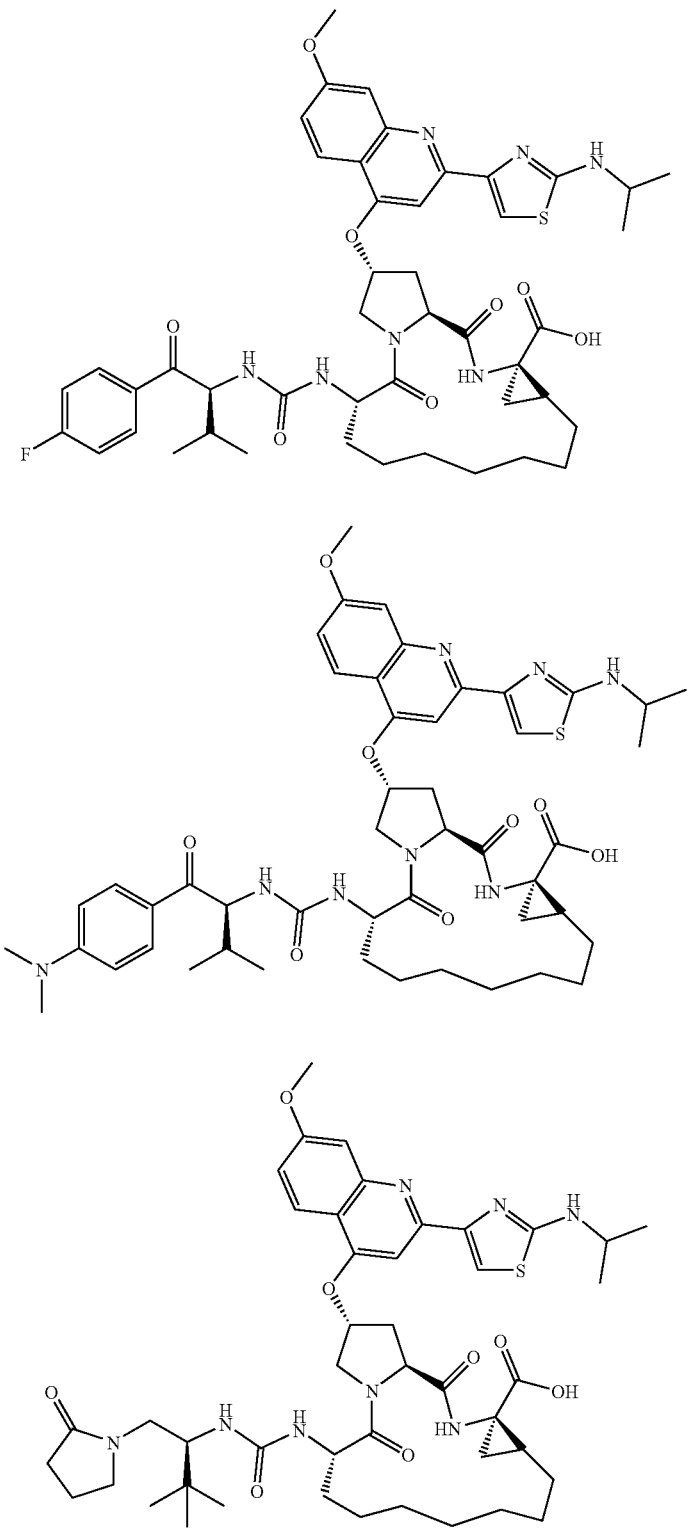

TABLE 3-continued

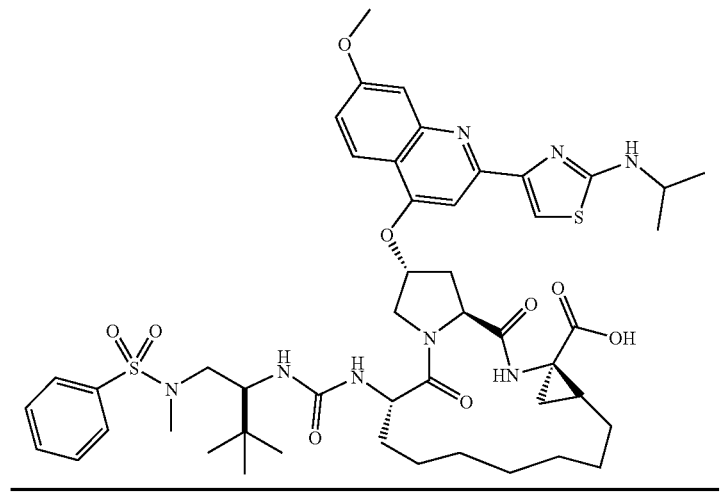

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), $Y_1Y_2N$—, $Y_1Y_2$N-alkyl-, $Y_1Y_2$NC(O)—, $Y_1Y_2$NSO$_2$— and —SO$_2$N$Y_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

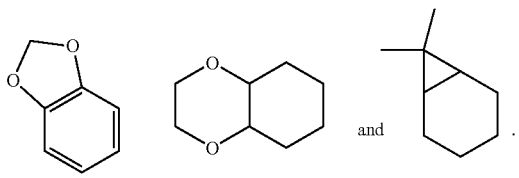

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

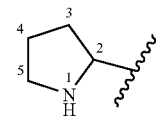

there is no —OH attached directly to carbons marked 2 and 5.

It should also be noted that tautomeric forms such as, for example, the moieties:

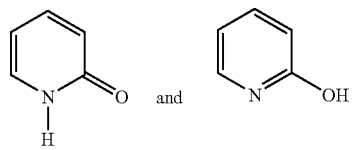

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formulas 1, 2 or 3, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formulas 1, 2 or 3 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formulas 1, 2 or 3 can form salts which are also within the scope of this invention. Reference to a compound of Formulas 1, 2 or 3 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulas 1, 2 or 3 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulas 1, 2 or 3 may be formed, for example, by reacting a compound of Formulas 1, 2 or 3 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

Compounds of Formulas 1, 2 or 3, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

It is to be understood that the utility of the compounds of Formulas 1, 2 or 3 for the therapeutic applications discussed herein is applicable to each compound by itself or to the combination or combinations of one or more compounds of Formulas 1, 2 or 3 with one or more compounds selected from within Formula 1, or from within Formula 2 or from within Formula 3, as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formulas 1, 2 or 3 can be inhibitors of HCV protease, each compound by itself or one or more compounds of Formulas 1, 2 or 3 can be combined with one or more compounds selected from within Formula 1, or from within Formula 2 or from within Formula 3. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formulas 1, 2 or 3 may be used for the manufacture of a medicament to treat disorders associated with the HCV protease, for example, the method comprising bringing into intimate contact a compound of Formulas 1, 2 or 3 a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, a compound of Formula I and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:

AcOH: Acetic acid
ADDP: 1,1'-(Azodicarbobyl)dipiperidine
Boc means t-butyloxy or tert-Butyloxycarbonyl
$^tBu$, TBu or $Bu^t$: tert-Butyl
Cbz: Benzyloxycarbonyl
Bop: Benzotriazol-1-yl-oxy-tris(dimethylamino) hexafluorophosphate
Bn or Bzl: Benzyl
Bz: Benzoyl
Chg: Cyclohexylglycine
Cp: Cylcopentyldienyl
DCM means diclhloromethane;
DCC: 1,3-Dicyclohexylcarbodiimide
DEAD: Diethylazodicarboxylate
DMAP: 4-N,N-Dimethylaminopyridine
DMF means N,N-dimethylformamide;
DMSO means dimethyl sulfoxide;

EDCl: 1-(3-dimethylaminopropyl)-3-ethylcarbodiimide hydrochloride;
EtOAc means ethyl acetate;
Et$_2$O: Diethyl ether;
HATU means O-(7-azabenzotriazol-1-yl)-1,1,3,3-tetramethyluronium;
HOOBt: 3-Hydroxy-1,2,3-benzotriazin-4(3H)-one;
HOBt: N-Hydroxybenzotriazole;
iBoc: isobutoxycarbonyl;
iPr: isopropyl;
KHMDS means Potassium hexamethyl disilylamide;
LiHMDS means hexamethyldisilazide;
MS means mass spectrum;
nBuLi means n-butyl lithium;
NMM means N-methyl morpholine;
NMR means nuclear magnetic resonance;
Phg: Phenylglycine;
Ph: Phenyl;
Pd/C means palladium on charcoal catalyst;
PyBrOP: Bromo-tris-pyrrolidinophosphonium hexafluorophosphate;
TBuNCO means t-butyl isocyanate;
TEMPO: 2,2,6,6-Tetramethyl-1-piperidinyloxy;
THF means tetrahydrofuran;
THP means tetrahydrofuran;
TMSI means trimethyl silyl iodide;
T$_3$N means triethylamine;
Ts: p-toluenesulfonyl.

Several of the intermediates and/or preparative examples used in the following synthetic procedures have been disclosed in WO 01/77113; WO 01/081325; WO 02/08198; WO 02/08256; WO 02/08187; WO 02/08244; WO 02/48172; WO 02/08251; and pending U.S. patent application, Ser. No. 10/052,386, filed Jan. 18, 2002. The disclosures of those applications are incorporated herein by reference thereto.

GENERAL PREPARATIVE SCHEMES AND PROCEDURES FOR PREPARATIVE EXAMPLES

Preparative Example 1

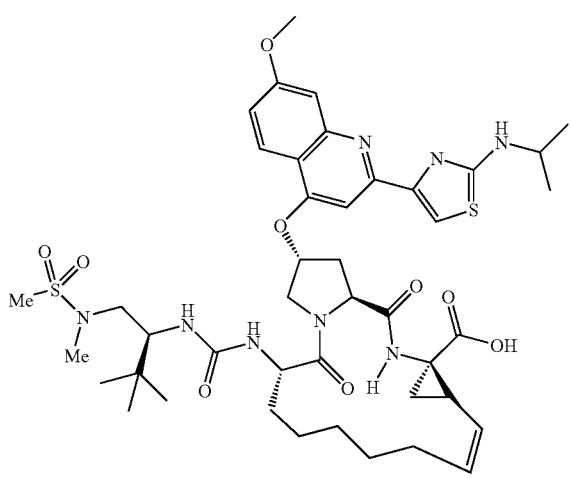

1

Step A:

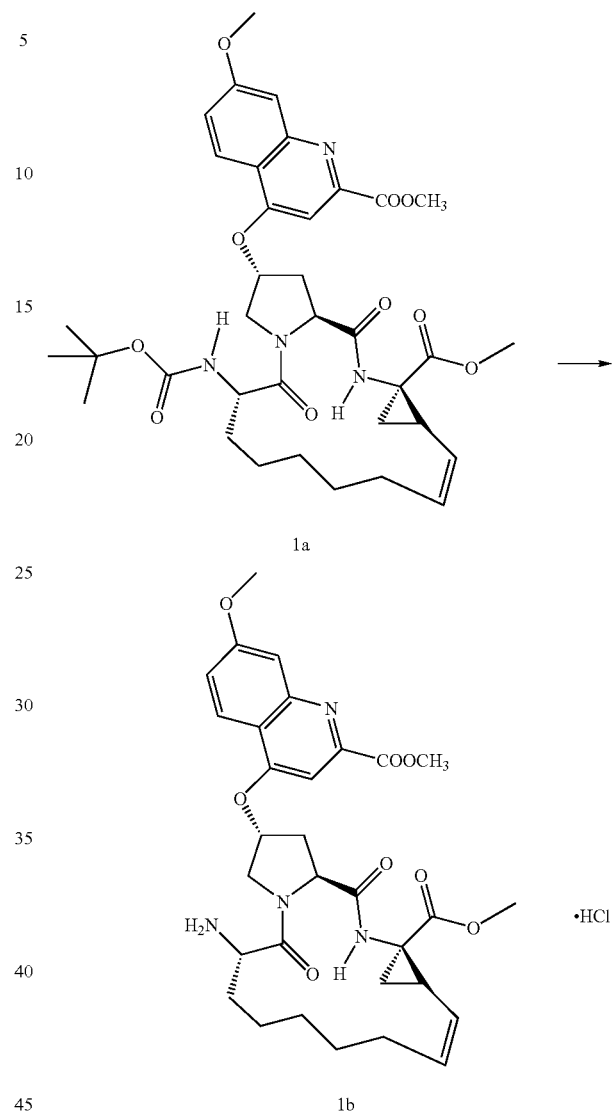

A solution of Boc protected compound 1a (Tsantrizos et al. U.S. Pat. No. 6,608,027 B1 (Boehringer Ingelheim, Canada), 2.2 g, 3.166 mmol) in HCl (4 M soln in dioxane 50 mL) and CH$_2$Cl$_2$ (50 mL) is stirred at rt. for 1 h and concentrated in vacuo. The disappearance of starting material is followed by TLC (acetone/hexanes 1:1). The gelatinous reaction mixture is concentrated in vacuo and dried to yield 1b that is used in next reaction without further purification.

Step B:

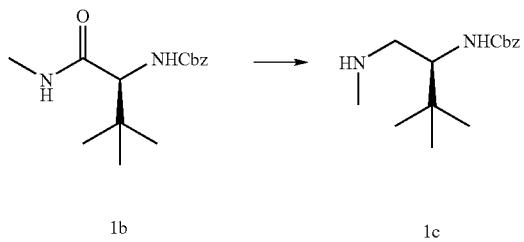

1b → 1c

A solution of amide 1b (18 g, 64.67 mmol) in toluene (200 mL) is treated with BH3.DMS (2 M soln. in THF, 65 mL, 130 mmol) and heated at 80° C. for 3 h. The reaction mixture is cooled to rt and treated carefully with aq NaOH (2 M) and extracted into $CH_2Cl_2$ (3×200 mL). The combined organic layers were extracted with aq. saturated $NaHCO_3$ (3×300 mL), brine (300 mL), dried ($MgSO_4$) and purified by chromatography ($SiO_2$, ammoniacal methanol (7M)/CH2Cl2 1:20) to yield 1c (3.5 g) as a colorless oil.

Step C:

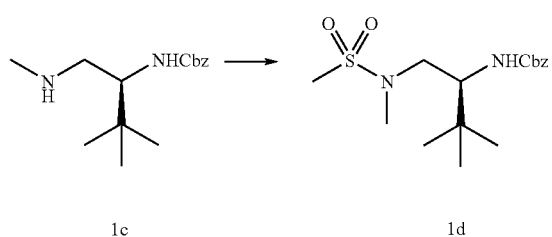

1c → 1d

A solution of amine 1c (900 mg, 3.40 mmol) in $CH_2Cl_2$ at 0° C. is treated with NMM (511 mg, 5.10 mmol) and methanesulfonyl chloride (585 mg, 5.10 mmol) and stirred at 0° C. for 12 h. The reaction mixture is diluted with $CH_2Cl_2$ (300 mL) and washed with excess aq. HCl (1M, 500 mL). The organic layer is dried ($MgSO_4$) filtered concentrated in vacuo and purified by chromatography ($SiO_2$, Hex/EtOAc 1:9→1:1) to yield methylsulfonamide 1d (1.00 g).

Step D:

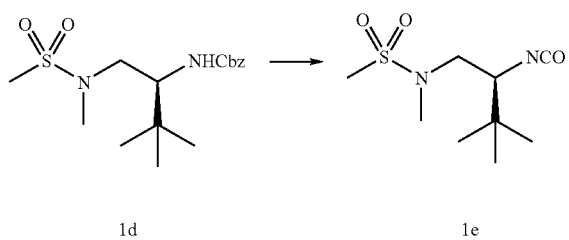

1d → 1e

A solution methanesulfonamide 1d (1.0 g, 2.9 mmol) in methanol (30 mL) is treated with palladium (200 mg, 10% wt/C) and hydrogenated at 60 psi for 3 h. The reaction mixture is filtered through a plug of celite and the filtrate is concentrated in vacuo. The residue is directly used in further reaction without further purification.

A solution of deprotected amine in $CH_2Cl_2$ (10 mL) aq. saturated $NaHCO_3$ (10 mL) at 0° C. is treated with phosgene (5 mL, 15% soln. in toluene) and stirred at 0° C. for 2 h. The reaction mixture is diluted with $CH_2Cl_2$ (50 mL) and the organic layer is washed with cold aq $NaHCO_3$. The organic layer is dried ($MgSO_4$) filtered and further diluted with 10 mL toluene, concentrated the methylene chloride layer and used as a solution of 1e in toluene.

Step E:

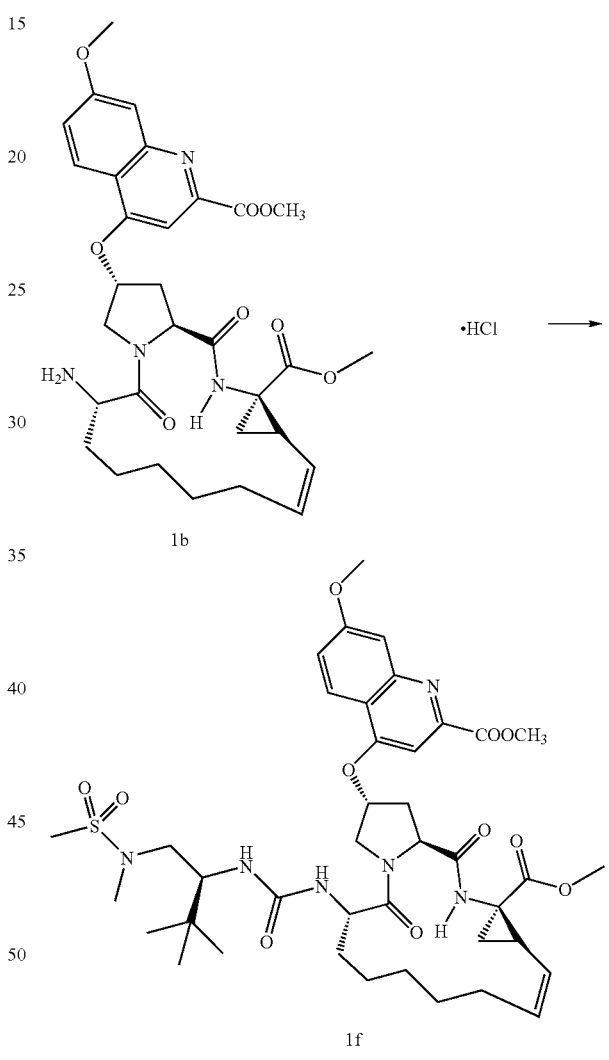

A solution of amine 1b in methylene chloride is treated with NMM and cooled to 0° C. A solution of isocyanate 1e in toluene is added and the reaction mixture is stirred at rt. The reaction mixture is diluted with methylene chloride (100 mL) and washed with water The organic layers were dried with ($MgSO_4$) filtered concentrated in vacuo and purified by chromatography to yield 1f.

Step F:

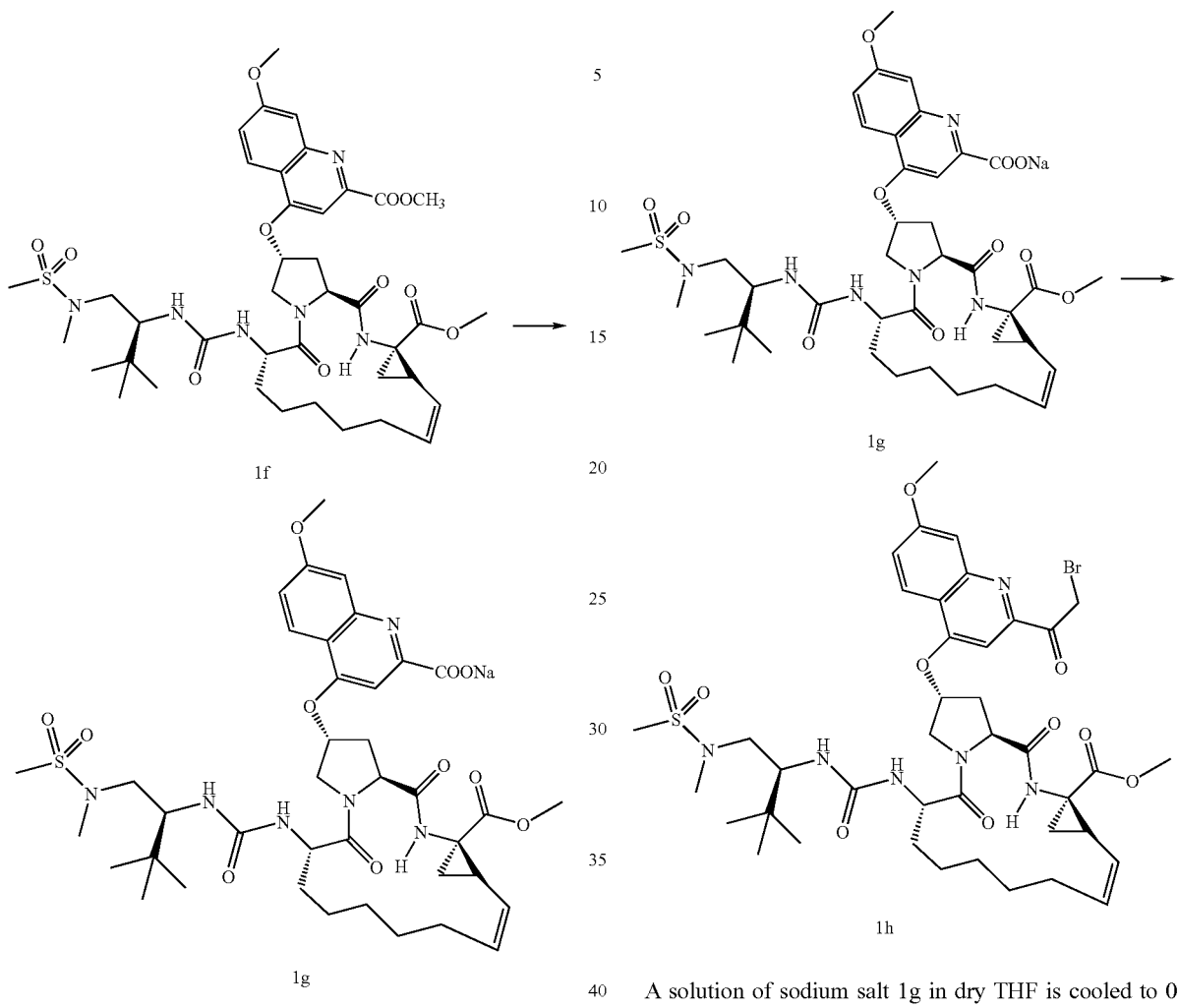

A solution of ester 1f in CH₃OH, THF and water is treated with aq NaOH (1M, 1. equiv) and stirred at rt. for 1.5 h. The reaction mixture is followed by TLC and the disappearance of starting material to base line is indicator of the completion of reaction. The reaction mixture is concentrated in vacuo to yield sodium salt 1g.

Step G:

A solution of sodium salt 1g in dry THF is cooled to 0° C. and treated with Et₃N and isobutylchloroformate. The reaction is stirred at 0° C. for 1.25 h and treated with diazomethane and stirred at 0° C. for 1 h and rt for. The reaction mixture is quenched with acetic acid and taken up with EtOAc. The organic layer is washed with satd. aq. NaHCO₃, brine, and dried (MgSO₄). It is filtered and concentrated in vacuo to yield diazo ketone which is directly used in next reaction without purification.

A solution of diazo compound in THF is cooled to 0° C. and treated with aq. HBr (48%) and stirred for 1 h. The reaction is quenched with aq. satd. NaHCO₃, and extracted into EtOAc. The organic layer is washed extensively with aq. NaHCO₃, brine and dried (MgSO₄). The ethyl acetate solution is filtered and concentrated in vacuo and purified by chromatography to yield 1 h.

Step H:

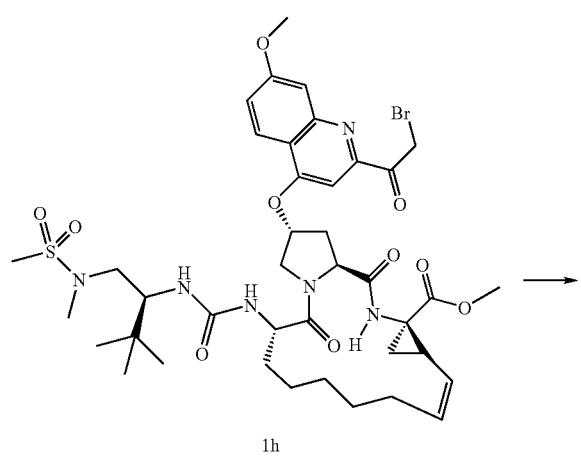

1h

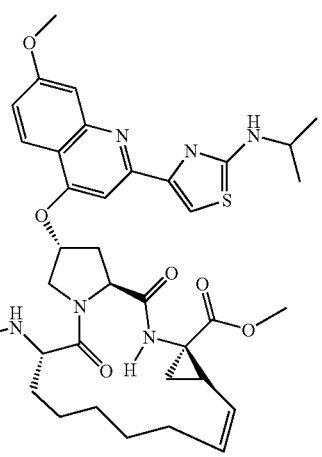

1

A solution of methyl ester 1i in THF, H₂O, and methanol is treated with LiOH hydrate and stirred at rt. The reaction mixture was concentrated in vacuo and purified by HPLC (C$_{18}$, CH$_3$CN/H$_2$O 10/90→100/0) to isolate the pure acid 1.

Preparative Example 2

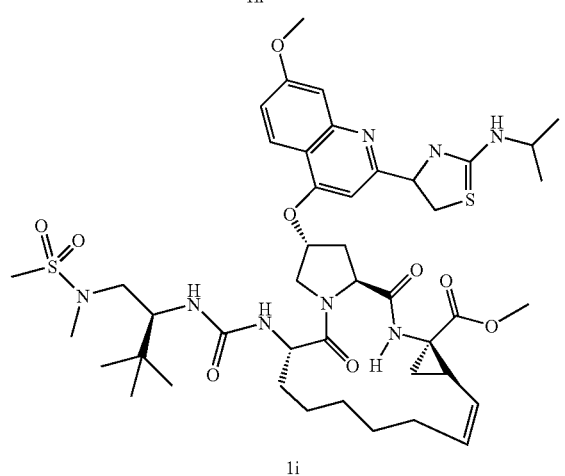

1i

A solution of bromoketone 1 h in 2-proponol is treated with ispropylthio urea and heated at 75° C. The reaction mixture is concentrated in vacuo and purified by chromatography to yield 1i.

Step I:

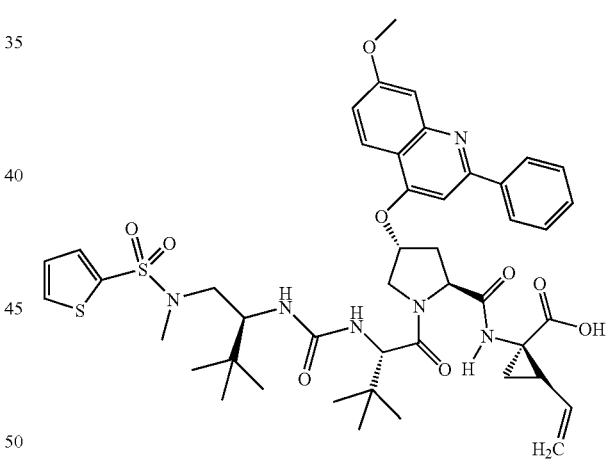

2

Step A:

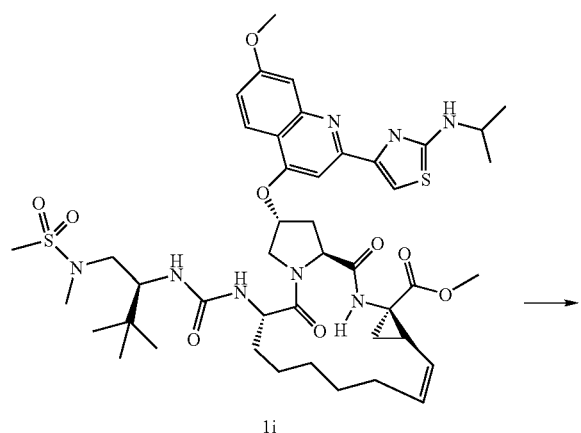

1i

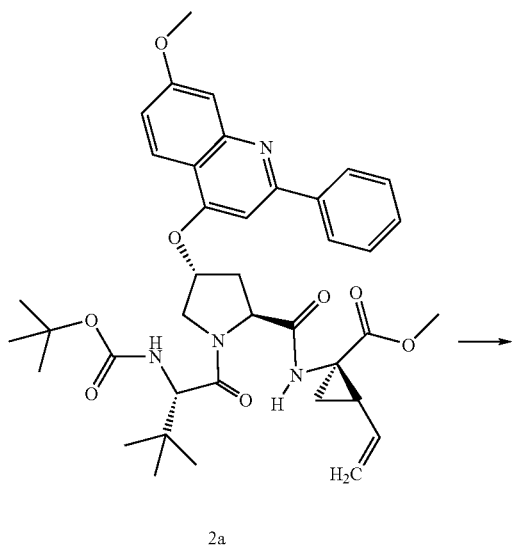

2a

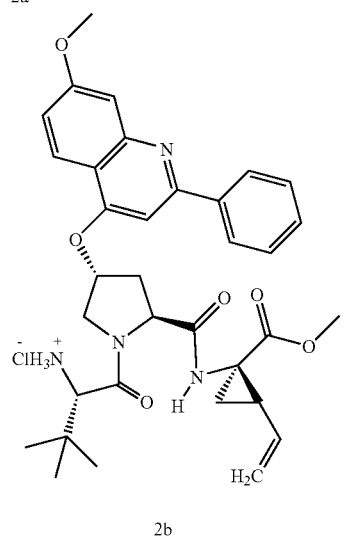

2b

A solution of Boc protected compound 2a (WO 00/09558 (Boehringer Ingelheim, Canada) in HCl (4 M soln in dioxane) and CH$_2$Cl$_2$ is stirred at rt. and concentrated in vacuo. The disappearance of starting material is followed by TLC (acetone/hexanes 1:1). The gelatinous reaction mixture is concentrated in vacuo and dried to yield 2b that is used in next reaction without further purification.

Step B:

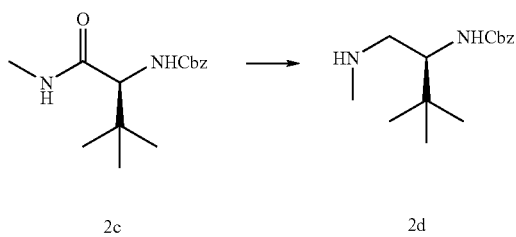

2c         2d

A solution of amide 2c (18 g, 64.67 mmol) in toluene (200 mL) is treated with BH3.DMS (2 M soln. in THF, 65 mL, 130 mmol) and heated at 80° C. for 3 h. The reaction mixture is cooled to rt and treated carefully with aq NaOH (2 M) and extracted into CH$_2$Cl$_2$ (3×200 mL). The combined organic layers were extracted with aq. saturated NaHCO$_3$ (3×300 mL), brine (300 mL), dried (MgSO$_4$) and purified by chromatography (SiO$_2$, ammoniacal methanol (7M)/CH2Cl2 1:20) to yield 2d (3.5 g) as a colorless oil.

Step C:

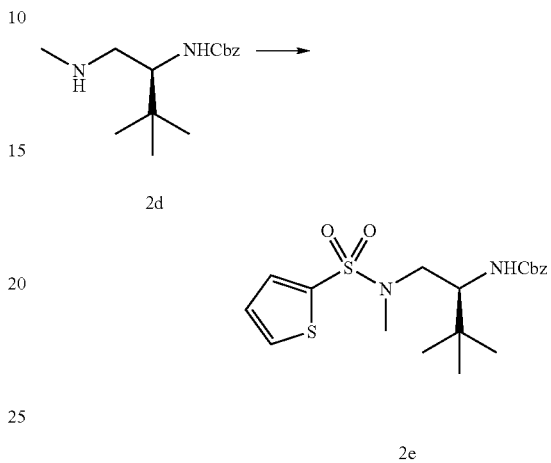

A solution of 2d (900 mg, 3.40 mmol) in CH$_2$Cl$_2$ at 0° C. was treated with NMM (511 mg, 5.10 mmol) and thiophenesulfonyl chloride (928 mg, 5.10 mmol) and stirred at 0° C. for 12 h. The reaction mixture was diluted with CH$_2$Cl$_2$ (300 mL) and washed with excess aq. HCl (1M, 500 mL). The organic layer was dried (MgSO$_4$) filtered concentrated in vacuo and purified by chromatography (SiO$_2$, Hex/EtOAc 1:9→1:1) to yield 2e.

Step D:

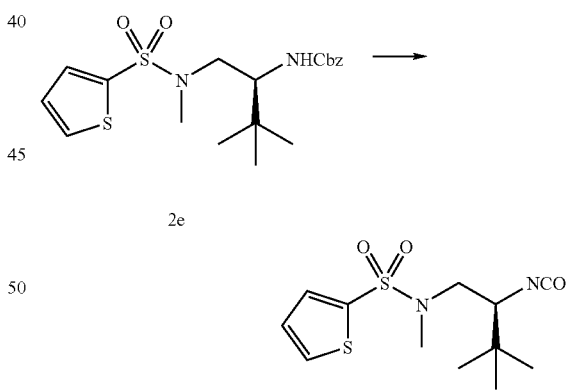

A solution of Cbz-protected compound 2e (1.00 g, 2.118 mmol) was treated with TFA (30 mL) and dimethylsulfide (7.78 mL) at 0° C. and stirred at rt. for 3 h. The reaction mixture was concentrated in vacuo and diluted with aq. NaOH (100 mL). The amine was extracted with methylene chloride (2×100 mL) and the combined organic layers were dried (MgSO$_4$), filtered, concentrated in vacuo to yield deprotected amine used directly in the next reaction.

A solution of deprotected amine in CH$_2$Cl$_2$ (10 mL), aq. saturated NaHCO$_3$ (10 mL) at 0° C. is treated with phosgene (5 mL, 15% soln. in toluene) and stirred at 0° C. for 2 h. The reaction mixture is diluted with CH$_2$Cl$_2$ (50 mL) and the organic layer is washed with cold aq NaHCO$_3$. The organic layer is dried (MgSO$_4$) filtered and further diluted with 10 mL toluene, concentrated the methylene chloride layer and used as a solution of 2f.

Step E:

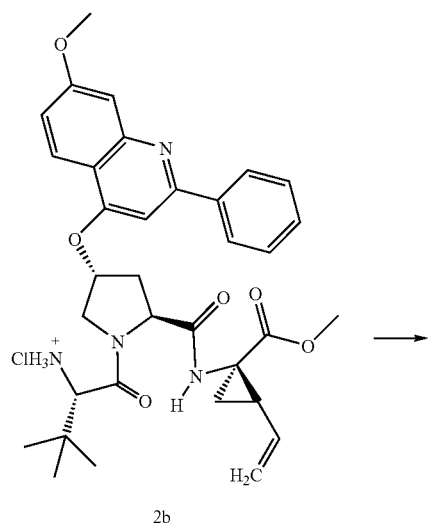

2b

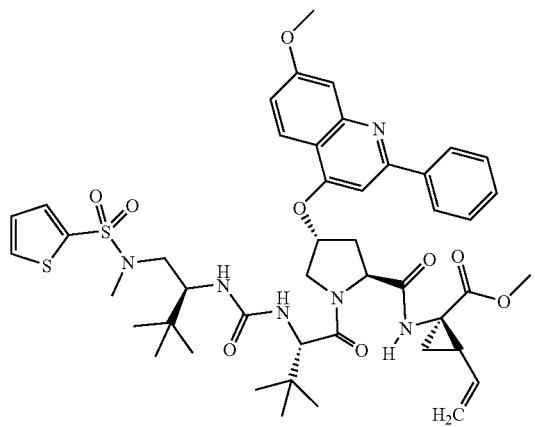

2g

A solution of amine 2b in CH$_2$Cl$_2$ is treated with NMM and cooled to 0° C. A solution of isocyanate 2f in toluene is added and the reaction mixture is stirred at rt. The reaction mixture is diluted with methylene chloride (100 mL) and washed with water The organic layer is dried with (MgSO$_4$), filtered, concentrated in vacuo and purified by chromatography to yield 2 g.

Step F:

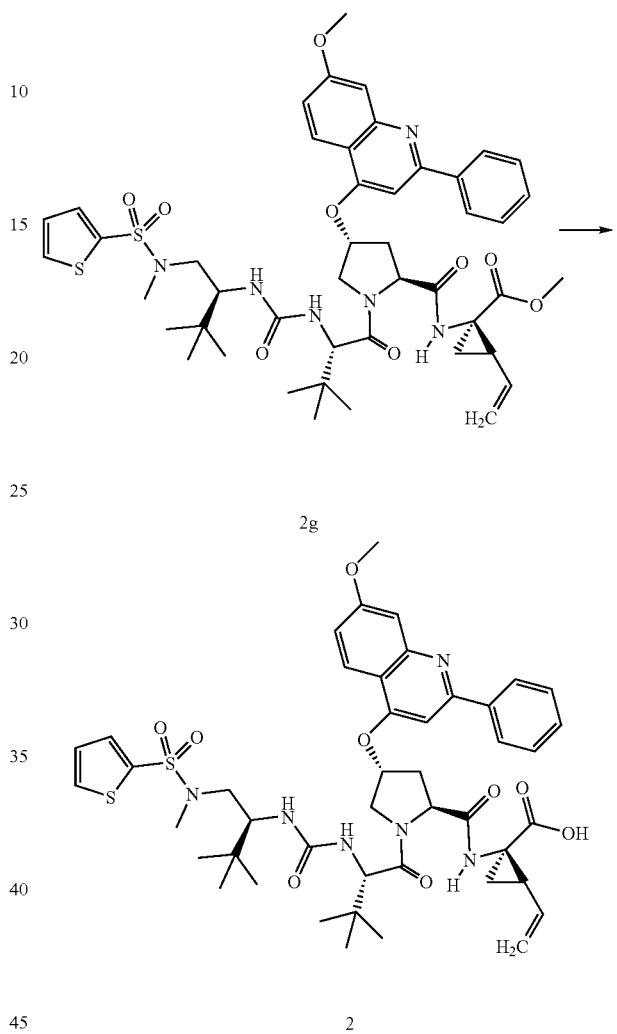

2g

2

A solution of methyl ester 2 g in THF, H$_2$O, and methanol is treated with LiOH monohydrate and stirred at rt. The reaction mixture is concentrated in vacuo and purified by HPLC (C$_{18}$, CH$_3$CN/H$_2$O 10/90→100/0) to isolate the pure acid 2.

Preparative Example 3

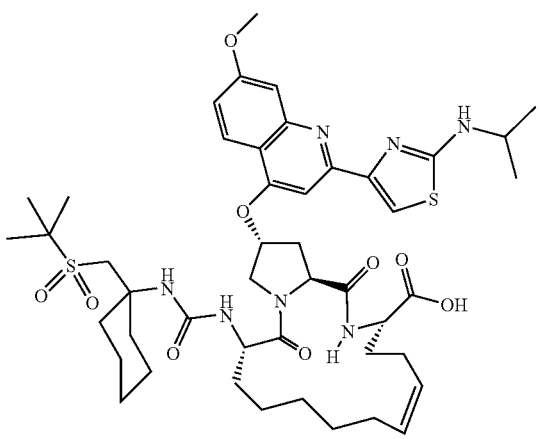

Step A:

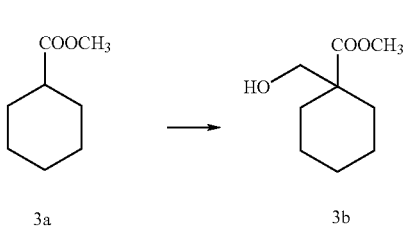

3a           3b

Potassium bis(trimethylsilylamide) (KHMDS), (200 ml of a 0.5M solution in toluene) was added, drop wise to a stirred solution of methyl cyclohexanecarboxylate 3a (11.1 g; 78 mmol) in anhydrous tetrahydrofuran (200 ml), at −78° C. under an atmosphere of nitrogen. When the addition was complete the reaction was maintained at this temperature for a further 0.5 h. before the addition of benzylchloromethyl ether (18.6 ml; 134 mmol). The reaction was allowed to warm to room temperature overnight and water (100 ml) was added. Aqueous work-up provided a residue which was purified by silica gel column chromatography using EtOAc; hexanes (1:10) as eluent to give the benzyl ether which was used in the next step (14.98 g)

A black suspension of 10% Pd/C (0.5 g) and the aforementioned crude ether (4.1 g) in methanol (80 ml) was exposed to an atmosphere of hydrogen (balloon) at room temp. overnight. The reaction was filtered through a pad of celite and the solid was washed thoroughly with methanol. The combined filtrate was concentrated under reduced pressure and the crude product was purified by silica gel column chromatography using EtOAc; hexanes (1:5) to give the primary alcohol 3b.

Step B:

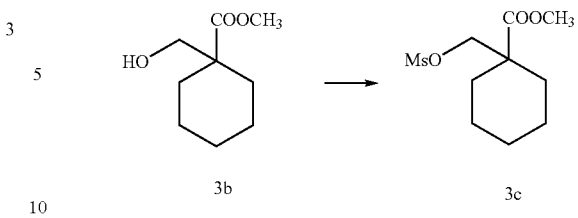

3b           3c

Methanesulfonyl chloride (0.31 ml) followed by triethylamine (0.75 ml) were added to a stirred solution of the primary alcohol (3b; 0.62 g) at 0° C., under an atmosphere of nitrogen. The resulting mixture was stirred at this temperature for 0.5 h. The reaction mixture was extracted into EtOAc and washed with 1M HCl, sat. aq. NaHCO$_3$, water, dried (MgSO$_4$) and concentrated. The residue (mesylate 3c; 0.74 g), was obtained as a yellow oil, which was used in subsequent steps without purification.

Step C:

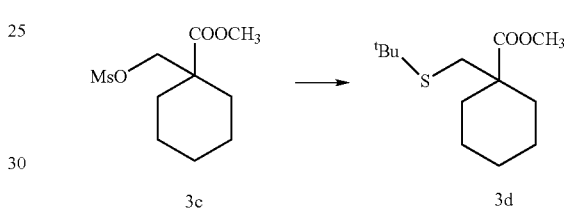

3c           3d

Sodium tert-butyl thiolate (2eq.) was added to a DMF solution of the mesylate and the mixture was heated to 100° C. for 1 h. Aqueous work-up and purification of the crude reaction product by silica gel column chromatography using EtOAc; hexanes (1:20) gave the sulfide 3d.

Step D:

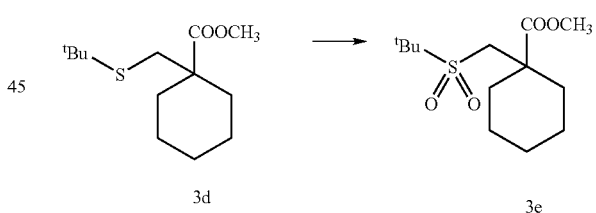

3d           3e

A solution of the sulfide 3d in water methanol (1:1) was treated with oxone® and stirred at rt. The oxidation was followed by TLC and the completion of oxidation the reaction mixture was carefully quenched with aq. solution of sodium thiosulfate and extracted into CH$_2$Cl$_2$. The organic layer was washed with water, dried (MgSO$_4$), filtered, concentrated in vacuo and purified by chromatography (SiO$_2$) to yield 3e.

Step E:

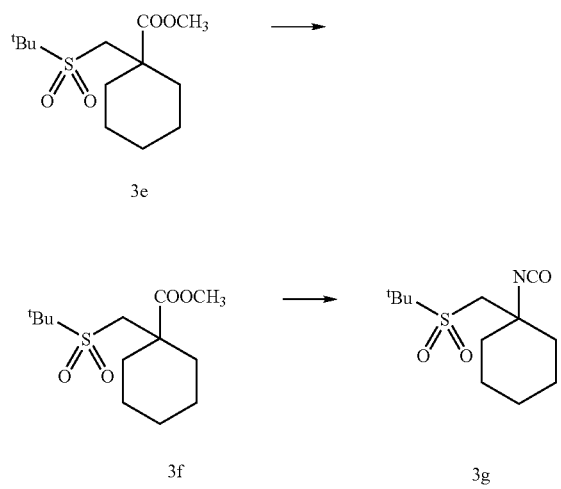

3e 3f 3g

Potassium hydroxide (0.25 g) was dissolved in a mixture of water (1 ml) and ethanol (5 ml) and added to the methyl ester (3e) and the resulting mixture was heated to reflux, under an atmosphere of nitrogen. After cooling, the reaction was partitioned between EtOAc and dilutes aq. HCl. The organic phase was separated, washed with brine, dried and concentrated to yield the crude intermediate carboxylic acid 3f, used without purification.

A solution of acid 3f (1.5 g, 5.71 mmol) in toluene (30 mL) was treated with DPPA (1.57 g, 5.71 mmol) and Et$_3$N (577 mg, 5.71 mmol) and stirred at reflux for 1.5 h. The reaction mixture was diluted with saturated NaHCO$_3$ (100 mL) and extracted into CH$_2$Cl$_2$ (2×100 mL). The combined organic layers were washed with aq. NaHCO$_3$ (100 mL), brine (100 mL), dried (MgSO$_4$), filtered, concentrated in vacuo, and used as a 0.2 M solution of isocyanate 3 g in toluene.

The syntheses of protected amino acids 3 h and 3i can be accomplished using the procedure of Myers$^i$ et al. ((1) A. G. Myers et al, *J. Org. Chem*, (1996), 61,813. (2) A. G. Myers et al, *J. Org. Chem*, (1999), 64, 3322. (3) A. G. Myers et al, *Org, Syntheses* (1998), 76, 57. (4) A. G. Myers et al, *J. Amer. Chem. Soc*, (1995), 117, 8488).

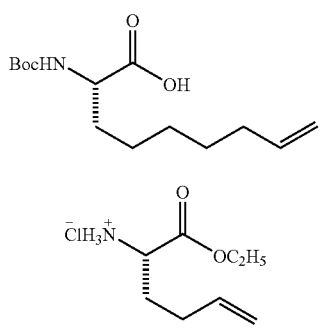

3h

3i

Step F:

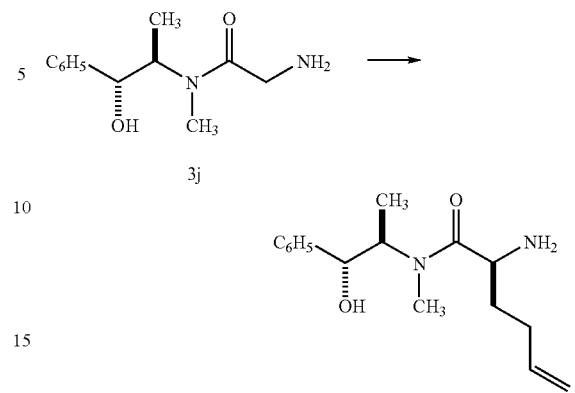

3j

3k

A solution of amine 3j in THF is treated with anhydrous LiCl over 0.5 h and stirred till the reaction mixture turns homogeneous. The reaction mixture is cooled to 0° C. and treated with a THF solution of LiHMDS over 20 min. The reaction mixture is stirred at 0° C. for 0.5 h and treated with 4-bromobutene and stirred at rt. for 24 h. The reaction mixture is dissolved in aq. 1 M HCl and concentrated in vacuo to remove THF. The mostly aq. layer is further diluted with 3M aq HCl (300 mL) and extracted with ether (2×200 mL). The aqueous layer is basified to pH 14 using aq. NaOH (50%) and extracted with CH$_2$Cl$_2$ (3×300 mL). The combined organic layers is dried with MgSO$_4$ filtered concentrated in vacuo to yield crude 3 k that is used in next step without further purification.

Step G:

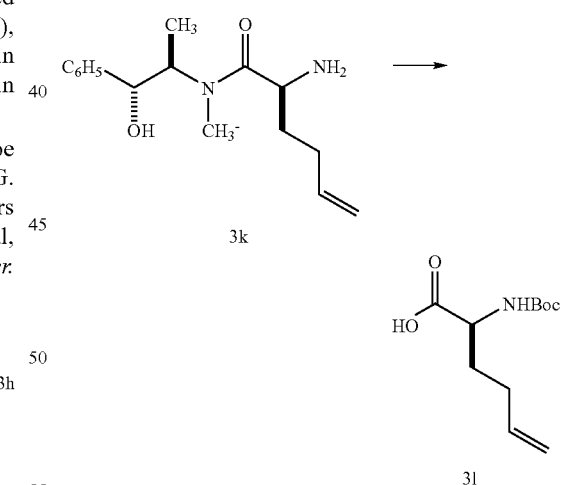

3k

3l

A solution of 3 k in aq. NaOH (1 M, 1 equiv) is heated at reflux for 3 h. The reaction mixture is cooled to rt. and extracted with CH$_2$Cl$_2$ (3×100 mL). The aq. layer is treated with dioxane followed by NaHCO$_3$ and di-tert-butyl dicarbonate and stirred at rt. for 5 h. The reaction mixture is extracted with ether and the aqueous layer was acidified to pH~2 with aq. HCl and extracted with CH$_2$Cl$_2$ (2×200 mL). The combined organic layers is dried with (MgSO$_4$), filtered, concentrated in vacuo to yield acid 3l.

Step H:

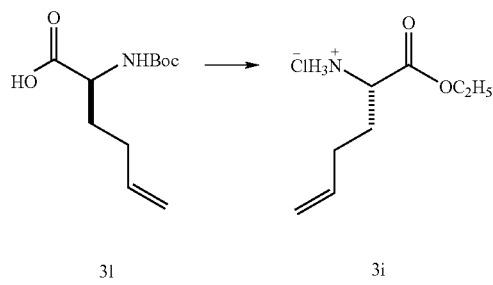

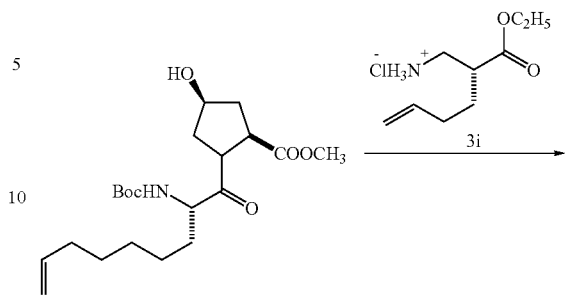

A solution of 3l in ethanol is saturated with anhydrous HCl at 0° C. and left standing for 12 h. The reaction mixture was concentrated in vacuo and used as it is in the following steps.

Note: A similar synthesis can be adapted for the synthesis of amino acid 3 h.

Step I:

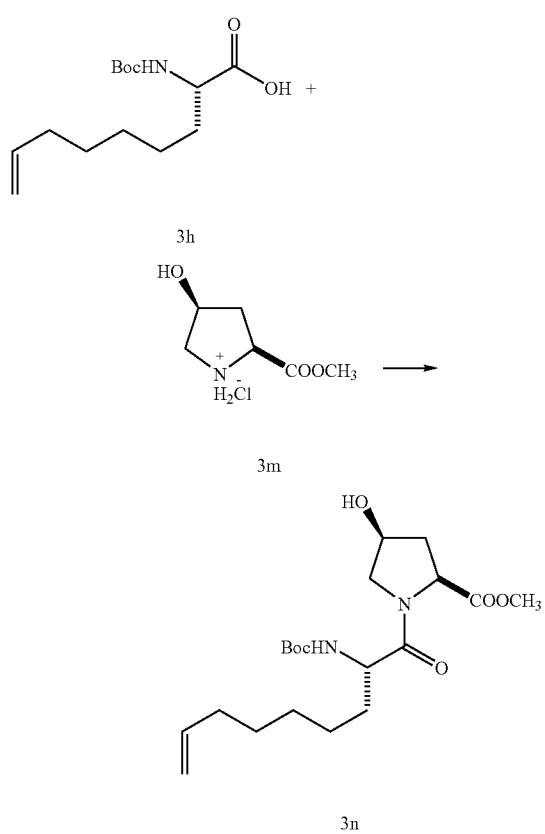

A solution of acid 3 h and amine 3m in CH$_2$Cl$_2$ (30 mL), DMF (30 mL) at 0° C. is treated with HATU and NMM and stirred overnight at 0° C. The reaction mixture is concentrated in vacuo and diluted with CH$_2$Cl$_2$. The organic layer was washed with aq. HCl (1M), aq. NaHCO$_3$ (1M). The organic layers were dried with MgSO$_4$, filtered concentrated in vacuo and purified by chromatography (SiO$_2$, to yield 3n.

Step J:

A solution of ester 3n in THF, H$_2$O, and MeOH is treated with LiOH·H$_2$O and stirred at rt for 4 h. The reaction mixture is concentrated in vacuo to remove THF and MeOH. The mostly aqueous layer is acidified with aq. HCl and extracted into CH$_2$Cl$_2$. The combined organic layers are dried with MgSO$_4$, filtered, concentrated in vacuo and used as it is.

A solution of acid obtained from hydrolysis of 3n, amine segment 3i in DMF, CH$_2$Cl$_2$, at 0° C. is treated with HATU and NMM and stirred at 0° C. for 24 h. The reaction mixture is concentrated in vacuo and diluted with aq. HCl. The aqueous layer is extracted with CH$_2$Cl$_2$. The combined organic layers are washed with aq saturated NaHCO$_3$, brine, dried with MgSO$_4$, filtered concentrated in vacuo and purified by silica gel chromatography to yield 3o.

Step K:

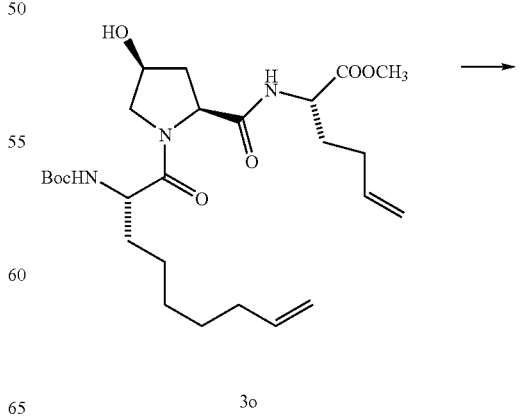

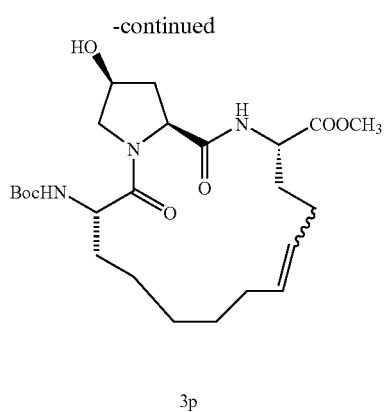

3p

A solution of diene 3o in dry toluene (0.05 M concentration) is treated with Grubbs catalyst [(Cy)$_3$RuCl$_2$=CHC$_6$H$_5$, 15 mol%) and heated at 60° C. The reaction mixture is concentrated in vacuo and purified by chromatography (SiO$_2$,) to yield 3p as a mixture of E/Z isomers.

Step L:

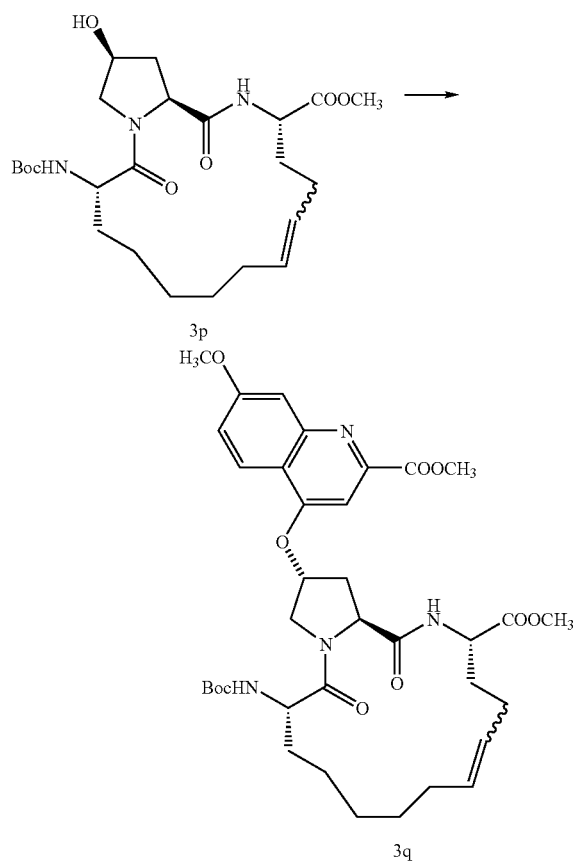

A solution of compound 3p in CH$_2$Cl$_2$ is treated with triphenylphosphine and quinoline derivative (WO 00/09558 (Boehringer Ingelheim, Canada) and cooled to 0° C. The reaction mixture is treated with DIAD and stirred at rt for 12 h. The reaction mixture is concentrated in vacuo and purified by chromatography obtain 3q. that was used in further reactions.

Step M:

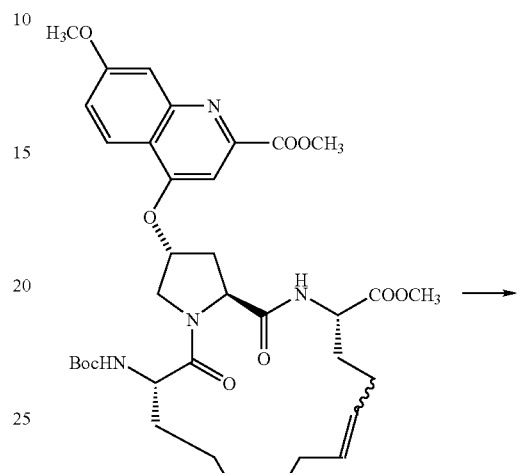

3q

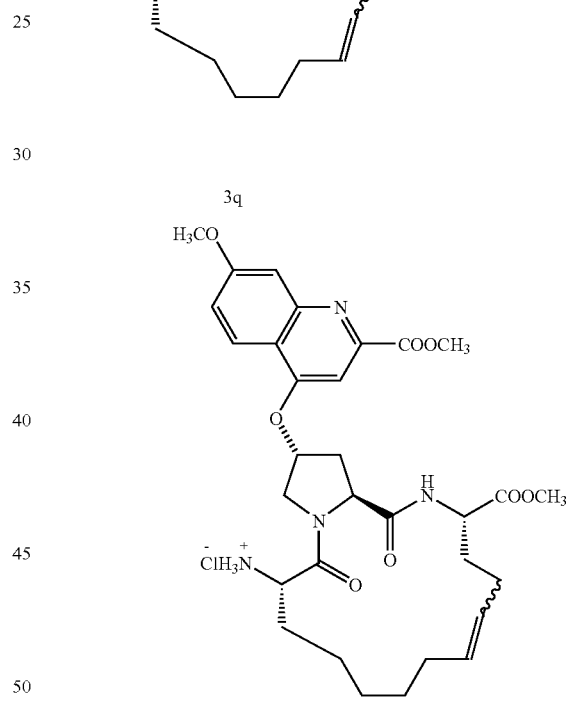

3r

A solution of Boc protected compound 3q in HCl (4 M soln in dioxane) and CH$_2$Cl$_2$ is stirred at rt. for 1 h and concentrated in vacuo. The disappearance of starting material is followed by TLC The reaction mixture is concentrated in vacuo and dried to yield 3r that is used in next reaction without further purification.

Step N:

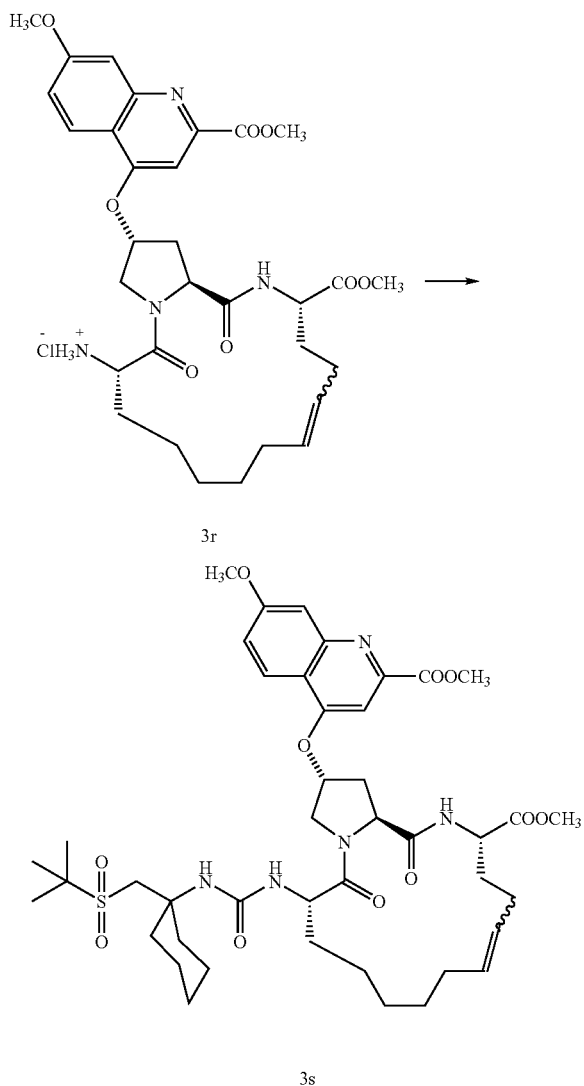

3r

3s

A solution of amine 3r in methylene chloride is treated with NMM and cooled to 0° C. A solution of isocyanate 3g in toluene is added and the reaction mixture is stirred at rt. The reaction mixture is diluted with methylene chloride (100 mL) and washed with water The organic layers were dried with (MgSO$_4$) filtered concentrated in vacuo and purified by chromatography to yield 3s.

Step O:

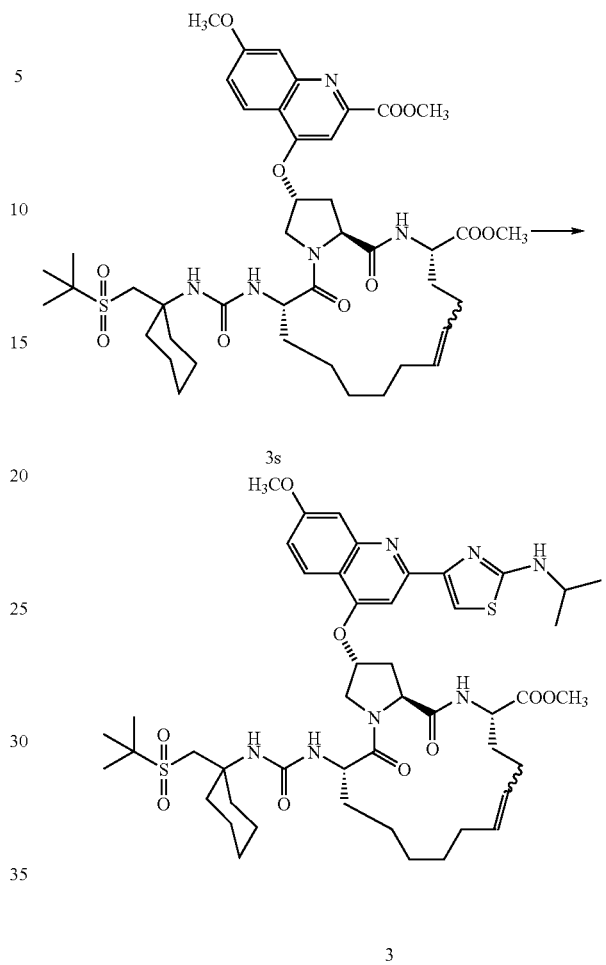

3s

3

The conversion of 3s to 3 can be achieved following steps F, G, H and I outlined in Preparative Example 1.

The present invention relates to novel HCV protease inhibitors. This utility can be manifested in their ability to inhibit the HCV NS2/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDWX (Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD—substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac—D-(D—Gla)-L—1-(Cha)-C—OH (27), Ac-DTEDVVA(Nva)-OH and Ac-DTEDVVP(Nva)-OH are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m)$, is used to calculate the $K_i$ value.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound having the structure shown in Formula 1:

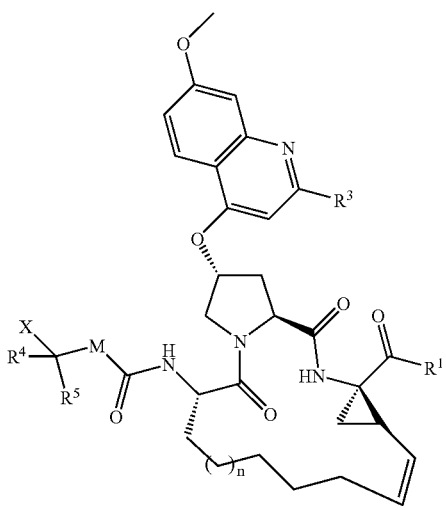

Formula 1 or a pharmaceutically acceptable salt, or ester thereof, wherein,

M is O, N(H), or CH$_2$;

n is 0-4;

R$^1$ is —OR$^6$, —NR$^6$R$^7$ or

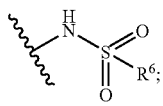

where R$^6$ and R$^7$ can be the same or different, each being independently selected from the group consisting of hydrogen, alkyl, alkenyl, alkynyl, heteroalkyl, (C$_3$-C$_{10}$)cycloalkyl, (C$_3$-C$_{10}$)cycloalkylalkyl, aryl, arylalkyl, heteroaryl, heteroarylalkyl, heterocyclyl, heterocyclylalkyl, hydroxyl, amino, arylamino and alkylamino;

R$^4$ and R$^5$ can be the same or different, each being independently selected from the group consisting of H, alkyl, aryl and (C$_3$-C$_{10}$)cycloalkyl; or alternatively R$^4$ and R$^5$ together form part of a cyclic 5- to 7-membered ring such that the moiety

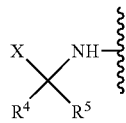

is represented by

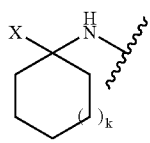

where k is 0 to 2;

X is selected from the group consisting of:

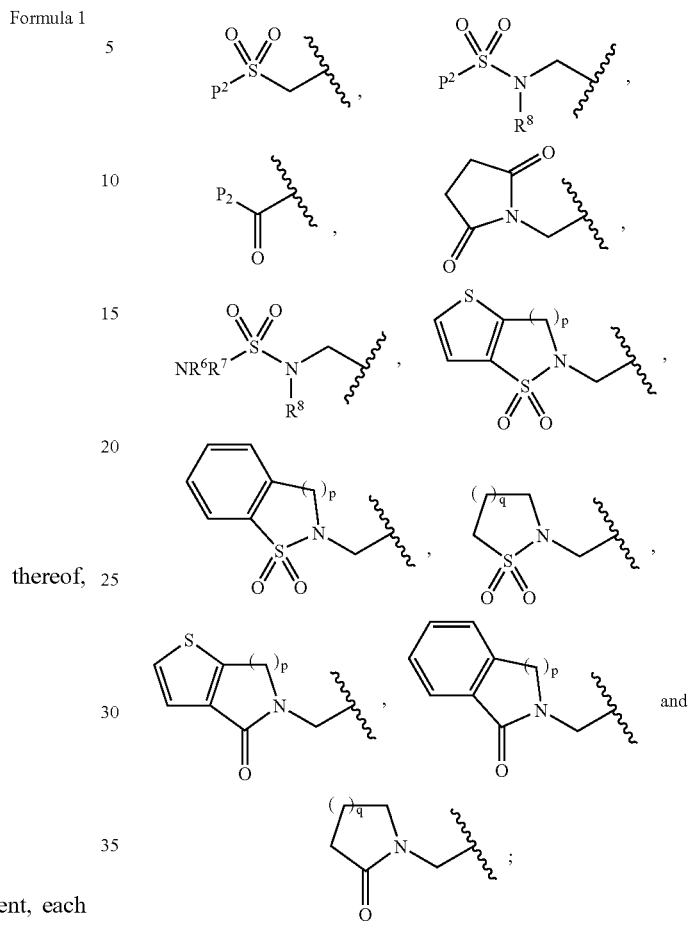

where p is 1 to 2, q is 1-3 and P$^2$ is alkyl, aryl, heteroaryl, heteroalkyl, (C$_3$-C$_{10}$)cycloalkyl, dialkylamino, alkylamino, arylamino or (C$_3$-C$_{10}$)cycloalkylamino; and R$^3$ is selected from the group consisting of: aryl, heterocyclyl, heteroaryl,

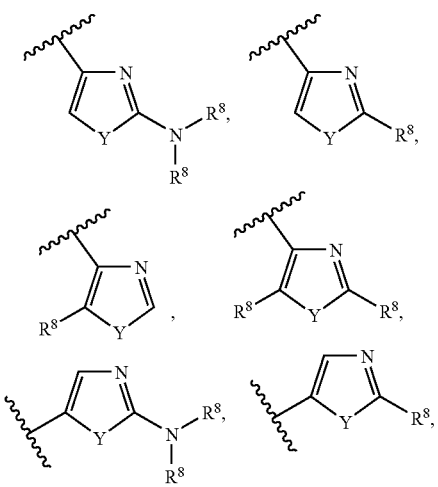

-continued

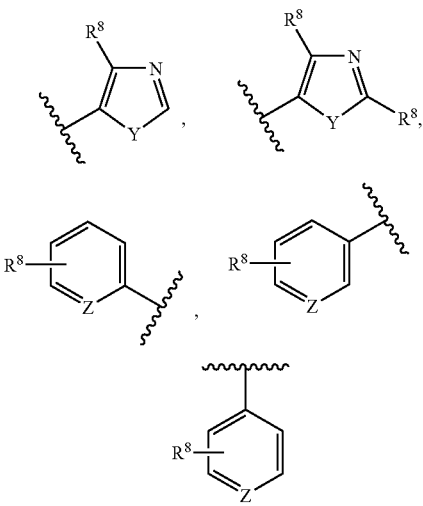

where Y is O, S or NH, and Z is CH or N, and the $R^8$ moieties can be the same or different, each $R^8$ being independently selected from the group consisting of hydrogen, alkyl, heteroalkyl, $(C_3-C_{10})$cycloalkyl, aryl, heteroaryl, heterocyclyl, hydroxyl, amino, arylamino, alkylamino, dialkylamino, halo, alkylthio, arylthio and alkyloxy;

wherein each of said heteroaryl and said heterocyclyl consist of 4-14 ring atoms, wherein 1 to 4 of said ring atoms are O, N, or S, further wherein each of said heteroaryl and heterocylyl can be monocyclic or bicyclic;

heteroalkyl is $(C_1-C_{12})$ alkyl, wherein 1-4 of the $(C_1-C_{12})$ atoms are replaced by heteroatoms selected from the group consisting of O, N and S.

2. The compound of claim 1, wherein M is NH or O.

3. The compound of claim 1, wherein n is 0 or 1.

4. The compound of claim 1, wherein $R^1$ is $OR^6$ or $NR^6R^7$, where $R^6$ and $R^7$ can be the same or different, each being independently selected from the group consisting of H, alkyl, alkenyl, $(C_3-C_{10})$cycloalkyl, alkylamino and $(C_3-C_{10})$cycloalkylalkyl.

5. The compound of claim 1, wherein $R^4$ and $R^5$ are the same or different, each being independently selected from the group consisting of:

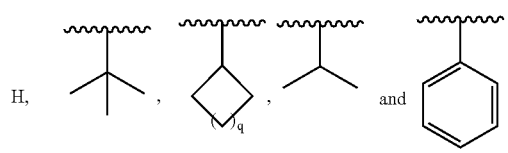

where q is 1 to 3, or $R^4$ and $R^5$ form part of a 5- or 6-membered ring such that the moiety

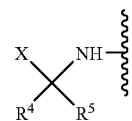

is represented by

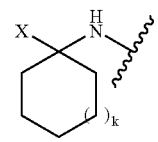

where k is 0 to 1.

6. The compound of claim 2, wherein M is NH.

7. The compound of claim 3, wherein n is 0.

8. The compound of claim 4, wherein $R^1$ is OH, $NH_2$ or N(H)(alkyl).

9. The compound of claim 5, wherein $R^4$ and $R^5$ are the same or different, each being independently selected from the group consisting of H, t-butyl, cyclobutyl or phenyl, or $R^4$ and $R^5$ together form a 6-membered ring such that the moiety

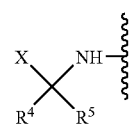

is represented by

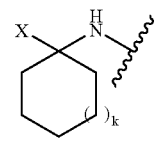

where k is 1.

10. A compound selected from the group consisting of:

211
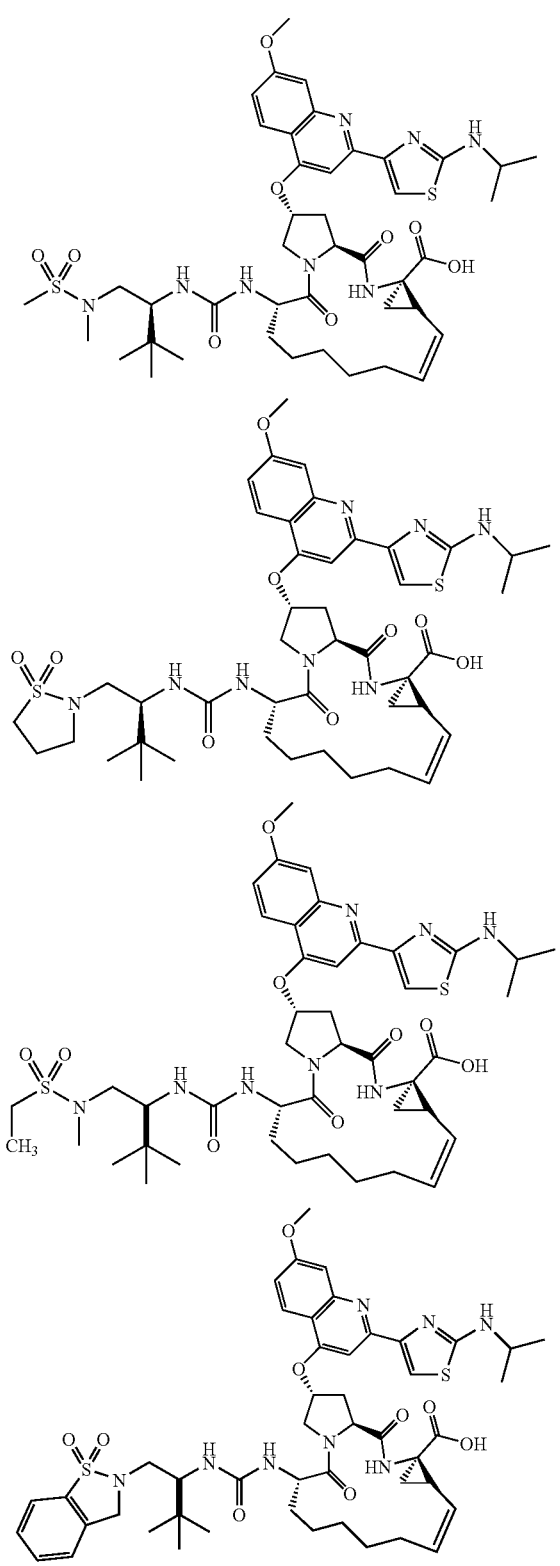
212
-continued
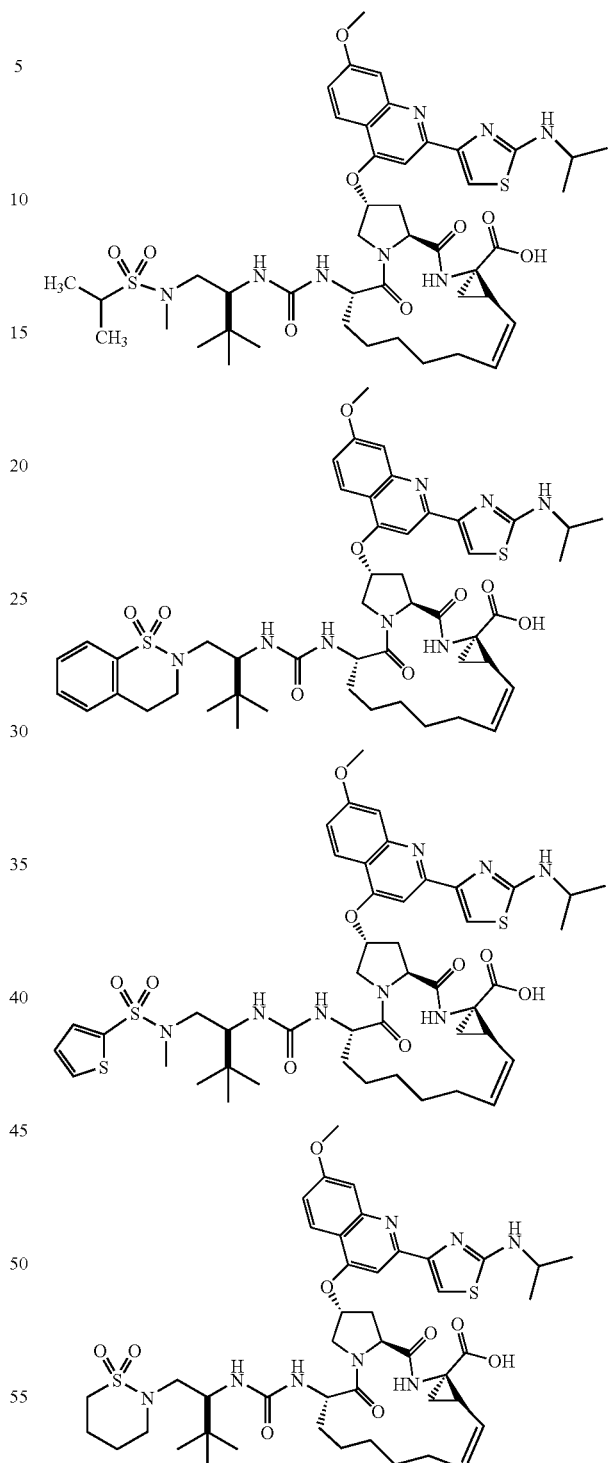

213
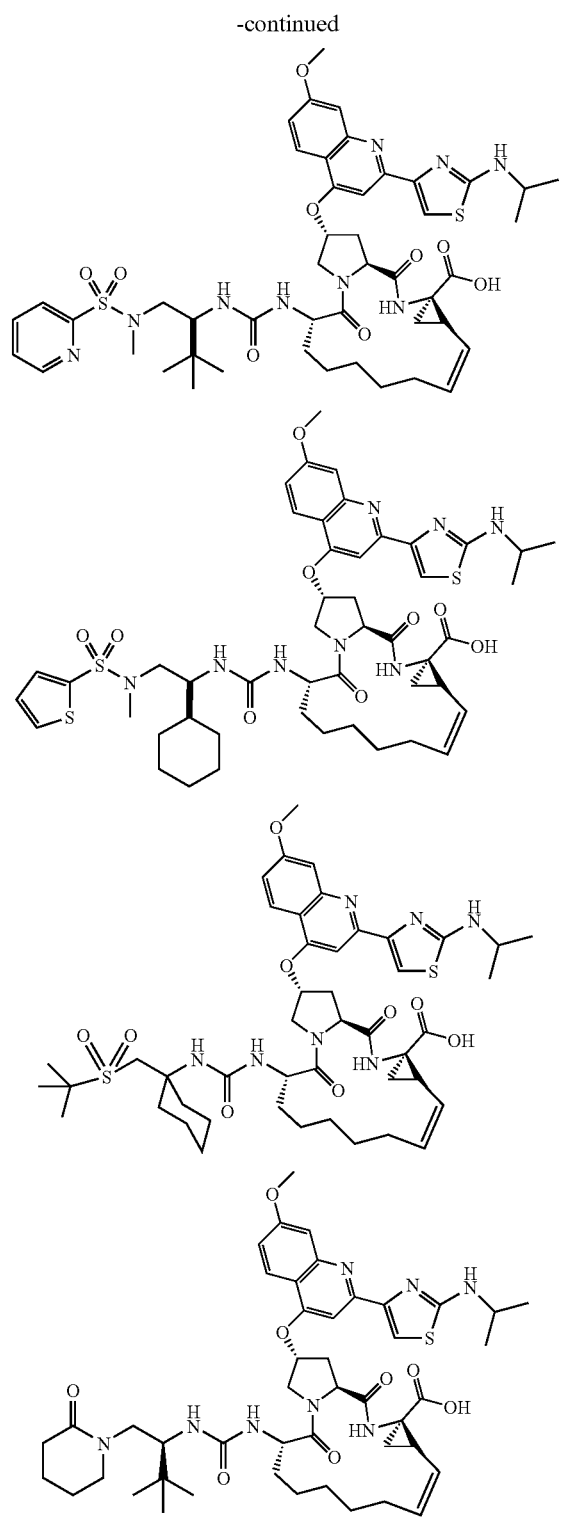
214
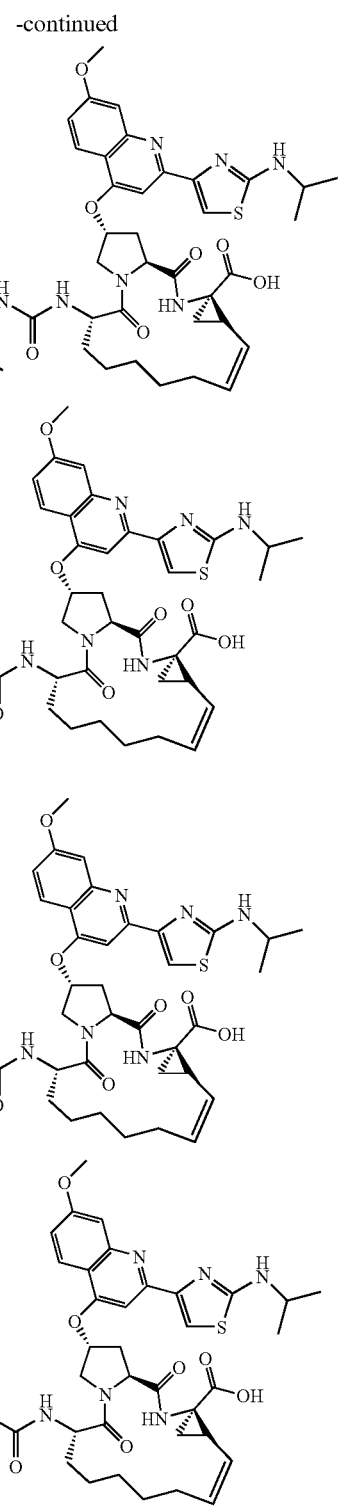

215
-continued
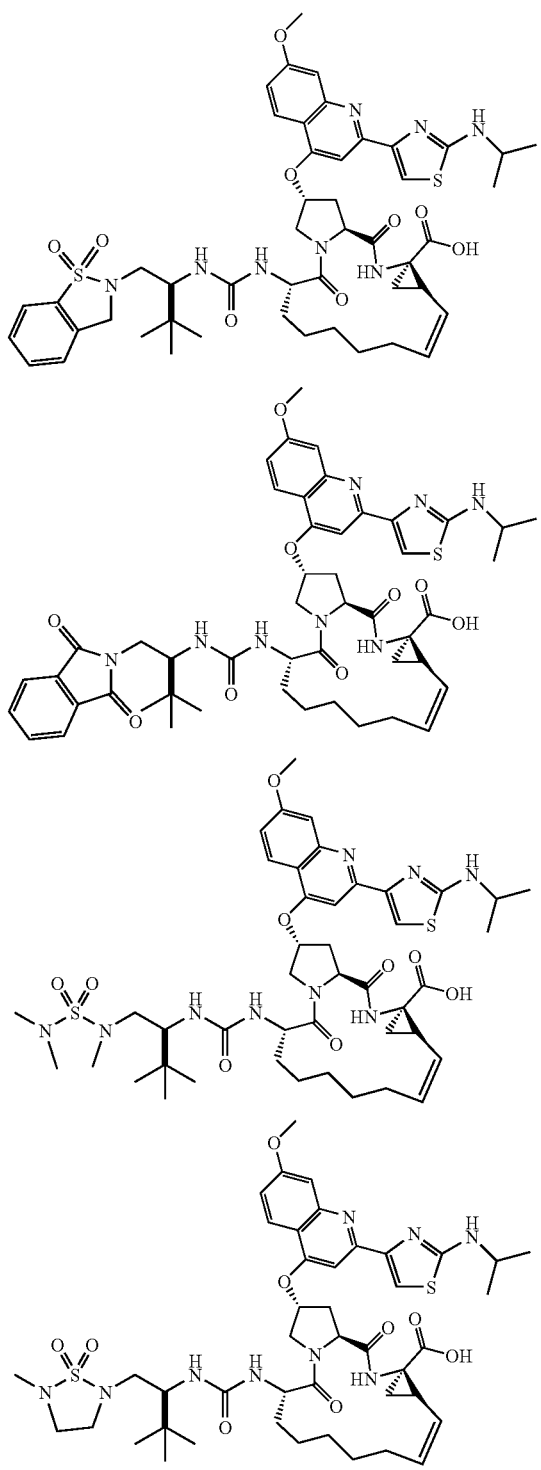
216
-continued
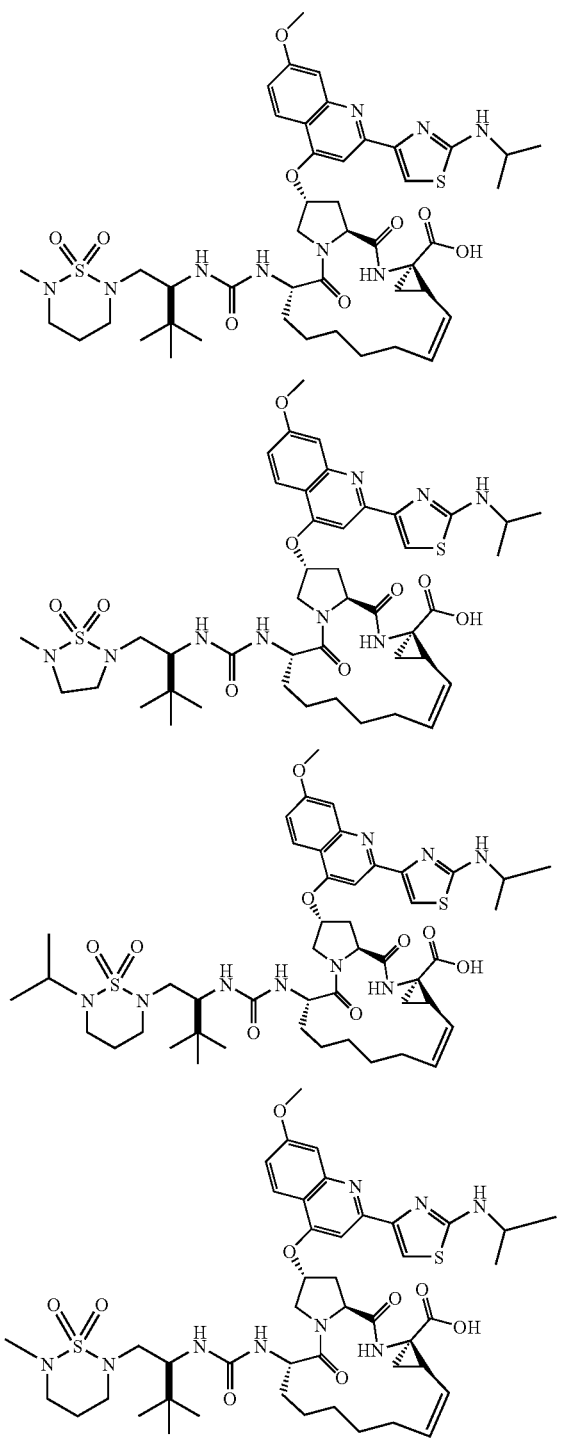

217
-continued
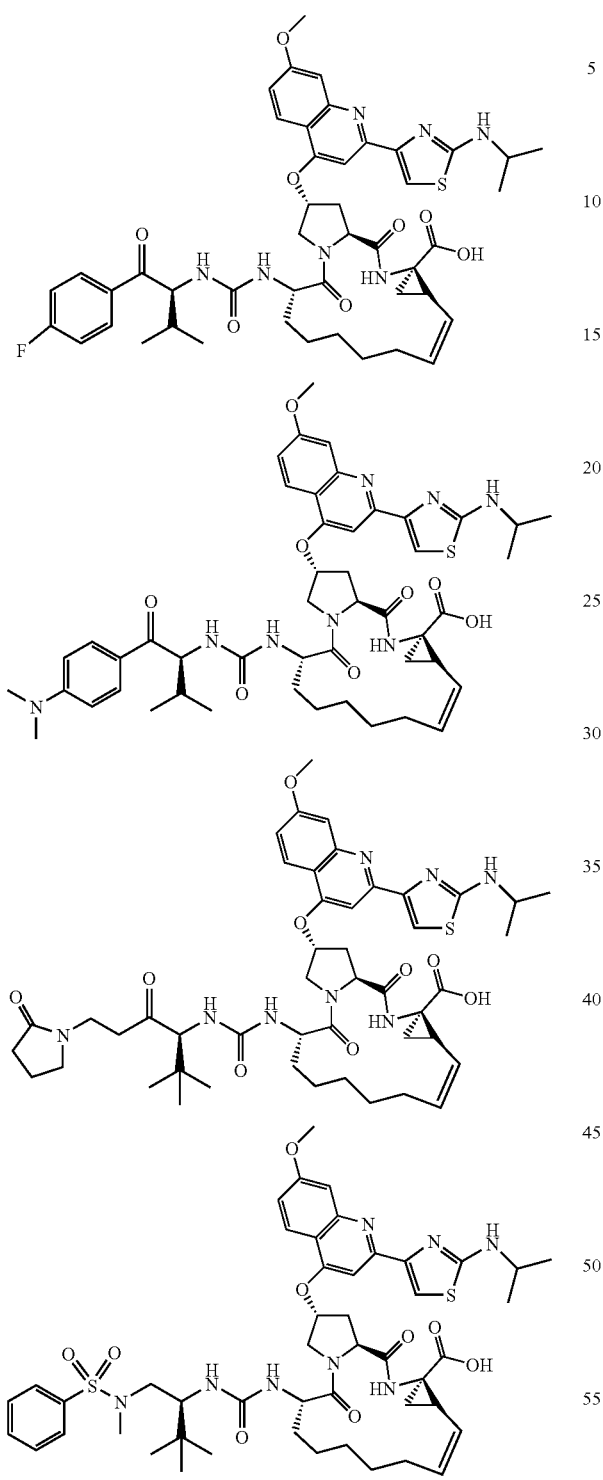
218
-continued
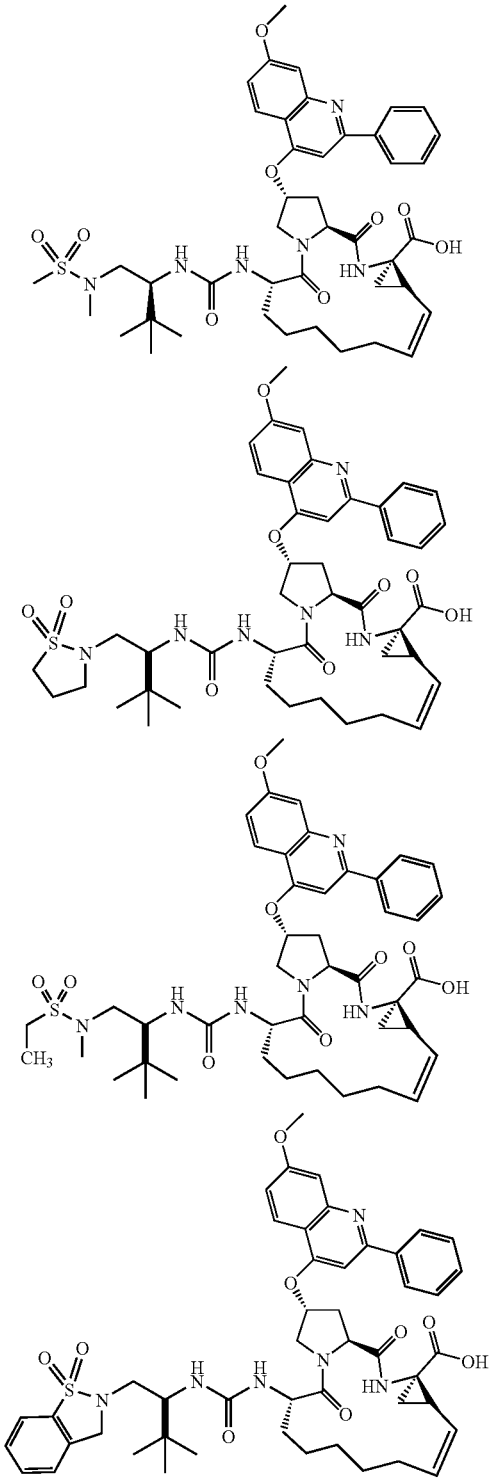

219
-continued
220
-continued
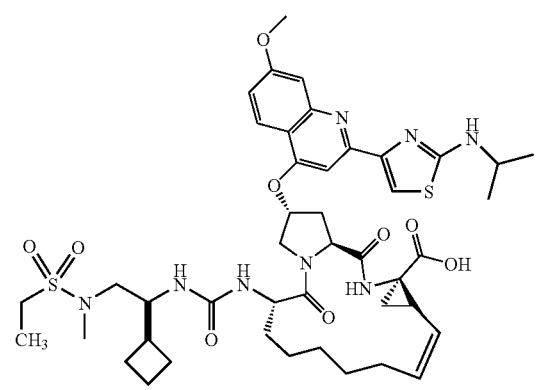
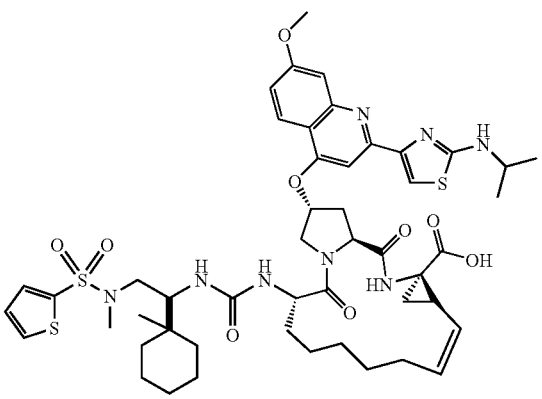

221
-continued
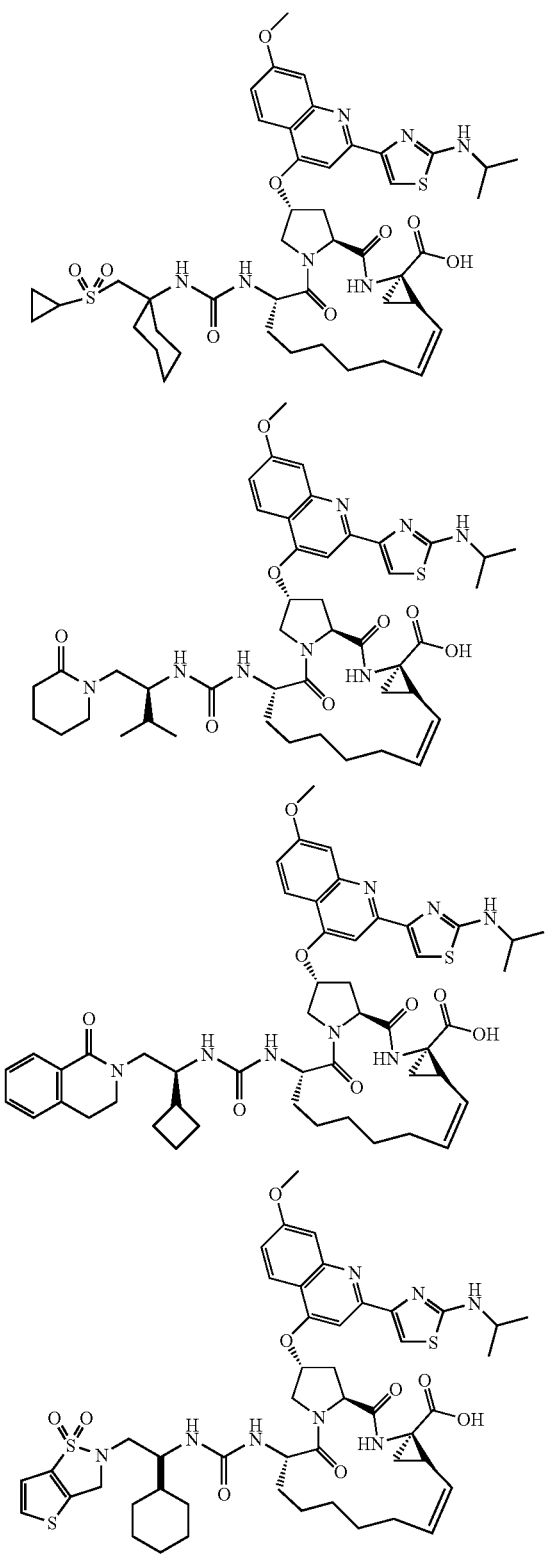
222
-continued
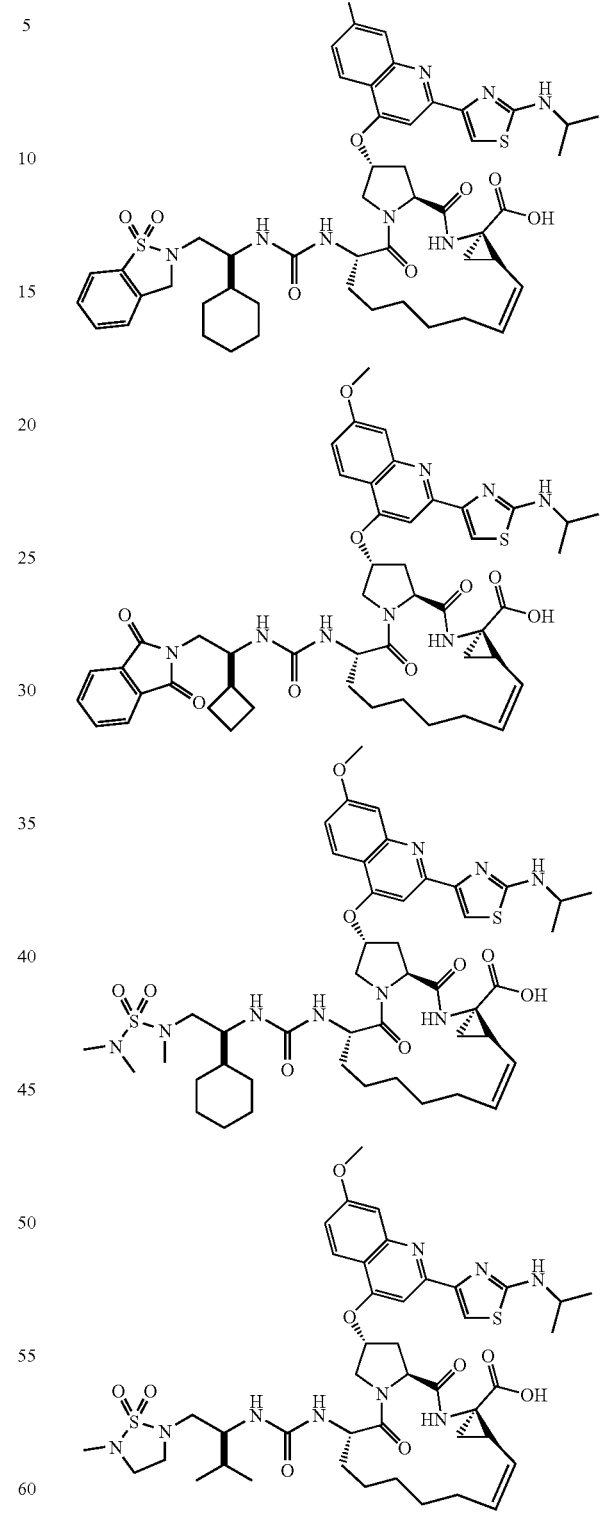

223
-continued
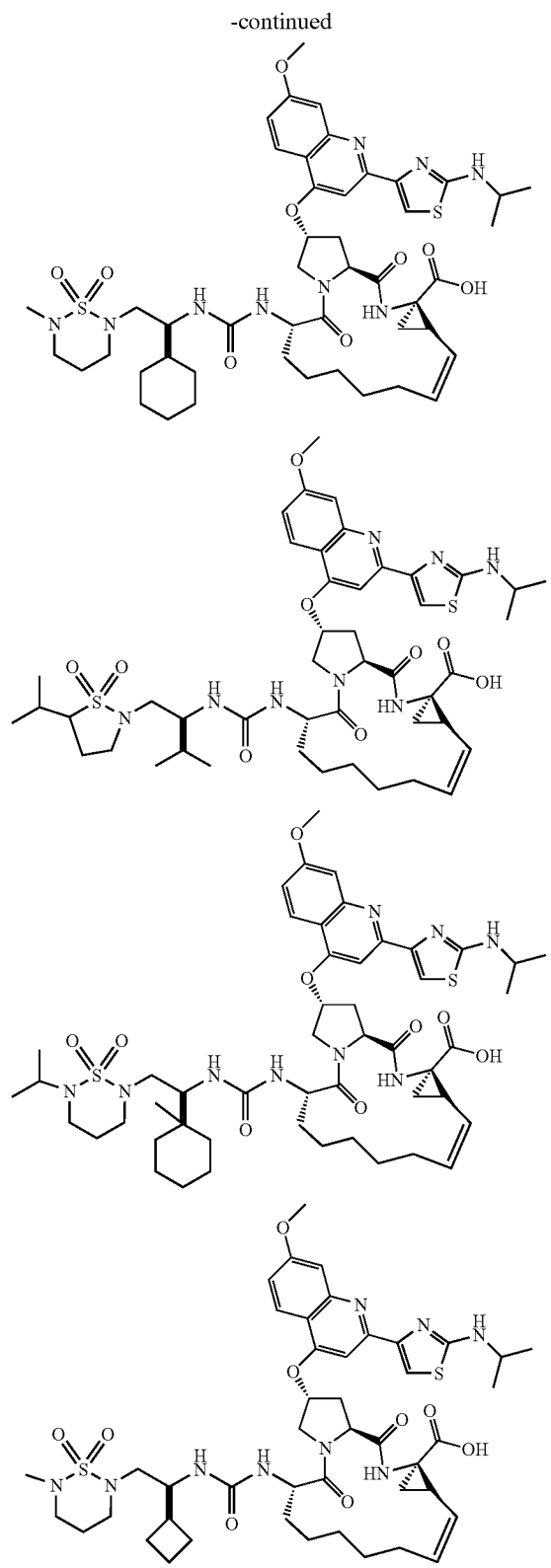
224
-continued
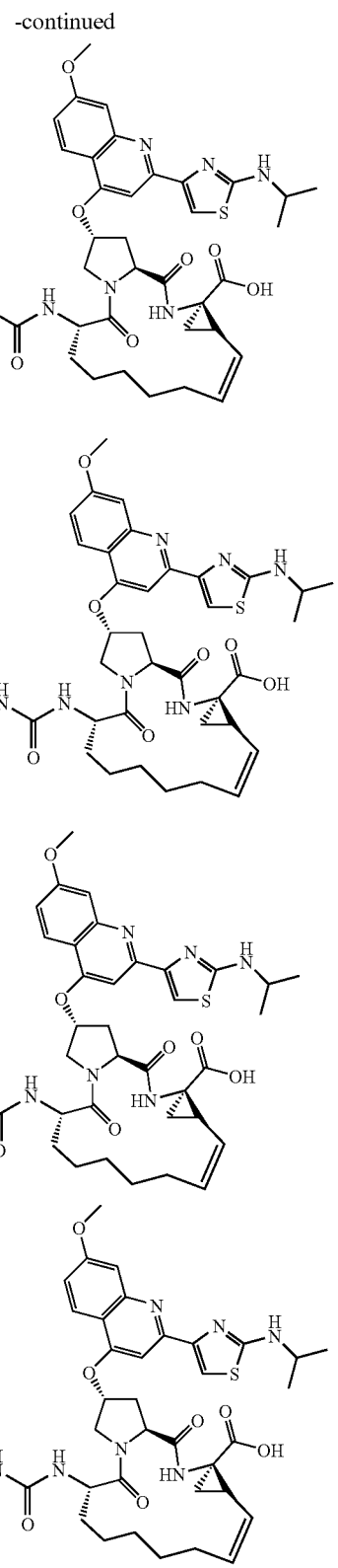

225
-continued
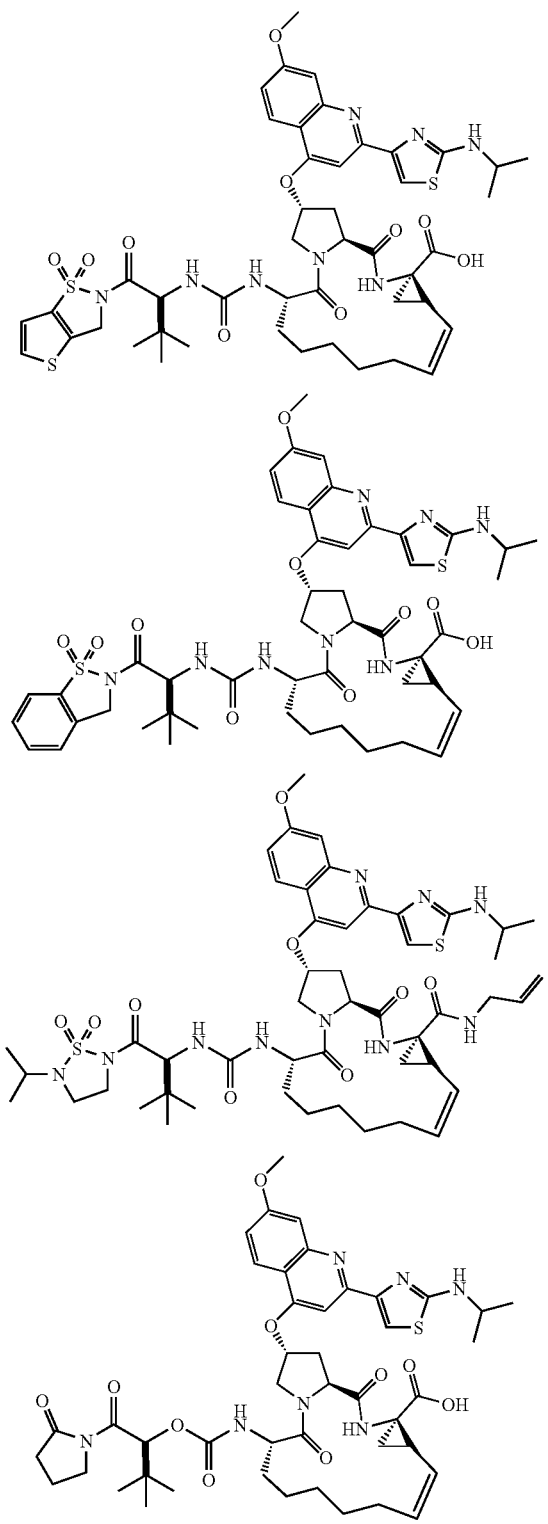
226
-continued
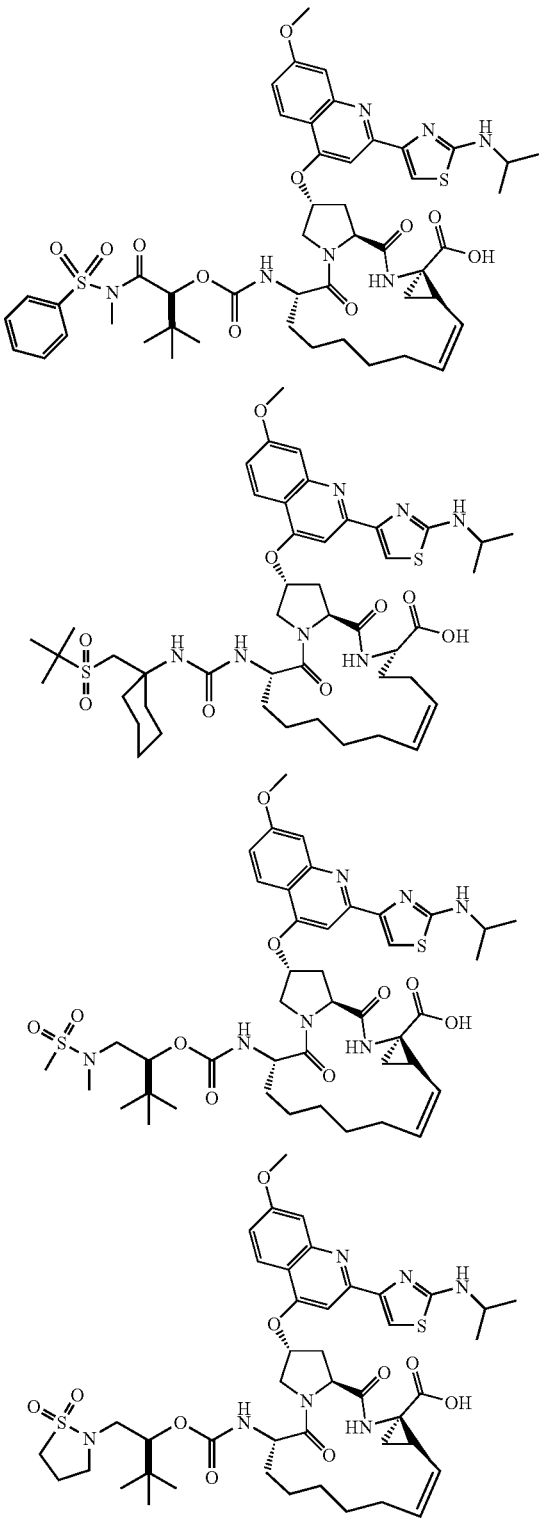

227
-continued
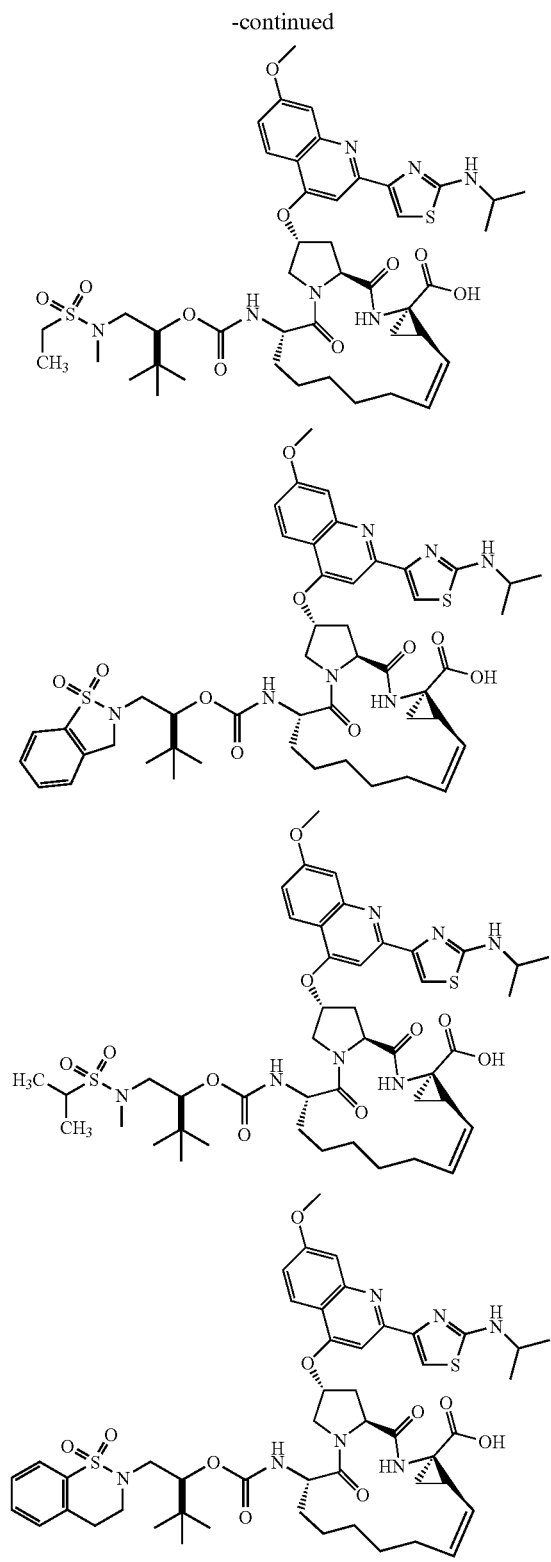
228
-continued
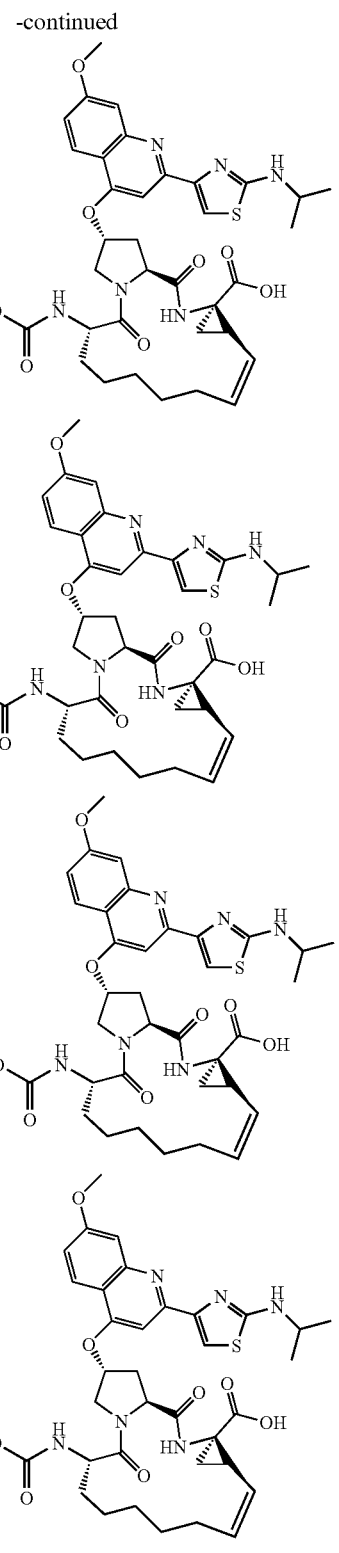

-continued
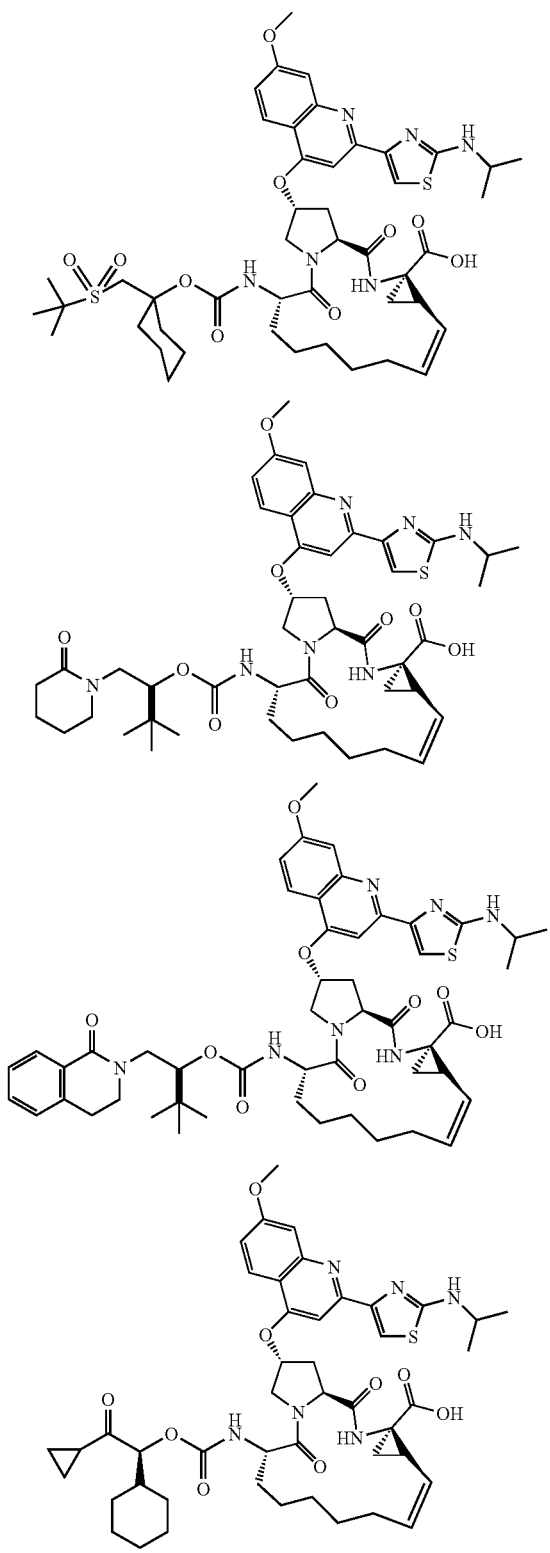
-continued
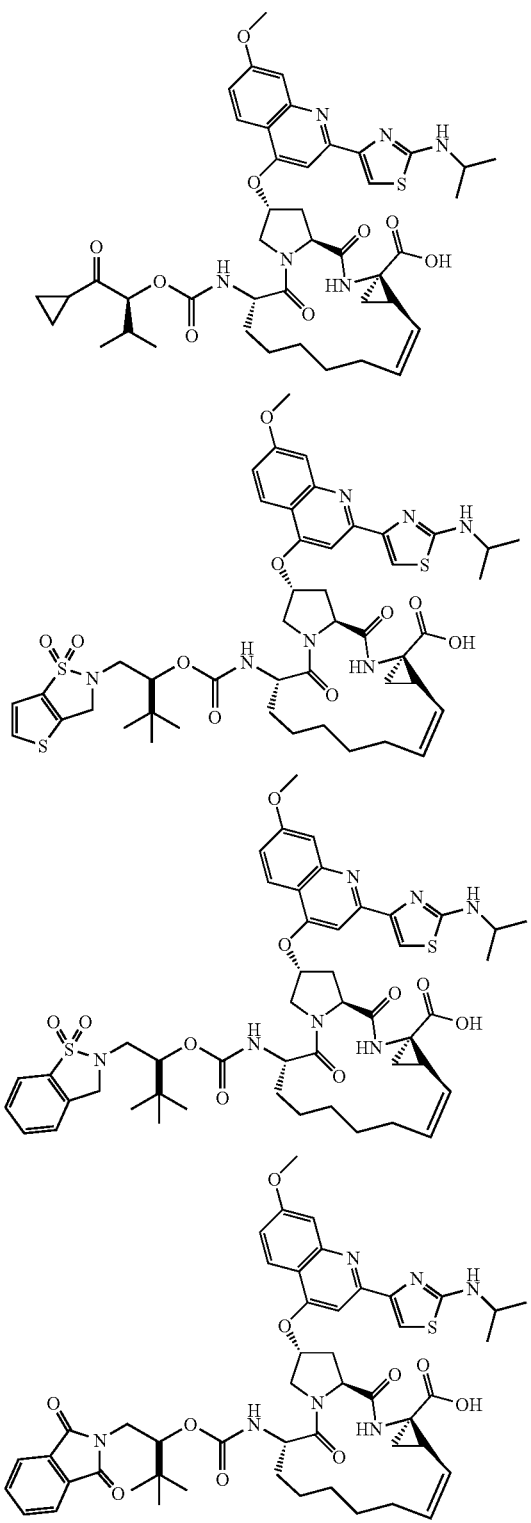

231
-continued
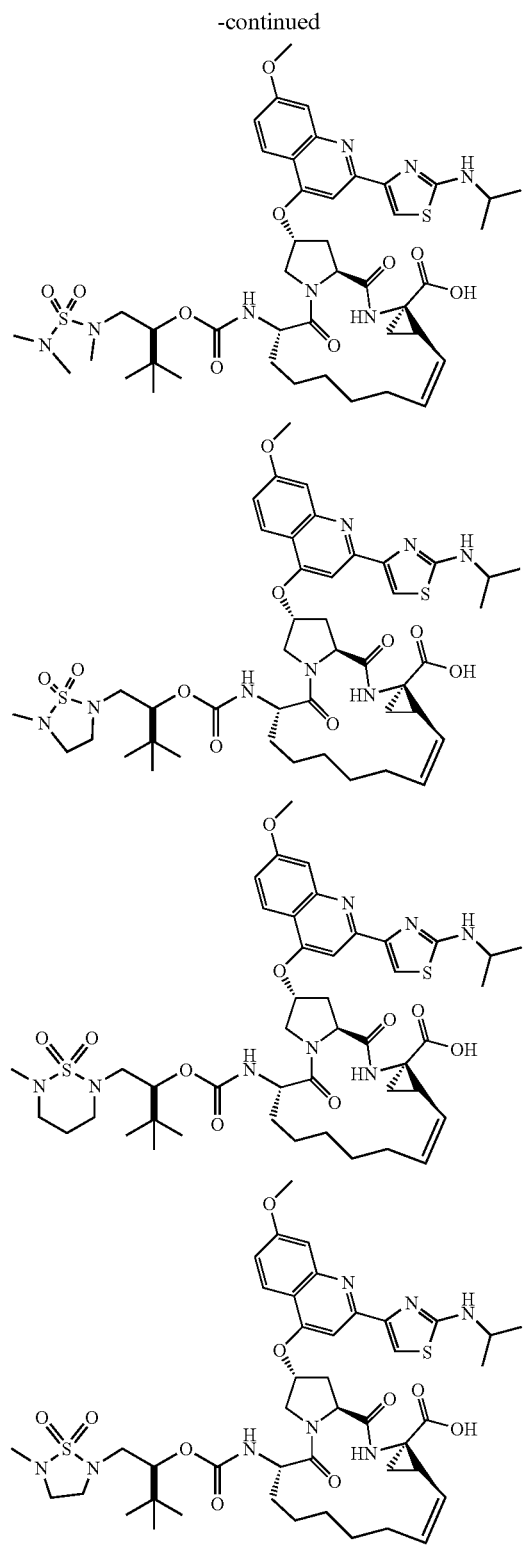
232
-continued
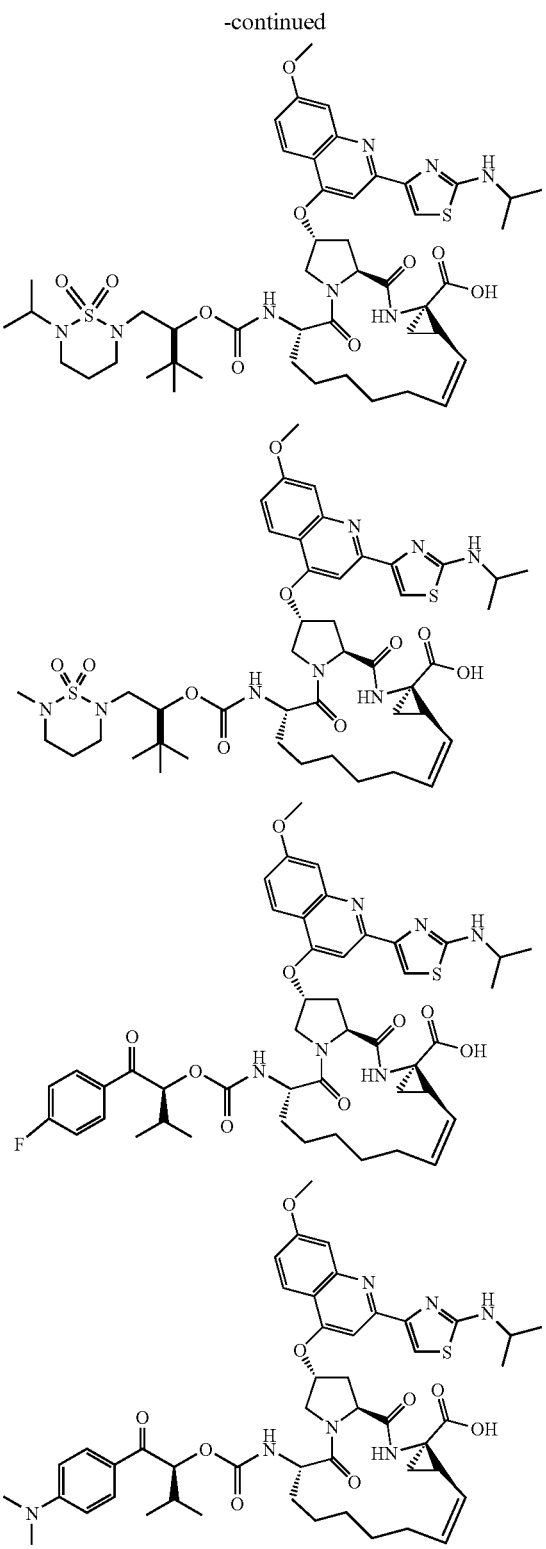

-continued

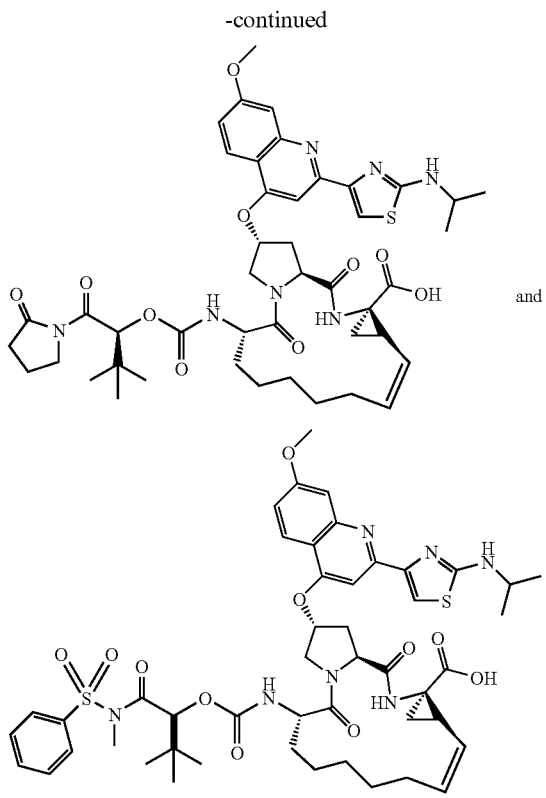

and

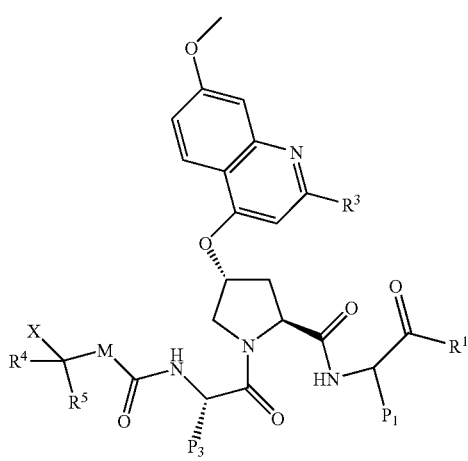

or a pharmaceutically acceptable salt, or ester thereof.

11. A compound having the general structure shown in Formula 2:

Formula 2

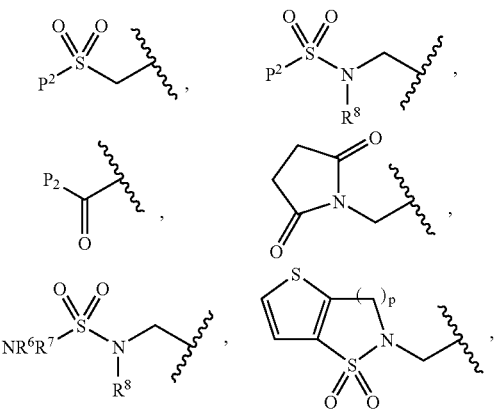

or a pharmaceutically acceptable salt, or ester thereof, wherein,

M is O, N(H), or CH₂;
R¹ is —OR⁶, —NR⁶R⁷ or

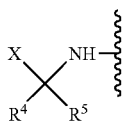

where R⁶ and R⁷ can be the same or different, each being independently selected from the group consisting of hydrogen, alkyl, alkenyl, alkynyl, heteroalkyl, $(C_3-C_{10})$cycloalkyl, $(C_3-C_{10})$cycloalkylalkyl, aryl, arylalkyl, heteroaryl, heteroarylalkyl, heterocyclyl, heterocyclylalkyl, hydroxyl, amino, arylamino and alkylamino;

$P_1$ is selected from the group consisting of alkyl, alkenyl, alkynyl, $(C_3-C_{10})$cycloalkyl haloalkyl;

$P_3$ is selected from the group consisting of alkyl, $(C_3-C_{10})$cycloalkyl, aryl and $(C_3-C_{10})$cycloalkyl fused with aryl;

$R^4$ and $R^5$ can be the same or different, each being independently selected from the group consisting of H, alkyl, aryl and $(C_3-C_{10})$cycloalkyl; or alternatively $R^4$ and $R^5$ together form part of a cyclic 5- to 7-membered ring such that the moiety

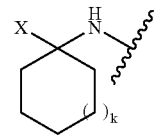

is represented by where k is 0 to 2;
X is selected from the group consisting of:

-continued

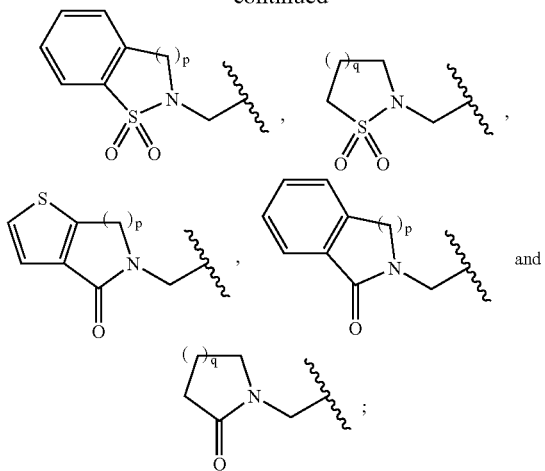

where p is 1 to 2, q is 1 to 3 and P² is alkyl, aryl, heteroaryl, heteroalkyl, (C₃-C₁₀)cycloalkyl, dialkylamino, alkylamino, arylamino or (C₃-C₁₀)cycloalkylamino; and R³ is selected from the group consisting of: aryl, heterocyclyl, heteroaryl,

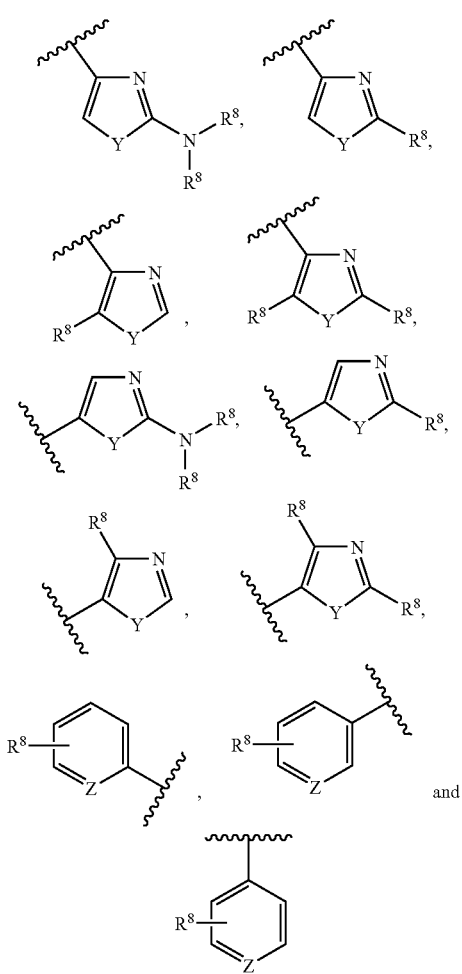

where Y is O, S or NH, and Z is CH or N, and the R⁸ moieties can be the same or different, each R⁸ being independently selected from the group consisting of hydrogen, alkyl, heteroalkyl, (C₃-C₁₀)cycloalkyl, aryl, heteroaryl, heterocyclyl, hydroxyl, amino, arylamino, alkylamino, dialkylamino, halo, alkylthio, arylthio and alkyloxy;

wherein each of said heteroaryl and said heterocyclyl consist of 4-14 ring atoms, wherein 1 to 4 of said ring atoms are O, N, or S, further wherein each of said heteroaryl and heterocylyl can be monocyclic or bicyclic and;

heteroalkyl is (C₁-C₁₂) alkyl, wherein 1-4 of the (C₁-C₁₂) atoms are replaced by heteroatoms selected from the group consisting of O, N and S.

12. The compound of claim 11, wherein M is NH or O.

13. The compound of claim 11, wherein R¹ is OR⁶ or NR⁶R⁷, where R⁶ and R⁷ can be the same or different, each being independently selected from the group consisting of H, alkyl, alkenyl, (C₃-C₁₀)cycloalkyl, alkylamino and (C₃-C₁₀)cycloalkylalkyl.

14. The compound of claim 11, wherein P₁ is selected from the group consisting of:

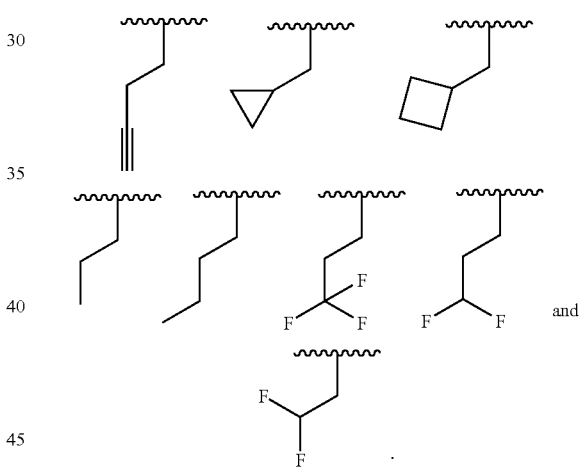

15. The compound of claim 11, wherein P₃ is selected from the group consisting of:

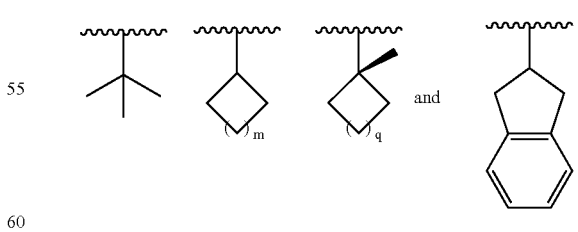

where m is 0 to 3 and q is 1 to 3.

16. The compound of claim 11, wherein R⁴ and R⁵ are the same or different, each being independently selected from the group consisting of:

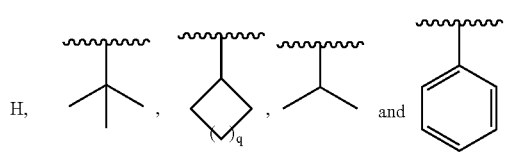

where q is 1 to 3, or $R^4$ and $R^5$ form part of a 5- or 6-membered ring such that the moiety

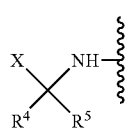

is represented by

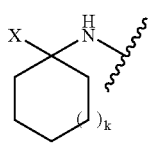

where k is 0 to 1.

17. The compound of claim 12, wherein M is NH.
18. The compound of claim 13, wherein $R^1$ is OH, $NH_2$ or N(H)(alkyl).
19. The compound of claim 14, wherein $P_1$ is cyclopropylalkyl, cyclobutylalkyl, n-propyl, n-butyl, 1,1,-difluoroethyl, 1,1-difluoropropyl or 1,1,1-trifluoropropyl.
20. The compound of claim 15, wherein $P_3$ is t-butyl, cyclohexyl or indanyl.
21. The compound of claim 16, wherein $R^4$ and $R^5$ are the same or different, each being independently selected from the group consisting of H, t-butyl, cyclobutyl or phenyl, or $R^4$ and $R^5$ together form a 6-membered ring such that the moiety

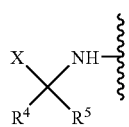

is represented by

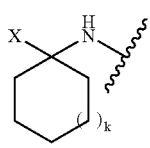

where k is 1.

22. A compound selected from the group consisting of:

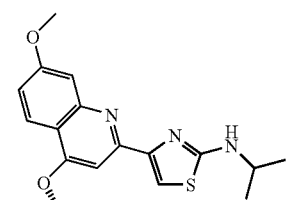

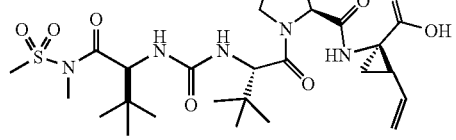

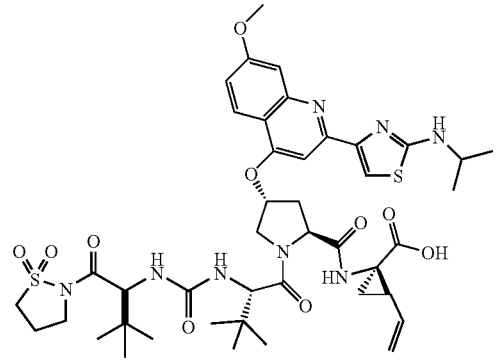

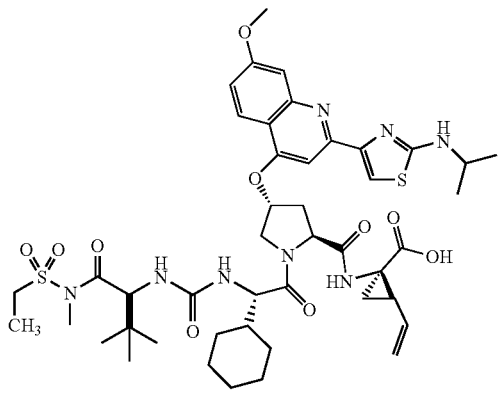

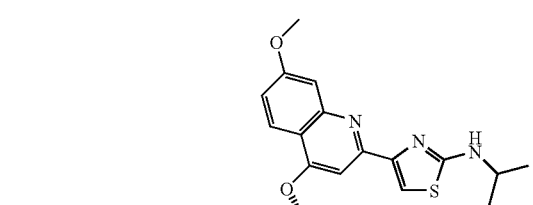

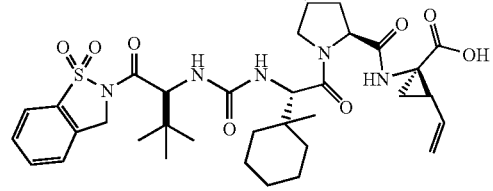

239
-continued
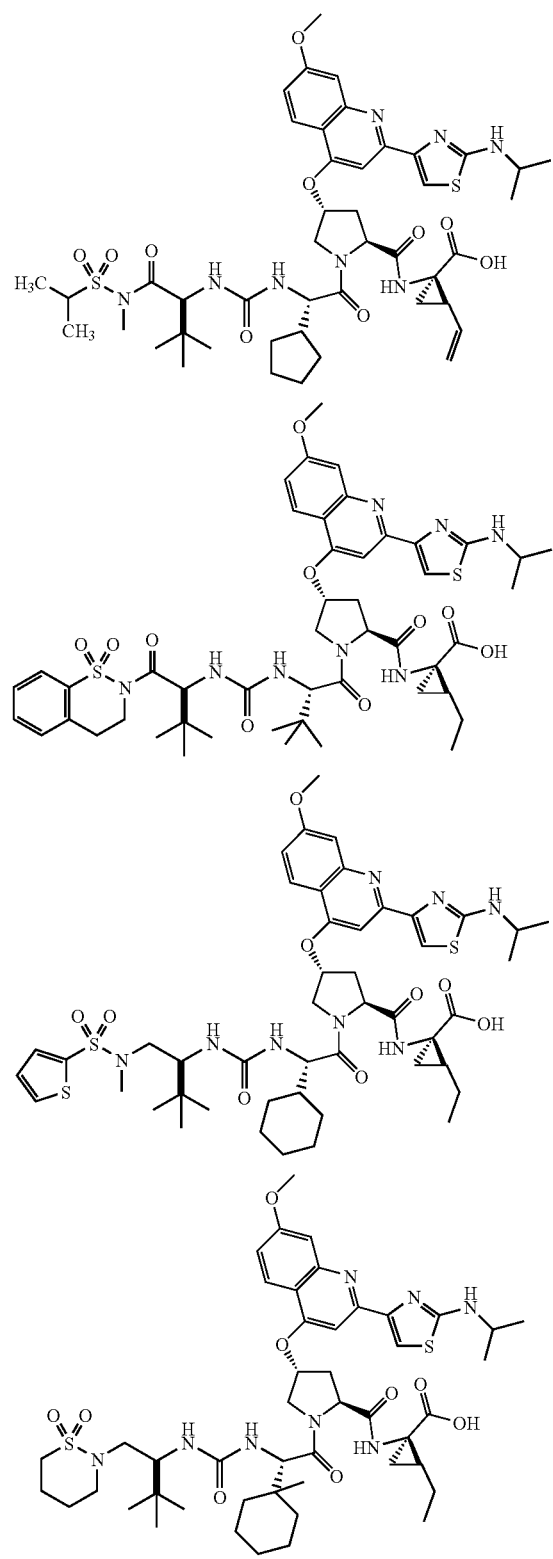
240
-continued
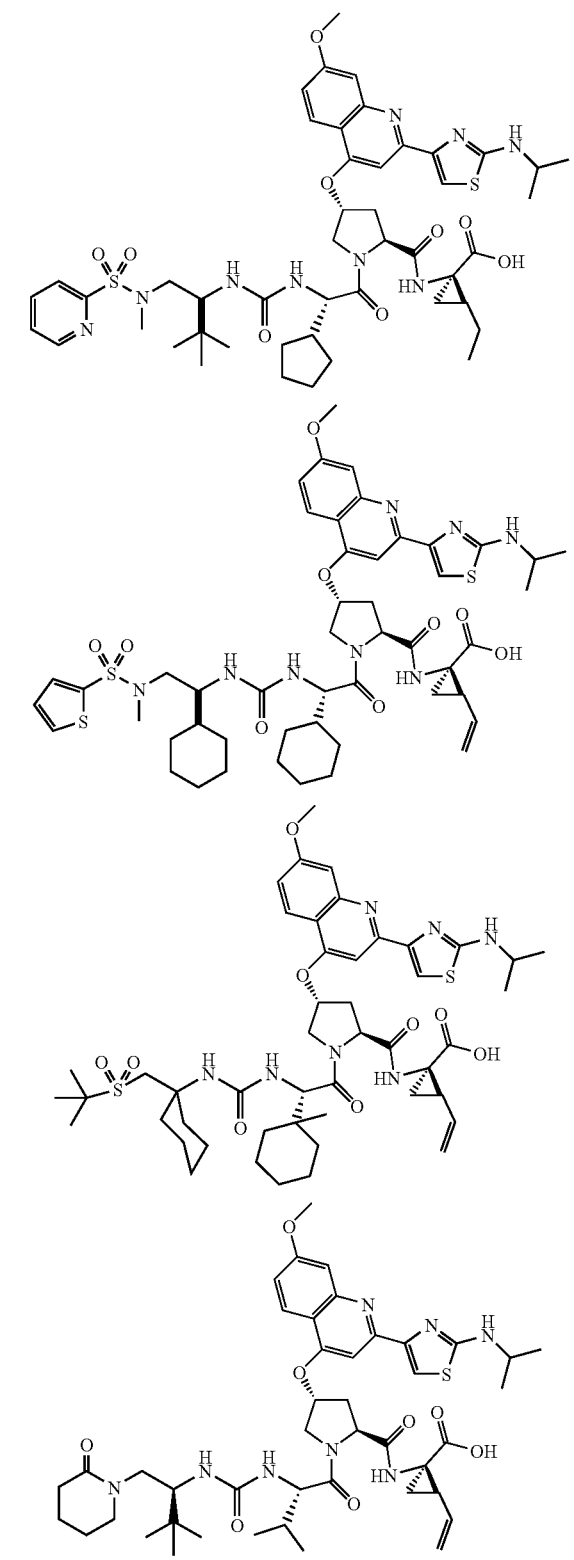

241
-continued
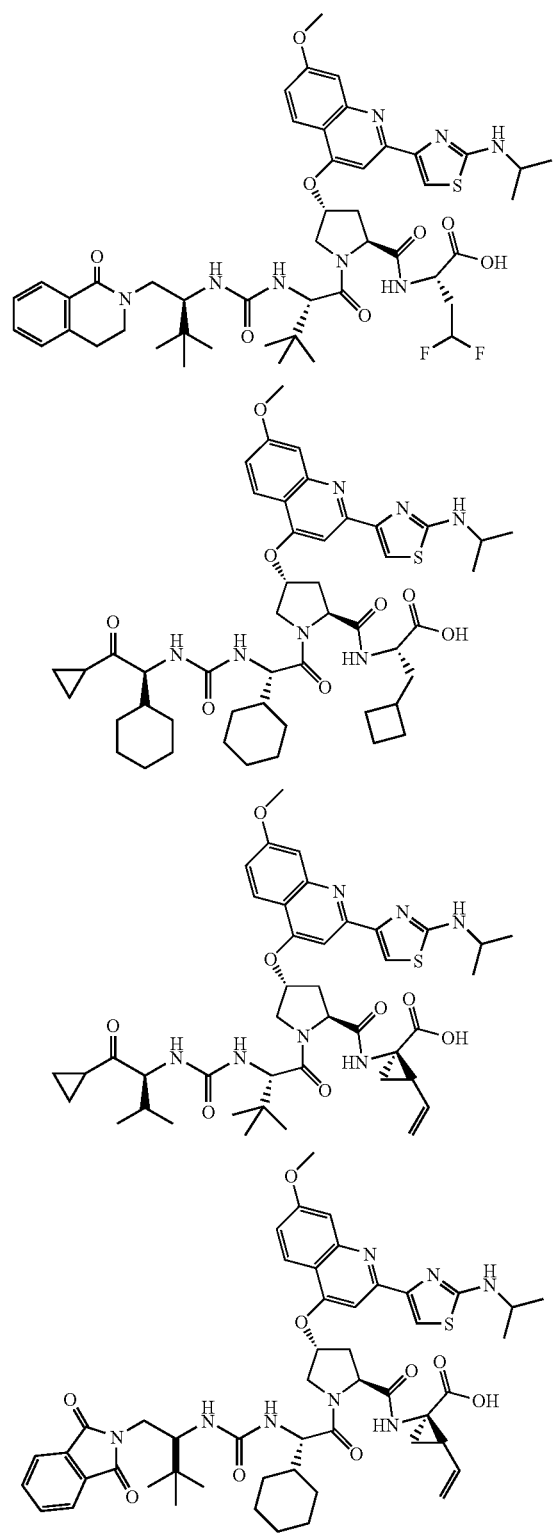
242
-continued
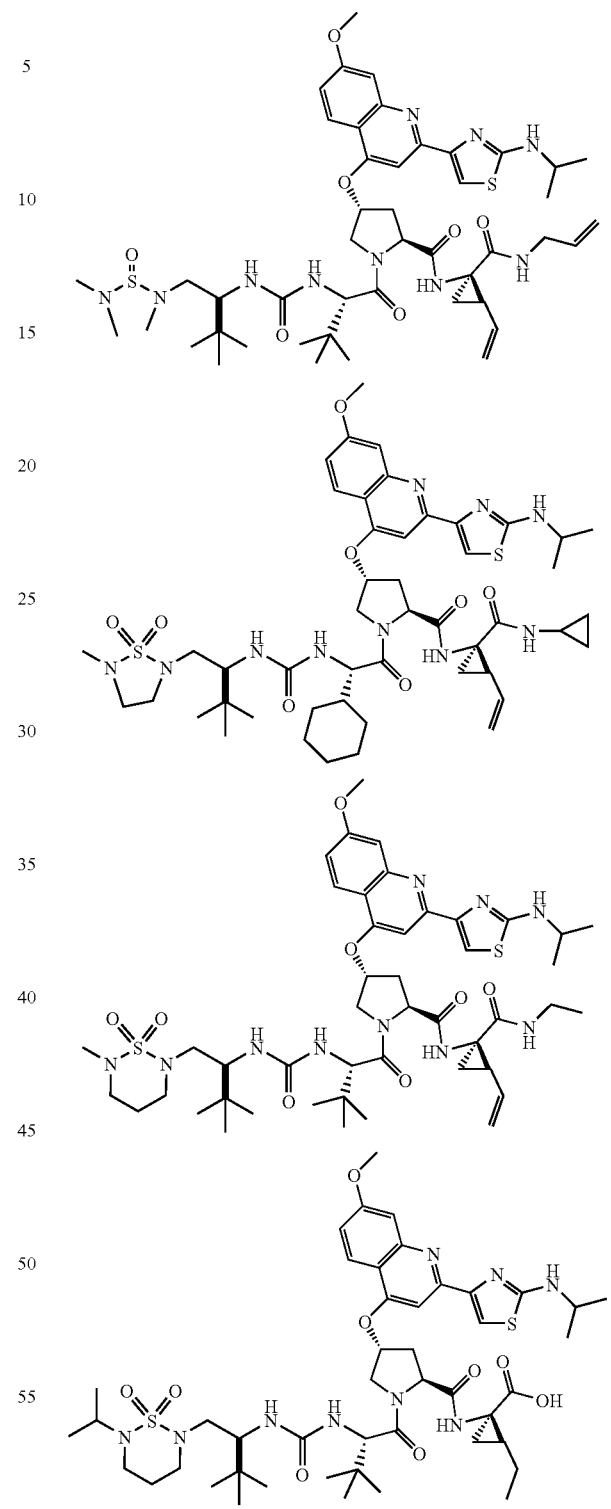

-continued

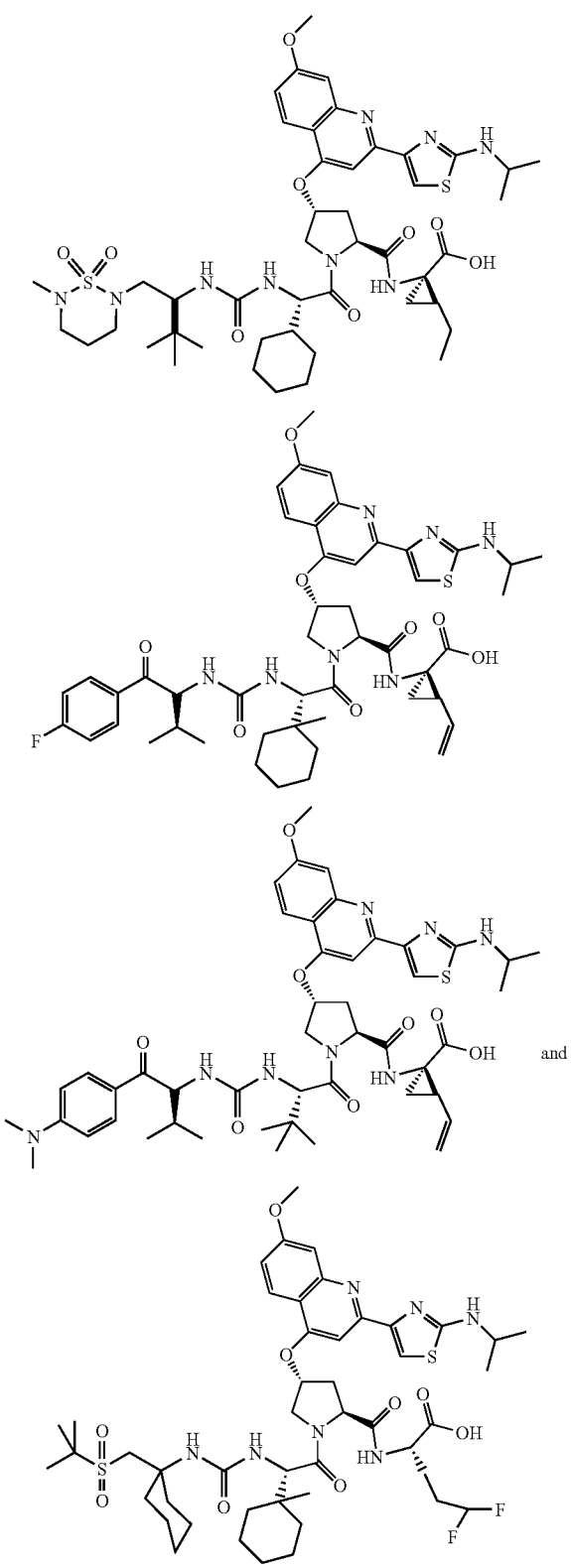

or a pharmaceutically acceptable salt, or ester thereof.

23. A compound having the general structure shown in Formula 3:

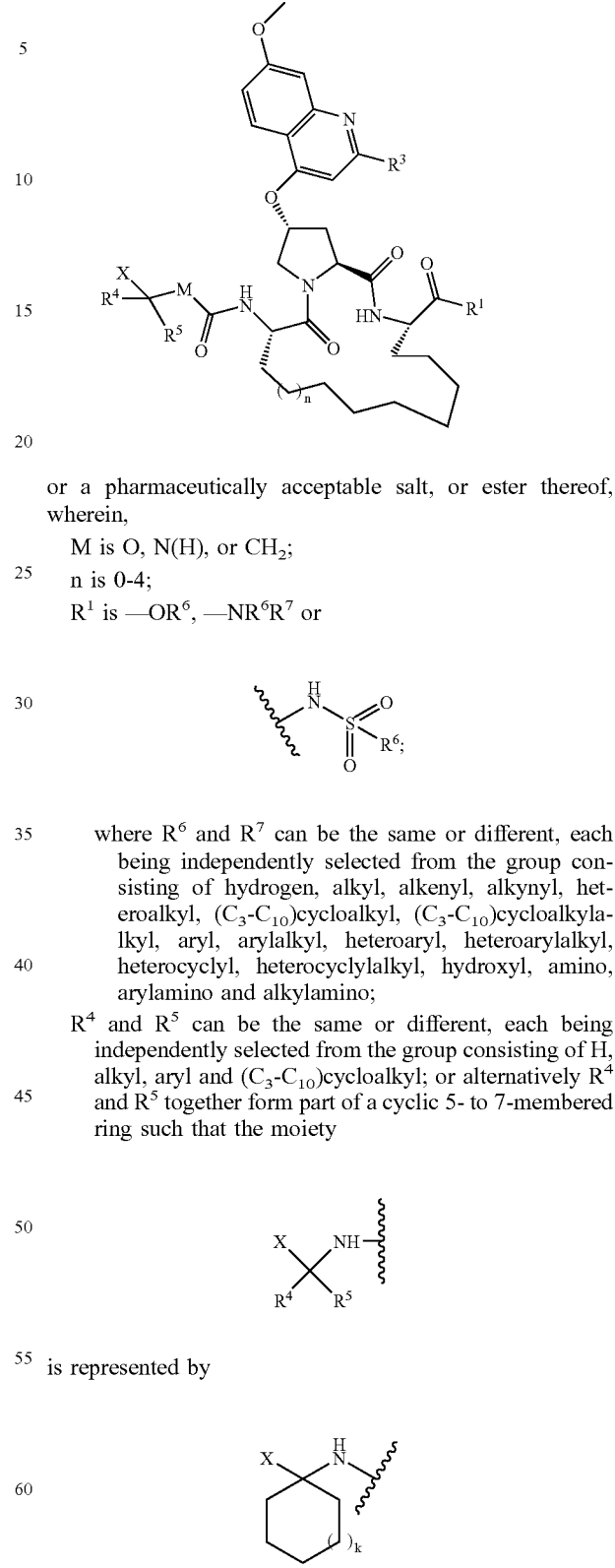

or a pharmaceutically acceptable salt, or ester thereof, wherein,

M is O, N(H), or CH$_2$;

n is 0-4;

R$^1$ is —OR$^6$, —NR$^6$R$^7$ or where R$^6$ and R$^7$ can be the same or different, each being independently selected from the group consisting of hydrogen, alkyl, alkenyl, alkynyl, heteroalkyl, (C$_3$-C$_{10}$)cycloalkyl, (C$_3$-C$_{10}$)cycloalkylalkyl, aryl, arylalkyl, heteroaryl, heteroarylalkyl, heterocyclyl, heterocyclylalkyl, hydroxyl, amino, arylamino and alkylamino;

R$^4$ and R$^5$ can be the same or different, each being independently selected from the group consisting of H, alkyl, aryl and (C$_3$-C$_{10}$)cycloalkyl; or alternatively R$^4$ and R$^5$ together form part of a cyclic 5- to 7-membered ring such that the moiety is represented by where k is 0 to 2;

X is selected from the group consisting of:

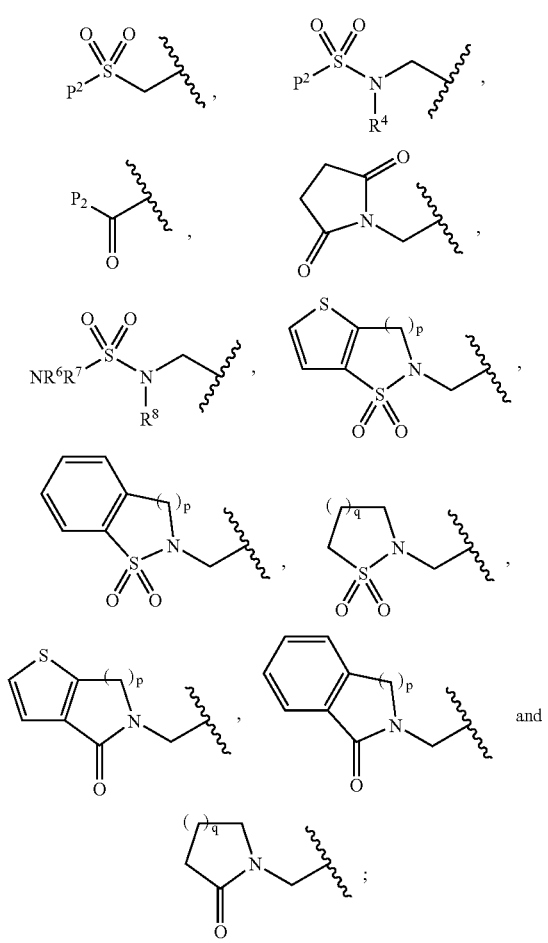

where p is 1 to 2, q is 1 to 3 and $P^2$ is alkyl, aryl, heteroaryl, heteroalkyl, $(C_3-C_{10})$cycloalkyl, dialkylamino, alkylamino, arylamino or $(C_3-C_{10})$cycloalkylamino; and $R^3$ is selected from the group consisting of: aryl, heterocyclyl, heteroaryl,

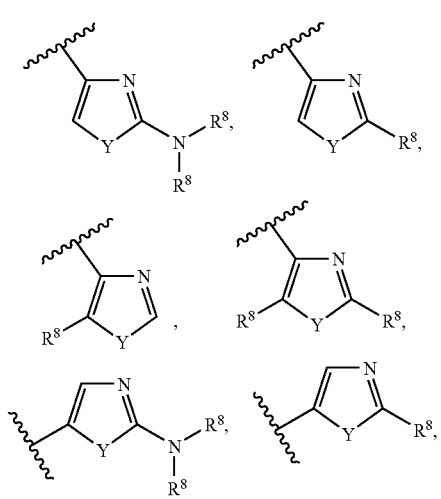

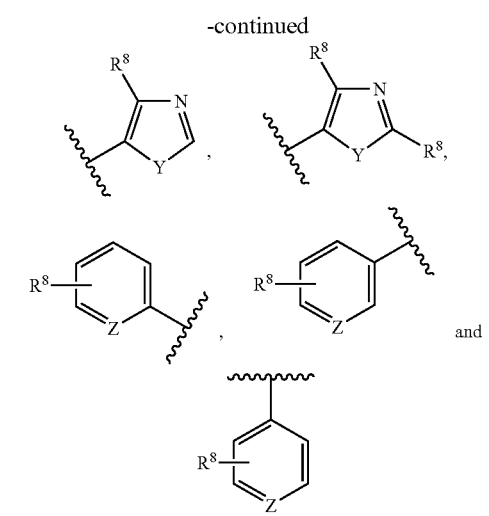

where Y is O, S or NH, and Z is CH or N, and the $R^8$ moieties can be the same or different, each $R^8$ being independently selected from the group consisting of hydrogen, alkyl, heteroalkyl, $(C_3-C_{10})$cycloalkyl, aryl, heteroaryl, heterocyclyl, hydroxyl, amino, arylamino, alkylamino, dialkylamino, halo, alkylthio, arylthio and alkyloxy;

wherein each of said heteroaryl and said heterocyclyl consist of 4-14 ring atoms, wherein 1 to 4 of said ring atoms are O, N, or S, further wherein each of said heteroaryl and heterocylyl can be monocyclic or bicyclic and;

heteroalkyl is $(C_1-C_{12})$ alkyl, wherein 1-4 of the $(C_1-C_{12})$ atoms are replaced by heteroatoms selected from the group consisting of O, N and S.

24. The compound of claim 23, wherein M is NH or O.

25. The compound of claim 23, wherein n is 0 or 1.

26. The compound of claim 23, wherein $R^1$ is $OR^6$ or $NR^6R^7$, where $R^6$ and $R^7$ can be the same or different, each being independently selected from the group consisting of H, alkyl, alkenyl, $(C_3-C_{10})$cycloalkyl, alkylamino and $(C_3-C_{10})$cycloalkylalkyl.

27. The compound of claim 23, wherein $R^4$ and $R^5$ are the same or different, each being independently selected from the group consisting of:

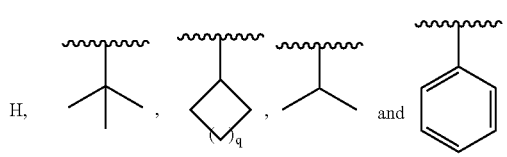

where q is 1 to 3, or $R^4$ and $R^5$ form part of a 5- or 6-membered ring such that the moiety

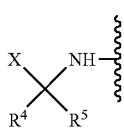

is represented by

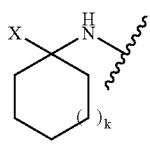

where k is 0 to 1.

28. The compound of claim 24, wherein M is NH.

29. The compound of claim 25, wherein n is 0 or 1.

30. The compound of claim 26, wherein $R^1$ is OH, $NH_2$ or N(H)(alkyl).

31. The compound of claim 27, wherein $R^4$ and $R^5$ are the same or different, each being independently selected from the group consisting of H, t-butyl, cyclobutyl or phenyl, or $R^4$ and $R^5$ together form a 6-membered ring such that the moiety

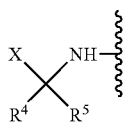

is represented by

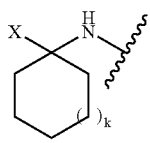

where k is 1.

32. A compound selected from the group consisting of:

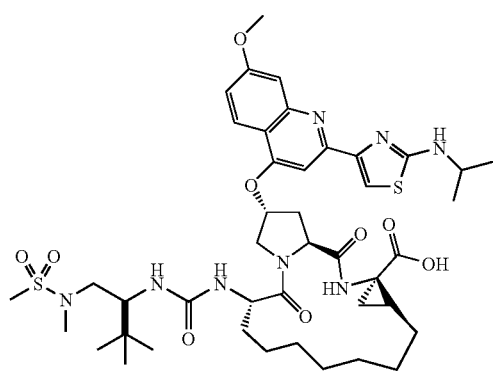

-continued

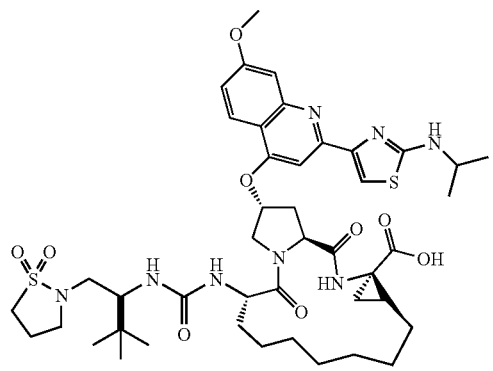

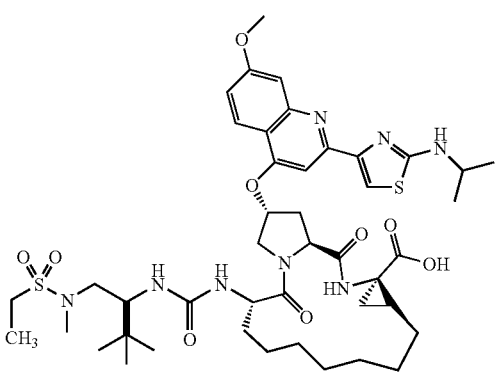

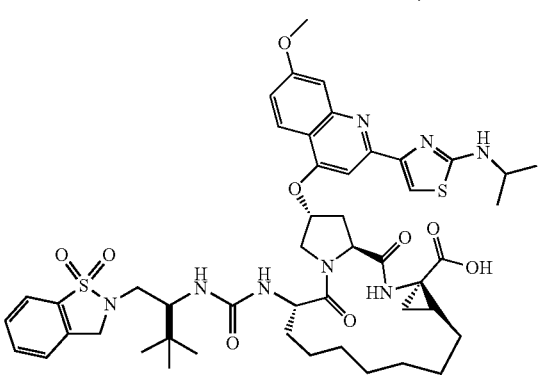

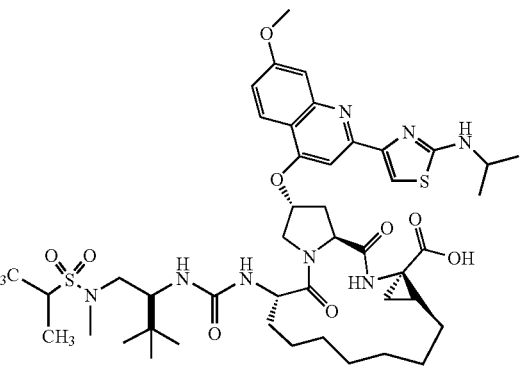

249
-continued
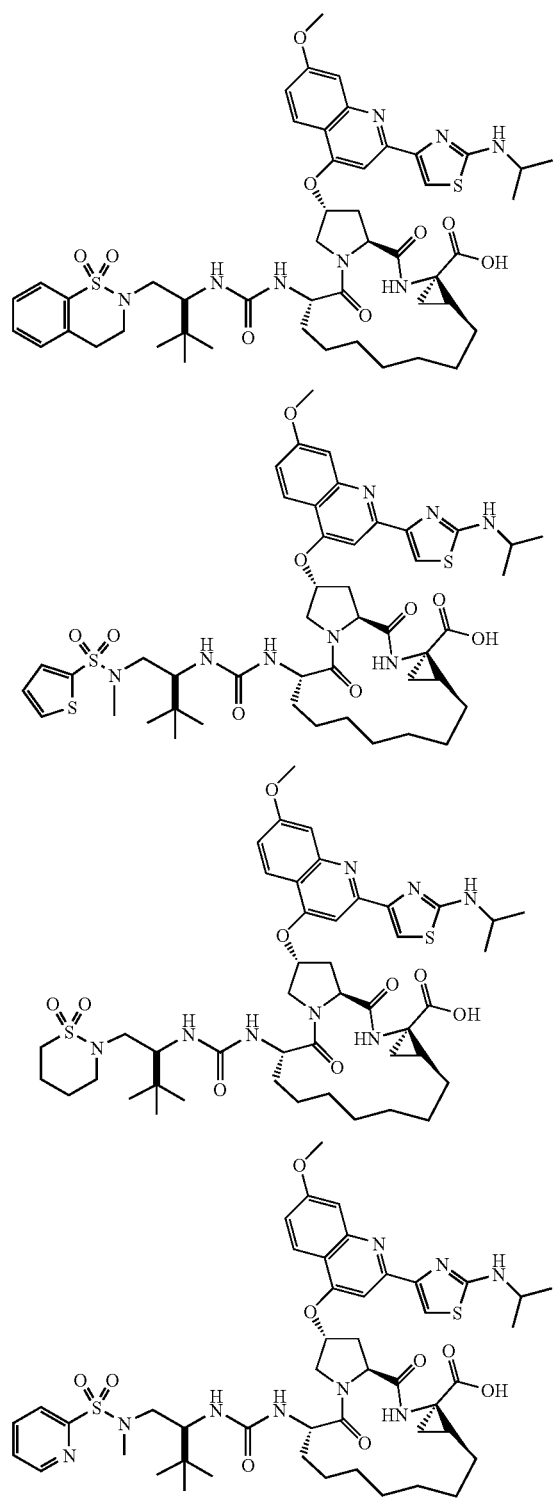
250
-continued
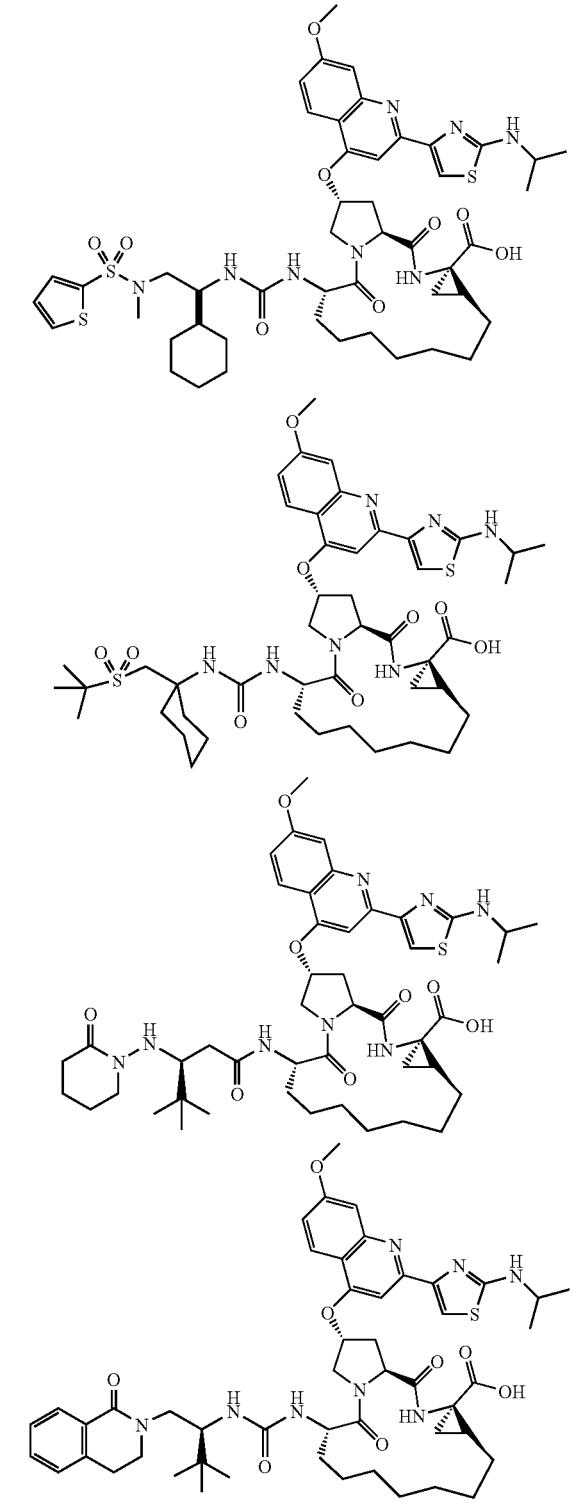

251
-continued
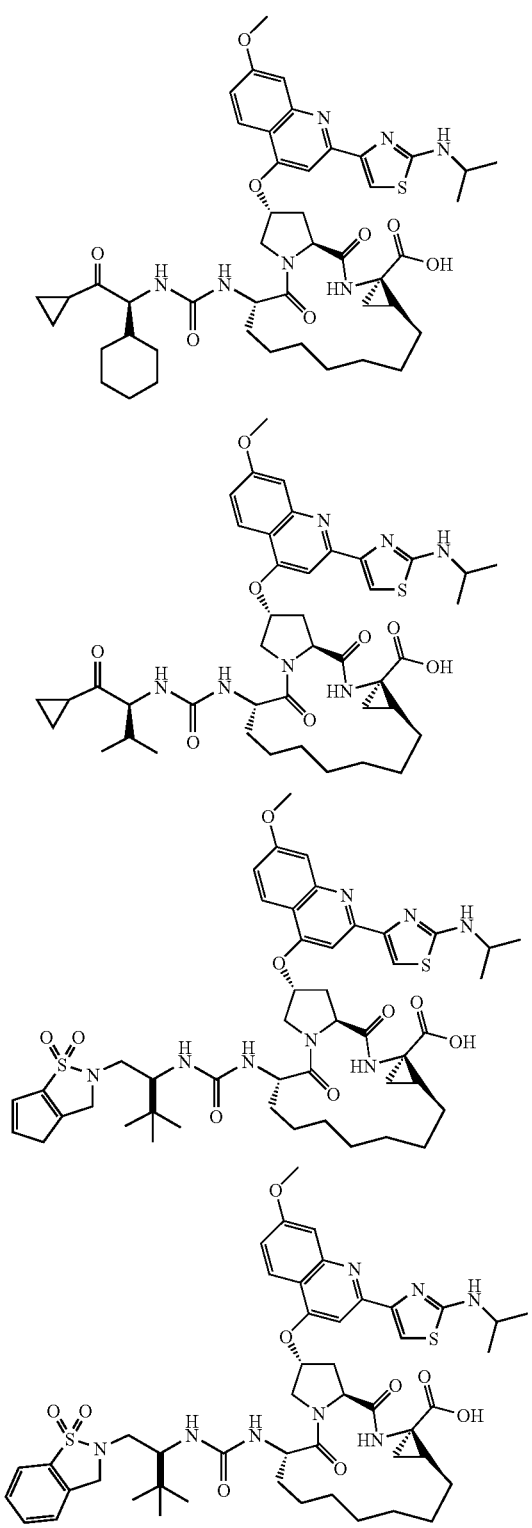
252
-continued
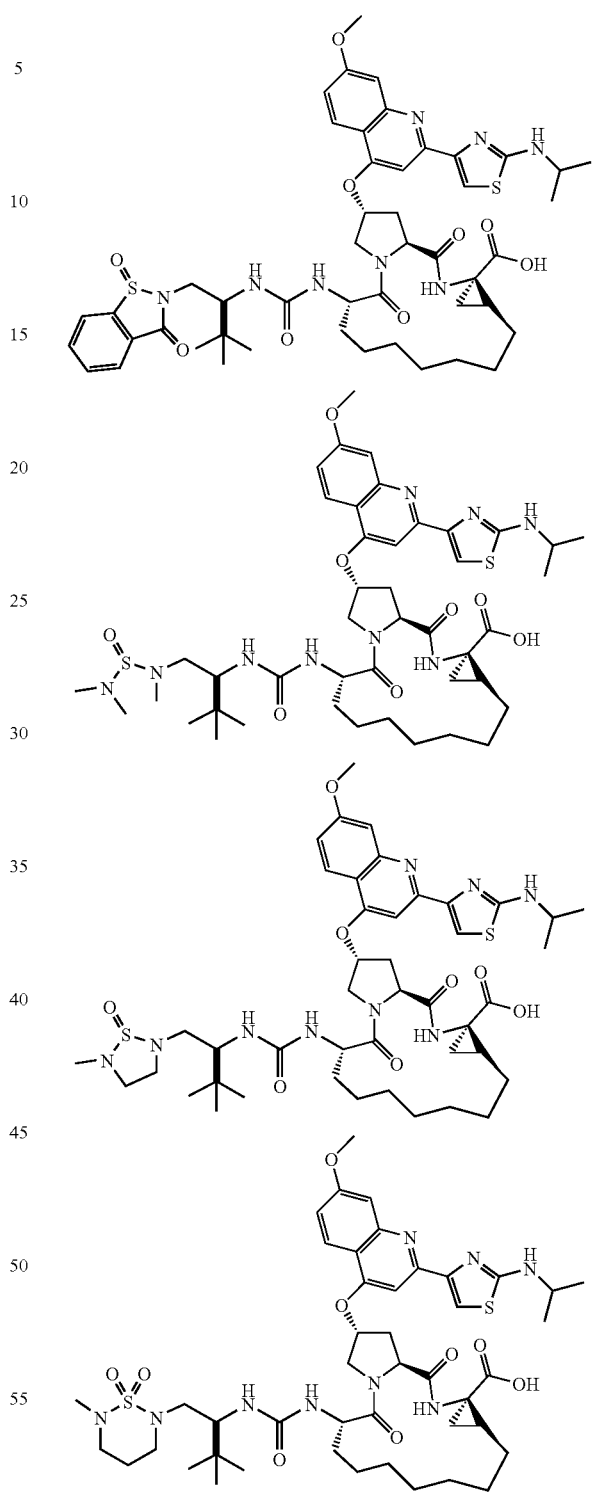

-continued
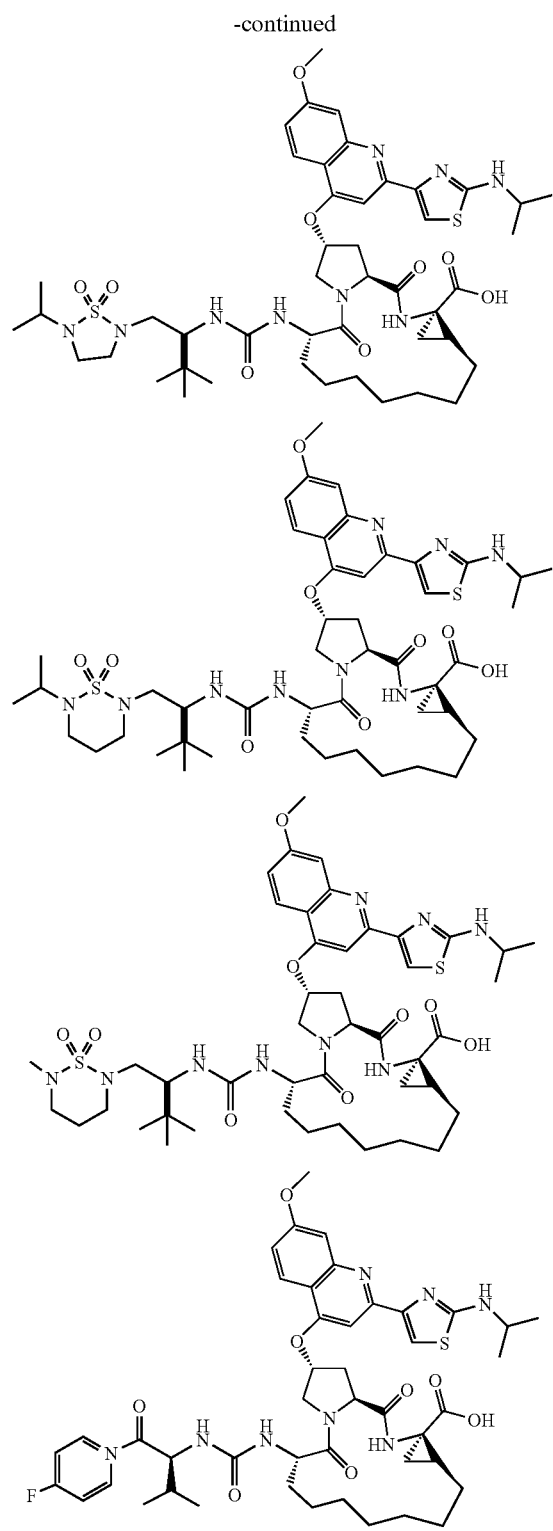
-continued
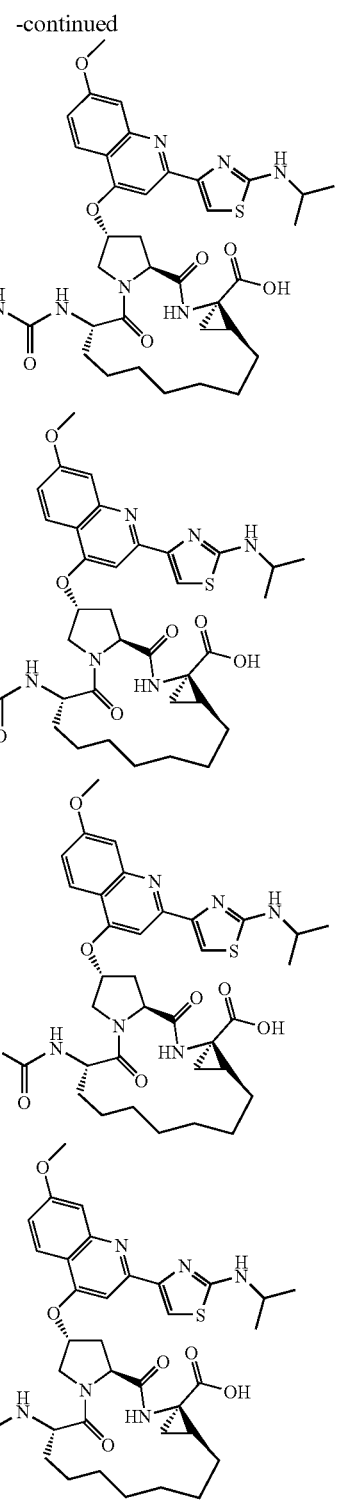

255
-continued
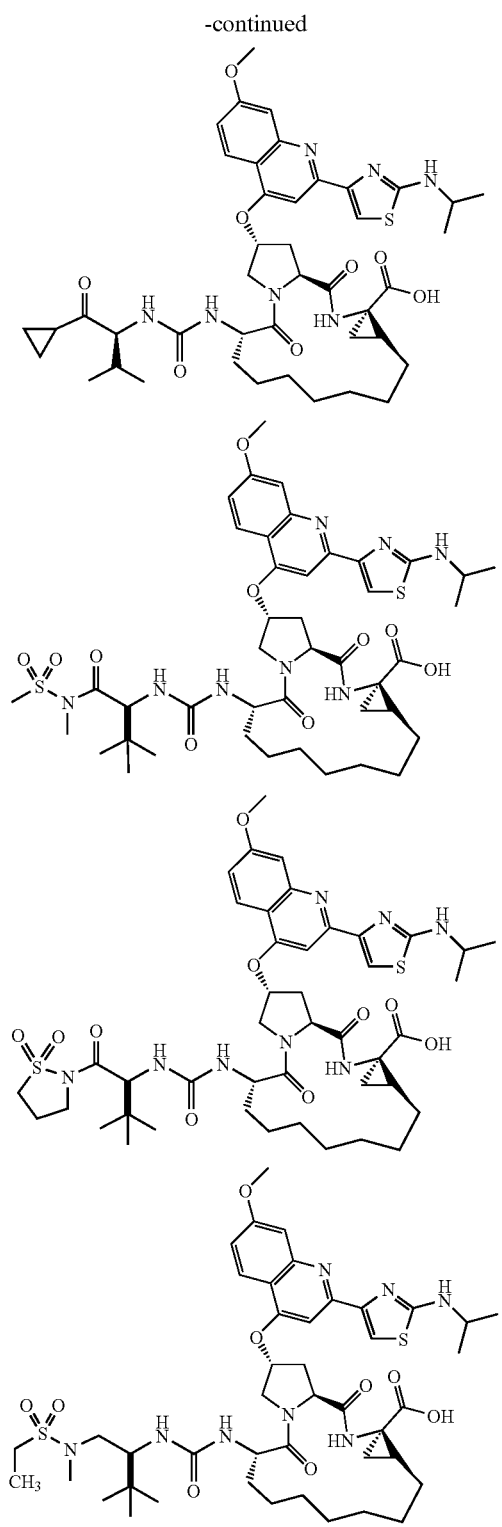
256
-continued
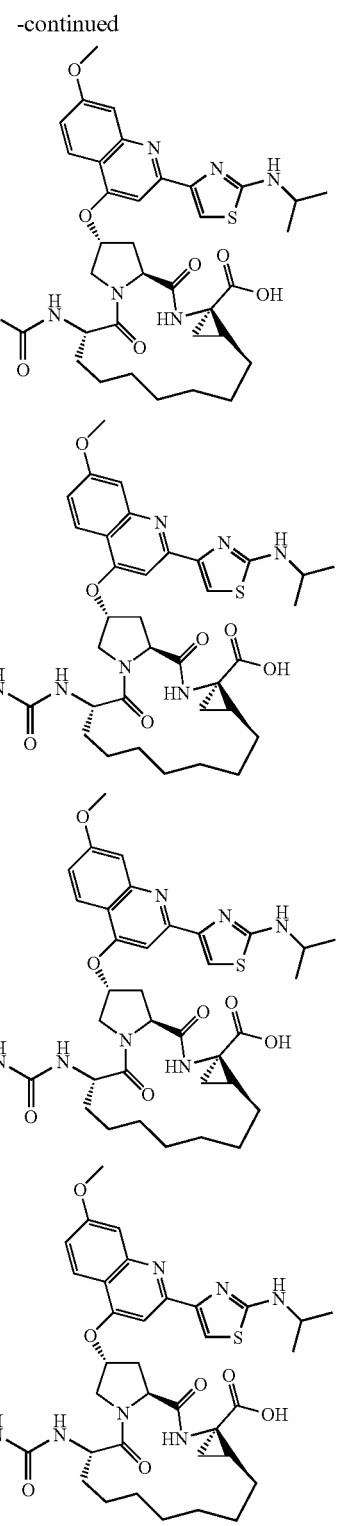

257
-continued
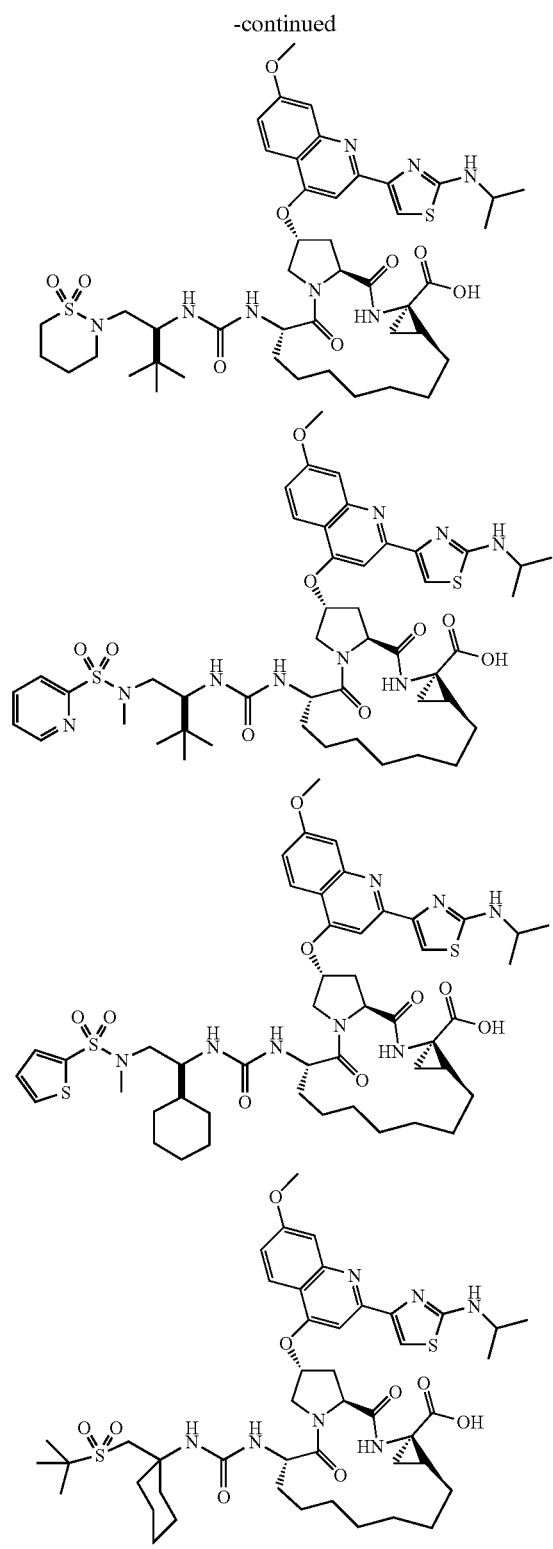
258
-continued
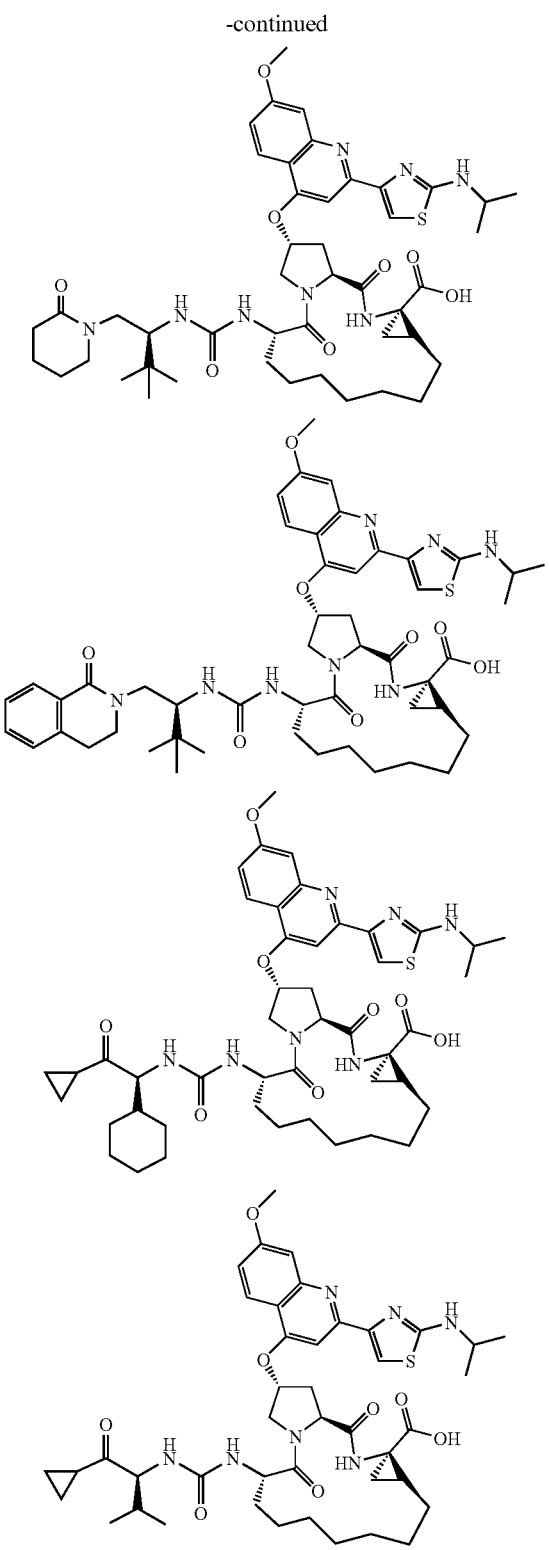

259
-continued
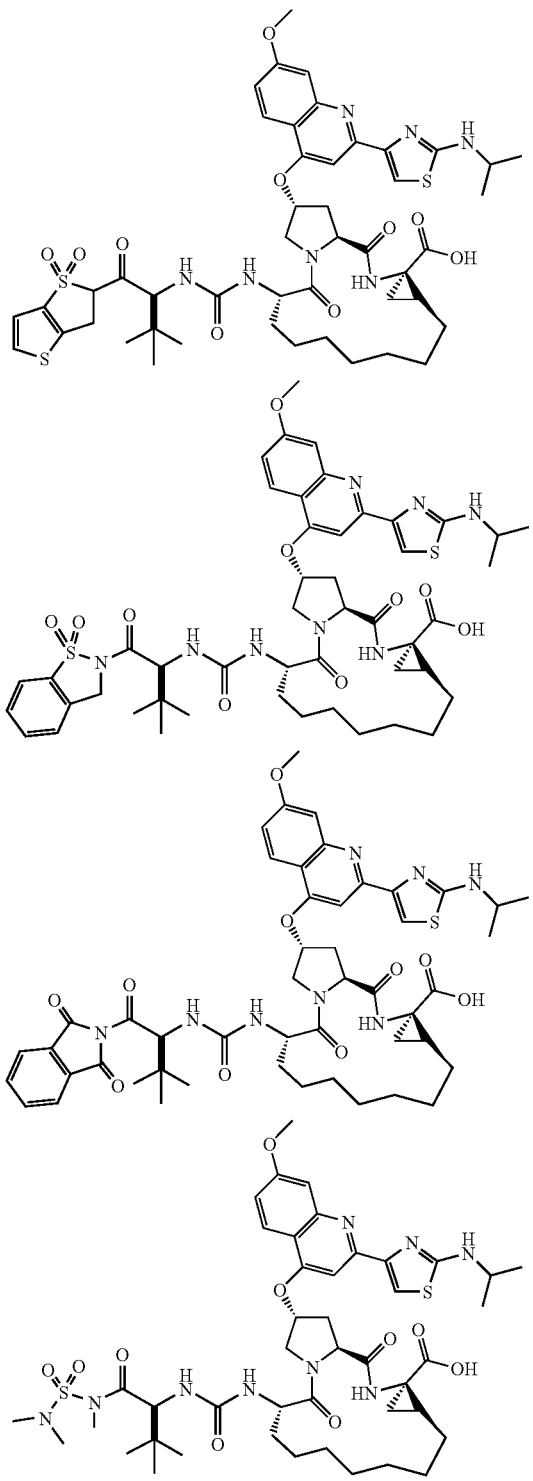
260
-continued
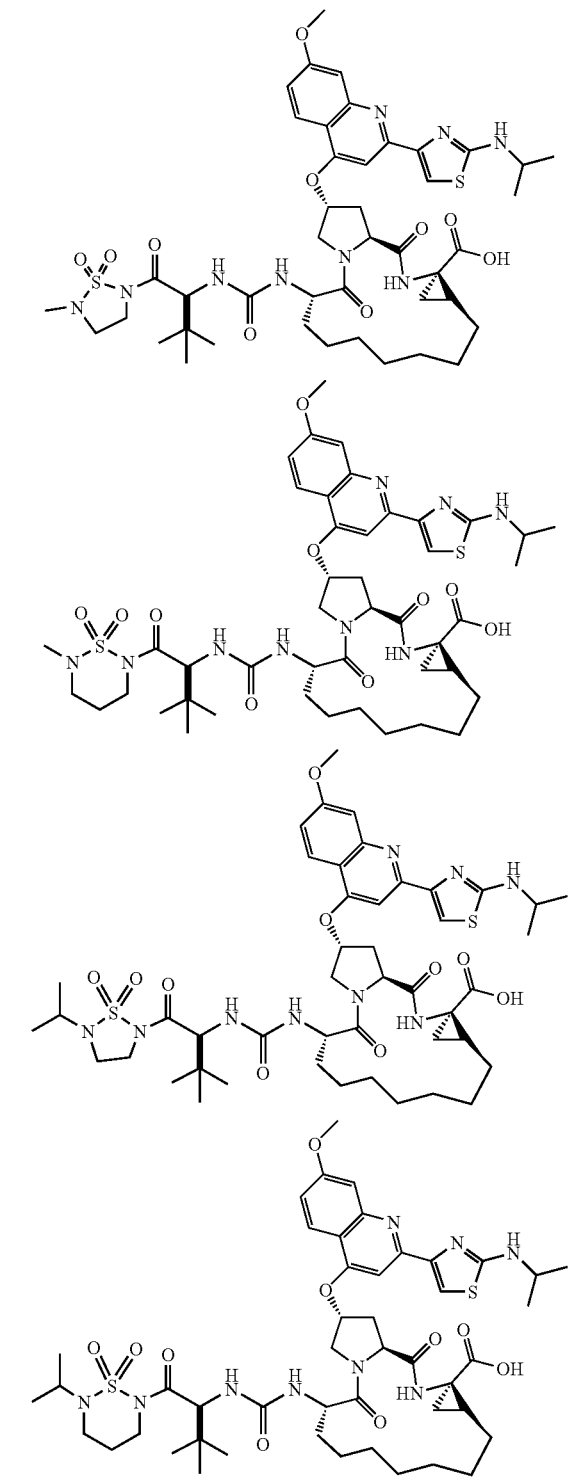

-continued

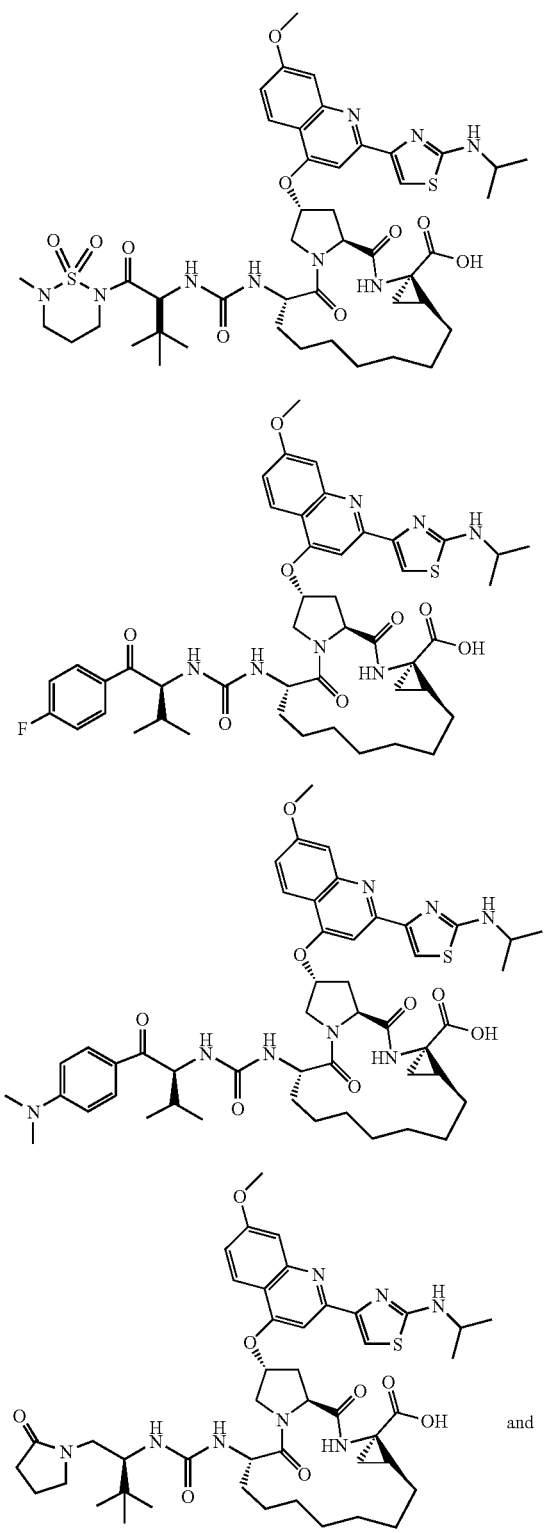

-continued

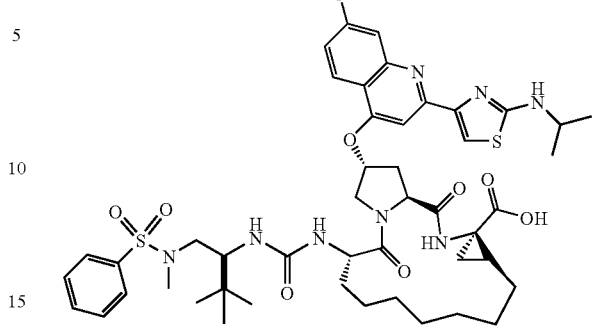

or a pharmaceutically acceptable salt, or ester thereof.

33. A pharmaceutical composition comprising as an active ingredient at least one compound according to claim 1 and at least one pharmaceutically acceptable carrier.

34. A method of treating HCV infection, said method comprising administering to a patient in need of such treatment a pharmaceutical composition which comprises therapeutically effective amounts of at least one compound according to claim 1.

35. The method according to claim 34, wherein said administration is subcutaneous.

36. A pharmaceutical composition for treating disorders associated with the HCV protease, said composition comprising therapeutically effective amount of one or more compounds in claim 10 and a pharmaceutically acceptable carrier.

37. A pharmaceutical composition comprising as an active ingredient at least one compound according to claim 11 and at least one pharmaceutically acceptable carrier.

38. A method of treating HCV infection, said method comprising administering to a patient in need of such treatment a pharmaceutical composition which comprises therapeutically effective amounts of at least one compound according to claim 11.

39. The method according to claim 38, wherein said administration is subcutaneous.

40. A pharmaceutical composition for treating disorders associated with the HCV protease, said composition comprising therapeutically effective amount of one or more compounds in claim 22 and a pharmaceutically acceptable carrier.

41. A pharmaceutical composition comprising as an active ingredient at least one compound according to claim 23 and at least one pharmaceutically acceptable carrier.

42. A method of treating HCV infection, said method comprising administering to a patient in need of such treatment a pharmaceutical composition which comprises therapeutically effective amounts of at least one compound according to claim 25.

43. The method according to claim 42, wherein said administration is subcutaneous.

44. A pharmaceutical composition for treating disorders associated with the HCV protease, said composition comprising therapeutically effective amount of one or more compounds in claim 32 and a pharmaceutically acceptable carrier.

* * * * *

UNITED STATES PATENT AND TRADEMARK OFFICE
CERTIFICATE OF CORRECTION

PATENT NO. : 7,253,160 B2
APPLICATION NO. : 10/993394
DATED : August 7, 2007
INVENTOR(S) : F. George Njoroge It is certified that error appears in the above-identified patent and that said Letters Patent is hereby corrected as shown below:

Claim 1, Col. 208, Lines 5-10        Please correct: "$R_8$"    to -- "$R_6$" --

Claim 1, Col. 208, Lines 15-20       Please correct: "$R_8$"    to -- "$R_6$" --

Claim 11, Col. 234, Lines 50-55      Please correct: "$R_8$"    to -- "$R_6$" --

Claim 11, Col. 234, Lines 60-65      Please correct: "$R_8$"    to -- "$R_6$" --

Claim 23, Col. 245, Lines 5-10       Please correct: "$R_8$"    to -- "$R_6$" --

Claim 23, Col. 245, Lines 15-20      Please correct: "$R_8$"    to -- "$R_6$" --

Signed and Sealed this

Twentieth Day of November, 2007

JON W. DUDAS
*Director of the United States Patent and Trademark Office*